(12) United States Patent
Singh

(10) Patent No.: US 11,370,847 B2
(45) Date of Patent: *Jun. 28, 2022

(54) SINGLE DOMAIN ANTIBODIES DIRECTED AGAINST INTRACELLULAR ANTIGENS

(71) Applicant: Singh Biotechnology, LLC, Hudson, FL (US)

(72) Inventor: Sunanda Singh, Lutz, FL (US)

(73) Assignee: Singh Molecular Medicine, LLC, Lutz, FL (US)

(*) Notice: Subject to any disclaimer, the term of this patent is extended or adjusted under 35 U.S.C. 154(b) by 681 days.

This patent is subject to a terminal disclaimer.

(21) Appl. No.: 16/195,542

(22) Filed: Nov. 19, 2018

(65) Prior Publication Data

US 2019/0177437 A1 Jun. 13, 2019

Related U.S. Application Data

(63) Continuation of application No. 15/823,295, filed on Nov. 27, 2017, now abandoned, which is a continuation-in-part of application No. 15/655,833, filed on Jul. 20, 2017, now Pat. No. 9,850,321, which is a continuation of application No. 15/608,255, filed on May 30, 2017, now abandoned, which is a continuation-in-part of application No. 14/922,093, filed on Oct. 23, 2015, now Pat. No. 9,695,234.

(60) Provisional application No. 62/210,795, filed on Aug. 27, 2015, provisional application No. 62/188,353, filed on Jul. 2, 2015, provisional application No. 62/148,656, filed on Apr. 16, 2015, provisional application No. 62/067,908, filed on Oct. 23, 2014.

(51) Int. Cl.
| | |
|---|---|
| *A61K 39/00* | (2006.01) |
| *C07K 16/46* | (2006.01) |
| *C12Q 1/68* | (2018.01) |
| *A61K 39/395* | (2006.01) |
| *A61K 45/06* | (2006.01) |
| *A61K 31/704* | (2006.01) |
| *C07K 16/18* | (2006.01) |
| *C07K 16/24* | (2006.01) |
| *C07K 16/30* | (2006.01) |
| *C07K 16/32* | (2006.01) |
| *C07K 16/00* | (2006.01) |
| *C12N 15/00* | (2006.01) |

(52) U.S. Cl.
CPC .......... *C07K 16/468* (2013.01); *A61K 31/704* (2013.01); *A61K 39/395* (2013.01); *A61K 39/39558* (2013.01); *A61K 45/06* (2013.01); *C07K 16/18* (2013.01); *C07K 16/241* (2013.01); *C07K 16/3015* (2013.01); *C07K 16/32* (2013.01); *C12Q 1/68* (2013.01); *A61K 39/00* (2013.01); *A61K 2039/505* (2013.01); *C07K 16/00* (2013.01); *C07K 2317/22* (2013.01); *C07K 2317/569* (2013.01); *C07K 2317/76* (2013.01); *C07K 2317/80* (2013.01); *C07K 2317/92* (2013.01); *C12N 15/00* (2013.01); *Y02A 50/30* (2018.01)

(58) Field of Classification Search
CPC ............................................. A61K 2039/6056
See application file for complete search history.

(56) References Cited

U.S. PATENT DOCUMENTS

| | | |
|---|---|---|
| 5,965,371 A | 10/1999 | Marasco et al. |
| 6,159,947 A | 12/2000 | Schweighoffer et al. |
| 6,265,160 B1 | 7/2001 | Leonard |

FOREIGN PATENT DOCUMENTS

| | | | |
|---|---|---|---|
| EP | 3590962 A1 | | 1/2020 |
| JP | 2011526619 A | | 10/2011 |
| WO | 2003077945 A1 | | 9/2003 |
| WO | 2004046186 A2 | | 6/2004 |
| WO | 2004046186 A3 | | 8/2004 |
| WO | WO 2007/092607 | * | 8/2007 |
| WO | 2014070868 A1 | | 5/2014 |
| WO | 2014144148 A1 | | 9/2014 |
| WO | 2014153495 A2 | | 9/2014 |
| WO | 2016065323 A3 | | 6/2016 |

OTHER PUBLICATIONS

Qiu et al Human Vaccin Immunother 10:964-967, Apr. 2014.*
Goodchild et al, Mol Immunol, 48:2027-2037, 2011.*
Wesolowski et al, Med Microbiol Immunol, 198:157-174, 2009.*
BRPTO, Non-Final Office Action on the Merits issued in related Brazilian Patent Application No. BR112017008165-2 dated Jan. 1, 2020 (6 pages).
CNIPA, Non-Final Office Action on the Merits issued in related Chinese Patent Application No. 201580056968.9 dated Jan. 21, 2020 (8 pages).

(Continued)

*Primary Examiner* — Mark Halvorson

(74) *Attorney, Agent, or Firm* — Laura M. King; Matrix Law Group, LLP

(57) ABSTRACT

This invention provides compositions and methods to prevent aberrant cell proliferation in a subject using a single-domain antibody (sdAb) directed against an intracellular component, wherein the aberrant cell proliferation can be cancer. The sdAb is synergistic with one or more chemotherapeutic drugs and improves therapeutic efficacy of the one or more chemotherapeutic drug against cancer. The invention also includes a method of treating viral infections using a sdAb, wherein the sbAb inhibits the replication of viruses such as Ebola virus and Zika virus in infected cells.

5 Claims, 26 Drawing Sheets

Specification includes a Sequence Listing.

(56) References Cited

OTHER PUBLICATIONS

CNIPA, Search Report issued by the China National Intellectual Property Administration in related Chinese Patent Application No. 201580056968.9 dated Jan. 21, 2020 (4 pages).
CIPO, Examiner Report on the Merits issued in related Canadian Patent Application No. 2,962,275 dated Mar. 5, 2019 (4 pages).
JPO, Notification of Reasons for Rejection issued in related patent family member Japanese Patent Application No. 2019-149269 dated Sep. 4, 2020. (5 pages total: 3 pages Rejection; 2 pages English translation).
Harrison B.C. et al, "Phosphorylation of glial fibrillary acidic protein and vimentin by cytoskeletal-associated intermediate filament protein kinase activity in astrocytes", Journal of Neurochemistry, Vol. 58, pp. 320-227, 1992.
Marschall, A.L.J., et al., "Targeting antibodies to the cytoplasm", Landes Bioscience mAbs, vol. 3(1), pp. 3-16, 2011.
USPTO, Non-Final Office Action on the Merits issued in related U.S. Appl. No. 15/608,255 dated Feb. 25, 2019, (11 pages).
AIPO, Examination Report No. 1 issued in related Australian Patent Application No. 2019204614 dated Jul. 31, 2020. (3 pages).
CIPO, Examiner Action on the Merits issued in related Canadian Patent Application No. 3,052,777 dated Jun. 12, 2020. (4 pages).
EPO, Examination Report issued in related European Patent Application No. 2019165430.0 dated Jul. 8, 2020. (4 pages).
IPO, Examination Report on the Merits issued in related Indian Patent Application No. 201717006629 dated Jul. 13, 2020. (7 pages).
MXIPO, Examination Report on the Merits issued in related Mexican Patent Application No. MX/a/2017/003268 dated Mar. 17, 2020. (10 pages: 1-5 Exam Report in Spanish; pp. 6-10 Google English translation).
BRPTO, Search Report issued in related Brazilian Patent Application No. BR122020006907-4 dated May 12, 2021, 4 pages total (2 pages of Portuguese translation and 2 pages of Google Translate English translation).
BRPTO, Technical Examination Report issued in related Brazilian Patent Application No. BR122020006907-4 dated May 12, 2021, 6 pages total (3 pages of Portuguese translation and 3 pages of Google Translate English translation).
USPTO, Non-Final Office Action on the Merits issued in related U.S. Appl. No. 15/608,255 dated Jun. 18, 2020 (13 pages).
ILPO, a Non-Final Office Action issued in related Israeli Patent Application No. 250961 dated Feb. 25, 2021, 2 pages.
JPO, a Final Notice of Reasons for Refusal issued in related Japanese Patent Application No. 2019-149269 dated Mar. 30, 2021, 4 pages total (2 pages of Japanese translation and 2 pages of English Translation).
JPO, Decision of Rejection issued in related Japanese Patent Application No. 2017-521577 dated May 15, 2019 (6 pages).
JPO, Office Action on the Merits issued in related Japanese Patent Application No. 2019-062231 (7 pages).
CIPO, Non-Final Office Action on the Merits issued in related Canadian Patent Application No. 2,962,275 dated Dec. 14, 2018 (4 pages).
EPO, Supplementary European Search Report issued in related European Patent Application No. 15853465.1 dated Jan. 2, 2018 (17 pages).
Siveen, Kodappully S. et. al., "Targeting the STAT3 signaling pathway in cancer: Role of synthetic and natural inhibitors", Biochimica et Biophysica Acta, vol. 1845, No. 2, pp. 136-154, Apr. 1, 2014, © 2013 Elsevier B.V.
ILPO, Non-Final Office Action on the Merits issued in related Israel Patent Application No. 250961 dated Feb. 20, 2020. (6 pages English translation, 4 pages Office Action).
Cochet, O., et. al., "Intracellular Expression of an Antibody Fragment-neutralizing p21 Ras Promotes Tumor Regression," Cancer Research, Vo.I 58, pp. 1170-1176, Mar. 15, 1998.
EPO, Extended European Search Report issued by the European Patent Office in related European Patent Application No. 19165430.0 dated Dec. 9, 2019, 8 pgs.
Liu, Pingyu, et. al., "Targeting the untargetable KRAS in cancer therapy," Acta Pharmaceutics Sinica B, 2019 Chinese Pharmaceutical Association and Institute of Materia Medica, Chinese Academy of Medical Sciences, 9(5): 871-879.
Singh, S., et. al., "Abstract 1544: Cell penetrating single domain antibody (sdAb) SBT-100 binds KRAS and inhibits growth of human cancers with KRAS activating mutations," Immunology, vol. 10, 1158/1538-7445.AM2019-1544, AACR American Association for Cancer Research Annual Meeting 2019; Mar. 29-Apr. 3, 2019, Atlanta, GA; AACR; Cancer Res 2019; 79(13 Suppl):Abstract nr 1544..
USPTO, Certificate of Correction for U.S. Pat. No. 5,865,371, Marasco, W., et. al. dated Sep. 25, 2001., 2 pgs., United States Patent and Trademark Office.
Japanese Patent Office, Office Action on the Merits issued in related Japanese Patent Application No. 2017-521577 dated Nov. 22, 2018 (8 pages, includes 3 pages of English translation).
Tanaka, et al., "Single Domain Intracellular Antibodies from Diverse Libraries Emphasizing Dual Functions of LMO2 Protein Interactions using a Single VH Domain," Journal of Biological Chemistry, vol. 286(5), pp. 3707-3716, Feb. 4, 2010.
BRPTO, Search Report and Technical Examination Report on the Merits issued in related Brazilian Patent Application No. BR122020006914-7 dated Jul. 12, 2021, (10 pages total, 5 pages in Portuguese, 5 pages English Google translation).
BRPTO, Search Report and Technical Examination Report on the Merits issued in related Brazilian Patent Application No. BR122020006918-0 dated Jul. 12, 2021, (10 pages total, 5 pages in Portuguese, 5 pages English Google translation).
BRPTO, Search Report and Technical Examination Report on the Merits issued in related Brazilian Patent Application No. BR122020006925-2 dated Jul. 12, 2021, (12 pages total, 6 pages in Portuguese, 6 pages English Google translation).
JPO, First Office Action/Notification of Reasons for Rejection on the merits in related Japanese Patent Application No. 2021-105631 dated Aug. 31, 2021, 4 pages (pp. 1-2 Japanese translation, pp. 3-4 English translation).
Wang, Li-meng, et. al., Construction and selection of camelized human sdAbs library against TNF, Mil. Med. Sci., May 2013, vol. 37, No. 5, pp. 1674-9960.

\* cited by examiner

Lanes:
M- Marker
1- STAT3 VHH13 (mammalian)
2- STAT3 VHH14 (mammalian)
3- STAT3 VHH13 (bacterial)
4- STAT3- VHH14 (bacterial)
5- Positive control (STAT-3)
6- Negative control (STAT-1)

Lanes:
M= Marker
1= PANC-1 with anti-STAT3 B VHH13
2= DU145 with anti-STAT3 B VHH13
3= HeLa + IFN-gamma with anti-STAT3 B VHH13
4= 4T1 with anti-STAT3 B VHH13
5= PANC-1 with anti-KRAS (G12D) VHH
6= PC-3 (negative control) with anti-STAT3 B VHH13

Top curve: G1 is control group with vehicle only IP; given twice daily
Second curve: G2 is given anti-STAT3 B VHH13 IP; 1mg/kg/twice daily
Third curve at the beginning: G3 is given anti-STAT3 B VHH13 IP; 2mg/kg/twice daily
Bottom curve at the beginning: G4 is given anti-STAT3 B VHH13 2mg/kg/once daily Mean IC$_{50}$ Staurosporine    (IC$_{50}$ Not determined)

SEQUENCE LISTING

<160> NUMBER OF SEQ ID NOS: 84

<210> SEQ ID NO 1
<211> LENGTH: 372

-continued

```
<212> TYPE: DNA
<213> ORGANISM: Artificial Sequence
<220> FEATURE:
<223> OTHER INFORMATION: Camelid

<400> SEQUENCE: 1
gaggtgcagc tggtggagtc tgggggaggc tcggtgcaga ctggagggtc tctgagactc    60
tcctgtgcag tttctggaaa tatcggcagc agctactgca tgggctggtt ccgccaggct   120
ccagggaaga agcgcgaggc ggtcgcacgt attgtacgtg atggtgccac tggctacgca   180
gactacgtga agggccgatt caccatctcc cgagacagcg ccaagaacac tctgtatctg   240
caaatgaaca ggctgatacc tgaggacact gccatctact actgtgcggc agacctgccc   300
ccaggttgtt tgactcaggc gatttggaat tttggttatc ggggccaggg aaccctggtc   360
accgtctcct ca                                                       372

<210> SEQ ID NO 2
<211> LENGTH: 124
<212> TYPE: PRT
<213> ORGANISM: Artificial Sequence
<220> FEATURE:
<223> OTHER INFORMATION: Camelid

<400> SEQUENCE: 2

Glu Val Gln Leu Val Glu Ser Gly Gly Gly Ser Val Gln Thr Gly Gly
  1               5                  10                  15

Ser Leu Arg Leu Ser Cys Ala Val Ser Gly Asn Ile Gly Ser Ser Tyr
             20                  25                  30

Cys Met Gly Trp Phe Arg Gln Ala Pro Gly Lys Lys Arg Glu Ala Val
         35                  40                  45

Ala Arg Ile Val Arg Asp Gly Ala Thr Gly Tyr Ala Asp Tyr Val Lys
     50                  55                  60

Gly Arg Phe Thr Ile Ser Arg Asp Ser Ala Lys Asn Thr Leu Tyr Leu
 65                  70                  75                  80

Gln Met Asn Arg Leu Ile Pro Glu Asp Thr Ala Ile Tyr Tyr Cys Ala
                 85                  90                  95

Ala Asp Leu Pro Pro Gly Cys Leu Thr Gln Ala Ile Trp Asn Phe Gly
            100                 105                 110

Tyr Arg Gly Gln Gly Thr Leu Val Thr Val Ser Ser
        115                 120

<210> SEQ ID NO 3
<211> LENGTH: 127
<212> TYPE: PRT
<213> ORGANISM: Artificial Sequence
<220> FEATURE:
<223> OTHER INFORMATION: Camelid

<400> SEQUENCE: 3

His Val Gln Leu Val Glu Ser Gly Gly Gly Ser Val Gln Ala Gly Gly
  1               5                  10                  15

Ser Leu Arg Leu Ser Cys Ala Ala Ser Gly Ala Asn Gly Gly Arg Ser
             20                  25                  30

Cys Met Gly Trp Phe Arg Gln Val Pro Gly Lys Glu Arg Glu Gly Val
         35                  40                  45

Ser Gly Ile Ser Thr Gly Gly Leu Ile Thr Tyr Tyr Ala Asp Ser Val
     50                  55                  60

Lys Gly Arg Phe Thr Ile Ser Gln Asp Asn Thr Lys Asn Thr Leu Tyr
 65                  70                  75                  80
```

```
Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125
```

<210> SEQ ID NO 4
<211> LENGTH: 126
<212> TYPE: PRT
<213> ORGANISM: Artificial Sequence
<220> FEATURE:
<223> OTHER INFORMATION: Camelid

<400> SEQUENCE: 4

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
        115                 120                 125
```

<210> SEQ ID NO 5
<211> LENGTH: 126
<212> TYPE: PRT
<213> ORGANISM: Artificial Sequence
<220> FEATURE:
<223> OTHER INFORMATION: Camelid

<400> SEQUENCE: 5

```
Asp Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Gln Val Thr Val Ser Ser
        115                 120                 125
```

```
<210> SEQ ID NO 6
<211> LENGTH: 126
<212> TYPE: PRT
<213> ORGANISM: Artificial Sequence
<220> FEATURE:
<223> OTHER INFORMATION: Camelid

<400> SEQUENCE: 6

Asp Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
                20                  25                  30

Trp Phe Arg Gln Ala Pro Gly Lys Glu Arg Glu Gly Val Ala Ala Leu
            35                  40                  45

Ser Ser Arg Gly Phe Ala Gly His Tyr Thr Asp Ser Val Lys Gly Arg
        50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Gln Val Thr Val Ser Ser
        115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Camelid

<400> SEQUENCE: 7

His Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
                20                  25                  30

Trp Phe Arg Gln Ala Pro Gly Lys Glu Arg Glu Gly Val Ala Ala Leu
            35                  40                  45

Ser Ser Arg Gly Phe Ala Gly His Tyr Thr Asp Ser Val Lys Gly Arg
        50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Gln Val Thr Val Ser Ser
        115                 120                 125

<210> SEQ ID NO 8
<211> LENGTH: 126
<212> TYPE: PRT
<213> ORGANISM: Artificial Sequence
<220> FEATURE:
<223> OTHER INFORMATION: Camelid

<400> SEQUENCE: 8

Gln Val Gln Leu Val Glu Ser Gly Gly Gly Ser Val Gln Ala Gly Gly
1               5                   10                  15
```

```
Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
            35                  40                  45

Ser Ser Arg Gly Phe Ala Gly His Tyr Thr Asp Ser Val Lys Gly Arg
50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
            115                 120                 125
```

<210> SEQ ID NO 9
<211> LENGTH: 126
<212> TYPE: PRT
<213> ORGANISM: Artificial Sequence
<220> FEATURE:
<223> OTHER INFORMATION: Camelid

<400> SEQUENCE: 9

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
            35                  40                  45

Ser Ser Arg Gly Phe Ala Gly His Tyr Thr Asp Ser Val Lys Gly Arg
50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
            115                 120                 125
```

<210> SEQ ID NO 10
<211> LENGTH: 126
<212> TYPE: PRT
<213> ORGANISM: Artificial Sequence
<220> FEATURE:
<223> OTHER INFORMATION: Camelid

<400> SEQUENCE: 10

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
            35                  40                  45

Ser Ser Arg Gly Phe Ala Gly His Tyr Thr Asp Ser Val Lys Gly Arg
50                  55                  60

Phe Ser Ile Ser Arg Asp Tyr Val Lys Asn Ala Val Tyr Leu Gln Met
```

```
                 65                  70                  75                  80
Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
           100                 105                 110

His Thr Tyr Trp Gly Gln Gly Thr Leu Val Thr Val Ser Ser
       115                 120                 125
```

<210> SEQ ID NO 11
<211> LENGTH: 126
<212> TYPE: PRT
<213> ORGANISM: Artificial Sequence
<220> FEATURE:
<223> OTHER INFORMATION: Camelid

<400> SEQUENCE: 11

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
           100                 105                 110

His Thr Tyr Trp Gly Gln Gly Thr Leu Val Thr Val Ser Ser
       115                 120                 125
```

<210> SEQ ID NO 12
<211> LENGTH: 126
<212> TYPE: PRT
<213> ORGANISM: Artificial Sequence
<220> FEATURE:
<223> OTHER INFORMATION: Camelid

<400> SEQUENCE: 12

```
Gln Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Ser
           100                 105                 110

His Thr Tyr Trp Gly Gln Gly Thr Leu Val Thr Val Ser Ser
       115                 120                 125
```

```
<210> SEQ ID NO 13
<211> LENGTH: 126
<212> TYPE: PRT
<213> ORGANISM: Artificial Sequence
<220> FEATURE:
<223> OTHER INFORMATION: Camelid

<400> SEQUENCE: 13

Glu Val Gln Leu Val Glu Ser Gly Gly Gly Ser Val Gln Ala Gly Gly
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
        115                 120                 125

<210> SEQ ID NO 14
<211> LENGTH: 126
<212> TYPE: PRT
<213> ORGANISM: Artificial Sequence
<220> FEATURE:
<223> OTHER INFORMATION: Camelid

<400> SEQUENCE: 14

Asp Val Gln Leu Val Glu Ser Gly Gly Gly Ser Val Gln Ala Gly Asp
1               5                   10                  15

Ser Leu Arg Leu Ser Cys Val Ala Ser Thr Tyr Thr Gly Cys Met Gly
            20                  25                  30

Trp Phe Arg Gln Ala Pro Gly Lys Glu Arg Glu Gly Val Ala Ala Leu
        35                  40                  45

Ser Ser Arg Gly Phe Ala Gly His Tyr Thr Asp Ser Val Lys Gly Arg
    50                  55                  60

Phe Ser Ile Ser Arg Asp Tyr Val Lys Asn Ala Val Tyr Leu Gln Met
65                  70                  75                  80

Asn Thr Val Lys Pro Glu Asp Ala Ala Met Tyr Tyr Cys Ala Ala Arg
                85                  90                  95

Glu Gly Trp Glu Cys Gly Glu Thr Trp Leu Asp Arg Thr Ala Gly Gly
            100                 105                 110

His Thr Tyr Trp Gly Gln Gly Thr Leu Val Thr Val Ser Ser
        115                 120                 125

<210> SEQ ID NO 15
<211> LENGTH: 127
<212> TYPE: PRT
<213> ORGANISM: Artificial Sequence
<220> FEATURE:
<223> OTHER INFORMATION: Camelid

<400> SEQUENCE: 15

Gln Val Gln Leu Val Glu Ser Gly Gly Gly Ser Val Gln Ala Gly Gly
```

```
1               5                   10                  15
Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
            50                  55                  60

Lys Gly Arg Phe Thr Ile Ser Gln Asp Asn Lys Asn Thr Leu Tyr
 65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
                100                 105                 110

Met Tyr Asn Ser Trp Gly Gln Gly Thr Leu Val Thr Val Ser Ser
                115                 120                 125
```

<210> SEQ ID NO 16
<211> LENGTH: 127
<212> TYPE: PRT
<213> ORGANISM: Artificial Sequence
<220> FEATURE:
<223> OTHER INFORMATION: Camelid

<400> SEQUENCE: 16

```
Gln Val Gln Leu Val Glu Ser Gly Gly Gly Ser Val Gln Ala Gly Gly
 1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
            50                  55                  60

Lys Gly Arg Phe Thr Ile Ser Gln Asp Asn Thr Asn Asn Thr Leu Tyr
 65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
                100                 105                 110

Met Tyr Asn Ser Trp Gly Gln Gly Thr Leu Val Thr Val Ser Ser
                115                 120                 125
```

<210> SEQ ID NO 17
<211> LENGTH: 127
<212> TYPE: PRT
<213> ORGANISM: Artificial Sequence
<220> FEATURE:
<223> OTHER INFORMATION: Camelid

<400> SEQUENCE: 17

```
Glu Val Gln Leu Val Glu Ser Gly Gly Gly Ser Val Gln Ala Gly Gly
 1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
            50                  55                  60
```

```
Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125

<210> SEQ ID NO 18
<211> LENGTH: 127
<212> TYPE: PRT
<213> ORGANISM: Artificial Sequence
<220> FEATURE:
<223> OTHER INFORMATION: Camelid

<400> SEQUENCE: 18

Asp Val Gln Leu Val Glu Ser Gly Gly Gly Ser Val Gln Ala Gly Gly
 1               5                  10                  15

Ser Leu Arg Leu Ser Cys Ala Ala Ser Gly Ala Asn Gly Gly Arg Ser
                 20                  25                  30

Cys Met Gly Trp Phe Arg Gln Val Pro Gly Lys Glu Arg Glu Gly Val
             35                  40                  45

Ser Gly Ile Ser Thr Gly Gly Leu Ile Thr Tyr Tyr Ala Asp Ser Val
         50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125

<210> SEQ ID NO 19
<211> LENGTH: 127
<212> TYPE: PRT
<213> ORGANISM: Artificial Sequence
<220> FEATURE:
<223> OTHER INFORMATION: Camelid

<400> SEQUENCE: 19

Asp Val Gln Leu Val Glu Ser Gly Gly Gly Ser Val Gln Ala Gly Gly
 1               5                  10                  15

Ser Leu Arg Leu Ser Cys Ala Ala Ser Gly Ala Asn Gly Gly Arg Ser
                 20                  25                  30

Cys Met Gly Trp Phe Arg Gln Val Pro Gly Lys Glu Arg Glu Gly Val
             35                  40                  45

Ser Gly Ile Ser Thr Gly Gly Leu Ile Thr Tyr Tyr Ala Asp Ser Val
         50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125
```

<210> SEQ ID NO 20
<211> LENGTH: 127
<212> TYPE: PRT
<213> ORGANISM: Artificial Sequence
<220> FEATURE:
<223> OTHER INFORMATION: Camelid

<400> SEQUENCE: 20

```
Asp Val Gln Leu Val Glu Ser Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
                35                  40                  45

Ser Gly Ile Ser Thr Gly Gly Leu Ile Thr Tyr Tyr Ala Asp Ser Val
        50                  55                  60

Lys Gly Arg Phe Thr Ile Ser Gln Asp Asn Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125
```

<210> SEQ ID NO 21
<211> LENGTH: 127
<212> TYPE: PRT
<213> ORGANISM: Artificial Sequence
<220> FEATURE:
<223> OTHER INFORMATION: Camelid

<400> SEQUENCE: 21

```
His Val Gln Leu Val Glu Ser Glu Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
                35                  40                  45

Ser Gly Ile Ser Thr Gly Gly Leu Ile Thr Tyr Tyr Ala Asp Ser Val
        50                  55                  60

Lys Gly Arg Phe Thr Ile Ser Gln Asp Asn Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Leu Val Thr Val Ser Ser
        115                 120                 125
```

<210> SEQ ID NO 22
<211> LENGTH: 127
<212> TYPE: PRT
<213> ORGANISM: Artificial Sequence
<220> FEATURE:
<223> OTHER INFORMATION: Camelid

<400> SEQUENCE: 22

Gln Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
50                  55                  60

Lys Gly Arg Phe Thr Ile Ser Gln Asp Asn Thr Lys Asn Thr Leu Tyr
65                  70                  75                  80

Leu Gln Met Asn Ser Leu Lys Pro Glu Asp Thr Ala Met Tyr Tyr Cys
            85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
            115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Camelid

<400> SEQUENCE: 23

Gln Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
50                  55                  60

Lys Gly Arg Phe Thr Ile Ser Gln Asp Asn Thr Lys Asn Thr Leu Tyr
65                  70                  75                  80

Leu Gln Met Asn Ser Leu Lys Pro Glu Asp Thr Ala Met Tyr Tyr Cys
            85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
            115                 120                 125

<210> SEQ ID NO 24
<211> LENGTH: 127
<212> TYPE: PRT
<213> ORGANISM: Artificial Sequence
<220> FEATURE:
<223> OTHER INFORMATION: Camelid

<400> SEQUENCE: 24

Glu Val Gln Leu Val Glu Ser Gly Gly Gly Ser Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
50                  55                  60

```
Lys Gly Arg Phe Thr Ile Ser Gln Asp Asn Thr Lys Asn Thr Leu Tyr
 65                  70                  75                  80

Leu Gln Met Ser Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125
```

<210> SEQ ID NO 25
<211> LENGTH: 127
<212> TYPE: PRT
<213> ORGANISM: Artificial Sequence
<220> FEATURE:
<223> OTHER INFORMATION: Camelid

<400> SEQUENCE: 25

```
Asp Val Gln Leu Val Glu Ser Gly Gly Ser Val Gln Ala Gly Gly
 1               5                  10                  15

Ser Leu Arg Leu Ser Cys Ala Ala Ser Gly Ala Asn Gly Gly Arg Ser
                 20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
        50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125
```

<210> SEQ ID NO 26
<211> LENGTH: 127
<212> TYPE: PRT
<213> ORGANISM: Artificial Sequence
<220> FEATURE:
<223> OTHER INFORMATION: Camelid

<400> SEQUENCE: 26

```
His Val Gln Leu Val Glu Ser Gly Gly Gly Ser Val Gln Ala Gly Gly
 1               5                  10                  15

Ser Leu Arg Leu Ser Cys Ala Ala Ser Gly Ala Asn Gly Gly Arg Ser
                 20                  25                  30

Cys Met Gly Trp Phe Arg Gln Val Pro Gly Lys Glu Arg Glu Gly Val
            35                  40                  45

Ser Gly Ile Ser Thr Gly Gly Leu Ile Thr Tyr Tyr Ala Asp Ser Val
        50                  55                  60

Lys Gly Arg Phe Thr Ile Ser Gln Asp Asn Thr Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
```

<210> SEQ ID NO 27
<211> LENGTH: 127
<212> TYPE: PRT
<213> ORGANISM: Artificial Sequence
<220> FEATURE:
<223> OTHER INFORMATION: Camelid

<400> SEQUENCE: 27

```
His Val Gln Leu Val Glu Ser Gly Gly Gly Ser Val Gln Ala Gly Gly
1               5                   10                  15
Ser Leu Arg Leu Ser Cys Ala Ala Ser Gly Ala Asn Gly Gly Arg Ser
            20                  25                  30
Cys Met Gly Trp Phe Arg Gln Val Pro Gly Lys Glu Arg Glu Gly Val
        35                  40                  45
Ser Gly Ile Ser Thr Gly Gly Leu Ile Thr Tyr Tyr Ala Asp Ser Val
    50                  55                  60
Lys Gly Arg Phe Thr Ile Ser Gln Asp Asn Thr Lys Asn Thr Leu Tyr
65                  70                  75                  80
Leu Gln Met Asn Ser Leu Lys Pro Glu Asp Thr Ala Met Tyr Tyr Cys
                85                  90                  95
Ala Thr Ser Arg Phe Asp Cys Tyr Arg Gly Ser Trp Phe Asn Arg Tyr
            100                 105                 110
Met Tyr Asn Ser Trp Gly Gln Gly Thr Gln Val Thr Val Ser Ser
        115                 120                 125
```

<210> SEQ ID NO 28
<211> LENGTH: 127
<212> TYPE: PRT
<213> ORGANISM: Artificial Sequence
<220> FEATURE:
<223> OTHER INFORMATION: Camelid

<400> SEQUENCE: 28

```
His Val Gln Leu Val Glu Ser Gly Gly Gly Ser Val Gln Ala Gly Gly
1               5                   10                  15
Ser Leu Arg Leu Ser Cys Ala Ala Ser Gly Ala Asn Gly Gly Arg Ser
            20                  25                  30
Cys Met Gly Trp Phe Arg Gln Val Pro Gly Lys Glu Arg Glu Gly Val
        35                  40                  45
Ser Gly Ile Ser Thr Gly Gly Leu Ile Thr Tyr Tyr Ala Asp Ser Val
    50                  55                  60
Lys Gly Arg Phe Thr Ile Ser Gln Asp Asn Thr Lys Asn Thr Leu Tyr
65                  70                  75                  80
Leu Gln Met Asn Ser Leu Lys Pro Glu Asp Thr Ala Met Tyr Tyr Cys
                85                  90                  95
Ala Thr Ser Arg Phe Asp Cys Tyr Arg Gly Ser Trp Phe Asn Arg Tyr
            100                 105                 110
Met Tyr Asn Ser Trp Gly Gln Gly Thr Gln Val Thr Val Ser Ser
        115                 120                 125
```

<210> SEQ ID NO 29
<211> LENGTH: 127
<212> TYPE: PRT
<213> ORGANISM: Artificial Sequence
<220> FEATURE:
<223> OTHER INFORMATION: Camelid

<400> SEQUENCE: 29

His Val Gln Leu Val Glu Ser Gly Gly Gly Val Gln Ala Gly Gly
1               5                   10                  15

Ser Leu Arg Leu Ser Cys Ala Ala Ser Gly Ala Asn Gly Gly Arg Ser
            20                  25                  30

Cys Met Gly Trp Phe Arg Gln Val Pro Gly Lys Glu Arg Glu Gly Val
        35                  40                  45

Ser Gly Ile Ser Thr Gly Gly Leu Ile Thr Tyr Tyr Ala Asp Ser Val
    50                  55                  60

Lys Gly Arg Phe Thr Ile Ser Gln Asp Asn Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Thr Ser Arg Phe Asp Cys Tyr Arg Gly Ser Trp Phe Asn Arg Tyr
            100                 105                 110

Met Tyr Asn Ser Trp Gly Gln Gly Thr Gln Val Thr Val Ser Ser
        115                 120                 125

```
<210> SEQ ID NO 30
<211> LENGTH: 378
<212> TYPE: DNA
<213> ORGANISM: Artificial Sequence
<220> FEATURE:
<223> OTHER INFORMATION: Camelid

<400> SEQUENCE: 30
gatgtgcagc tggtggagtc tgggggaggc tcggtgcagg ctggaggctc tctgagactc      60
tcctgtgtag cctctacata caccggctgc atgggctggt tccgccaggc tcctggaaag     120
gagcgcgagg gagtcgcagc tcttagtagc cgtggttttg ccgggcacta taccgactcc     180
gtgaagggcc gattctccat ctcccgagac tacgtcaaga atgcggtgta tctgcaaatg     240
aacactgtga aacctgagga cgctgccatg tactactgtg cagcacggga gggatgggag     300
tgcggtgaga cctggttgga ccggaccgcc ggggccata cctactgggg ccaggggacc     360
caggtcaccg tctcctca                                                   378

<210> SEQ ID NO 31
<211> LENGTH: 378
<212> TYPE: DNA
<213> ORGANISM: Artificial Sequence
<220> FEATURE:
<223> OTHER INFORMATION: Camelid

<400> SEQUENCE: 31
caggtgcagc tggtggagtc tgggggaggc tcggtgcagg ctggaggctc tctgagactc      60
tcctgtgtag cctctacata caccggctgc atgggctggt tccgccaggc tcctggaaag     120
gagcgcgagg gagtcgcagc tcttagtagc cgtggttttg ccgggcacta taccgactcc     180
gtgaagggcc gattctccat ctcccgagac tacgtcaaga atgcggtgta tctgcaaatg     240
aacactgtga aacctgagga cgctgccatg tactactgtg cagcacggga gggatgggag     300
tgcggtgaga cctggttgga ccggaccgcc ggggccata cctactgggg ccaggggacc     360
ctggtcaccg tctcctca                                                   378

<210> SEQ ID NO 32
<211> LENGTH: 381
<212> TYPE: DNA
<213> ORGANISM: Artificial Sequence
<220> FEATURE:
```

<223> OTHER INFORMATION: Camelid

<400> SEQUENCE: 32

```
caggtgcagc tggtggagtc tgggggaggc tcggtgcagg ctggagggtc tctgagactc    60
tcctgtgcag cctctggagc caatggtggt cggagctgca tgggctggtt ccgccaggtt   120
ccagggaagg agcgcgaggg ggtttctggt atttcaaccg gtggtcttat tacatactat   180
gccgactccg tgaagggccg attcaccatc tcccaagaca acaccaagaa cacgctgtat   240
ctgcaaatga acagcctgaa acctgaggac actgccatgt actactgtgc gacgagtcgg   300
tttgactgct atagaggctc ttggttcaac cgatatatgt ataacagttg gggccagggg   360
accctggtca ccgtctcctc a                                             381
```

<210> SEQ ID NO 33
<211> LENGTH: 381
<212> TYPE: DNA
<213> ORGANISM: Artificial Sequence
<220> FEATURE:
<223> OTHER INFORMATION: Camelid

<400> SEQUENCE: 33

```
catgtgcagc tggtggagtc tgggggaggc tcggtgcagg ctggagggtc tctgagactc    60
tcctgtgcag cctctggagc caacggtggt cggagctgca tgggctggtt ccgccaggtt   120
ccagggaagg agcgcgaggg ggtttctggt atttcaaccg gtggtcttat tacatactat   180
gccgactccg tgaagggccg attcaccatc tcccaagaca acaccaagaa cacgctgtat   240
ctgcaaatga acagcctgaa acctgaggac actgccatgt actactgtgc gacgagtcgg   300
tttgactgct atagaggctc ttggttcaac cgatatatgt ataacagttg gggccagggg   360
acccaggtca ctgtctcctc a                                             381
```

<210> SEQ ID NO 34
<211> LENGTH: 381
<212> TYPE: DNA
<213> ORGANISM: Artificial Sequence
<220> FEATURE:
<223> OTHER INFORMATION: Camelid

<400> SEQUENCE: 34

```
gatgtgcagc tggtggagtc tgggggaggc tcggtgcagg ctggagggtc tctgagactc    60
tcctgtgcag cctctggagc caatggtggt cggagctgca tgggctggtt ccgccaggtt   120
ccagggaagg agcgcgaggg ggtttctggt atttcaaccg gtggtcttat tacatactat   180
gccgactccg tgaagggccg attcaccatc tcccaagaca acaccaagaa cacgctgtat   240
ctgcaaatga acagcctgaa acctgaggac actgccatgt actactgtgc gacgagtcgg   300
tttgactgct atagaggctc ttggttcaac cgatatatgt ataacagttg gggccagggg   360
accctggtca ccgtctcctc a                                             381
```

<210> SEQ ID NO 35
<211> LENGTH: 378
<212> TYPE: DNA
<213> ORGANISM: Artificial Sequence
<220> FEATURE:
<223> OTHER INFORMATION: Camelid

<400> SEQUENCE: 35

```
caggtgcagc tggtggagtc tgggggaggc tcggtgcagg ctggaggctc tctgagactc    60
tcctgtgtag cctctacata caccggctgc atgggctggt tccgccaggc tcctggaaag   120
```

-continued

```
gagcgcgagg gagtcgcagc tcttagcagc cgtggttttg ccgggcacta taccgactcc    180
gtgaagggcc gattctccat ctcccgagac tacgtcaaga atgcggtgta tctgcaaatg    240
aacactgtga aacctgagga cgctgccatg tactactgtg cagcacggga gggatgggag    300
tgcggtgaga cctggttgga ccggaccgcc gggagccata cctactgggg ccaggggacc    360
ctggtcaccg tctcctca                                                  378
```

<210> SEQ ID NO 36
<211> LENGTH: 378
<212> TYPE: DNA
<213> ORGANISM: Artificial Sequence
<220> FEATURE:
<223> OTHER INFORMATION: Camelid

<400> SEQUENCE: 36

```
gaggtgcagc tggtggagtc tgggggaggc tcggtgcagg ctggaggctc tctgagactc    60
tcctgtgtag cctctacata caccggctgc atgggctggt tccgccaggc tcctggaaag    120
gagcgcgagg gagtcgcagc tcttagtagc cgtggttttg ccgggcacta taccgactcc    180
gtgaagggcc gattctccat ctcccgagac tacgtcaaga atgcggtgta tctgcaaatg    240
aacactgtga aacctgagga cgctgccatg tactactgtg cagcacggga gggatgggag    300
tgcggtgaga cctggttgga ccgaaccgcc ggggccata cctactgggg ccaggggacc    360
ctggtcaccg tctcctca                                                  378
```

<210> SEQ ID NO 37
<211> LENGTH: 381
<212> TYPE: DNA
<213> ORGANISM: Artificial Sequence
<220> FEATURE:
<223> OTHER INFORMATION: Camelid

<400> SEQUENCE: 37

```
gaggtgcagc tggtggagtc tgggggaggc tcggtgcagg ctggagggtc tctgagactc    60
tcctgtgcag cctctggagc caatggtggt cggagctgca tggctggtt ccgccaggtt    120 ccagggaagg agcgcgaggg ggtttctggt atttcaaccg tggtcttat tacatactat    180 gccgactccg tgaagggtcg attcaccatc tcccaagaca acaccaagaa cacgctgtat    240
ctgcaaatga gcagcctgaa acctgaggac actgccatgt actactgtgc gacgagtcgg    300
tttgactgct atagaggctc ttggttcaac cgatatatgt ataacagttg gggccagggg    360
acccaggtca ccgtctcctc a                                              381
```

<210> SEQ ID NO 38
<211> LENGTH: 378
<212> TYPE: DNA
<213> ORGANISM: Artificial Sequence
<220> FEATURE:
<223> OTHER INFORMATION: Camelid

<400> SEQUENCE: 38

```
catgtgcagc tggtggagtc tgggggggc tcggtgcagg ctggaggctc tctgagactc    60
tcctgtgtag cctctacata caccggctgc atgggctggt tccgccaggc tcctggaaag    120
gagcgcgagg gagtcgcagc tcttagtagc cgtggttttg ccgggcacta taccgactcc    180
gtgaagggcc gattctccat ctcccgagac tacgtcaaga atgcggtgta tctgcaaatg    240
aacactgtga aacctgagga cgctgccatg tactactgtg cagcacggga gggatgggag    300
```

```
tgcggtgaga cctggttgga ccggaccgcc gggggccata cctactgggg ccaggggacc    360
caggtcaccg tctcctca                                                  378
```

<210> SEQ ID NO 39
<211> LENGTH: 381
<212> TYPE: DNA
<213> ORGANISM: Artificial Sequence
<220> FEATURE:
<223> OTHER INFORMATION: Camelid

<400> SEQUENCE: 39

```
gatgtgcagc tggtggagtc tgggggaggc tcggtgcagg ctggagggtc tctgagactc    60
tcctgtgcag cctctggagc caatggtggt cggagctgca tgggctggtt ccgccaggtt   120
ccagggaagg agcgcgaggg ggtttctggt atttcaaccg gtggtcttat tacatactat   180
gccgactccg tgaagggccg attcaccatc tcccaagaca caccaagaa cacgctgtat   240 ctgcaaatga acagcctgaa acctgaggac actgccatgt actactgtgc gacgagtcgg   300
tttgactgct atagaggctc ttggttcaac cgatatatgt ataacagttg gggccagggg   360
acccaggtca ccgtctcctc a                                             381
```

<210> SEQ ID NO 40
<211> LENGTH: 381
<212> TYPE: DNA
<213> ORGANISM: Artificial Sequence
<220> FEATURE:
<223> OTHER INFORMATION: Camelid

<400> SEQUENCE: 40

```
caggtgcagc tggtggagtc tgggggaggc tcggtgcagg ctggagggtc tctgagactc    60
tcctgtgcag cctctggagc caatggtggt cggagctgca tgggctggtt ccgccaggtt   120
ccagggaagg agcgcgaggg ggtttctggt atttcaaccg gtggtcttat tacatactat   180
gccgactccg tgaagggccg attcaccatc tcccaagaca caccaagaa cacgctgtat   240 ctgcaaatga acagcctgaa acctgaggac actgccatgt actactgtgc gacgagtcgg   300
tttgactgct atagaggctc ttggttcaac cgatatatgt ataacagttg gggccagggg   360
acccaggtca ccgtctcctc a                                             381
```

<210> SEQ ID NO 41
<211> LENGTH: 378
<212> TYPE: DNA
<213> ORGANISM: Artificial Sequence
<220> FEATURE:
<223> OTHER INFORMATION: Camelid

<400> SEQUENCE: 41

```
gatgtgcagc tggtggagtc tgggggaggc tcggtgcagg ctggagactc tctgagactc    60
tcctgtgtag cctctacata caccggctgc atgggctggt ccgccaggc tcctggaaag   120 gagcgcgagg gagtcgcagc tcttagtagc cgtggttttg ccgggcacta taccgactcc   180
gtgaagggcc gattctccat ctcccgagac tacgtcaaga atgcggtgta tctgcaaatg   240
aacactgtga aacctgagga cgctgccatg tactactgtg cagcacggga gggatgggag   300
tgcggtgaga cctggttgga ccggaccgcc gggggccata cctactgggg ccaggggacc   360
ctggtcactg tctcctca                                                 378
```

<210> SEQ ID NO 42
<211> LENGTH: 378

<212> TYPE: DNA
<213> ORGANISM: Artificial Sequence
<220> FEATURE:
<223> OTHER INFORMATION: Camelid

<400> SEQUENCE: 42

| | | | | | |
|---|---|---|---|---|---|
| gtgcagctgg | tggagtctgg | gggaggctcg | gtgcaggctg | gagggtctct | gagactctcc | 60 |
| tgtgcagcct | ctggagccaa | tggtggtcgg | agctgcatgg | gctggttccg | ccaggttcca | 120 |
| gggaaggagc | gtgaggggt | ttctggtatt | tcaaccggtg | gtcttattac | atactatgcc | 180 |
| gactccgtga | agggccgatt | caccatctcc | caagacaaca | ccaagaacac | gctgtatctg | 240 |
| caaatgaaca | gcctgaaacc | tgaggacact | gccatgtact | actgtgcgac | gagtcggttt | 300 |
| gactgctata | gaggctcttg | gttcaaccga | tatatgtata | acagttgggg | ccaggggacc | 360 |
| ctggtcactg | tctcctca | | | | | 378 |

<210> SEQ ID NO 43
<211> LENGTH: 378
<212> TYPE: DNA
<213> ORGANISM: Artificial Sequence
<220> FEATURE:
<223> OTHER INFORMATION: Camelid

<400> SEQUENCE: 43

| | | | | | |
|---|---|---|---|---|---|
| gtgcagctgg | tggagtctga | gggaggctcg | gtgcaggctg | gagggtctct | gagactctcc | 60 |
| tgtgcagcct | ctggagccaa | tggtggtcgg | agctgcatgg | gctggttccg | ccaggttcca | 120 |
| gggaaggagc | gcgaggggt | ttctggtatt | tcaaccggtg | gtcttattac | atactatgcc | 180 |
| gactccgtga | agggccgatt | caccatctcc | caagacaaca | ccaagaacac | gctgtatctg | 240 |
| caaatgaaca | gcctgaaacc | tgaggacact | gccatgtact | actgtgcgac | gagtcggttt | 300 |
| gactgctata | gaggctcttg | gttcaaccga | tatatgtata | acagttgggg | ccaggggacc | 360 |
| ctggtcaccg | tctcctca | | | | | 378 |

<210> SEQ ID NO 44
<211> LENGTH: 378
<212> TYPE: DNA
<213> ORGANISM: Artificial Sequence
<220> FEATURE:
<223> OTHER INFORMATION: Camelid

<400> SEQUENCE: 44

| | | | | | |
|---|---|---|---|---|---|
| gtgcagctgg | tggagtctgg | gggaggctcg | gtgcaggctg | gagggtctct | gagactctcc | 60 |
| tgtgcagcct | ctggagccaa | tggtggtcgg | agctgcatgg | gctggttccg | ccaggttcca | 120 |
| gggaaggagc | gcgaggggt | ttctggtatt | tcaaccggtg | gtcttattac | atactatgcc | 180 |
| gactccgtga | agggccgatt | caccatctcc | caagacaaca | ccaataacac | gctgtatctg | 240 |
| caaatgaaca | gcctgaaacc | tgaggacact | gccatgtact | actgtgcgac | gagtcggttt | 300 |
| gactgctata | gaggctcttg | gttcaaccga | tatatgtata | acagttgggg | ccaggggacc | 360 |
| ctggtcactg | tctcctca | | | | | 378 |

<210> SEQ ID NO 45
<211> LENGTH: 123
<212> TYPE: PRT
<213> ORGANISM: Artificial Sequence
<220> FEATURE:
<223> OTHER INFORMATION: Camelid

<400> SEQUENCE: 45

-continued

```
His Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
                35                  40                  45

Ala Thr Ile Asp Ile Asp Gly Leu Thr Thr His Ala Asp Ser Val Lys
        50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
                100                 105                 110

Arg Gly Gln Gly Thr Leu Val Thr Val Ser Ser
            115                 120
```

<210> SEQ ID NO 46
<211> LENGTH: 124
<212> TYPE: PRT
<213> ORGANISM: Artificial Sequence
<220> FEATURE:
<223> OTHER INFORMATION: Camelid

<400> SEQUENCE: 46

```
Glu Val Gln Leu Val Glu Ser Gly Gly Gly Val Leu Ala Gly Gly
1               5                   10                  15

Ser Leu Arg Leu Ser Cys Val Ala Ser Gly Phe Thr Ser Arg Tyr Asn
            20                  25                  30

Tyr Met Ala Trp Phe Arg Gln Ala Pro Gly Lys Glu Arg Glu Gly Val
                35                  40                  45

Ala Thr Ile Gly Thr Ala Ser Gly Ser Ala Asp Tyr Tyr Gly Ser Val
        50                  55                  60

Lys Asp Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Thr Tyr Gly Thr Ile Ser Leu Thr Pro Ser Asp Tyr Arg
                100                 105                 110

Tyr Trp Gly Gln Gly Thr Leu Val Thr Val Ser Ser
            115                 120
```

<210> SEQ ID NO 47
<211> LENGTH: 129
<212> TYPE: PRT
<213> ORGANISM: Artificial Sequence
<220> FEATURE:
<223> OTHER INFORMATION: Camelid

<400> SEQUENCE: 47

```
Gln Val Gln Leu Val Glu Ser Gly Gly Gly Pro Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
                35                  40                  45

Ser Thr Ile Thr Thr Glu Gly Ile Thr Ser Glu Ala Ser Ser Tyr Tyr
        50                  55                  60
```

```
Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                 85                  90                  95

Val Tyr Tyr Cys Ala Pro Asp Pro Tyr Ala Tyr Ser Thr Tyr Ser Asp
            100                 105                 110

Tyr Cys Ser Trp Ala Gln Gly Thr Gln Gly Thr Leu Val Thr Val Ser
        115                 120                 125

Ser

<210> SEQ ID NO 48
<211> LENGTH: 123
<212> TYPE: PRT
<213> ORGANISM: Artificial Sequence
<220> FEATURE:
<223> OTHER INFORMATION: Camelid

<400> SEQUENCE: 48

Gln Val Gln Leu Val Glu Ser Gly Gly Gly Ser Val Glu Ala Gly Arg
 1               5                  10                  15

Ser Leu Arg Leu Ser Cys Ala Ala Ser Gly Phe Arg Tyr Ala Ala Tyr
                20                  25                  30

Cys Met Gly Trp Phe Arg Gln Ala Asp Gly Lys Glu Arg Glu Gly Val
            35                  40                  45

Ala Thr Ile Asp Ile Asp Gly Gln Thr Thr His Ala Asp Ser Val Lys
        50                  55                  60

Gly Arg Phe Thr Ile Ser Arg Asp Asn Ala Lys Asn Thr Leu Ser Leu
 65                  70                  75                  80

Gln Met Asn Asp Leu Lys Pro Glu Asp Thr Ala Met Tyr Tyr Cys Ala
                 85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
        115                 120

<210> SEQ ID NO 49
<211> LENGTH: 123
<212> TYPE: PRT
<213> ORGANISM: Artificial Sequence
<220> FEATURE:
<223> OTHER INFORMATION: Camelid

<400> SEQUENCE: 49

Gln Val Gln Leu Val Glu Ser Gly Gly Gly Ser Val Glu Ala Gly Gly
 1               5                  10                  15

Ser Leu Arg Leu Ser Cys Ala Ala Ser Gly Phe Arg Tyr Ala Ala Tyr
                20                  25                  30

Cys Met Gly Trp Phe Arg Gln Ala Asp Gly Lys Glu Arg Glu Gly Val
            35                  40                  45

Ala Thr Ile Asp Ile Asp Gly Gln Thr Thr His Ala Asp Ser Val Lys
        50                  55                  60

Gly Arg Phe Thr Ile Ser Arg Asp Asn Val Lys Asn Thr Leu Ser Leu
 65                  70                  75                  80

Gln Met Asn Asp Leu Lys Pro Glu Asp Thr Ala Met Tyr Tyr Cys Ala
                 85                  90                  95

Ala Asp Arg Asp Arg Cys Gly Ser Ile Trp Thr Tyr Ala Tyr Lys Tyr
            100                 105                 110
```

Arg Gly Gln Gly Thr Gln Val Thr Val Ser Ser
        115                 120

<210> SEQ ID NO 50
<211> LENGTH: 123
<212> TYPE: PRT
<213> ORGANISM: Artificial Sequence
<220> FEATURE:
<223> OTHER INFORMATION: Camelid

<400> SEQUENCE: 50

Gln Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Leu Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
        115                 120

<210> SEQ ID NO 51
<211> LENGTH: 123
<212> TYPE: PRT
<213> ORGANISM: Artificial Sequence
<220> FEATURE:
<223> OTHER INFORMATION: Camelid

<400> SEQUENCE: 51

Gln Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Gln Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
        115                 120

<210> SEQ ID NO 52
<211> LENGTH: 123
<212> TYPE: PRT
<213> ORGANISM: Artificial Sequence
<220> FEATURE:
<223> OTHER INFORMATION: Camelid

<400> SEQUENCE: 52

```
Glu Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Gln Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
        115                 120
```

<210> SEQ ID NO 53
<211> LENGTH: 123
<212> TYPE: PRT
<213> ORGANISM: Artificial Sequence
<220> FEATURE:
<223> OTHER INFORMATION: Camelid

<400> SEQUENCE: 53

```
Glu Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45

Ala Thr Ile Asp Ile Asp Gly Leu Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120
```

<210> SEQ ID NO 54
<211> LENGTH: 123
<212> TYPE: PRT
<213> ORGANISM: Artificial Sequence
<220> FEATURE:
<223> OTHER INFORMATION: Camelid

<400> SEQUENCE: 54

```
Asp Val Gln Leu Val Glu Ser Gly Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Glu Arg Glu Gly Val
        35                  40                  45
```

Ala Thr Ile Asp Ile Asp Gly Gln Thr Thr His Ala Asp Ser Val Lys
            50                  55                  60

Gly Arg Phe Thr Ile Ser Arg Asp Asn Ala Lys Asn Thr Leu Ser Leu
 65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
            115                 120

<210> SEQ ID NO 55
<211> LENGTH: 123
<212> TYPE: PRT
<213> ORGANISM: Artificial Sequence
<220> FEATURE:
<223> OTHER INFORMATION: Camelid

<400> SEQUENCE: 55

His Val Gln Leu Val Glu Ser Gly Gly Gly Val Glu Ala Gly Gly
 1               5                  10                  15

Ser Leu Arg Leu Ser Cys Ala Ala Ser Gly Phe Arg Tyr Ala Ala Tyr
                20                  25                  30

Cys Met Gly Trp Phe Arg Gln Ala Asp Gly Lys Glu Arg Glu Gly Val
            35                  40                  45

Ala Thr Ile Asp Ile Asp Gly Leu Thr Thr His Ala Asp Ser Val Lys
            50                  55                  60

Gly Arg Phe Thr Ile Ser Arg Asp Asn Ala Lys Asn Thr Leu Ser Leu
 65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
            115                 120

<210> SEQ ID NO 56
<211> LENGTH: 123
<212> TYPE: PRT
<213> ORGANISM: Artificial Sequence
<220> FEATURE:
<223> OTHER INFORMATION: Camelid

<400> SEQUENCE: 56

His Val Gln Leu Val Glu Ser Gly Gly Gly Ser Val Glu Ala Gly Gly
 1               5                  10                  15

Ser Leu Arg Leu Ser Cys Ala Ala Ser Gly Phe Arg Tyr Ala Ala Tyr
                20                  25                  30

Cys Met Gly Trp Phe Arg Gln Ala Asp Gly Lys Glu Arg Glu Gly Val
            35                  40                  45

Ala Thr Ile Asp Ile Asp Gly Leu Ala Thr His Ala Asp Ser Val Lys
            50                  55                  60

Gly Arg Phe Thr Ile Ser Arg Asp Asn Ala Lys Asn Thr Leu Ser Leu
 65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr

```
                100               105               110
Arg Gly Gln Gly Thr Leu Val Thr Val Ser Ser
        115                 120

<210> SEQ ID NO 57
<211> LENGTH: 123
<212> TYPE: PRT
<213> ORGANISM: Artificial Sequence
<220> FEATURE:
<223> OTHER INFORMATION: Camelid

<400> SEQUENCE: 57

His Val Gln Leu Val Glu Ser Gly Gly Ser Val Glu Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Arg Lys Glu Arg Glu Gly Val
        35                  40                  45

Ala Thr Ile Asp Ile Asp Gly Gln Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Gln Val Thr Val Ser Ser
        115                 120

<210> SEQ ID NO 58
<211> LENGTH: 123
<212> TYPE: PRT
<213> ORGANISM: Artificial Sequence
<220> FEATURE:
<223> OTHER INFORMATION: Camelid

<400> SEQUENCE: 58

His Val Gln Leu Val Glu Ser Gly Gly Ser Val Gln Ala Gly Gly
1               5                   10                  15

Ser Leu Arg Leu Ser Cys Ala Ala Ser Gly Phe Arg Tyr Ala Ala Tyr
            20                  25                  30

Cys Met Gly Trp Phe Arg Gln Ala Asp Gly Lys Val Arg Glu Gly Val
        35                  40                  45

Ala Thr Ile Asp Ile Asp Gly Gln Thr Thr His Ala Asp Ser Val Lys
    50                  55                  60

Gly Arg Phe Thr Ile Ser Arg Asp Asn Ala Lys Asn Thr Leu Ser Leu
65                  70                  75                  80

Gln Met Asn Asp Leu Lys Pro Glu Asp Thr Ala Met Tyr Tyr Cys Ala
                85                  90                  95

Ala Asp Arg Asp Arg Cys Gly Ser Ile Trp Thr Tyr Ala Tyr Lys Tyr
            100                 105                 110

Arg Gly Gln Gly Thr Leu Val Thr Val Ser Ser
        115                 120

<210> SEQ ID NO 59
<211> LENGTH: 123
<212> TYPE: PRT
<213> ORGANISM: Artificial Sequence
<220> FEATURE:
```

<223> OTHER INFORMATION: Camelid

<400> SEQUENCE: 59

Gln Val Gln Leu Val Glu Ser Gly Gly Gly Ser Val Gln Ala Gly Gly
1               5                   10                  15

Ser Leu Arg Leu Ser Cys Ala Ala Ser Gly Phe Ile Asp Ser Phe Gly
            20                  25                  30

Val Met Ala Trp Phe Arg Gln Ala Pro Gly Lys Glu Arg Glu Gly Val
        35                  40                  45

Ala Ala Val Tyr Arg Arg Ala Gly Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Met Tyr Tyr Cys
                85                  90                  95

Ala Ala Arg Thr Tyr Gly Ser Val Ser Ser Trp Thr Gly Tyr Lys Tyr
            100                 105                 110

Trp Gly Gln Gly Thr Gln Val Thr Val Ser Ser
        115                 120

<210> SEQ ID NO 60
<211> LENGTH: 123
<212> TYPE: PRT
<213> ORGANISM: Artificial Sequence
<220> FEATURE:
<223> OTHER INFORMATION: Camelid

<400> SEQUENCE: 60

Asp Val Gln Leu Val Glu Ser Gly Gly Gly Ser Val Gln Ala Gly Gly
1               5                   10                  15

Ser Leu Arg Leu Ser Cys Ala Ala Ser Gly Phe Ile Asp Ser Phe Gly
            20                  25                  30

Val Met Ala Trp Phe Arg Gln Thr Pro Gly Lys Glu Arg Glu Gly Val
        35                  40                  45

Ala Ala Val Tyr Arg Arg Ala Gly Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Ser Ala Met Tyr Tyr Cys
                85                  90                  95

Ala Ala Arg Thr Tyr Gly Ser Val Ser Ser Trp Thr Gly Tyr Lys Tyr
            100                 105                 110

Trp Gly Gln Gly Thr Gln Val Thr Val Ser Ser
        115                 120

<210> SEQ ID NO 61
<211> LENGTH: 123
<212> TYPE: PRT
<213> ORGANISM: Artificial Sequence
<220> FEATURE:
<223> OTHER INFORMATION: Camelid

<400> SEQUENCE: 61

Asp Val Gln Leu Val Glu Ser Gly Gly Gly Ser Val Gln Val Gly Gly
1               5                   10                  15

Ser Leu Thr Leu Ser Cys Ala Val Ser Gly Tyr Thr Asp Ser Tyr Gly
            20                  25                  30

Val Met Ala Trp Phe Arg Gln Ala Pro Gly Lys Glu Arg Glu Gly Val

```
                35                  40                  45

Ala Ser Ile Tyr Arg Asn Ser Gly Ile Thr Tyr Tyr Pro Asp Ser Val
 50                  55                  60

Lys Gly Arg Phe Thr Ile Ser Arg Asp Asn Ala Lys Asn Thr Val Leu
 65                  70                  75                  80

Leu Gln Met Asn Ser Leu Lys Pro Glu Asp Ser Ala Thr Tyr Tyr Cys
                 85                  90                  95

Ala Val Arg Ser Phe Gly Ser Val Ser Thr Trp Ala Gly Tyr Val Tyr
                100                 105                 110

Trp Gly Gln Gly Thr Gln Val Thr Val Ser Ser
            115                 120

<210> SEQ ID NO 62
<211> LENGTH: 123
<212> TYPE: PRT
<213> ORGANISM: Artificial Sequence
<220> FEATURE:
<223> OTHER INFORMATION: Camelid

<400> SEQUENCE: 62

Asp Val Gln Leu Val Glu Ser Gly Gly Gly Ser Val Gln Ala Gly Gly
 1               5                  10                  15

Ser Leu Arg Leu Ser Cys Ala Ala Ser Gly Phe Ile Asp Ser Phe Gly
                20                  25                  30

Val Met Ala Trp Phe Arg Gln Ala Pro Gly Lys Glu Arg Glu Gly Val
                35                  40                  45

Ala Ala Val Tyr Arg Arg Ala Gly Asp Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Ser Ala Met Tyr Tyr Cys
                 85                  90                  95

Ala Ala Arg Thr Tyr Gly Ser Val Ser Ser Trp Thr Gly Tyr Lys Tyr
                100                 105                 110

Trp Gly Arg Gly Thr Gln Val Thr Val Ser Ser
            115                 120

<210> SEQ ID NO 63
<211> LENGTH: 125
<212> TYPE: PRT
<213> ORGANISM: Artificial Sequence
<220> FEATURE:
<223> OTHER INFORMATION: Camelid

<400> SEQUENCE: 63

Asp Val Gln Leu Val Glu Ser Gly Gly Gly Ser Val Arg Ala Gly Gly
 1               5                  10                  15

Ser Leu Arg Leu Ser Cys Thr Ala Ser Gly Asp Thr Ser Lys Ser Asp
                20                  25                  30

Cys Met Ala Trp Phe Arg Gln Ala Pro Gly Lys Glu Arg Glu Arg Val
                35                  40                  45

Gly Ala Ile Tyr Thr Arg Asn Gly Tyr Thr His Tyr Ala Asp Ser Val
 50                  55                  60

Asn Gly Arg Phe Thr Ile Ser Gln Asp Asn Ala Lys Asn Ala Leu Tyr
 65                  70                  75                  80

Leu Gln Met Ser Gly Leu Lys Pro Glu Asp Thr Ala Met Tyr Tyr Cys
                 85                  90                  95
```

Ala Ala Arg Phe Arg Ile Tyr Gly Gln Cys Val Glu Asp Asp Ile
            100                 105                 110

Asp Tyr Trp Gly Gln Gly Thr Leu Val Thr Val Ser Ser
        115                 120                 125

<210> SEQ ID NO 64
<211> LENGTH: 124
<212> TYPE: PRT
<213> ORGANISM: Artificial Sequence
<220> FEATURE:
<223> OTHER INFORMATION: Camelid

<400> SEQUENCE: 64

Glu Val Gln Leu Val Glu Ser Gly Gly Gly Ser Val Leu Ala Gly Gly
1               5                   10                  15

Ser Leu Arg Leu Ser Cys Val Ala Ser Gly Phe Thr Ser Arg Tyr Asn
            20                  25                  30

Tyr Met Ala Trp Phe Arg Gln Ala Pro Gly Lys Glu Arg Glu Gly Val
        35                  40                  45

Ala Thr Ile Gly Thr Ala Ser Gly Ser Ala Asp Tyr Tyr Gly Ser Val
    50                  55                  60

Lys Asp Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Thr Tyr Gly Thr Ile Ser Leu Thr Pro Ser Asp Tyr Arg
            100                 105                 110

Tyr Trp Gly Gln Gly Thr Leu Val Thr Val Ser Ser
        115                 120

<210> SEQ ID NO 65
<211> LENGTH: 128
<212> TYPE: PRT
<213> ORGANISM: Artificial Sequence
<220> FEATURE:
<223> OTHER INFORMATION: Camelid

<400> SEQUENCE: 65

Gln Val Gln Val Val Glu Tyr Gly Gly Gly Ser Val Gln Ala Gly Glu
1               5                   10                  15

Thr Val Arg Leu Ser Cys Thr Ala Ser Gly Phe Thr Phe Ala Glu Ala
            20                  25                  30

Asp Met Gly Trp Tyr Arg Gln Ala Pro Gly His Glu Trp Glu Leu Val
        35                  40                  45

Ser Asn Ile Thr Thr Glu Gly Ile Thr Ser Glu Ala Ser Ser Ser Tyr
    50                  55                  60

Ala Asp Ser Val Arg Gly Arg Phe Thr Ile Phe Asp Asn Ala Lys Asn
65                  70                  75                  80

Met Val Tyr Leu Gln Met Asn Ser Leu Lys His Glu Asp Thr Ala Val
                85                  90                  95

Tyr Tyr Cys Ala Pro Asp Pro Tyr Ala Tyr Ser Thr Tyr Arg Glu Tyr
            100                 105                 110

Cys Thr Trp Ala Gln Gly Thr Gln Gly Thr Leu Val Thr Val Ser Ser
        115                 120                 125

<210> SEQ ID NO 66
<211> LENGTH: 129
<212> TYPE: PRT
<213> ORGANISM: Artificial Sequence

```
<220> FEATURE:
<223> OTHER INFORMATION: Camelid

<400> SEQUENCE: 66

Gln Val Gln Leu Val Glu Ser Gly Gly Gly Pro Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Ser Trp Ala Gln Gly Thr Gln Gly Thr Leu Val Thr Val Ser
        115                 120                 125

Ser

<210> SEQ ID NO 67
<211> LENGTH: 129
<212> TYPE: PRT
<213> ORGANISM: Artificial Sequence
<220> FEATURE:
<223> OTHER INFORMATION: Camelid

<400> SEQUENCE: 67

Gln Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Leu Val Thr Val Ser
        115                 120                 125

Ser

<210> SEQ ID NO 68
<211> LENGTH: 129
<212> TYPE: PRT
<213> ORGANISM: Artificial Sequence
<220> FEATURE:
<223> OTHER INFORMATION: Camelid

<400> SEQUENCE: 68

Gln Val Gln Pro Val Glu Ser Gly Gly Gly Ser Val Gln Ala Gly Glu
1               5                   10                  15
```

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
            35                  40                  45

Ser Thr Ile Thr Thr Glu Gly Ile Thr Ser Glu Ala Ser Ser Tyr Tyr
50                      55                  60

Ala Asp Ser Val Arg Gly Arg Phe Thr Ile Ser Arg Asp Asn Ala Lys
65                      70                  75                  80

Asn Met Val Tyr Leu Gln Met Asn Ser Leu Lys Pro Glu Asp Thr Ala
            85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Ala Gln Gly Thr Leu Val Thr Val Ser
            115                 120                 125

Ser

<210> SEQ ID NO 69
<211> LENGTH: 129
<212> TYPE: PRT
<213> ORGANISM: Artificial Sequence
<220> FEATURE:
<223> OTHER INFORMATION: Camelid

<400> SEQUENCE: 69

Gln Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
            35                  40                  45

Ser Thr Ile Thr Thr Glu Gly Ile Thr Ser Glu Ala Ser Ser Tyr Tyr
50                      55                  60

Ala Asp Ser Val Arg Gly Arg Phe Thr Ile Ser Arg Asp Asn Ala Lys
65                      70                  75                  80

Asn Met Val Tyr Leu Gln Met Asn Ser Leu Lys Pro Glu Asp Thr Ala
            85                  90                  95

Val Tyr Tyr Cys Ala Pro Asp Pro Tyr Ala Tyr Ser Thr Tyr Ser Asp
            100                 105                 110

Tyr Cys Ser Trp Ala Gln Gly Thr Gln Gly Thr Gln Val Thr Val Ser
            115                 120                 125

Ser

<210> SEQ ID NO 70
<211> LENGTH: 129
<212> TYPE: PRT
<213> ORGANISM: Artificial Sequence
<220> FEATURE:
<223> OTHER INFORMATION: Camelid

<400> SEQUENCE: 70

Gln Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
            35                  40                  45

```
Ser Thr Ile Thr Thr Glu Gly Ile Thr Ser Glu Ala Ser Ser Tyr Tyr
        50                  55                  60

Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                    85                  90                  95

Val Tyr Tyr Cys Ala Pro Asp Pro Tyr Ala Tyr Ser Thr Tyr Ser Asp
               100                 105                 110

Tyr Cys Thr Trp Ala Gln Gly Thr Gln Gly Thr Gln Val Thr Val Ser
            115                 120                 125

Ser

<210> SEQ ID NO 71
<211> LENGTH: 129
<212> TYPE: PRT
<213> ORGANISM: Artificial Sequence
<220> FEATURE:
<223> OTHER INFORMATION: Camelid

<400> SEQUENCE: 71

Gln Val Gln Leu Val Glu Ser Gly Gly Gly Ser Val Gln Ala Gly Glu
 1               5                  10                  15

Thr Leu Arg Leu Ser Cys Thr Ala Ser Gly Phe Thr Phe Ala Glu Ala
                20                  25                  30

Asp Met Gly Trp Tyr Arg Gln Ala Pro Gly His Glu Cys Glu Leu Val
            35                  40                  45

Ser Thr Ile Thr Thr Glu Gly Ile Thr Ser Glu Ala Ser Ser Tyr Tyr
        50                  55                  60

Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                    85                  90                  95

Val Tyr Tyr Cys Ala Pro Asp Pro Tyr Ala Tyr Ser Thr Tyr Ser Asp
               100                 105                 110

Tyr Cys Thr Trp Ala Gln Gly Thr Gln Gly Thr Leu Val Thr Val Ser
            115                 120                 125

Ser

<210> SEQ ID NO 72
<211> LENGTH: 129
<212> TYPE: PRT
<213> ORGANISM: Artificial Sequence
<220> FEATURE:
<223> OTHER INFORMATION: Camelid

<400> SEQUENCE: 72

His Val Gln Leu Val Glu Ser Gly Gly Gly Ser Val Gln Ala Gly Glu
 1               5                  10                  15

Thr Leu Arg Leu Ser Cys Thr Ala Ser Gly Phe Thr Phe Ala Glu Ala
                20                  25                  30

Asp Met Gly Trp Tyr Arg Gln Ala Pro Gly His Glu Cys Glu Leu Val
            35                  40                  45

Ser Thr Ile Thr Thr Glu Gly Ile Thr Ser Glu Ala Ser Ser Tyr Tyr
        50                  55                  60

Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
```

```
                    85                  90                  95
Val Tyr Tyr Cys Ala Pro Asp Pro Tyr Ala Tyr Ser Thr Tyr Ser Asp
                100                 105                 110
Tyr Cys Thr Trp Ala Gln Gly Thr Gln Gly Thr Gln Val Thr Val Ser
            115                 120                 125
Ser
```

<210> SEQ ID NO 73
<211> LENGTH: 129
<212> TYPE: PRT
<213> ORGANISM: Artificial Sequence
<220> FEATURE:
<223> OTHER INFORMATION: Camelid

<400> SEQUENCE: 73

```
Glu Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
                100                 105                 110

Tyr Cys Thr Trp Ala Gln Gly Thr Gln Gly Ala Leu Val Thr Val Ser
            115                 120                 125

Ser
```

<210> SEQ ID NO 74
<211> LENGTH: 129
<212> TYPE: PRT
<213> ORGANISM: Artificial Sequence
<220> FEATURE:
<223> OTHER INFORMATION: Camelid

<400> SEQUENCE: 74

```
Glu Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
                100                 105                 110

Tyr Cys Thr Trp Ala Gln Gly Thr Gln Gly Thr Leu Val Thr Val Ser
            115                 120                 125
```

Ser

<210> SEQ ID NO 75
<211> LENGTH: 129
<212> TYPE: PRT
<213> ORGANISM: Artificial Sequence
<220> FEATURE:
<223> OTHER INFORMATION: Camelid

<400> SEQUENCE: 75

```
Glu Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Ser Trp Ala Gln Gly Thr Gln Gly Thr Gln Val Thr Val Ser
        115                 120                 125

Ser
```

<210> SEQ ID NO 76
<211> LENGTH: 129
<212> TYPE: PRT
<213> ORGANISM: Artificial Sequence
<220> FEATURE:
<223> OTHER INFORMATION: Camelid

<400> SEQUENCE: 76

```
Glu Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Gln Val Thr Val Ser
        115                 120                 125

Ser
```

<210> SEQ ID NO 77
<211> LENGTH: 129
<212> TYPE: PRT

```
<213> ORGANISM: Artificial Sequence
<220> FEATURE:
<223> OTHER INFORMATION: Camelid

<400> SEQUENCE: 77

Asp Val Gln Leu Val Glu Ser Arg Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Glu Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Leu Val Thr Val Ser
        115                 120                 125

Ser

<210> SEQ ID NO 78
<211> LENGTH: 129
<212> TYPE: PRT
<213> ORGANISM: Artificial Sequence
<220> FEATURE:
<223> OTHER INFORMATION: Camelid

<400> SEQUENCE: 78

Asp Val Gln Leu Val Glu Ser Gly Gly Gly Ser Val Gln Ala Gly Glu
1               5                   10                  15

Thr Leu Arg Leu Ser Cys Thr Ala Ser Gly Phe Thr Phe Ala Glu Ala
            20                  25                  30

Asp Met Gly Trp Tyr Arg Gln Ala Pro Gly His Val Cys Glu Leu Val
        35                  40                  45

Ser Thr Ile Thr Thr Glu Gly Ile Thr Ser Glu Ala Ser Ser Tyr Tyr
    50                  55                  60

Ala Asp Ser Val Arg Gly Arg Phe Thr Ile Ser Arg Asp Asn Ala Lys
65                  70                  75                  80

Asn Met Val Tyr Leu Gln Met Asn Ser Leu Lys Pro Glu Asp Thr Ala
                85                  90                  95

Val Tyr Tyr Cys Ala Pro Asp Pro Tyr Ala Tyr Ser Thr Tyr Ser Asp
            100                 105                 110

Tyr Cys Ser Trp Ala Gln Gly Thr Gln Gly Thr Gln Val Thr Val Ser
        115                 120                 125

Ser

<210> SEQ ID NO 79
<211> LENGTH: 128
<212> TYPE: PRT
<213> ORGANISM: Artificial Sequence
<220> FEATURE:
<223> OTHER INFORMATION: Camelid

<400> SEQUENCE: 79

Asp Val Gln Leu Val Glu Ser Gly Gly Gly Ser Val Gln Ala Gly Glu
```

-continued

```
                1               5                  10                 15
          Thr Leu Arg Leu Ser Cys Thr Ala Ser Gly Phe Thr Phe Ala Glu Ala
                          20                  25                 30

Asp Met Gly Trp Tyr Arg Gln Ala Pro Gly Leu Glu Cys Glu Leu Val
                          35                  40                 45

Ser Thr Ile Thr Thr Glu Gly Ile Thr Ser Glu Ala Ser Ser Tyr Ala
                      50                  55                 60

Asp Ser Val Arg Gly Arg Phe Thr Ile Ser Arg Asp Asn Ala Lys Asn
          65                  70                  75                 80

Met Val Tyr Leu Gln Met Asn Ser Leu Lys Pro Glu Asp Thr Ala Val
                              85                  90                 95

Tyr Tyr Cys Ala Pro Asp Pro Tyr Ala Tyr Ser Thr Tyr Ser Glu Tyr
                          100                 105                110

Cys Thr Trp Ala Gln Gly Thr Gln Gly Thr Leu Val Thr Val Ser Ser
                          115                 120                125
```

<210> SEQ ID NO 80
<211> LENGTH: 129
<212> TYPE: PRT
<213> ORGANISM: Artificial Sequence
<220> FEATURE:
<223> OTHER INFORMATION: Camelid

<400> SEQUENCE: 80

```
          Asp Val Gln Leu Val Glu Ser Gly Gly Gly Ser Val Gln Ala Gly Glu
          1               5                  10                 15

Thr Leu Arg Leu Ser Cys Thr Ala Ser Gly Phe Thr Phe Ala Glu Ala
                          20                  25                 30

Asp Met Gly Trp Tyr Arg Gln Ala Pro Gly His Glu Cys Glu Leu Val
                          35                  40                 45

Ser Thr Ile Thr Thr Glu Gly Ile Thr Ser Glu Ala Ser Ser Tyr Tyr
                      50                  55                 60

Ala Asp Ser Val Arg Gly Arg Phe Thr Ile Ser Arg Asp Asn Ala Lys
          65                  70                  75                 80

Asn Met Val Tyr Leu Gln Met Asn Ser Leu Lys Pro Glu Asp Thr Ala
                              85                  90                 95

Val Tyr Tyr Cys Ala Pro Asp Pro Tyr Ala Tyr Ser Thr Tyr Ser Asp
                          100                 105                110

Tyr Cys Thr Trp Ala Gln Gly Thr Gln Gly Thr Leu Val Thr Val Ser
                          115                 120                125

Ser
```

<210> SEQ ID NO 81
<211> LENGTH: 129
<212> TYPE: PRT
<213> ORGANISM: Artificial Sequence
<220> FEATURE:
<223> OTHER INFORMATION: Camelid

<400> SEQUENCE: 81

```
          Asp Val Gln Leu Val Glu Ser Gly Gly Gly Ser Val Gln Ala Gly Glu
          1               5                  10                 15

Thr Leu Arg Leu Ser Cys Thr Ala Ser Gly Phe Thr Phe Ala Glu Ala
                          20                  25                 30

Asp Met Gly Trp Tyr Arg Gln Ala Pro Gly His Glu Cys Glu Leu Val
                          35                  40                 45

Ser Thr Ile Thr Thr Glu Gly Ile Thr Ser Val Ala Ser Ser Tyr Tyr
```

```
Ala Asp Ser Val Arg Gly Arg Phe Thr Ile Ser Arg Asp Asn Ala Lys
 65                  70                  75                  80

Asn Met Val Tyr Leu Gln Met Asn Ser Leu Lys Pro Glu Asp Thr Ala
                 85                  90                  95

Val Tyr Tyr Cys Ala Pro Asp Pro Tyr Ala Tyr Ser Thr Tyr Ser Asp
            100                 105                 110

Tyr Cys Thr Trp Ala Gln Gly Thr Gln Gly Thr Gln Val Thr Val Ser
                115                 120                 125

Ser
```

<210> SEQ ID NO 82
<211> LENGTH: 372
<212> TYPE: DNA
<213> ORGANISM: Artificial Sequence
<220> FEATURE:
<223> OTHER INFORMATION: Camelid

<400> SEQUENCE: 82

```
gaggtgcagc tggtggagtc tgggggaggc tcggtgcaga ctggagggtc tctgagactc      60
tcctgcgcag cctctggatt ccccttttagt agtcacgtta tgggctggtt ccgccaggct    120
ccagggaaga aacgcgaggg ggtcgcagct atttcggttg atagtggtag cacatggtat    180
gccgactccg tgaagggccg attcaccatc tccctgacac gccaagaa cacgctgtat     240
ctgcaaatga acagcctgaa acctgaggac actgccatgt actactgtgc gactagacgt    300
ggagttattc ttacactaag cccagagacc tatgactact ggggccaggg gacccaggtc    360
accgtctcct ca                                                        372
```

<210> SEQ ID NO 83
<211> LENGTH: 124
<212> TYPE: PRT
<213> ORGANISM: Artificial Sequence
<220> FEATURE:
<223> OTHER INFORMATION: Camelid

<400> SEQUENCE: 83

```
Glu Val Gln Leu Val Glu Ser Gly Gly Gly Ser Val Gln Thr Gly Gly
 1               5                  10                  15

Ser Leu Arg Leu Ser Cys Ala Ala Ser Gly Phe Pro Phe Ser Ser His
                 20                  25                  30

Val Met Gly Trp Phe Arg Gln Ala Pro Gly Lys Lys Arg Glu Gly Val
             35                  40                  45

Ala Ala Ile Ser Val Asp Ser Gly Ser Thr Trp Tyr Ala Asp Ser Val
 50                  55                  60

Lys Gly Arg Phe Thr Ile Ser Leu Asp Ser Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

Ala Thr Arg Arg Gly Val Ile Leu Thr Leu Ser Pro Glu Thr Tyr Asp
            100                 105                 110

Tyr Trp Gly Gln Gly Thr Gln Val Thr Val Ser Ser
            115                 120
```

<210> SEQ ID NO 84
<211> LENGTH: 141
<212> TYPE: PRT
<213> ORGANISM: Artificial Sequence

```
<220> FEATURE:
<223> OTHER INFORMATION: Camelid

<400> SEQUENCE: 84

Met Gly Asp Val Gln Leu Val Glu Ser Gly Gly Asp Ser Val Arg Ala
1               5                   10                  15

Gly Gly Ser Leu Gln Leu Ser Cys Lys Ala Ser Gly Tyr Thr Tyr Asn
            20                  25                  30

Ser Arg Val Asp Ile Arg Ser Met Gly Trp Phe Arg Gln Tyr Pro Gly
        35                  40                  45

Lys Glu Arg Glu Gly Val Ala Thr Ile Asn Ile Arg Asn Ser Val Thr
    50                  55                  60

Tyr Tyr Ala Asp Ser Val Lys Gly Arg Phe Thr Ile Ser Gln Asp Asn
65                  70                  75                  80

Ala Lys Asn Thr Val Tyr Leu Gln Met Asn Ala Leu Lys Pro Glu Asp
                85                  90                  95

Thr Ala Met Tyr Tyr Cys Ala Leu Ser Asp Arg Phe Ala Ala Gln Val
                100                 105                 110

Pro Ala Arg Tyr Gly Ile Arg Pro Ser Asp Tyr Asn Tyr Trp Gly Glu
            115                 120                 125

Gly Thr Leu Val Thr Val Ser Ser Ser Ser Gly Leu Glu
            130                 135                 140
```

SINGLE DOMAIN ANTIBODIES DIRECTED AGAINST INTRACELLULAR ANTIGENS

CROSS-REFERENCE TO RELATED APPLICATIONS

This application is a continuation of pending U.S. application Ser. No. 15/823,295, titled "Single Domain Antibodies Directed Against Intracellular Antigens," filed Nov. 27, 2017, which is a continuation-in-part of pending U.S. application Ser. No. 15/655,833, titled "Single Domain Antibodies Directed Against Intracellular Antigens," filed Jul. 20, 2017, which is a continuation of pending U.S. patent application Ser. No. 15/608,255 titled "Single Domain Antibodies Directed Against Intracellular Antigens," filed May 30, 2017, which is continuation-in-part of U.S. patent application Ser. No. 14/922,093 titled "Single Domain Antibodies Directed Against STAT3" filed Oct. 23, 2015, now U.S. Pat. No. 9,695,234 issued on Jul. 4, 2017, which claims the benefit of U.S. Provisional Patent Application No. 62/067,908, filed on Oct. 23, 2014; U.S. Provisional Patent Application No. 62/148,656, filed on Apr. 16, 2015; U.S. Provisional Patent Application No. 62/188,353 filed on Jul. 2, 2015; and U.S. Provisional Patent Application No. 62/210,795, filed on Aug. 27, 2015, the contents of which are incorporated herein by reference in their entirety.

SEQUENCE LISTING

The present application is being filed along with a Sequence Listing in electronic format. The Sequence Listing is provided as a file titled "Sequence listing 51293-14" created Oct. 20, 2017, and is 89,000 bytes in size. The information in the electronic format of the Sequence Listing is incorporated herein by reference in its entirety.

BACKGROUND

The use of single-domain antibodies (sdAbs) as single antigen-binding proteins or as an antigen-binding domain in a larger protein or polypeptide offers a number of significant advantages over the use of conventional antibodies or antibody fragments. The advantages of sdAbs include: only a single domain is required to bind an antigen with high affinity and with high selectivity; sdAbs can be expressed from a single gene and require no post-translational modification; sdAbs are highly stable to heat, pH, proteases and other denaturing agents or conditions; sdAbs are inexpensive to prepare; and sdAbs can access targets and epitopes not accessible to conventional antibodies.

There are a number of diseases or conditions, such as cancer, that are caused by aberrant cell proliferation, including aberrant intracellular or transmembrane components such as nucleotides and proteins. Aberrant cell proliferation is abnormal cell growth, usually linked to cancer. Elimination of the aberrant components can be used to prevent or treat the diseases or conditions. There are a number of pharmacological compounds available for treatment, but the compounds can be ineffective, undeliverable, or toxic to unaffected cells.

Other treatments include the use of therapeutic proteins or agents that contain an exogenous targeting sequence so that the therapeutic agent can be recognized by receptors in the cell membrane, enabling the therapeutic agent to cross the cell membrane and enter the cell. Once the therapeutic agent is inside the cell, the therapeutic agent can interact with the target component in order to treat the disease. However, the use of exogenous targeting sequence can limit the cell type that is targeted by the therapeutic agent, and adds to the cost of manufacturing the therapeutic agent.

For the foregoing reasons, there is a need for compositions and methods to treat or prevent a disease that do not rely on exogenous targeting sequences or chemical compositions in order to enter the cell, and that are effective in targeting only the affected cells in the body.

The present invention relates to single-domain antibodies (sdAbs), proteins and polypeptides comprising the sdAbs. The sdAbs are directed against intracellular components that cause a condition or disease. The invention also includes nucleic acids encoding the sdAbs, proteins and polypeptides, and compositions comprising the sdAbs. The invention includes the use of the compositions, sdAbs, proteins or polypeptides for prophylactic, therapeutic or diagnostic purposes. The invention also includes the use of monoclonal antibodies directed towards the sdAbs of the invention.

SUMMARY

The invention includes a method of preventing aberrant cell proliferation in a subject using a single-domain antibody (sdAb) directed against an intracellular component. The aberrant cell proliferation can be cancer, and the cancer can be osteosarcoma, fibrosarcoma or glioblastoma.

The sdAb is synergistic with one or more chemotherapeutic drugs and improves therapeutic efficacy of the one or more chemotherapeutic drug against cancer. The one or more chemotherapeutic drugs can be doxorubicin.

The sbAb decreases the toxicity of one or more chemotherapeutic drugs and improves survival in the treated subject. Optionally, the sbAb is used in combination with one or more compounds. The intracellular component comprises a protein, and the protein can be STAT1, STAT2, STAT3, STAT4, STAT5a, STAT5b, or STAT6. Optionally, the sdAb comprises anti-STAT3 VHH13 (SEQ ID NO:3) sdAb.

Another embodiment of the invention is a method of treating viral infections using a single-domain antibody (sdAb). The viral infection is caused by one or more of a DNA virus, an RNA virus, or a retrovirus. The virus can be hepatitis A virus, hepatitis B virus, hepatitis C virus, human papillomavirus, polio virus, rabies virus, herpesvirus, West Nile virus, Ebola virus, and Zika virus. The sbAb can inhibit the replication of Ebola viruses in infected cells. The sdAb inhibits the replication of Zika virus in infected cells. Optionally, the sdAb is used in combination with one or more compounds.

DRAWINGS

These and other features, aspects, and advantages of the present invention will become better understood with regard to the following description, appended claims, and accompanying drawings where:

Figure 6:
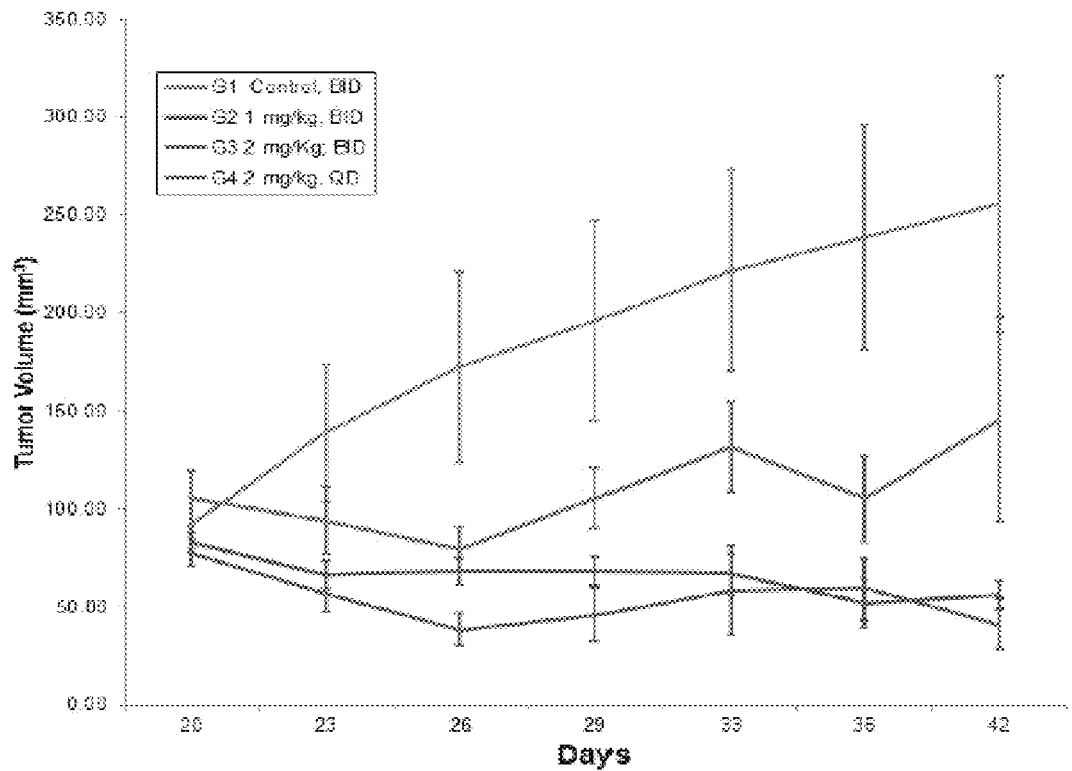
Figure 7:
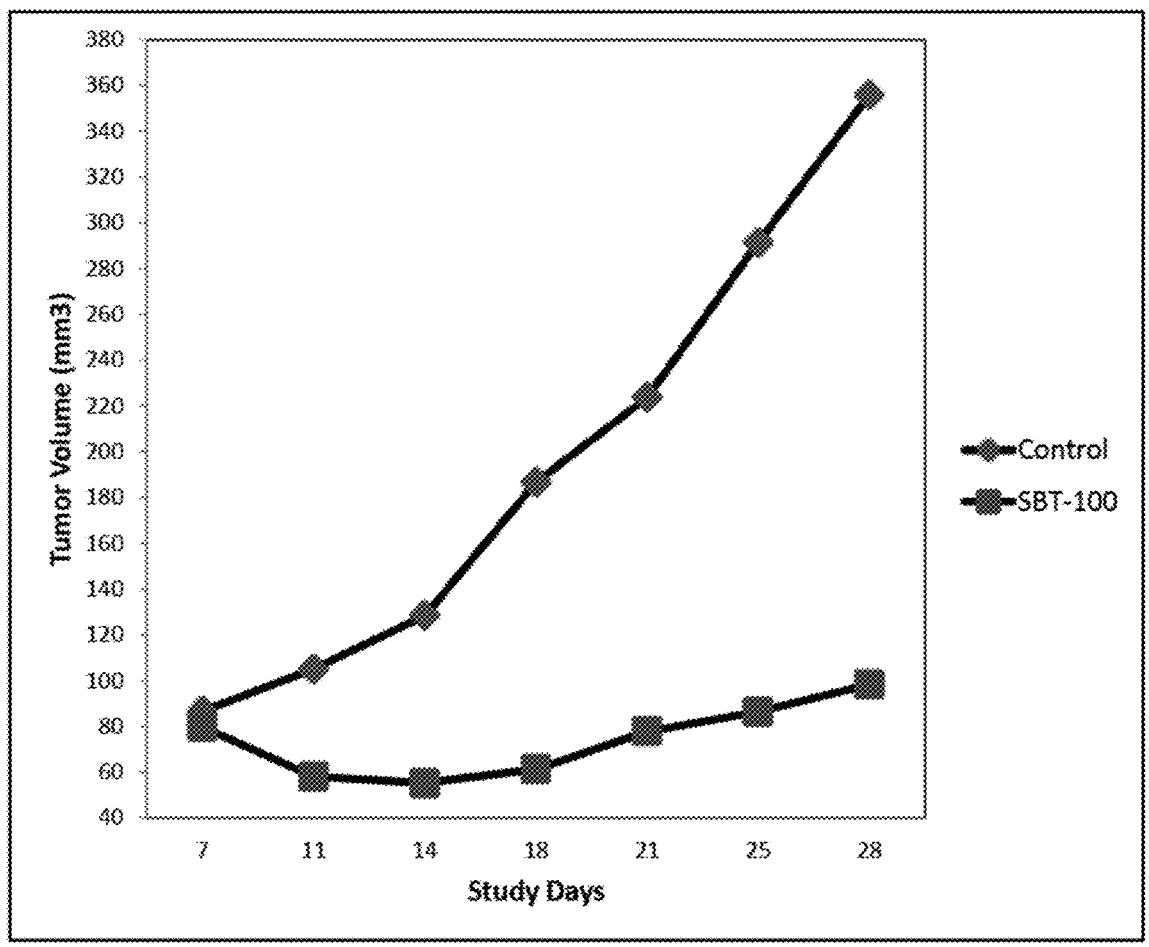
Figure 8:
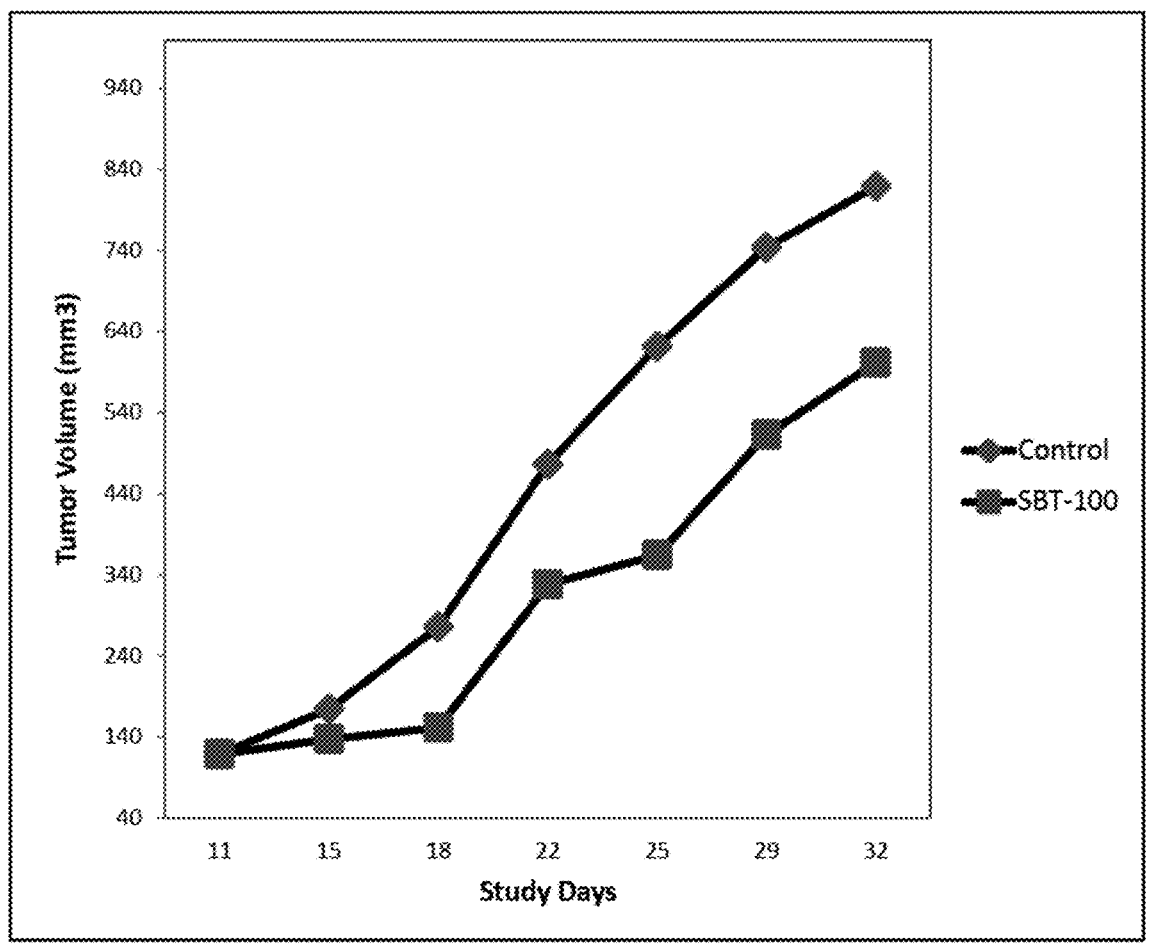
Figure 9:
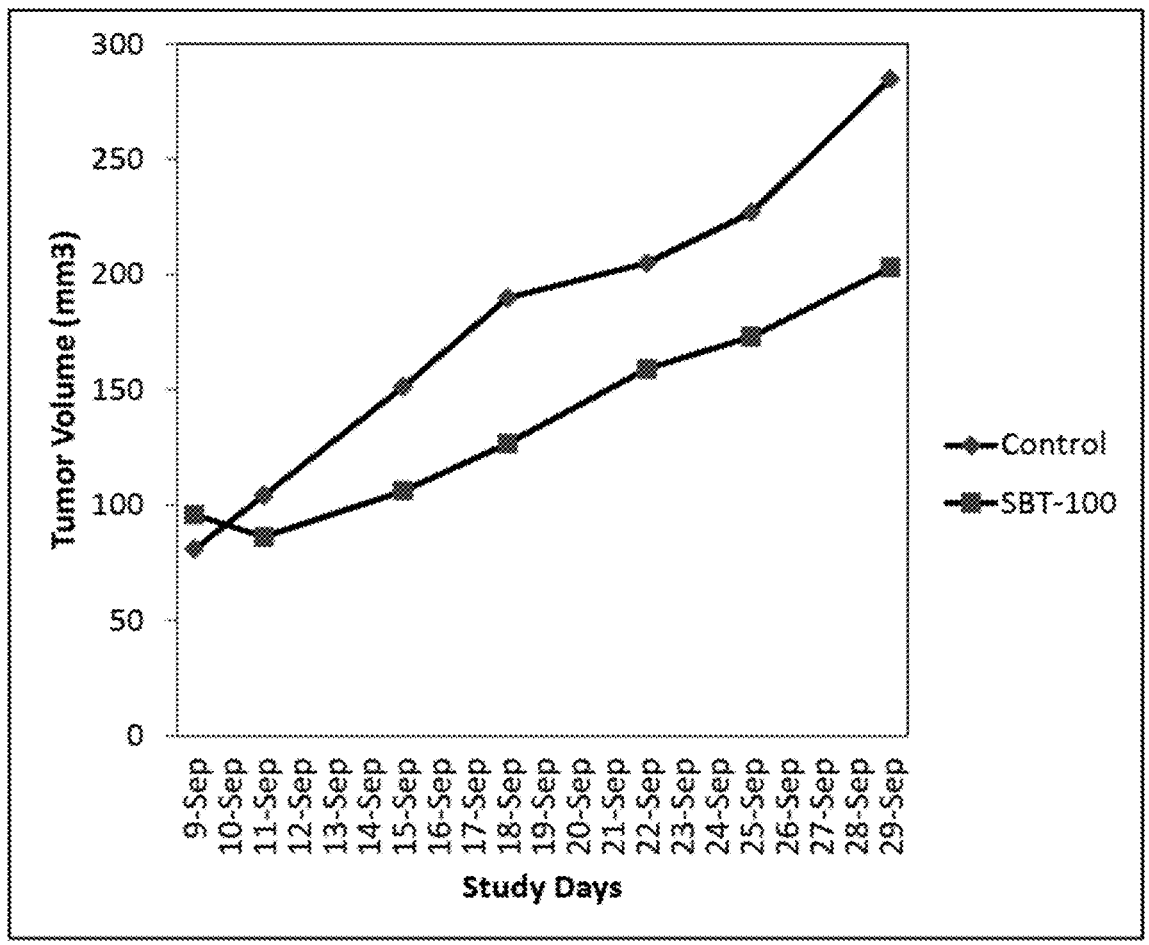
Figure 10:
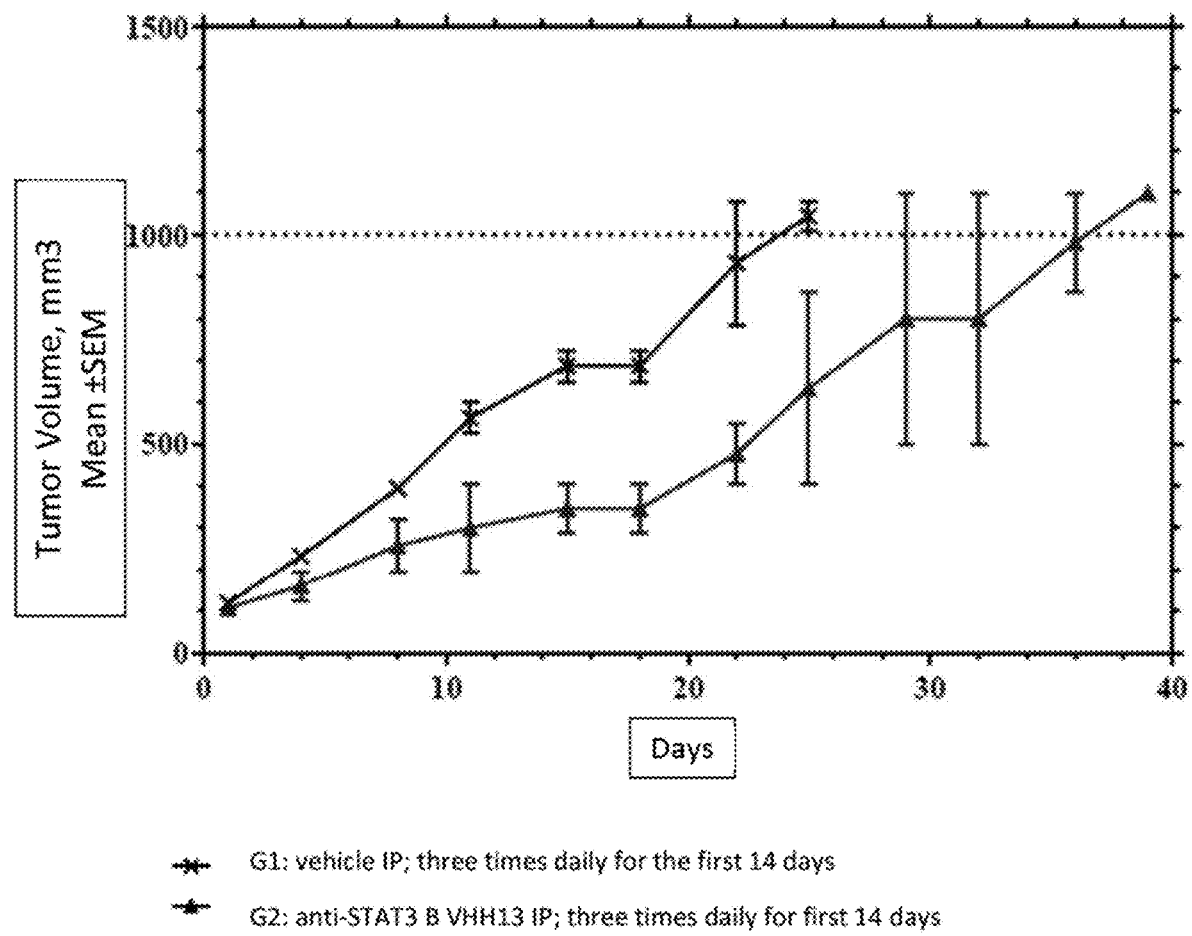
Figure 11:
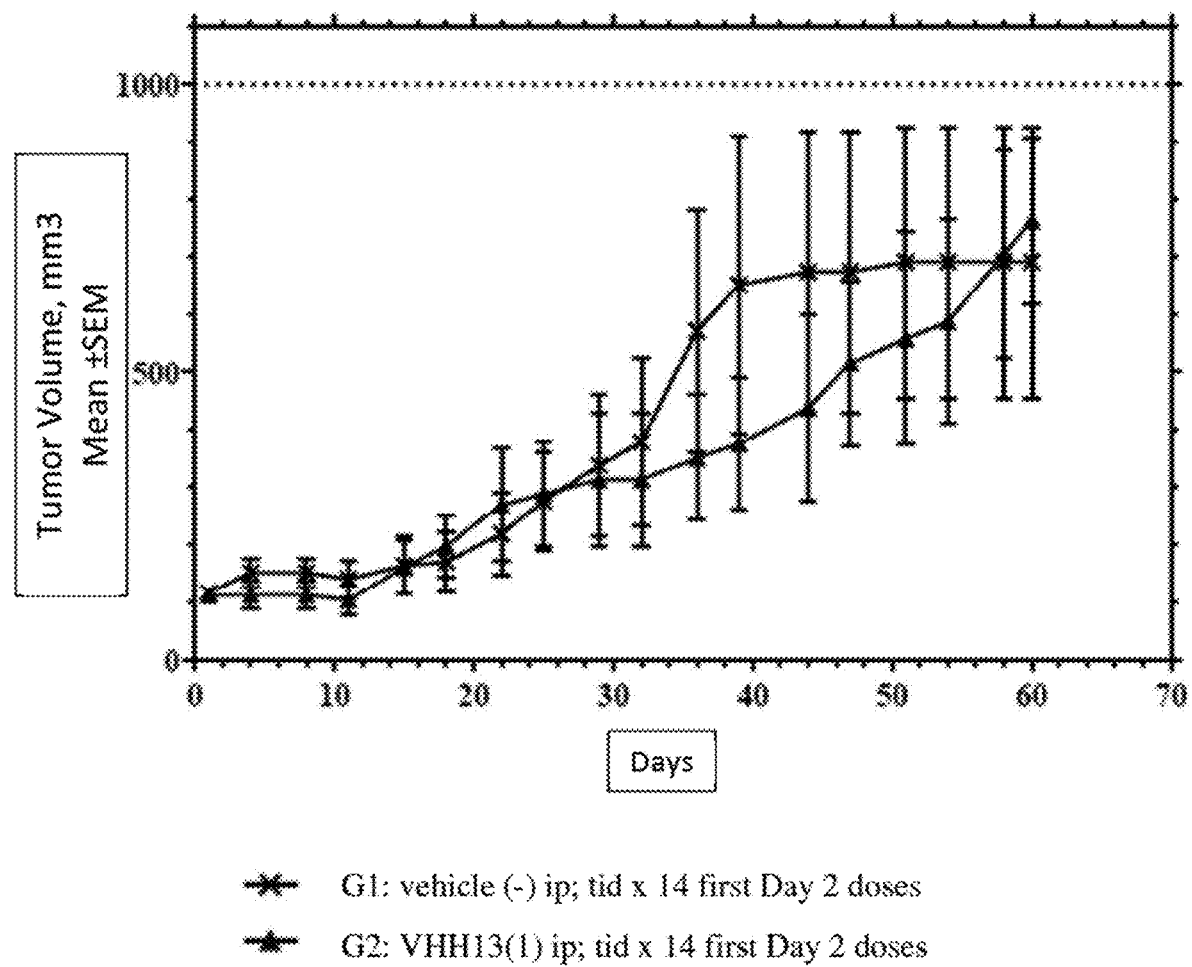
Figure 12:
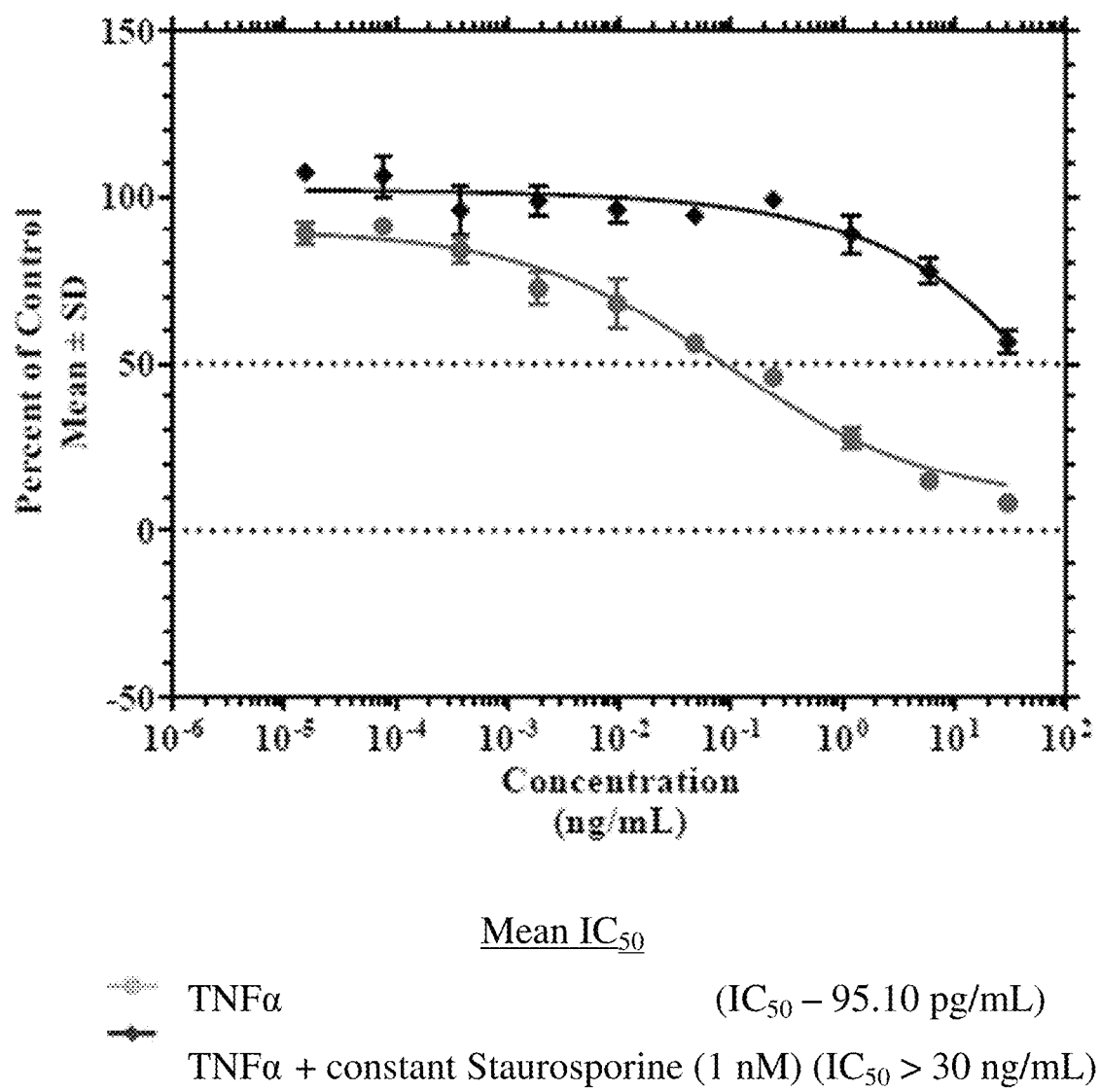
Figure 13:
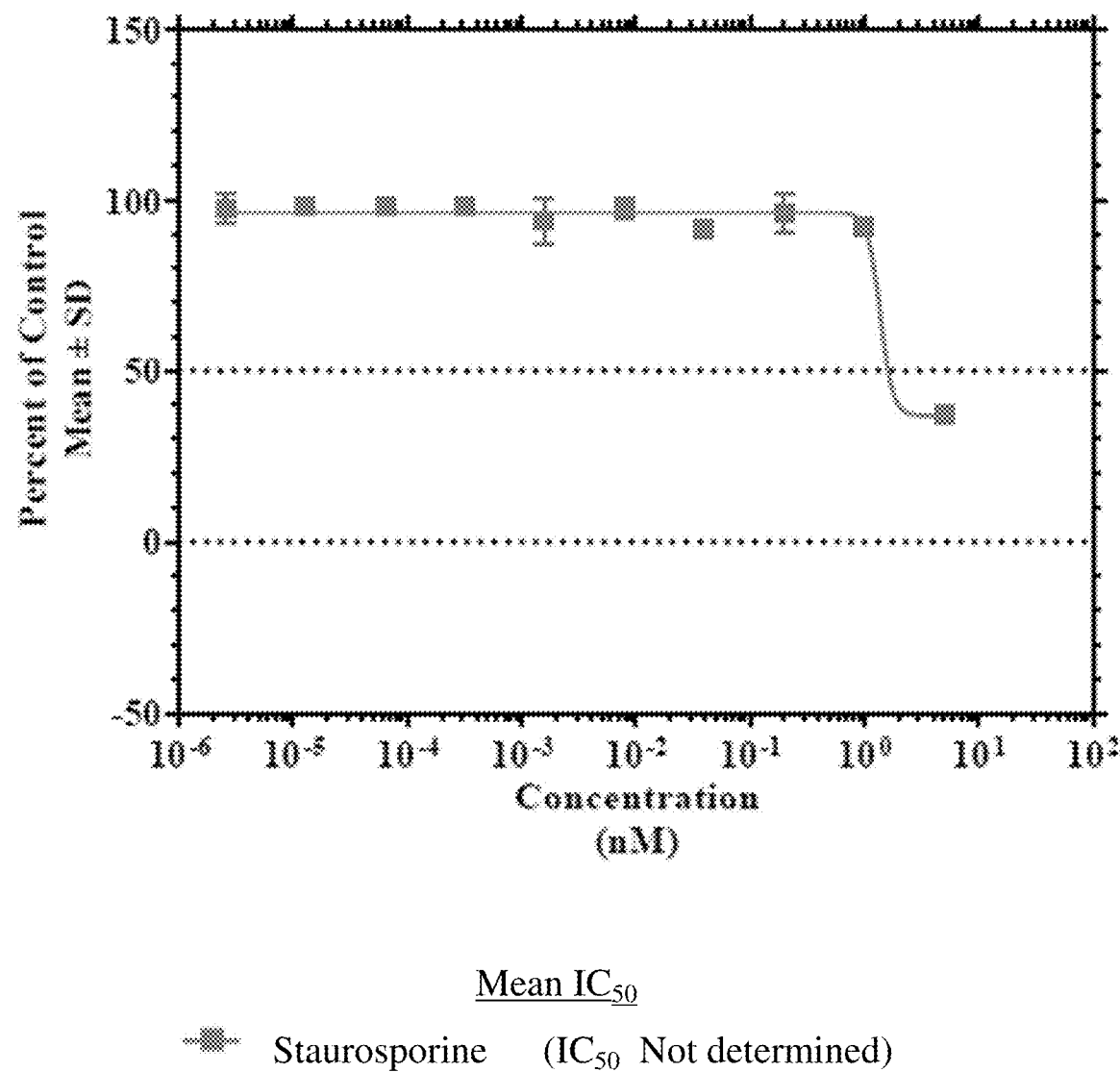
Figure 14:
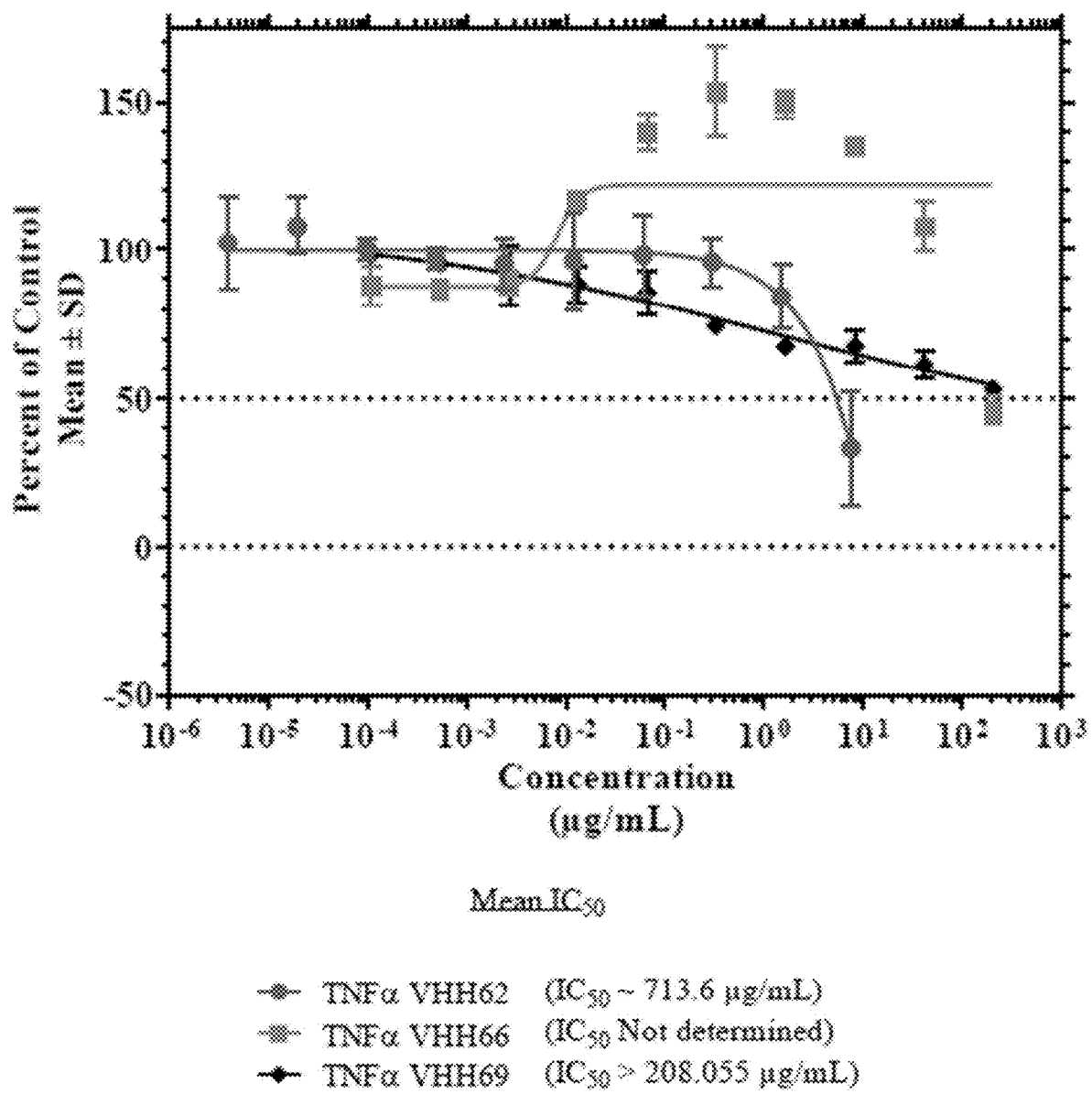
Figure 15:
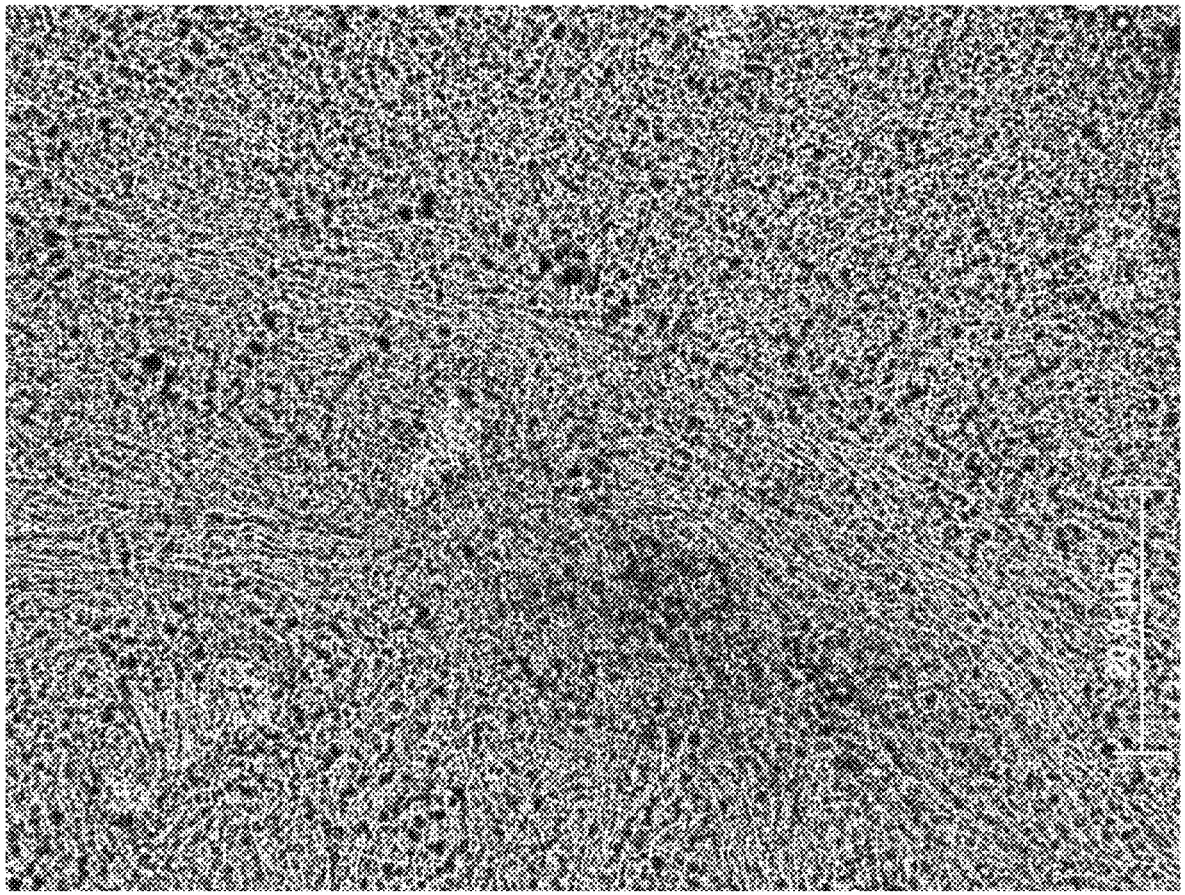
Figure 16:
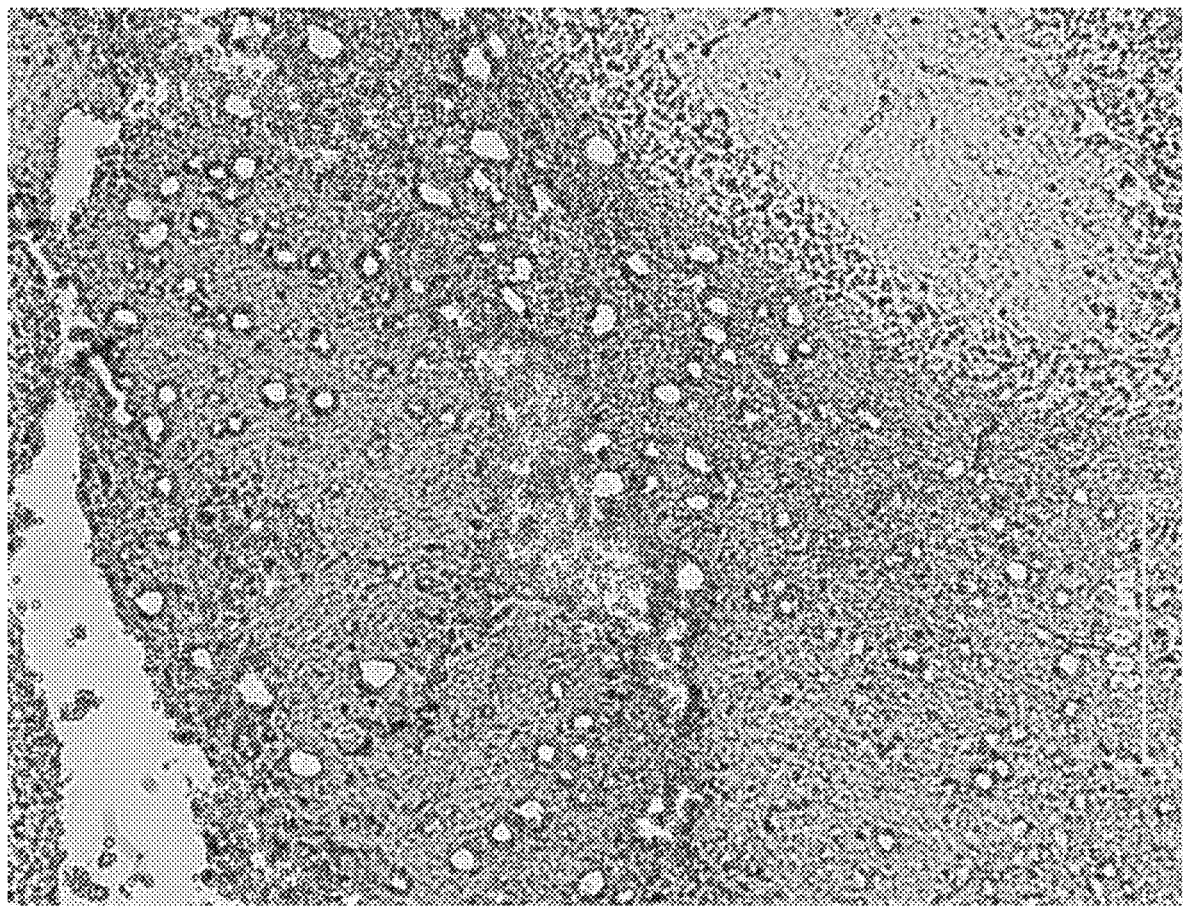
Figure 17:
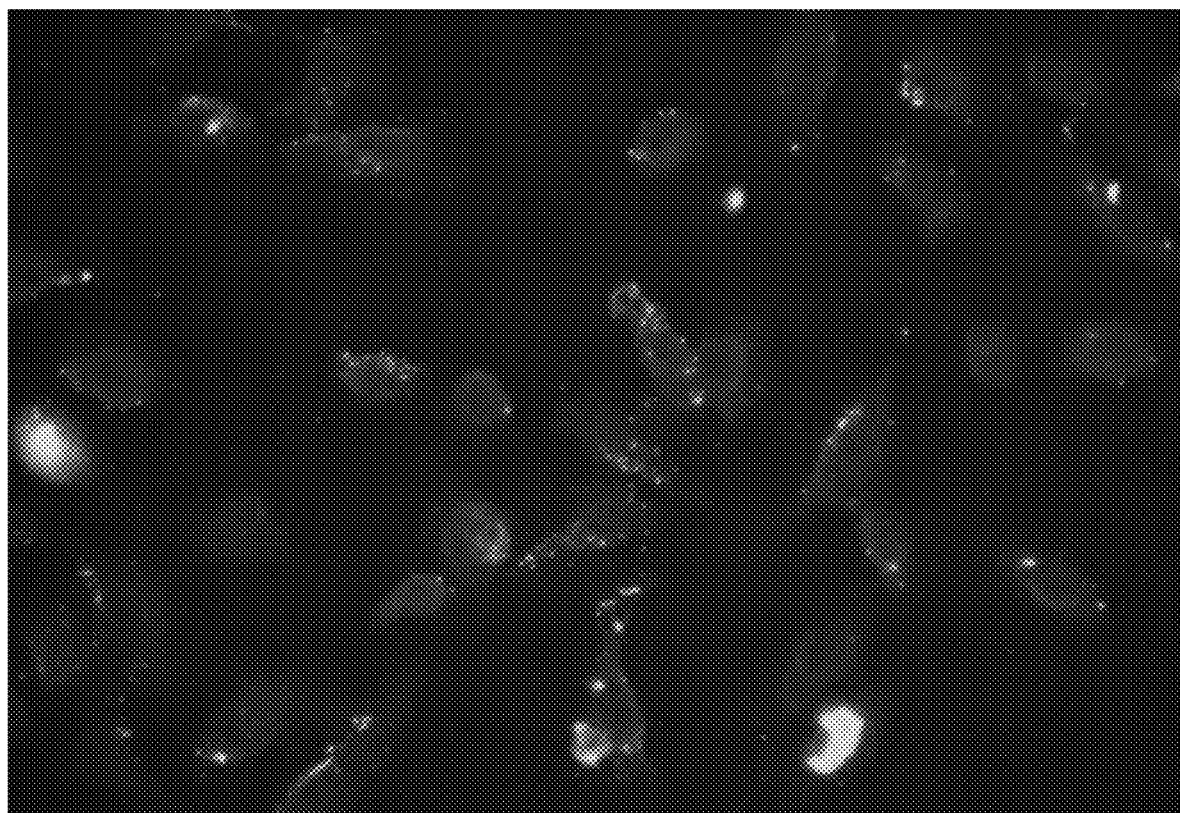
Figure 18:
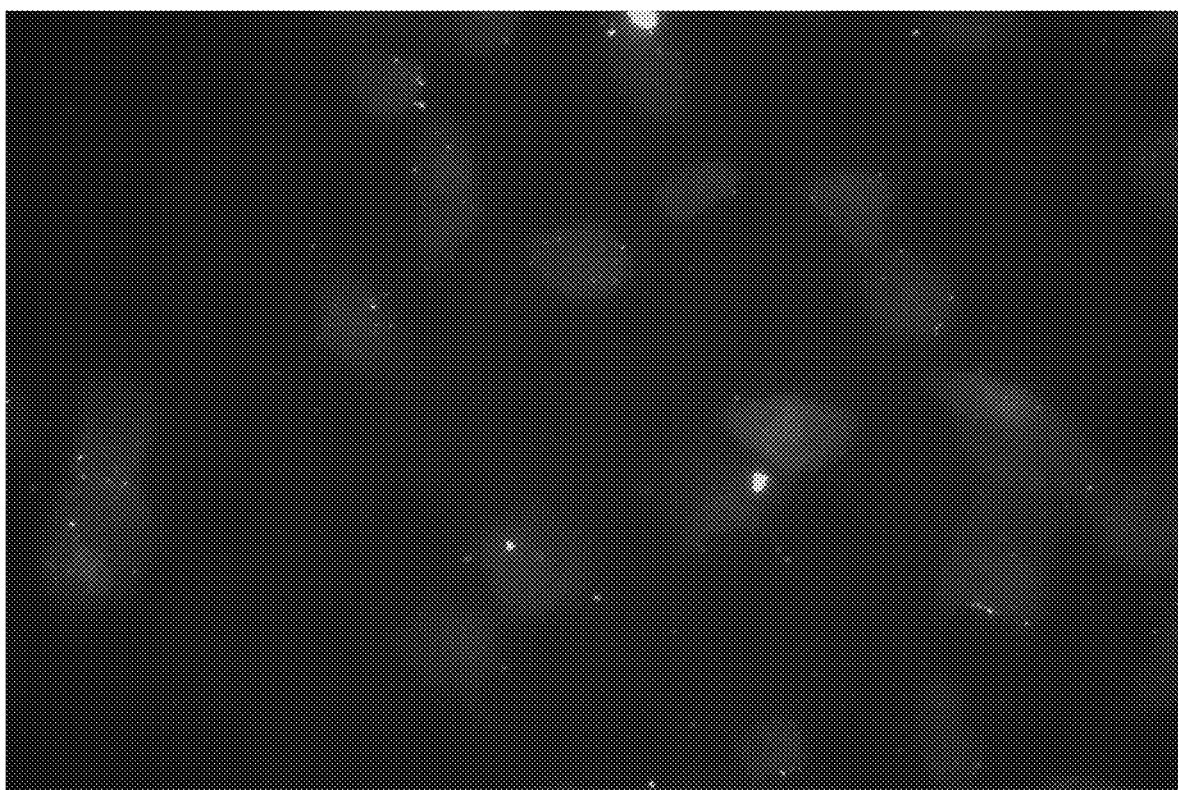
Figure 19:
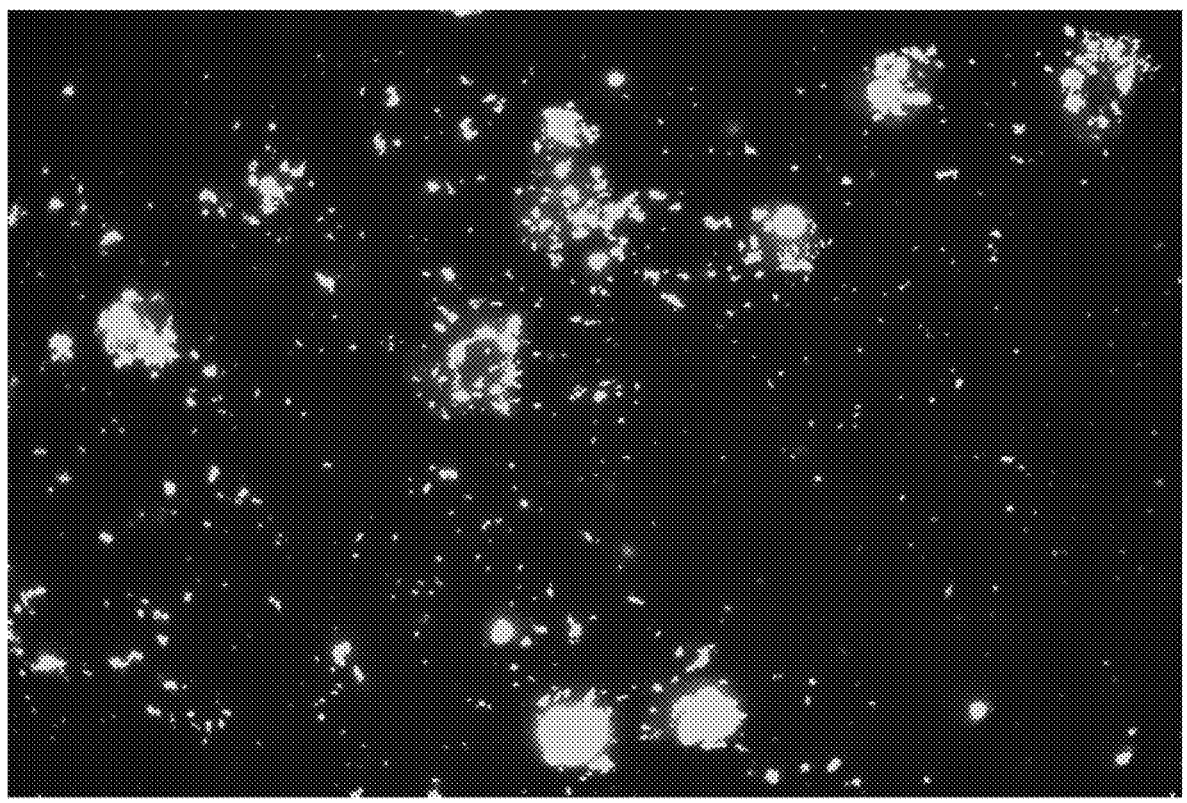
Figure 20:
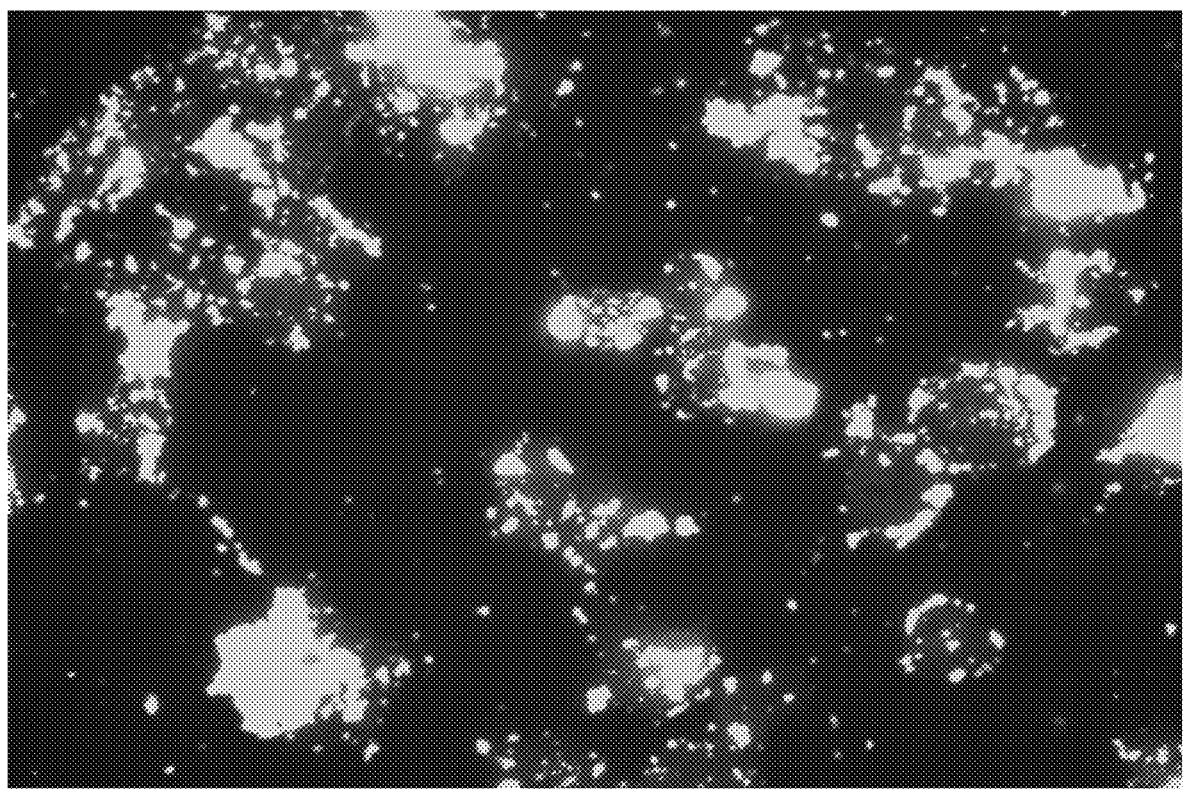
Figure 21:
Figure 22:
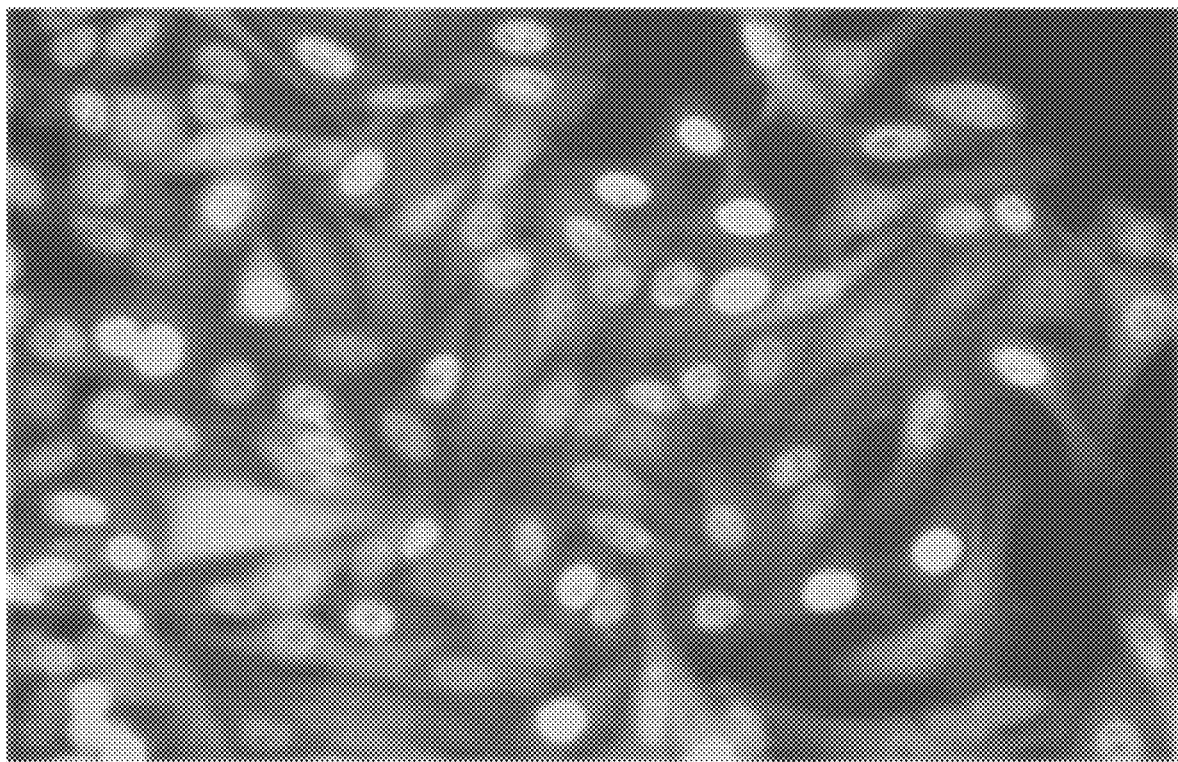
Figure 23:
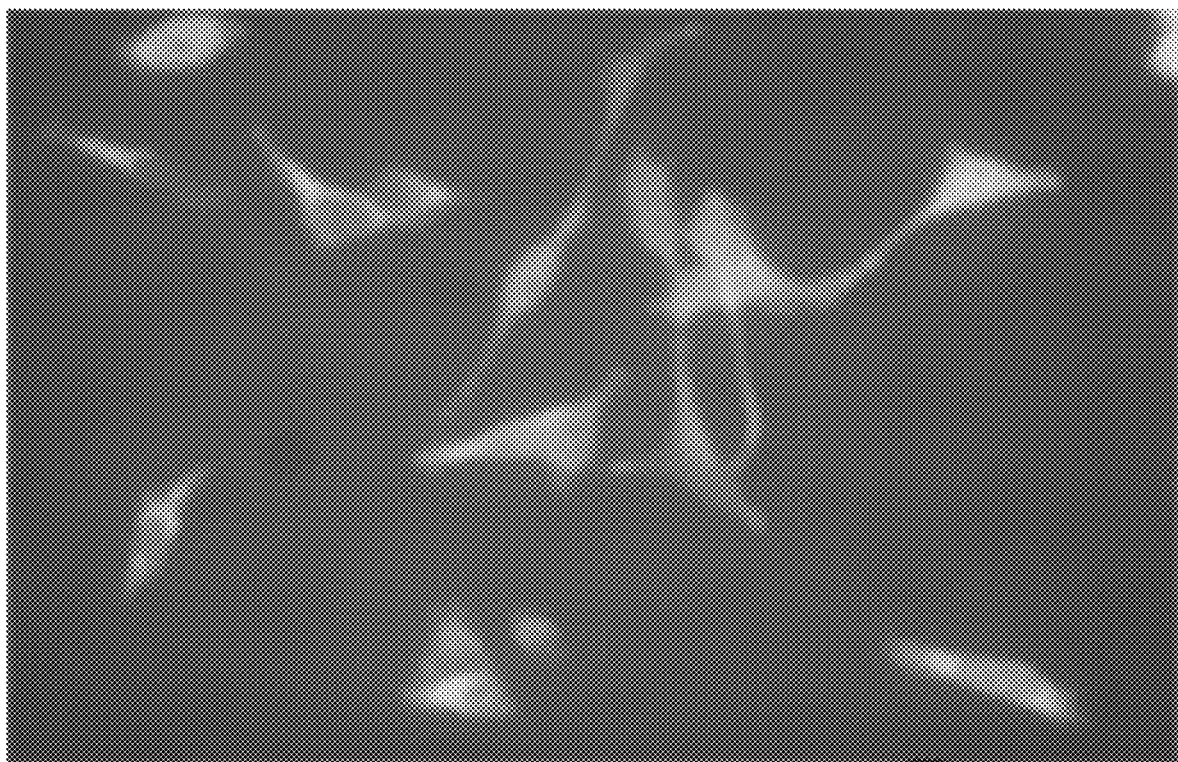
Figure 24:
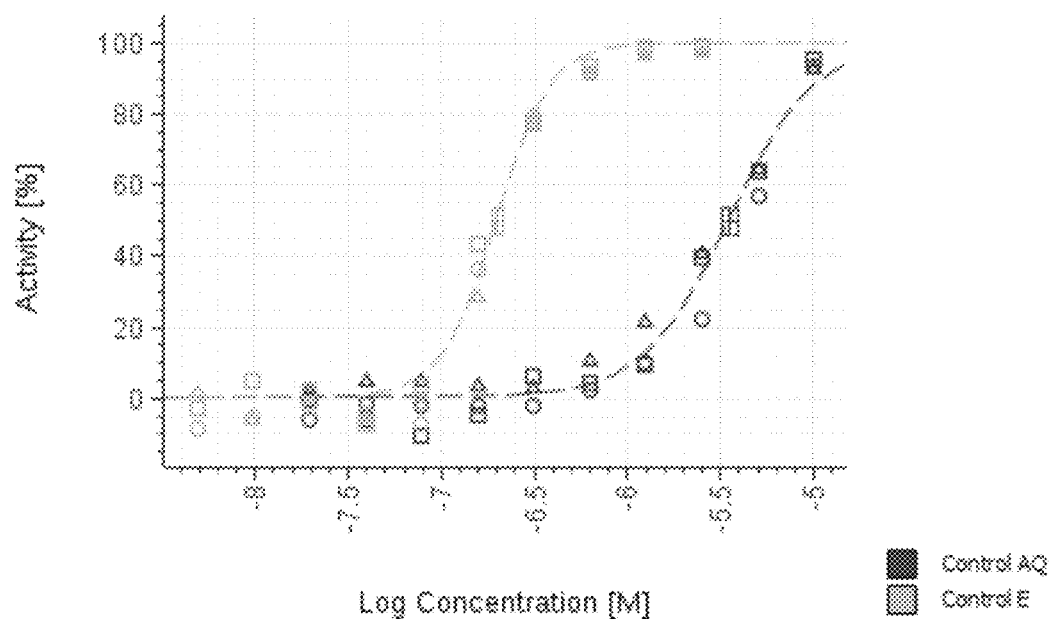
Figure 25:
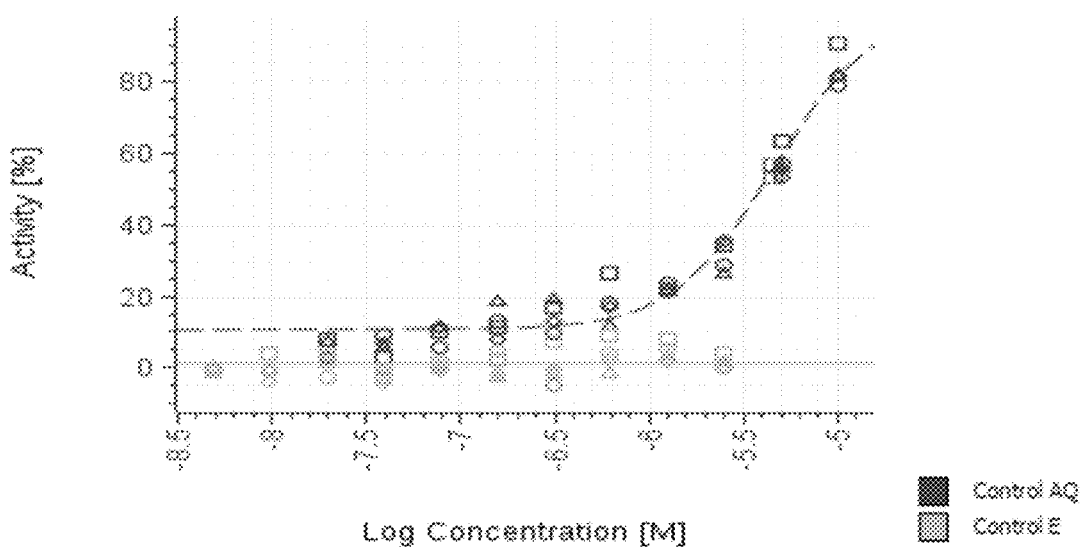
Figure 26:
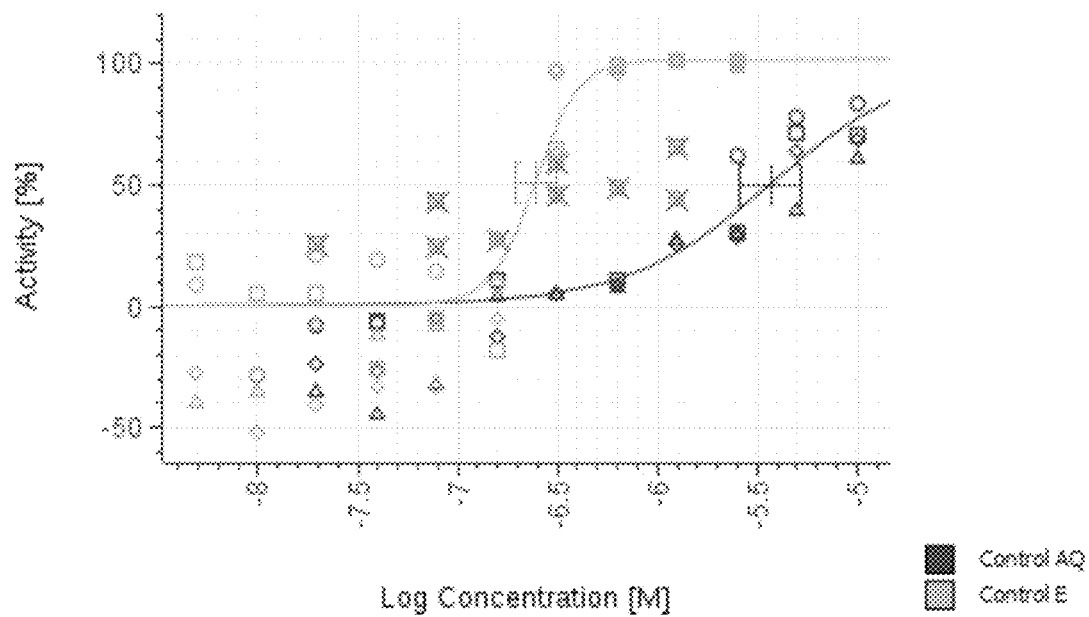
Figure 27:
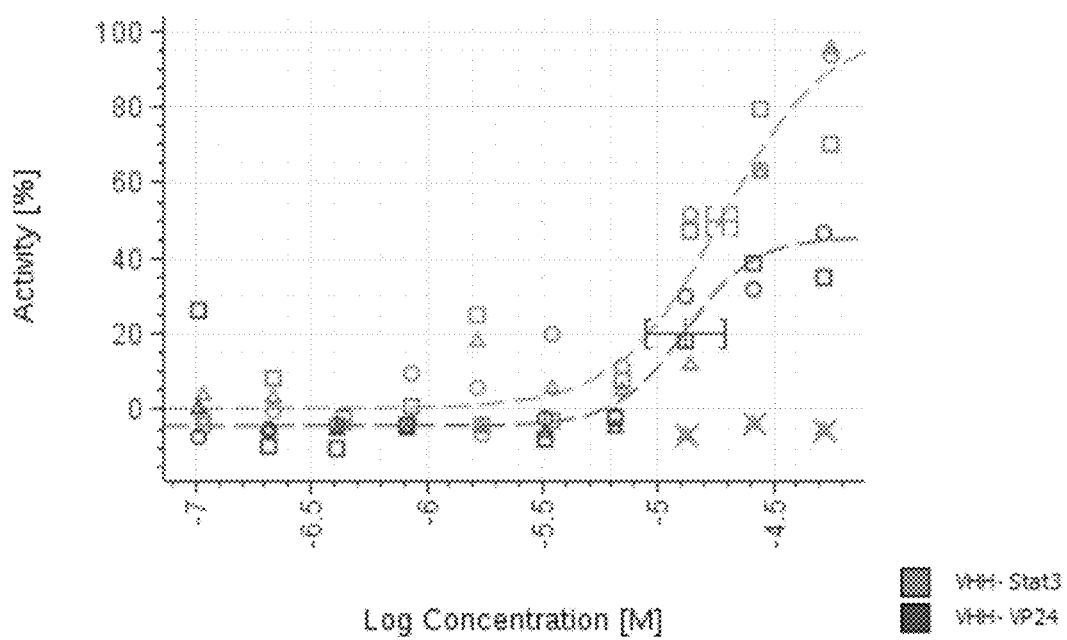
Figure 28:
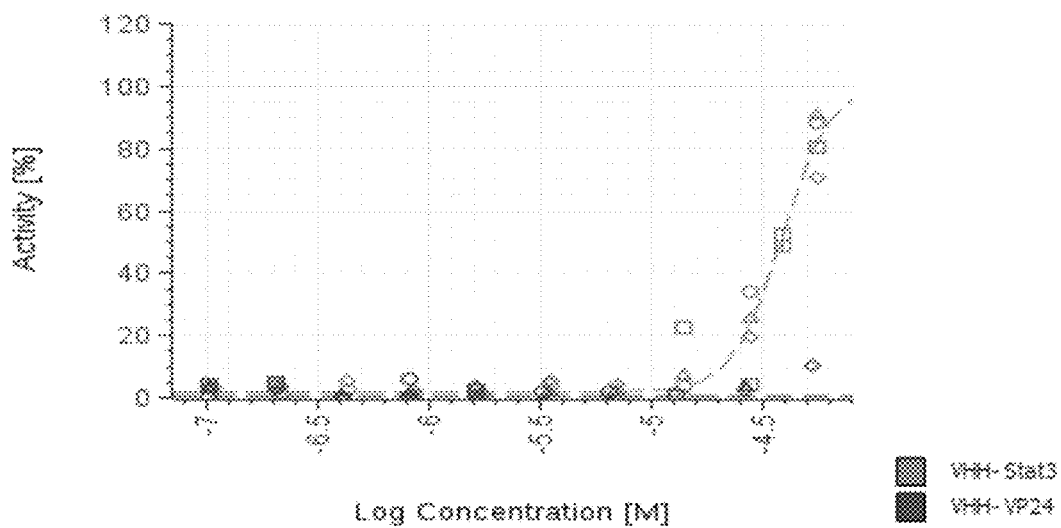

FIG. 6 illustrates the growth inhibition of anti-STAT3 bacterial VHH13 (SEQ. ID. NO. 3) sdAb in MDA-MB-231 xenograft model at doses ranging from 1 mg/kg twice daily to 2 mg/kg twice daily or 2 mg/kg/day;

FIG. 7 illustrates the growth inhibition of anti-STAT3 bacterial VHH13 (SEQ ID NO:3) sdAb in the MDA-MB-231 xenograft model, dosed at 5 mg/kg/twice daily;

FIG. 8 illustrates the growth inhibition of anti-STAT3 bacterial VHH13 (SEQ ID NO:3) sdAb in the DU145 xenograft model, dosed at 5 mg/kg/twice daily;

FIG. 9 illustrates the growth inhibition of anti-STAT3 bacterial VHH13 (SEQ ID NO:3) sdAb in the PANC-1 xenograft model, dosed at 5 mg/kg/twice daily;

FIG. 10 illustrates the growth inhibition of anti-STAT3 bacterial VHH13 (SEQ ID NO:3) sdAb in the MCF-7 xenograft model, dosed at 1 mg/kg/three times daily;

FIG. 11 illustrates the growth inhibition of anti-STAT3 bacterial VHH13 (SEQ ID NO:3) sdAb in the BT-474 xenograft model, dosed at 1 mg/kg/three times daily;

FIG. 12 illustrates the cytotoxicity of TNF-alpha in U937 cells;

FIG. 13 illustrates the cytotoxicity of Staurosporine in U937 cells;

FIG. 14 illustrates inhibition of TNF-alpha cytotoxicity by anti-TNF-α sdAbs;

FIG. 15 shows staining of anti-STAT3 VHH13 (SEQ ID NO:3) sdAb in neurons and glial cells;

FIG. 16 shows staining of anti-STAT3 VHH13 (SEQ ID NO:3) sdAb in cancer cells;

FIG. 17 shows MDA-MB 231 cells incubated with STAT3 VHH13 (SEQ ID NO:3) sdAb;

FIG. 18 shows PANC-1 cells incubated with STAT3 VHH13 (SEQ ID NO:3) sdAb;

FIG. 19 shows MDA-MB 231 cells incubated with TNF-α VHH66 (SEQ ID NO:45) sdAb;

FIG. 20 shows PANC-1 cells incubated with TNF-α VHH66 (SEQ ID NO:45) sdAb;

FIG. 21 shows cytoplasmic staining of Stat3 in HEp-2 cells incubated with STAT3 VHH13 (SEQ ID NO:3) sdAb;

FIG. 22 shows nuclear staining of Stat3 in HEp-2 cells incubated with recombinant IL-6;

FIG. 23 shows cytoplasmic staining of Stat3 in HEp-2 cells incubated with STAT3 VHH13 (SEQ ID NO:3) sdAb and recombinant IL-6;

FIG. 24 illustrates the dose response curves for controls E864 and AQ for EBOV/Hela;

FIG. 25 illustrates the dose response curves for controls E864 and AQ for EBOV/HFF;

FIG. 26 illustrates the dose response curves for controls E864 and AQ for Zika/Vero;

FIG. 27 illustrates the dose response curves with test drugs for EBOV/Hela;

FIG. 28 illustrates the dose response curves with test drugs for EBOV/HFF; and

Figure 29:
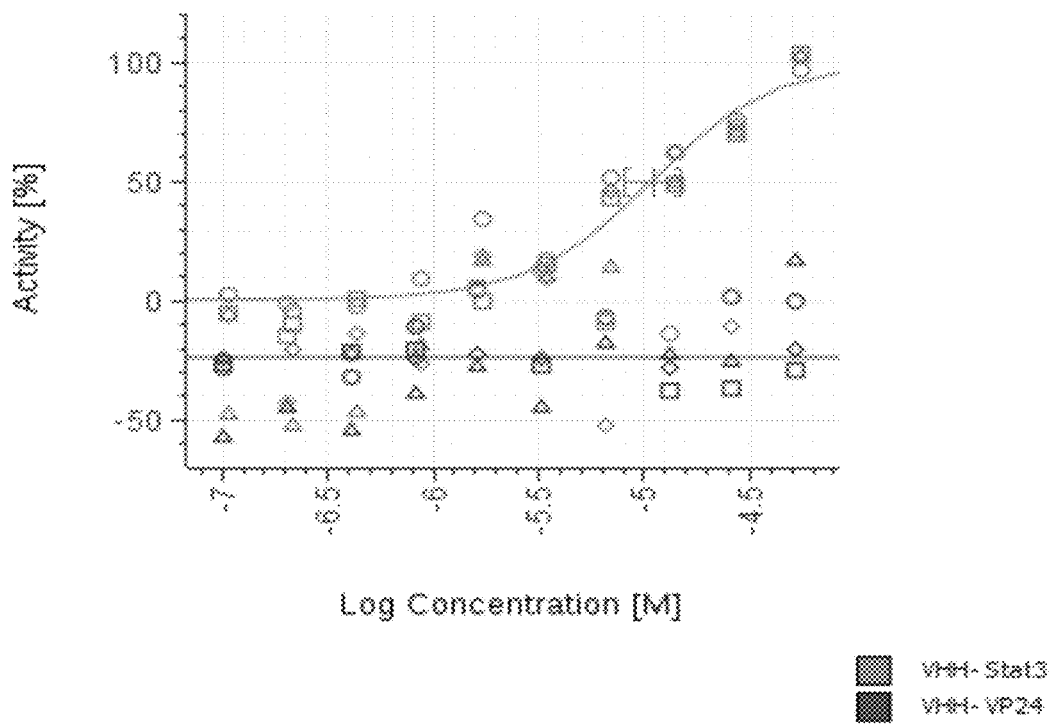

FIG. 29 illustrates the dose response curves with test drugs for Zika/Vero.

DESCRIPTION

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

The term "antigenic determinant" refers to the epitope on the antigen recognized by the antigen-binding molecule (such as an sdAb or polypeptide of the invention) and more in particular by the antigen-binding site of the antigen-binding molecule. The terms "antigenic determinant" and "epitope" may also be used interchangeably. An amino acid sequence that can bind to, that has affinity for and/or that has specificity for a specific antigenic determinant, epitope, antigen or protein is said to be "against" or "directed against" the antigenic determinant, epitope, antigen or protein.

As used herein, the term "comprise" and variations of the term, such as "comprising" and "comprises," are not intended to exclude other additives, components, integers or steps.

It is contemplated that the sdAbs, polypeptides and proteins described herein can contain so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Conservative amino acid substitutions are well known in the art. Conservative substitutions are substitutions in which one amino acid within the following groups (a)-(e) is substituted by another amino acid within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Other conservative substitutions include: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A "domain" as used herein generally refers to a globular region of an antibody chain, and in particular to a globular region of a heavy chain antibody, or to a polypeptide that essentially consists of such a globular region.

The amino acid sequence and structure of an sdAb is typically made up of four framework regions or "FRs," which are referred to as "Framework region 1" or "FR1"; as "Framework region 2" or "FR2"; as "Framework region 3" or "FR3"; and as "Framework region 4" or "FR4," respectively. The framework regions are interrupted by three complementarity determining regions or "CDRs," which are referred as "Complementarity Determining Region 1" or "CDR1"; as "Complementarity Determining Region 2" or "CDR2"; and as "Complementarity Determining Region 3" or "CDR3," respectively.

As used herein, the term "humanized sdAb" means an sdAb that has had one or more amino acid residues in the amino acid sequence of the naturally occurring VHH sequence replaced by one or more of the amino acid residues that occur at the corresponding position in a VH domain from a conventional 4-chain antibody from a human. This can be performed by methods that are well known in the art. For example, the FRs of the sdAbs can be replaced by human variable FRs.

As used herein, an "isolated" nucleic acid or amino acid has been separated from at least one other component with which it is usually associated, such as its source or medium, another nucleic acid, another protein/polypeptide, another biological component or macromolecule or contaminant, impurity or minor component.

The term "mammal" is defined as an individual belonging to the class Mammalia and includes, without limitation, humans, domestic and farm animals, and zoo, sports, and pet animals, such as cows, horses, sheep, dogs and cats.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, PBS (phosphate-buffered saline), and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined above, use thereof in the composition of the present invention is contemplated.

A "quantitative immunoassay" refers to any means of measuring an amount of antigen present in a sample by using an antibody. Methods for performing quantitative immunoassays include, but are not limited to, enzyme-linked immunosorbent assay (ELISA), specific analyte labeling and recapture assay (SALRA), liquid chromatography, mass spectrometry, fluorescence-activated cell sorting, and the like.

The term "solution" refers to a composition comprising a solvent and a solute, and includes true solutions and suspensions. Examples of solutions include a solid, liquid or gas dissolved in a liquid and particulates or micelles suspended in a liquid.

The term "specificity" refers to the number of different types of antigens or antigenic determinants to which a particular antigen-binding molecule or antigen-binding protein molecule can bind. The specificity of an antigen-binding protein can be determined based on affinity and/or avidity. The affinity, represented by the equilibrium constant for the dissociation of an antigen with an antigen-binding protein (KD), is a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the affinity constant (KA), which is 1/KD). As will be clear to one of skill in the art, affinity can be determined depending on the specific antigen of interest. Avidity is the measure of the strength of binding between an antigen-binding molecule and the antigen. Avidity is related to both the affinity between an antigenic determinant and its antigen binding site on the antigen-binding molecule and the number of pertinent binding sites present on the antigen-binding molecule. Specific binding of an antigen-binding protein to an antigen or antigenic determinant can be determined by any known manner, such as, for example, Scatchard analysis and/or competitive binding assays, such as radioimmunoassays (RIA), enzyme immunoassays (EIA) and sandwich competition assays.

As used herein, the term "recombinant" refers to the use of genetic engineering methods (for example, cloning, and amplification) used to produce the sdAbs of the invention.

A "single domain antibody," "sdAb" or "VHH" can be generally defined as a polypeptide or protein comprising an amino acid sequence that is comprised of four framework regions interrupted by three complementarity determining regions. This is represented as FR1-CDR1-FR2-CDR2-FR3-CDR3-FR4. An sdAb of the invention also includes a polypeptide or protein that comprises the sdAb amino acid sequence. Typically, sdAbs are produced in camelids such as llamas, but can also be synthetically generated using techniques that are well known in the art. As used herein, the variable domains present in naturally occurring heavy chain antibodies will also be referred to as "VHH domains," in order to distinguish them from the heavy chain variable domains that are present in conventional 4-chain antibodies, referred to as "VH domains," and from the light chain variable domains that are present in conventional 4-chain antibodies, referred to as "VL domains." "VHH" and "sdAb" are used interchangeably herein. The numbering of the amino acid residues of a sdAb or polypeptide is according to the general numbering for VH domains given by Kabat et al. ("Sequence of proteins of immunological interest," US Public Health Services, NIH Bethesda, Md., Publication No. 91). According to this numbering, FR1 of a sdAb comprises the amino acid residues at positions 1-30, CDR1 of a sdAb comprises the amino acid residues at positions 31-36, FR2 of a sdAb comprises the amino acids at positions 36-49, CDR2 of a sdAb comprises the amino acid residues at positions 50-65, FR3 of a sdAb comprises the amino acid residues at positions 66-94, CDR3 of a sdAb comprises the amino acid residues at positions 95-102, and FR4 of a sdAb comprises the amino acid residues at positions 103-113.

The term "synthetic" refers to production by in vitro chemical or enzymatic synthesis.

The term "target" as used herein refers to any component, antigen, or moiety that is recognized by the sdAb. The term "intracellular target" refers to any component, antigen, or moiety present inside a cell. A "transmembrane target" is a component, antigen, or moiety that is located within the cell membrane. An "extracellular target" refers to a component, antigen, or moiety that is located outside of the cell.

A "therapeutic composition" as used herein means a substance that is intended to have a therapeutic effect such as pharmaceutical compositions, genetic materials, biologics, and other substances. Genetic materials include substances intended to have a direct or indirect genetic therapeutic effect such as genetic vectors, genetic regulator elements, genetic structural elements, DNA, RNA and the like. Biologics include substances that are living matter or derived from living matter intended to have a therapeutic effect.

As used herein, the phrases "therapeutically effective amount" and "prophylactically effective amount" refer to an amount that provides a therapeutic benefit in the treatment, prevention, or management of a disease or an overt symptom of the disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The specific amount that is therapeutically effective can be readily determined by an ordinary medical practitioner, and may vary depending on factors known in the art, such as, e.g., the type of disease, the patient's history and age, the stage of disease, and the administration of other therapeutic agents.

The present invention relates to single-domain antibodies (sdAbs) that are directed against intracellular components, as well as to proteins and polypeptides comprising the sdAbs and nucleotides encoding the proteins and polypeptides. The invention can also relate to sdAbs that are directed against intercellular, transcellular and extracellular targets or antigens. The invention also includes nucleic acids encoding the sdAbs, proteins and polypeptides, and compositions comprising the sdAbs. The invention includes the use of the compositions, sdAbs, proteins or polypeptides for prophylactic, therapeutic or diagnostic purposes.

SdAbs have a number of unique structural characteristics and functional properties which make sdAbs highly advantageous for use as functional antigen-binding domains or proteins. SdAbs functionally bind to an antigen in the absence of a light chain variable domain, and can function as a single, relatively small, functional antigen-binding structural unit, domain or protein. This distinguishes sdAbs from the domains of conventional antibodies, which by themselves do not function as an antigen-binding protein or domain, but need to be combined with conventional antibody fragments such as Fab fragments or ScFv's fragment in order to bind an antigen.

SdAbs can be obtained using methods that are well known in the art. For example, one method for obtaining sdAbs includes (a) immunizing a Camelid with one or more antigens, (b) isolating peripheral lymphocytes from the immunized Camelid, obtaining the total RNA and synthesizing the corresponding cDNAs, (c) constructing a library of cDNA fragments encoding VHH domains, (d) transcribing the VHH domain-encoding cDNAs obtained in step (c) to mRNA using PCR, converting the mRNA to ribosome display format, and selecting the VHH domain by ribosome display, and (e) expressing the VHH domain in a suitable vector and, optionally purifying the expressed VHH domain.

Another method of obtaining the sdAbs of the invention is by preparing a nucleic acid encoding an sdAb using techniques for nucleic acid synthesis, followed by expression of the nucleic acid in vivo or in vitro. Additionally, the sdAb, polypeptides and proteins of the invention can be prepared using synthetic or semi-synthetic techniques for preparing proteins, polypeptides or other amino acid sequences.

The sdAbs of the invention will generally bind to all naturally occurring or synthetic analogs, variants, mutants, alleles, parts and fragments of the target, or at least to those analogs, variants, mutants, alleles, parts and fragments of the target that contain one or more antigenic determinants or epitopes that are essentially the same as the antigenic determinant or epitope to which the sdAbs of the invention bind in the wild-type target. The sdAbs of the invention may bind to such analogs, variants, mutants, alleles, parts and fragments with an affinity and/or specificity that is the same as, or that is higher than or lower than the affinity and specificity with which the sdAbs of the invention bind to the wild-type target. It is also contemplated within the scope of the invention that the sdAbs of the invention bind to some analogs, variants, mutants, alleles, parts and fragments of the target but not to others. In addition, the sdAb of the invention may be humanized, and may be monovalent or multivalent, and/or multispecific. Additionally, the sdAbs of the invention can bind to the phosphorylated form of the target protein as well as the unphosphorylated form of the target protein. SdAbs can be linked to other molecules such as albumin or other macromolecules.

In addition, it is within the scope of the invention that the sdAbs are multivalent, that is, the sdAb can have two or more proteins or polypeptides which are directed against two or more different epitopes of the target. In such a multivalent sdAb, the protein or polypeptide may be directed, for example, against the same epitopes, substantially equivalent epitopes, or different epitopes. The different epitopes may be located on the same target, or it could be on two or more different targets.

It is also contemplated that the sequence of one or more sdAbs of the invention may be connected or joined with one or more linker sequences. The linker can be, for example, a protein sequence containing a combination of serines, glycines and alanines.

It is also within the scope of the invention to use parts, fragments, analogs, mutants, variants, alleles and/or derivatives of the sdAbs of the invention, as long as these are suitable for the described uses.

Since the sdAbs of the invention are mainly intended for therapeutic and/or diagnostic use, they are directed against mammalian, preferably human, targets. However, it is possible that the sdAbs described herein are cross-reactive with targets from other species, for example with targets from one or more other species of primates or other animals (for example, mouse, rat, rabbit, pig or dog), and in particular in animal models for diseases and disorders associated with the disease associated with the targets.

In another aspect, the invention relates to a nucleic acid that encodes an sdAb of the invention. Such a nucleic acid may be, for example, in the form of a genetic construct.

In another aspect, the invention relates to host or host cell that expresses or is capable of expressing an sdAb of the invention, and/or that contains a nucleic acid encoding a sdAb of the invention. Sequences of the sdAbs can be used to insert into the genome of any organism to create a genetically modified organism (GMO). Examples include, but are not limited to, plants, bacteria, viruses, and animals.

The invention further relates to methods for preparing or generating the sdAbs, nucleic acids encoding the sdAbs, host cells expressing or capable of expressing such sdAbs, products and compositions containing the sdAbs of the invention.

The invention further relates to applications and uses of the sdAb, the nucleic acids encoding the sdAbs, host cells, products and compositions described herein. Such a product or composition may, for example, be a pharmaceutical composition for treatment or prevention of a disease, or a product or composition for diagnostic use. The sdAb of the invention can also be used to deliver a therapeutic agent or can be covalently linked to a molecule in order to deliver the therapeutic agent into a cell or across the blood-brain barrier of a person in need thereof. The sdAb can be used to target primary malignancies of the central nervous system, metastatic cancer, and central nervous system diseases such as multiple sclerosis, dementia, and the like. Furthermore, sdAbs can be used in a variety of assays, for example ELISA assays and mass spectrometry assays to measure the serum and tissue levels of the sdAbs.

In another aspect, a nucleic acid encoding one or more sdAb of the invention can be inserted into the genome of an organism to treat or prevent diseases.

The present invention generally relates to sdAbs, as well as to proteins or polypeptides comprising or essentially consisting of one or more of such sdAbs, that can be used for prophylactic, therapeutic and/or diagnostic purposes.

The methods and compositions detailed in the present invention can be used to treat disease described herein, and can be used with any dosage and/or formulation described herein or otherwise known, as well as with any route of administration described herein or otherwise known to one of skill in the art.

The sdAbs of the invention, in particular the anti-STAT3 VHH, the anti-KRAS VHH, and the anti-TNF-α VHH of the present invention, can be used for treatment and prevention of malignant diseases including, but not limited to: multiple myeloma, leukemias (HTLV-1 dependent, erythroleukemia, acute myelogenous leukemia (AML), chronic myelogenous leukemia (CML), and large granular lymphocyte leukemia (LGL), lymphomas (EBV-related/Burkitt's, mycosis fungoides, cutaneous T-cell lymphoma, non-Hodgkins lymphoma (NHL), anaplastic large-cell lymphoma (ALCL), breast cancers, triple-negative breast cancers, head and neck cancers, melanoma, ovarian cancers, lung cancers, pancreatic cancers, prostate cancers, sarcomas, osteosarcoma, Kaposi's sarcoma, Ewing's sarcoma, hepatocellular cancers, glioma, neuroblastoma, astrocytoma, colorectal cancers, Wilm's tumors, renal cancers, bladder cancers, endometrial cancers, cervical cancers, esophageal cancers, cutaneous squamous cell cancers, basal cell cancers, and any metastatic cancers. The sdAbs can be used in cancer patients to help prevent or reduce weight loss or cachexia due to cancer.

The sdAb, in particular the anti-STAT3 and the anti-TNF-α sdAbs of the present invention, can also be used for treatment and prevention of diseases such as, but not limited to: autoimmune diseases (e.g., rheumatoid arthritis, ulcerative colitis, Crohn's disease, bacterial induced colitis, asthma, scleroderma, lupus, encephalomyelitis, arteritis, vasculitis, glomerulonephritis, uveitis, uveoretinitis, multiple sclerosis), polycystic kidney disease, dermatologic diseases (e.g., psoriasis, alopecia areata, atopic dermatitis, keloids/hypertrophic scars, lipoma, Paget's disease, and actinic keratosis), Hidradenitis suppurativa, transplantation (e.g., solid organ, bone marrow, hand, face, limbs, any body part), muscular dystrophy and muscle wasting associated with cancers and aging, endometriosis, macular degeneration, retinal degeneration, stroke, epilepsy, traumatic brain and spinal cord injuries, hypertension, cardiac hypertrophy, Alzheimer's disease, pulmonary artery hypertension, type 2 diabetes mellitus, and ankylosing spondylitis.

Additionally, sdAbs can target orphan diseases. Examples of these rare orphan diseases include, but are not limited to, triple negative breast cancers, pancreatic cancers, AML (acute myeloid leukemia), head and neck cancers, multiple myeloma, and chemo-resistant cancers.

Viruses are small particles of genetic material (either DNA or RNA) that are surrounded by a protein coat. Some viruses also have a fatty "envelope" covering. They are incapable of reproducing on their own. Viruses depend on the organisms they infect (hosts) for their very survival. A viral infection is a proliferation of a harmful virus inside the body. Viruses infect a host by introducing their genetic material into the cells and hijacking the cell's internal machinery to make more virus particles. With an active viral infection, a virus makes copies of itself and bursts the host cell (killing it) to set the newly-formed virus particles free. In other cases, virus particles "bud" off the host cell over a period of time before killing the host cell. Either way, new virus particles are then free to infect other cells. Symptoms of the viral illness occur as a result of cell damage, tissue destruction, and the associated immune response.

Viral infections can be treated by targeting intracellular viral proteins in infected cells. Viral proteins, such as HIV reverse transcriptase, can block viral life-cycle. The sdAb of the invention can also target intracellular viral proteins such as Ebola VP24 and thus block Ebola's ability to shut down the host's anti-viral immune response. The sdAbs of the invention can be used to target diseases when there is an overexpression of an intracellular molecule. Huntington's disease can be treated with sdAbs. The sdAb can be used to treat additional viral infections caused by RNA viruses, DNA viruses, or retroviruses such as, for example, hepatitis A, hepatitis B, hepatitis C, cancer-causing strains of human papillomavirus (HPV), polio, rabies, Varicella-Zoster, Epstein-Barr, Human Immunodeficiency Virus, West Nile, Ebola virus, and Zika. In the event ebola or zika is targeted, the sbAb inhibits the replication of ebola viruses in infected cells.

The sdAbs of the invention can be used with one or more compounds. For example, the sdAb of the invention can be used with JAK/STAT inhibitors such as, for example, Curcumin, Resveratrol, Cucurbitacin A, B, E, I, Q, Flavopiridol, Deoxytetrangomycin, Cyclopentenone derivatives, N-Acyl-homoserine Lactone, Indirubin derivatives, Meisoindigo, Tyrphostins, Platinum-containing compounds (e.g., IS3-295), Peptidomimetics, antisense oligonucleotides, S3I-201, phosphotyrosin tripeptide derivatives, HIV protease inhibitors (e.g., nelfinavir, indinavir, saquinavir, & ritornavir), JSI-124, XpYL, Ac-pYLPQTV-NH2, ISS 610, CJ-1383, pyrimethamine, Metformin, Atiprimod, S3I-M2001, STX-0119; N-[2-(1,3,4-oxadiazolyl)]-4 quinolinecarboxamide derivative, S3I-1757, LYS; 5,8-dioxo-6(pyridin-3-ylamino)-5,8,-dihydro-naphthalene-1-sulfonamide, withacinstin, Stattic, STA-21, LLL-3, LLL12, XZH-5, SF-1066, SF-1087, 17o, Cryptotanshinone, FLL32, FLL62, C188-9, BP-1108 and BP-1075, Galiellalactone, JQ1, 5, 15 DPP, WP1066, Niclosamide, SD1008, Nifuroxazide, Cryptotanshinone, BBI quinone, and Ruxolitnib Phosphate. The one or more compounds can increase the therapeutic response and augment the effectiveness of the sdAb of the invention. In addition, the effectiveness of the sdAb can be increased by combining it with peptides, peptidomimetics, and other drugs, such as, for example, but not limited to, cimetidine, atorvastatin, celecoxib, metformin, and cimetidine. In addition, anti-STAT3 sdAbs can convert radioresistant cancers to radiosensitive cancers with respect to radiation therapy.

It is also contemplated that one or more sdAbs of the invention can be combined, or the sdAbs of the invention can be combined with other sdAbs.

It is contemplated that certain sdAbs of the invention can cross the cell membrane and enter the cell without the aid of additional targeting protein sequences on the sdAb, and without the aid of exogenous compounds that direct the sdAb to bind to the cell surface receptors and cross the cell membrane. Additionally, sdAbs of the invention can cross the blood-brain barrier.

After crossing the cell membrane, these sdAbs can target transmembrane or intracellular molecules or antigens. These intracellular or transmembrane targets can be, for example, proteins, carbohydrates, lipids, nucleic acids, mutated proteins, viral proteins, and prions. The sdAb targets may function as enzymes, structural proteins of the cell, intracellular portions of cell membrane molecules, molecules within the membranes of organelles, any type of RNA molecule, any regions of DNA or chromosome, methylated or unmethylated nucleic acids, partially assembled molecules within the synthesis mechanism of the cell, second messenger molecules, and molecules within cell signaling mechanisms. Targets may include all molecules in the cytoplasm, nucleus, organelles, and cell membrane. Molecules destined for secretion or placement in the cell membrane can be targeted within the cytoplasm before leaving the cell.

The sdAbs of the invention can cross the blood-brain barrier and target brain cells in vivo without exogenous compounds. The sdAbs of the invention can also be used as carriers to transport therapeutics or other molecules across the blood-brain barrier.

The sdAb targets can be in humans, animals, plants, fungi, parasites, protists, bacteria, viruses, prions, prokaryotic cells, and eukaryotic cells. Some examples of inter- and intracellular signaling molecules and protein groups that can be targeted by the sdAbs of the invention are: oncogene products, hormones, cytokines, growth factors, neurotransmitters, kinases (including tyrosine kinase, serine kinase, and threonine kinase), phosphatases, ubiquitin, cyclic nucleotides, cyclases (adenylyl and guanylyl), G proteins, phosphodiesterases, GTPase superfamily, immunoglobulins (antibodies, Fab fragments, binders, sdAbs), immunoglobulin superfamily, inositol phosphate lipids, steroid receptors, calmodulin, CD group (e.g., CD4, CD8, CD28, etc.), transcription factors, TGF-beta, TNF-α and beta, TNF ligand superfamily, notch receptor signaling molecules, hedgehog receptor signaling molecules, Wnt receptor signaling molecules, toll-like receptor signaling molecules, caspases, actin, myosin, myostatin, 12-lipoxygenase, 15-lipoxygenase, lipoxygenase superfamily, reverse transcriptase, viruses and their proteins, amyloid proteins, collagen, G protein coupled receptors, mutated normal proteins, prions, Ras, Raf, Myc, Src, BCR/ABL, MEK, Erk, Mos, Tpl2, MLK3, TAK, DLK, MKK, p38, MAPK, MEKK, ASK, SAPK, JNK, BMK, MAP, JAK, PI3K, cyclooxygenase, STAT1, STAT2, STAT3, STAT4, STAT5a, STAT5b, STAT6, Myc, p53, BRAF, NRAS, KRAS, HRAS and chemokines. IL-6 production can also be regulated by the sdAbs of the invention. Increased IL-6 production can result in cell growth and wound healing, while decreased IL-6 production can result in decreased cell proliferation.

KRAS is a Kirsten ras oncogene homolog from the mammalian ras gene family. KRAS encodes a protein that is a member of the small GTPase superfamily. The protein is implicated in various malignancies, including lung adenocarcinoma, mucinous adenoma, ductal carcinoma of the pancreas, and colorectal carcinoma. Under normal conditions, Ras family members influence cell growth and differentiation events in a subcellular membrane compartmentalization-based signaling system. However, oncogenic Ras can deregulate processes that control both cell proliferation and apoptosis.

Anti-KRAS sdAbs were developed to target wild-type and mutated KRAS (G12D) in order to disrupt its role in malignant cells such as, for example, cells involved in colorectal cancer, pancreatic cancer, biliary tract cancer, lung cancer, leukemias, and other metastatic malignancies. Without being bound by a particular mechanism, it is thought that the anti-KRAS sdAb binds KRAS and blocks the downstream signaling of KRAS in malignant cells. Additionally, the anti-KRAS sdAb may successfully treat malignancies that are resistant to anti-EGFR biologics (e.g., cetuximab and panitumumab).

Using methods that are well-known in the art, recombinant human mutant KRAS (G12D) protein was used to generate sdAbs that are directed against or can bind to an epitope of KRAS or mutant KRAS (G12D), or other KRAS mutants. Additionally, sdAbs can be generated to other KRAS mutants. To generate the anti-KRAS sdAbs, recombinant full-length human KRAS (Gene ID: 3845) was expressed in *Escherichia coli.*

Several sdAbs were obtained and screened. The DNA sequence of one anti-KRAS (G12D) sdAb, named KRAS_13 (SEQ ID NO:1), is shown below:

5'Gaggtgcagctggtggagtctgggggaggctcggtgcagactggaggg tctctgagactctcctgtgcagtttctggaaatatcggcagcagctactg catgggctggttccgccaggctccagggaagaagcgcgaggcggtcgcac gtattgtacgtgatggtgccactggctacgcagactacgtgaagggccga ttcaccatctcccgagacagcgccaagaacactctgtatctgcaaatgaa caggctgatacctgaggacactgccatctactactgtgcggcagacctgc ccccaggttgtttgactcaggcgatttggaattttggttatcggggccag ggaaccctggtcaccgtctcctca-3'

The amino acid sequence of the anti-KRAS (G12D) sdAb (SEQ ID NO:2), KRAS_13, is shown below, with the CDRs underlined:

EVQLVESGGGSVQTGGSLRLSCAVSGNIGS<u>SYCMGW</u>FRQAPGKKREAVA<u>R
IVRDGATGYADYVKGRFTI</u>SRDSAKNTLYLQMNRLIPEDTAIYYCAA<u>DLP
PGCLTQAIWNFGY</u>RGQGTLVTVSS

Additionally, the present invention comprises one or more mouse monoclonal antibodies which are directed against one or more domains of the anti-KRAS sdAb of the invention. The mouse monoclonal antibody can be generated by methods that are known by one of skill in the art, for example, the mouse monoclonal antibody can be produced by a mouse hybridoma. The mouse monoclonal antibody can be used in diagnostic assays, for example, the antibody can be used in an immunoassay such as an ELISA or mass spectrometry assay in order to measure the amount of anti-KRAS sdAb present in a patient's serum. The cytotoxicity of KRAS (G12D) sdAbs on PANC-1 human pancreatic cancer cells was tested, as described below.

STAT3 is a member of the signal transducers and activators of transcription (STAT) family of proteins that carry both signal transduction and activation of transcription functions. STAT3 is widely expressed and becomes activated through phosphorylation on tyrosine and/or serine as a DNA binding protein in response to a various cytokines and growth factors such as EGF, IL-6, PDGF, IL-2 and G-CSF. The STAT3 phosphoprotein forms homodimers and heterodimers with other members of the STAT family and translocates to the nucleus in order to modulate the transcription of various genes, and as a result plays a key role in many cellular processes such as cell growth, apoptosis, angiogenesis, immune evasion, and survival.

An anti-STAT3 sdAb can be given to patients and other organisms to treat diseases caused by phosphorylated and non-phosphorylated STAT3, as well as to prevent the development of disease or recurrence of disease. For example, patients who have undergone organ transplant and bone marrow transplant are at higher risk for cutaneous SCCA and BCCA due to the immunosuppressive medications they take. Administration of an anti-STAT3 sdAb can reduce or eliminate this risk. Patients treated for a malignancy who are at risk for recurrence will benefit from treatment with the anti-STAT3 sdAb. Based on family medical history and HLA-type, some individuals will be at increased risk for some types of autoimmune diseases and may benefit from treatment with sdAbs to reduce risk of developing that autoimmune disease. Breast cancer risk can be reduced with administration of anti-STAT3 medication such as GLG-302, as demonstrated in a recent NCI study.

In addition to inhibiting STAT3, the anti-STAT3 sdAb can also inhibit STAT1, STAT2, STAT4, STAT5a, STAT5b, and STAT6 due to the high degree of homology between these molecules.

Figure 1:
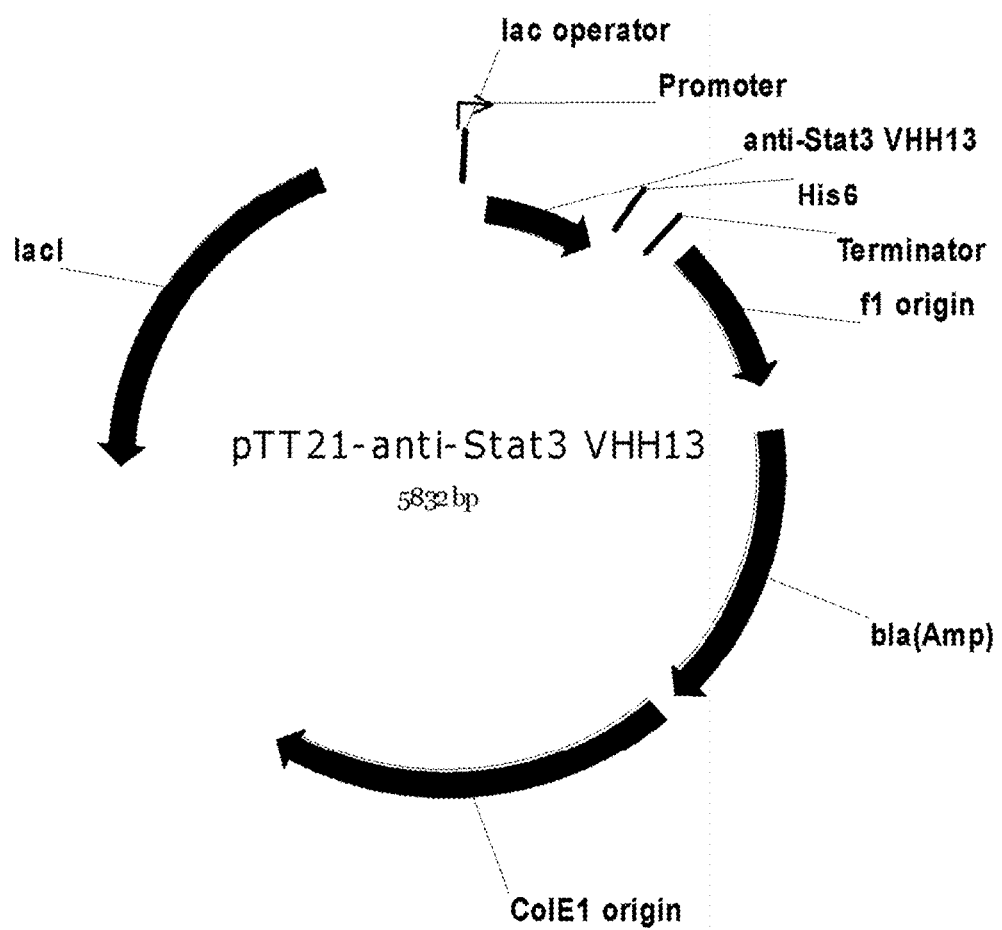
FIG. 1 is a schematic map of VHH13 anti-STAT3 sdAb expression vector pTT21-stt VHH13.
Figure 2:
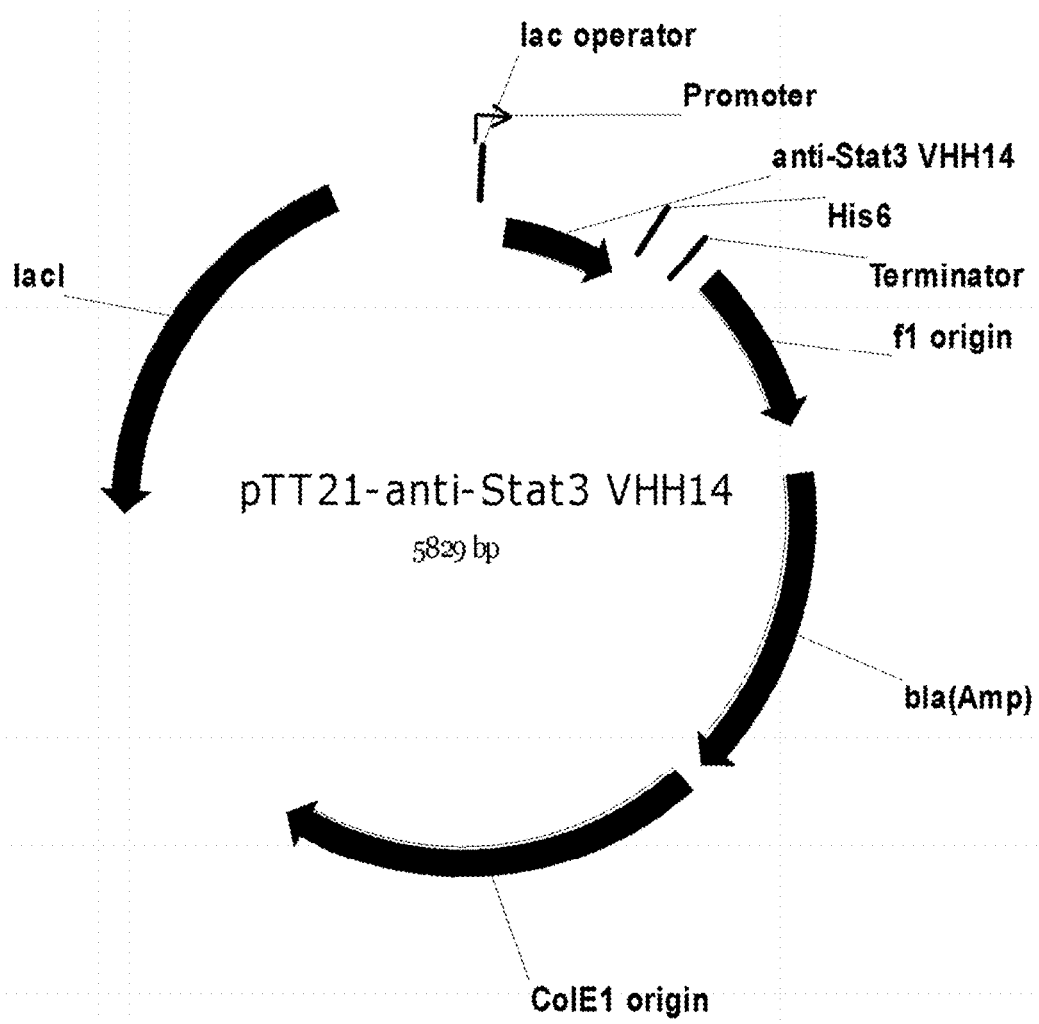
FIG. 2 is a schematic map of VHH14 anti-STAT3 sdAb expression vector pTT21-stt VHH14.

Recombinant human STAT3 protein was used to produce anti-STAT sdAbs that were directed against or can bind to an epitope of STAT3. To generate the anti-STAT3 sdAbs, recombinant full-length human STAT3 (Gene ID: 6774) was expressed by baculovirus in Sf9 insect cells. The anti-STAT sdAbs were cloned into vectors that can be expressed in both bacterial and mammalian cells, as shown in FIGS. 1 and 2.

The anti-STAT3 sdAb of the invention can be used to target STAT3 and all other STAT molecules inside the cell in order to inhibit cell growth, such as, for example, suppression of cancer cell growth. In addition, the anti-STAT3 sdAb can inhibit cell growth in other proliferative diseases such as psoriasis, diabetic retinopathy, and macular degeneration via inhibition of the production of VEGF.

Without being limited to a particular mechanism of action, it is thought that anti-STAT3 sdAb can eliminate cancer induced immune suppression by decreasing STAT3 levels in antigen presenting cells such as, for example, host dendritic cells. STAT3 inhibition promotes anti-cancer response by patient's innate and adaptive immune systems (i.e., dendritic cells, macrophages, neutrophils, T cells, NK cells, and B cells).

Using methods that are well known in the art, several anti-STAT sdAbs were obtained and screened for the ability to suppress cancer cell growth and induce apoptosis in cancer cell lines, as described below. The cytotoxicity and anti-proliferative activities of the anti-STAT3 sdAbs was tested. In addition, the tolerance of anti-STAT3 sdAbs was tested in vitro and in vivo. The production of mouse monoclonal antibody directed against one or more domains of the anti-STAT sdAbs is described below.

The amino acid sequence of one anti-STAT3 sdAb, named VHH13 (SEQ ID NO:3), is shown below:

```
HVQLVESGGGSVQAGGSLRLSCAASGANGGRSCMGWFRQVPGKEREGVSG
ISTGGLITYYADSVKGRFTISQDNTKNTLYLQMNSLKPEDTAMYYCATSR
FDCYRGSWFNRYMYNSWGQGTQVTVSS
```

The three CDRs are underlined.

The amino acid sequence of a second anti-STAT3 sdAb, named VHH14 (SEQ ID NO:4), is shown below:

```
QVQLVESGGGSVQAGGSLRLSCVASTYTGCMGWFRQAPGKEREGVAA
LSSRGFAGHYTDSVKGRFSISRDYVKNAVYLQMNTVKPEDAAMYYCAARE
GWECGETWLDRTAGGHTYWGQGTLVTVSS
```

Again, the three CDRs are underlined. The protein sequences of other anti-STAT3 sdAbs that were obtained are as follows:

```
STAT3_10 (SEQ ID NO: 5):
(1)  DVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTQVTVSS

STAT3_34 (SEQ ID NO: 6):
(1)  DVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTQVTVSS

STAT3_19 (SEQ ID NO: 7):
(1)  HVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTQVTVSS

STAT3_14 (SEQ ID NO: 8):
(1)  QVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTLVTVSS

STAT3_35 (SEQ ID NO: 9):
(1)  QVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTLVTVSS

STAT3_9 (SEQ ID NO: 10):
(1)  QVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTLVTVSS
```

-continued

```
STAT3_30 (SEQ ID NO: 11):
(1) QVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTLVTVSS

STAT3_23 (SEQ ID NO: 12):
(1) QVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGSHTYWGQGTLVTVSS

STAT3_24 (SEQ ID NO: 13):
(1) EVQLVESGGGSVQAGGSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTLVTVSS

STAT3_36 (SEQ ID NO: 14):
(1) DVQLVESGGGSVQAGDSLRLSCVASTYTGCMGWFRQAPGKEREGVAA

(48) LSSRGFAGHYTDSVKGRFSISRDYVKNAVYLQMNTVKPEDAAMYYCAARE

(98) GWECGETWLDRTAGGHTYWGQGTLVTVSS

STAT3_12 (SEQ ID NO: 15):
(1) QVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTLVTVSS

STAT3_16 (SEQ ID NO:16):
(1) QVQLVESGGGSVQAGGSLRLSCAASGANGGRSCMGWFRQVPGKEREGVSG

(51) ISTGGLITYYADSVKGRFTISQDNTNNTLYLQMNSLKPEDTAMYYCATSR (101) FDCYRGSWFNRYMYNSWGQGTLVTVSS

STAT3_11 (SEQ ID NO: 17):
(1) EVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTLVTVSS

STAT3_20 (SEQ ID NO: 18):
(1) DVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTLVTVSS

STAT3_2 (SEQ ID NO: 19):
(1) DVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTLVTVSS

STAT3_15 (SEQ ID NO: 20):
(1) DVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTLVTVSS

STAT3_6 (SEQ ID NO: 21):
(1) HVQLVESEGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTLVTVSS
```

-continued

STAT3_33 (SEQ ID NO: 22):
(1) QVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTQVTVSS

STAT3_17 (SEQ ID NO: 23):
(1) QVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTQVTVSS

STAT3_25 (SEQ ID NO: 24):
(1) EVQLVESGGGSVQAGGSLRLSCAASGANGGRSCMGWFRQVPGKEREGVSG

(51) ISTGGLITYYADSVKGRFTISQDNTKNTLYLQMSSLKPEDTAMYYCATSR (101) FDCYRGSWFNRYMYNSWGQGTQVTVSS

STAT3_32 (SEQ ID NO: 25):
(1) DVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTQVTVSS

STAT3_13 (SEQ ID NO: 26):
(1) HVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTQVTVSS

STAT3_39 (SEQ ID NO: 27):
(1) HVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTQVTVSS

STAT3_4 (SEQ ID NO: 28):
(1) HVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTQVTVSS

STAT3_29 (SEQ ID NO: 29):
(1) HVQLVESGGGSVQAGGSLRLSCAASGANGGRSCMGWFRQVPGKEREGVSG

(51) ISTGGLITYYADSVKGRFTISQDNTKNTLYLQMNSLKPEDTAMYYCATSR (101) FDCYRGSWFNRYMYNSWGQGTQVTVSS

The corresponding anti-STAT3 DNA sequences are as follows:

Stat3_VHH-10 (SEQ ID NO: 30):
5'-gatgtgcagctggtggagtctgggggaggctcggtgcaggctggagg ctctctgagactctcctgtgtagcctctacatacaccggctgcatgggct ggttccgccaggctcctggaaaggagcgcgagggagtcgcagctcttagt agccgtggttttgccgggcactataccgactccgtgaagggccgattctc catctcccgagactacgtcaagaatgcggtgtatctgcaaatgaacactg tgaaacctgaggacgctgccatgtactactgtgcagcacgggagggatgg gagtgcggtgagacctggttggaccggaccgccgggggccatacctactg gggccaggggacccaggtcaccgtctcctca-3'

Stat3_VHH-14 (SEQ ID NO: 31):
5'-caggtgcagctggtggagtctgggggaggctcggtgcaggctggagg ctctctgagactctcctgtgtagcctctacatacaccggctgcatgggct ggttccgccaggctcctggaaaggagcgcgagggagtcgcagctcttagt agccgtggttttgccgggcactataccgactccgtgaagggccgattctc catctcccgagactacgtcaagaatgcggtgtatctgcaaatgaacactg tgaaacctgaggacgctgccatgtactactgtgcagcacgggagggatgg gagtgcggtgagacctggttggaccggaccgccgggggccatacctactg gggccaggggacccaggtcaccgtctcctca-3'

Stat3_VHH-12 (SEQ ID NO: 32):
5'-caggtgcagctggtggagtctgggggaggctcggtgcaggctggagg gtctctgagactctcctgtgcagcctctggagccaatggtggtcggagct -continued
gcatgggctggttccgccaggttccagggaaggagcgcgagggggtttct ggtatttcaaccggtggtcttattacatactatgccgactccgtgaaggg ccgattcaccatctcccaagacaacaccaagaacacgctgtatctgcaaa tgaacagcctgaaacctgaggacactgccatgtactactgtgcgacgagt cggtttgactgctatagaggctcttggttcaaccgatatatgtataacag ttggggccaggggaccctggtcaccgtctcctca-3'

Stat3_VHH-13 (SEQ ID NO: 33):
5'-catgtgcagctggtggagtctgggggaggctcggtgcaggctggagg gtctctgagactctcctgtgcagcctctggagccaacggtggtcggagct gcatgggctggttccgccaggttccagggaaggagcgcgagggggtttct ggtatttcaaccggtggtcttattacatactatgccgactccgtgaaggg ccgattcaccatctcccaagacaacaccaagaacacgctgtatctgcaaa tgaacagcctgaaacctgaggacactgccatgtactactgtgcgacgagt cggtttgactgctatagaggctcttggttcaaccgatatatgtataacag ttggggccaggggacccaggtcactgtctcctca-3'

Stat3_VHH-20 (SEQ ID NO: 34):
5'-gatgtgcagctggtggagtctgggggaggctcggtgcaggctggagg gtctctgagactctcctgtgcagcctctggagccaatggtggtcggagct gcatgggctggttccgccaggttccagggaaggagcgcgagggggtttct ggtatttcaaccggtggtcttattacatactatgccgactccgtgaaggg ccgattcaccatctcccaagacaacaccaagaacacgctgtatctgcaaa tgaacagcctgaaacctgaggacactgccatgtactactgtgcgacgagt cggtttgactgctatagaggctcttggttcaaccgatatatgtataacag ttggggccaggggaccctggtcaccgtctcctca-3'

Stat3_VHH-23 (SEQ ID NO: 35):
5'-caggtgcagctggtggagtctgggggaggctcggtgcaggctggagg ctctctgagactctcctgtgtagcctctacatacaccggctgcatgggct ggttccgccaggctcctggaaaggagcgcgagggagtcgcagctcttagc agccgtggttttgccgggcactataccgactccgtgaagggccgattctc catctcccgagactacgtcaagaatgcggtgtatctgcaaatgaacactg tgaaacctgaggacgctgccatgtactactgtgcagcacgggagggatgg gagtgcggtgagacctggttggaccggaccgccgggagccatacctactg gggccaggggaccctggtcaccgtctcctca-3'

Stat3_VHH-24 (SEQ ID NO: 36):
5'-gaggtgcagctggtggagtctgggggaggctcggtgcaggctggagg ctctctgagactctcctgtgtagcctctacatacaccggctgcatgggct ggttccgccaggctcctggaaaggagcgcgagggagtcgcagctcttagt agccgtggttttgccgggcactataccgactccgtgaagggccgattctc catctcccgagactacgtcaagaatgcggtgtatctgcaaatgaacactg tgaaacctgaggacgctgccatgtactactgtgcagcacgggagggatgg gagtgcggtgagacctggttggaccgaaccgccggggccatacctactg gggccaggggaccctggtcaccgtctcctca-3'

Stat3_VHH-25 (SEQ ID NO: 37):
5'-gaggtgcagctggtggagtctgggggaggctcggtgcaggctggagg gtctctgagactctcctgtgcagcctctggagccaatggtggtcggagct gcatgggctggttccgccaggttccagggaaggagcgcgagggggtttct ggtatttcaaccggtggtcttattacatactatgccgactccgtgaaggg tcgattcaccatctcccaagacaacaccaagaacacgctgtatctgcaaa tgagcagcctgaaacctgaggacactgccatgtactactgtgcgacgagt cggtttgactgctatagaggctcttggttcaaccgatatatgtataacag ttggggccaggggacccaggtcaccgtctcctca-3'

Stat3_VHH-19 (SEQ ID NO: 38):
5'-catgtgcagctggtggagtctggggggggctcggtgcaggctggagg ctctctgagactctcctgtgtagcctctacatacaccggctgcatgggct ggttccgccaggctcctggaaaggagcgcgagggagtcgcagctcttagt agccgtggttttgccgggcactataccgactccgtgaagggccgattctc catctcccgagactacgtcaagaatgcggtgtatctgcaaatgaacactg tgaaacctgaggacgctgccatgtactactgtgcagcacgggagggatgg gagtgcggtgagacctggttggaccggaccgccgggggccatacctactg gggccaggggaccccaggtcaccgtctcctca-3'

Stat3_VHH-32 (SEQ ID NO: 39):
5'-gatgtgcagctggtggagtctgggggaggctcggtgcaggctggagg gtctctgagactctcctgtgcagcctctggagccaatggtggtcggagct gcatgggctggttccgccaggttccagggaaggagcgcgagggggtttct ggtatttcaaccggtggtcttattacatactatgccgactccgtgaaggg ccgattcaccatctcccaagacaacaccaagaacacgctgtatctgcaaa tgaacagcctgaaacctgaggacactgccatgtactactgtgcgacgagt cggtttgactgctatagaggctcttggttcaaccgatatatgtataacag ttggggccaggggacccaggtcaccgtctcctca-3'

Stat3_VHH-33 (SEQ ID NO: 40):
5'-caggtgcagctggtggagtctgggggaggctcggtgcaggctggagg gtctctgagactctcctgtgcagcctctggagccaatggtggtcggagct gcatgggctggttccgccaggttccagggaaggagcgcgagggggtttct ggtatttcaaccggtggtcttattacatactatgccgactccgtgaaggg ccgattcaccatctcccaagacaacaccaagaacacgctgtatctgcaaa tgaacagcctgaaacctgaggacactgccatgtactactgtgcgacgagt cggtttgactgctatagaggctcttggttcaaccgatatatgtataacag ttggggccaggggacccaggtcaccgtctcctca-3'

Stat3_VHH-36 (SEQ ID NO: 41):
5'-gatgtgcagctggtggagtctgggggaggctcggtgcaggctggaga ctctctgagactctcctgtgtagcctctacatacaccggctgcatgggct ggttccgccaggctcctggaaaggagcgcgagggagtcgcagctcttagt agccgtggttttgccgggcactataccgactccgtgaagggccgattctc catctcccgagactacgtcaagaatgcggtgtatctgcaaatgaacactg tgaaacctgaggacgctgccatgtactactgtgcagcacgggagggatgg -continued

```
gagtgcggtgagacctggttggaccggaccgccgggggccatacctactg gggccaggggaccctggtcactgtctcctca-3'
```

Stat3_VHH-11 (SEQ ID NO: 42):
```
5'-gtgcagctggtggagtctggggggaggctcggtgcaggctggagggtc tctgagactctcctgtgcagcctctggagccaatggtggtcggagctgca tgggctggttccgccaggttccagggaaggagcgtgagggggtttctggt atttcaaccggtggtcttattacatactatgccgactccgtgaagggccg attcaccatctcccaagacaacaccaagaacacgctgtatctgcaaatga acagcctgaaacctgaggacactgccatgtactactgtgcgacgagtcgg tttgactgctatagaggctcttggttcaaccgatatatgtataacagttg gggccaggggaccctggtcactgtctcctca-3'
```

Stat3_VHH-6 (SEQ ID NO: 43):
```
5'-gtgcagctggtggagtctgagggaggctcggtgcaggctggagggtc tctgagactctcctgtgcagcctctggagccaatggtggtcggagctgca tgggctggttccgccaggttccagggaaggagcgcgagggggtttctggt atttcaaccggtggtcttattacatactatgccgactccgtgaagggccg attcaccatctcccaagacaacaccaagaacacgctgtatctgcaaatga acagcctgaaacctgaggacactgccatgtactactgtgcgacgagtcgg tttgactgctatagaggctcttggttcaaccgatatatgtataacagttg gggccaggggaccctggtcaccgtctcctca-3'
```

Stat3_VHH-1 (SEQ ID NO: 44):
```
5'-gtgcagctggtggagtctggggggaggctcggtgcaggctggagggtc tctgagactctcctgtgcagcctctggagccaatggtggtcggagctgca tgggctggttccgccaggttccagggaaggagcgcgagggggtttctggt atttcaaccggtggtcttattacatactatgccgactccgtgaagggccg attcaccatctcccaagacaacaccaataacacgctgtatctgcaaatga acagcctgaaacctgaggacactgccatgtactactgtgcgacgagtcgg tttgactgctatagaggctcttggttcaaccgatatatgtataacagttg gggccaggggaccctggtcactgtctcctca-3'
```

Additionally, the present invention comprises one or more mouse monoclonal antibodies which are directed against one or more domains of the anti-STAT3 sdAb of the invention. The mouse monoclonal antibody can be generated by methods that are known by one of skill in the art, for example, the mouse monoclonal antibody can be produced by a mouse hybridoma. The mouse monoclonal antibody can be used in diagnostic assays, for example, the antibody can be used in an immunoassay such as an ELISA in order to measure the amount of anti-STAT3 sdAb present in a patient's serum. It should be appreciated that the method is not limited to anti-STAT3 sdAbs, and could be used to produce a mouse antibody directed towards any of the sdAbs of the present invention.

Anti-STAT5a sdAbs were also generated. The DNA and corresponding protein sequences for one clone is listed below.

Stat5-31
(SEQ ID NO: 82)
```
5'-gaggtgcagctggtggagtctggggggaggctcggtgcagactgga gggtctctgagactctcctgcgcagcctctggattcccctttagtagtca cgttatgggctggttccgccaggctccagggaagaaacgcgagggggtcg cagctatttcggttgatagtggtagcacatggtatgccgactccgtgaag ggccgattcaccatctccctggacagcgccaagaacacgctgtatctgca aatgaacagcctgaaacctgaggacactgccatgtactactgtgcgacta gacgtggagttattcttacactaagcccagagacctatgactactgggc caggggacccaggtcaccgtctcctca-3'
```

STAT5-31
(SEQ ID NO: 83)
EVQLVESGGGSVQTGGSLRLSCAASGFPFSSHVMGWFRQA

PGKKREGVAAISVDSGSTWYADSVKGRFTISLDSAKNTLYLQMNSLKPED

TAMYYCATRRGVILTLSPETYDYWGQGTQVTVSS

The TNF-α gene encodes a multifunctional proinflammatory cytokine that belongs to the tumor necrosis factor (TNF) superfamily. This cytokine is mainly secreted by macrophages. The cytokine is involved in the regulation of a wide spectrum of biological processes including growth regulation, differentiation, inflammation, viral replication, tumorigenesis, and autoimmune diseases; and in viral, bacterial, fungal, and parasitic infections. Besides inducing hemorrhagic necrosis of tumors, TNF was found to be involved in tumorigenesis, tumor metastasis, viral replication, septic shock, fever, inflammation, cachexia, and autoimmune diseases including Crohn's disease, and rheumatoid arthritis as well as graft-versus-host disease.

The present invention provides sdAbs, proteins, and polypeptides that are directed against TNF-α, in particular against human TNF-α inside the cell or cell membrane, so as to prevent the secretion of TNF-α by cells.

It is contemplated that the anti-TNF-α sdAbs and polypeptides of the invention can be used for the prevention and/or treatment of diseases and disorders associated with and/or mediated by TNF-α, such as inflammation, rheumatoid arthritis, Crohn's disease, ulcerative colitis, inflammatory bowel syndrome, multiple sclerosis, Addison's disease, autoimmune hepatitis, autoimmune parotitis, diabetes type 1, epididymitis, glomerulonephritis, Graves' disease, Guillain-Barre syndrome, Hashimoto's disease, hemolytic anemia, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, vasculitis, and weight loss due to cancer and cachexia.

TNF-α exists in different forms; there are monomeric and multimeric forms, including a trimeric form. It is within the scope of the invention that the sdAbs, proteins and polypeptides of the invention bind to TNF-α in its different form, i.e., monomeric form or multimeric forms. Thus, when sdAbs, proteins and polypeptides of the invention are directed to TNF-α, it should be understood that this also comprises sdAbs, proteins and polypeptides directed against TNF-α in its trimeric form.

It is known that signal transduction by TNF involves crosslinking by TNF receptors by a trimer of TNF molecules, which contains three receptor binding sites (see, for example, Peppel et al., J. Exp. Med., 174 (1991), 1483-1489).

Recombinant human TNF-α protein was used to generate sdAbs that are directed against or can bind to an epitope of TNF-α. To generate the anti-TNF-α sdAbs, recombinant full-length human TNF-α (Gene ID: 7124) was expressed in *Escherichia coli* and used as the target antigen.

Thirty-five sdAbs against the TNF-α protein were obtained. These anti-TNF-α antibodies were divided into three groups based on sequence homology.

The amino acid sequence of the first anti-TNF-α sdAb, named TNF-α VHH66 (SEQ ID NO:45) sdAb, is shown below:

```
HVQLVESGGGSVEAGGSLRLSCAASGFRYAAYCMGWFRQADGKERE
GVATIDIDGLTTHADSVKGRFTISRDNAKNTLSLQMNDLKPEDTA
MYYCAADRDRCGSIWTYAYKYRG-QGTLVTVSS
```

The three CDRs are underlined.

The amino acid sequence of the second anti-TNF-α sdAb, named TNF-α VHH69 (SEQ ID NO:46) sdAb, is shown below:

```
EVQLVESGGGSVLAGGSLRLSCVASGFTSRYNYMAWFRQAPGKERE
GVATIGTASGSADYYGSVKDRFTISQDNAKNTVYLQMNSLKPEDTA
MYYCAARTYGTISLTPSDYRYWGQGTLVTVSS
```

The three CDRs are underlined.

The amino acid sequence of the third anti-TNF-α sdAb, named TNF-α VHH62 (SEQ ID NO:47) sdAb, is shown below:

```
QVQLVESGGGPVQAGETLRLSCTASGFTFAEADMGWYRQAPGHECE
LVSTITTEGITSEASSYYADSVRGRFTISRDNAKNMVYLQMNSLKPEDTA
VYYCAPDPYAYSTYSDYCSWAQGTQGTLVTVSS
```

The three CDRs are underlined. Other anti-TNF-α sdAbs that were found include the sequences below, again with the CDRs underlined:

```
TNF_2 (SEQ ID NO: 48):
QVQLVESGGGSVEAGRSLRLSCAASGFRYAAYCMGWFRQADGKERE
GVATIDIDGQTTHADSVKGRFTISRDNAKNTLSLQMNDLKPEDTA
MYYCAADRDRCGSIWTYAYKYRGQGTQVTVSS

TNF_46 (SEQ ID NO: 49):
QVQLVESGGGSVEAGGSLRLSCAASGFRYAAYCMGWFRQADGKERE
GVATIDIDGQTTHADSVKGRFTISRDNVKNTLSLQMNDLKPEDTA
MYYCAADRDRCGSIWTYAYKYRGQGTQVTVSS

TNF_71 (SEQ ID NO: 50):
QVQLVESGGGSVEAGGSLRLSCAASGFRYAAYCMGWFRQADGKERE
GVATIDIDGLTTHADSVKGRFTISRDNAKNTLSLQMNDLKPEDTA
MYYCAADRDRCGSIWTYAYKYRGQGTQVTVSS

TNF_21 (SEQ ID NO: 51):
QVQLVESGGGSVEAGGSLRLSCAASGFRYAAYCMGWFRQADGKERE
GVATIDIDGQTTHADSVKGRFTISRDNAKNTLSLQMNDLKPEDTA
MYYCAADRDRCGSIWTYAYKYRGQGTQVTVSS

TNF_38 (SEQ ID NO: 52):
EVQLVESGGGSVEAGGSLRLSCAASGFRYAAYCMGWFRQADGKERE
GVATIDIDGQTTHADSVKGRFTISRDNAKNTLSLQMNDLKPEDTA
MYYCAADRDRCGSIWTYAYKYRGQGTQVTVSS

TNF_18 (SEQ ID NO: 53):
EVQLVESGGGSVEAGGSLRLSCAASGFRYAAYCMGWFRQADGKERE
GVATIDIDGLTTHADSVKGRFTISRDNAKNTLSLQMNDLKPEDTA
MYYCAADRDRCGSIWTYAYKYRGQGTLVTVSS

TNF_37 (SEQ ID NO: 54):
DVQLVESGGGSVEAGGSLRLSCAASGFRYAAYCMGWFRQADGKERE
GVATIDIDGQTTHADSVKGRFTISRDNAKNTLSLQMNDLKPEDTA
MYYCAADRDRCGSIWTYAYKYRGQGTLVTVSS

TNF_66 (SEQ ID NO: 55):
HVQLVESGGGSVEAGGSLRLSCAASGFRYAAYCMGWFRQADGKERE
GVATIDIDGLTTHADSVKGRFTISRDNAKNTLSLQMNDLKPEDTA
MYYCAADRDRCGSIWTYAYKYRGQGTLVTVSS

TNF_68 (SEQ ID NO: 56):
HVQLVESGGGSVEAGGSLRLSCAASGFRYAAYCMGWFRQADGKERE
GVATIDIDGLATHADSVKGRFTISRDNAKNTLSLQMNDLKPEDTA
MYYCAADRDRCGSIWTYAYKYRGQGTLVTVSS

TNF_78 (SEQ ID NO: 57):
HVQLVESGGGSVEAGGSLRLSCAASGFRYAAYCMGWFRQADRKERE
GVATIDIDGQTTHADSVKGRFTISRDNAKNTLSLQMNDLKPEDTA
MYYCAADRDRCGSIWTYAYKYRGQGTQVTVSS

TNF_67 (SEQ ID NO: 58):
HVQLVESGGGSVQAGGSLRLSCAASGFRYAAYCMGWFRQADGKVRE
GVATIDIDGQTTHADSVKGRFTISRDNAKNTLSLQMNDLKPEDTA
MYYCAADRDRCGSIWTYAYKYRGQGTLVTVSS

TNF_6 (SEQ ID NO: 59):
QVQLVESGGGSVQAGGSLRLSCAASGFIDSFGVMAWFRQAPGKERE
GVAAVYRRAGDTYYADSVKGRFTISRDNAKNTVYLQMNSLKPEDSA
MYYCAARTYGSVSSWTGYKYWGQGTQVTVSS

TNF_7 (SEQ ID NO: 60):
DVQLVESGGGSVQAGGSLRLSCAASGFIDSFGVMAWFRQTPGKERE
GVAAVYRRAGDTYYADSVKGRFTISRDNAKNTVYLQMNSLKPEDSA
MYYCAARTYGSVSSWTGYKYWGQGTQVTVSS

TNF_13 (SEQ ID NO: 61):
DVQLVESGGGSVQVGGSLTLSCAVSGYTDSYGVMAWFRQAPGKERE
GVASIYRNSGITYYPDSVKGRFTISRDNAKNTVLLQMNSLKPEDSA
TYYCAVRSFGSVSTWAGYVYWGQGTQVTVSS

TNF_60 (SEQ ID NO: 62):
DVQLVESGGGSVQAGGSLRLSCAASGFIDSFGVMAWFRQAPGKERE
GVAAVYRRAGDTYYADSVKGRFTISRDNAKNTVYLQMNSLKPEDSA
MYYCAARTYGSVSSWTGYKYWGRGTQVTVSS

TNF_73 (SEQ ID NO: 63):
DVQLVESGGGSVRAGGSLRLSCTASGDTSKSDCMAWFRQAPGKERE
RVGAIYTRNGYTHYADSVNGRFTISQDNAKNALYLQMSGLKPEDTA
MYYCAARFRIYGQCVEDDDIDYWGQGTLVTVSS

TNF_69 (SEQ ID NO: 64):
EVQLVESGGGSVLAGGSLRLSCVASGFTSRYNYMAWFRQAPGKERE
GVATIGTASGSADYYGSVKDRFTISQDNAKNTVYLQMNSLKPEDTA
MYYCAARTYGTISLTPSDYRYWGQGTQVTVSS

TNF_76 (SEQ ID NO: 65):
QVQVVEYGGGSVQAGETVRLSCTASGFTFAEADMGWYRQAPGHEWE
LVSNITTEGITSEASSYYADSVRGRFTIFDNAKNMVYLQMNSLKHEDTA
VYYCAPDPYAYSTYREYCTWAQGTQGTLVTVSS

TNF_62 (SEQ ID NO: 66):
QVQLVESGGGPVQAGETLRLSCTASGFTFAEADMGWYRQAPGHECE
LVSTITTEGITSEASSYYADSVRGRFTISRDNAKNMVYLQMNSLKPEDTA
VYYCAPDPYAYSTYSDYCSWAQGTQGTLVTVSS

TNF_43 (SEQ ID NO: 67):
QVQLVESGGGSVQAGETLRLSCTASGFTFAEADMGWYRQAPGHECE
LVSTITTEGITSEASSYYADSVRGRFTISRDNAKNMVYLQMNSLKPEDTA
VYYCAPDPYAYSTYSDYCTWAQGTQGTLVTVSS

TNF_15 (SEQ ID NO: 68):
QVQPVESGGGSVQAGETLRLSCTASGFTFAEADMGWYRQAPGHECE
LVSTITTEGITSEASSYYADSVRGRFTISRDNAKNMVYLQMNSLKPEDTA
VYYCAPDPYAYSTYSDYCTWAQGAQGTLVTVSS

TNF_11 (SEQ ID NO: 69):
QVQLVESGGGSVQAGETLRLSCTASGFTFAEADMGWYRQAPGHECE
LVSTITTEGITSEASSYYADSVRGRFTISRDNAKNMVYLQMNSLKPEDTA
VYYCAPDPYAYSTYSDYCSWAQGTQGTQVTVSS
```

-continued

TNF_17 (SEQ ID NO: 70):
QVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGTQVTVSS

TNF_63 (SEQ ID NO: 71):
QVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGTLVTVSS

TNF_20 (SEQ ID NO: 72):
HVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGTQVTVSS

TNF_58 (SEQ ID NO: 73):
EVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGALVTVSS

TNF_27 (SEQ ID NO: 74):
EVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGTLVTVSS

TNF_28 (SEQ ID NO: 75):
EVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCS</u>WAQGTQGTQVTVSS

TNF_4 (SEQ ID NO: 76):
EVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGTQVTVSS

TNF_14 (SEQ ID NO: 77):
DVQLVESRGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGTLVTVSS

TNF_3 (SEQ ID NO: 78):
DVQLVESGGGSVQAGETLRLSCTASGFTFA<u>EADMG</u>WYRQAPGHVCE
LVS<u>TITTEGITSEASSYYADSVRGRFT</u>ISRDNAKNMVYLQMNSLKPEDTA
VYYCAP<u>DPYAYSTYSDYCS</u>WAQGTQGTQVTVSS

TNF_1 (SEQ ID NO: 79):
DVQLVESGGGSVQAGETLRLSCTASGFTFA<u>EADMG</u>WYRQAPGLECE
LVS<u>TITTEGITSEASSYADSVRGRFT</u>ISRDNAKNMVYLQMNSLKPEDTA
VYYCAP<u>DPYAYSTYSEYCT</u>WAQGTQGTLVTVSS

TNF_45 (SEQ ID NO: 80):
DVQLVESGGGSVQAGETLRLSCTASGFTFA<u>EADMG</u>WYRQAPGHECE
LVS<u>TITTEGITSEASSYYADSVRGRFT</u>ISRDNAKNMVYLQMNSLKPEDTA
VYYCAP<u>DPYAYSTYSDYCT</u>WAQGTQGTLVTVSS

TNF_22 (SEQ ID NO: 81):
DVQLVESGGGSVQAGETLRLSCTASGFTFA<u>EADMG</u>WYRQAPGHECE
LVS<u>TITTEGITSVASSYYADSVRGRFT</u>ISRDNAKNMVYLQMNSLKPEDTA
VYYCAP<u>DPYAYSTYSDYCT</u>WAQGTQGTQVTVSS

The in vitro growth inhibition of several TNF-α sdAbs was tested, as described below. The present invention also comprises one or more mouse monoclonal antibodies which are directed against one or more domains of the anti-TNF-α sdAb of the invention. The mouse monoclonal antibody can be generated by methods that are known by one of skill in the art. The mouse monoclonal antibody can be used in diagnostic assays, such as, for example, an immunoassay such as an ELISA in order to measure the amount of anti-TNF-α sdAb present in a patient's serum.

The RAF proteins are a family of serine/threonine-specific kinases that serve as a central intermediate in transmitting extracellular signals to the mitogen-activated protein kinase cascade, which controls cell growth, differentiation and survival. BRAF is a member of the RAF family that is activated by members of the Ras family upon growth factor-induced stimulation. Active Ras can induce heterodimerization of cRaf and BRAF and this may explain the observed cooperativity of cRaf and BRaf in cells responding to growth factor signals. Activating mutations in the BRAF gene are present in a large percentage of human malignant melanomas and in a proportion of colon cancers. The vast majority of these mutations result in a valine to glutamic acid change at residue 599 within the activation segment of BRAF.

Anti-BRAF sdAbs were developed to target wild-type and mutated BRAF in order to disrupt its role in malignant cells such as, for example, cells involved in colon cancer and other malignancies.

Using methods that are well-known in the art, recombinant human BRAF protein was used to generate sdAbs that are directed against or can bind to an epitope of BRAF.

Additionally, the present invention comprises one or more mouse monoclonal antibodies which are directed against one or more domains of the anti-BRAF sdAb of the invention. The mouse monoclonal antibody can be generated by methods that are known by one of skill in the art. The mouse monoclonal antibody can be used in diagnostic assays, for example, the antibody can be used in an immunoassay such as an ELISA in order to measure the amount of anti-BRAF sdAb present in a patient's serum.

EXAMPLES

Example 1

Anti-STAT3 VHH13 (SEQ ID NO:3) SDAB Binds STAT3

In this example, the affinity of two VHH targets against STAT3 was measured using Octet based label-free binding assay. Anti-STAT3 VHH13 (SEQ ID NO:3) sdAb, anti-KRAS (negative control) and GST-STAT3 (16 kDa monovalent antigen, Creative BioMart #STAT3-1476H) were used as antigen probes in this assay. The GST-STAT3 protein was captured at 20 μg/ml in PBS using aminopropylsilane (APS) dip and read biosensors, specifically meant for hydrophobic protein. The probes were then dipped into wells with the GST-STAT3 protein, anti-STAT3 VHH13 (SEQ ID NO:3) sdAb or anti-KRAS at a concentration as indicated. The association rate (on rate) of the antigen was measured. The sensors were quenched with 1% BSA in water. The probes were dipped into assay buffer (PBS) and the dissociation rate (off rate) was measured.

The affinity, represented by the equilibrium constant for the dissociation of an antigen with an antigen-binding protein (KD) was determined from the obtained affinity constant (KA), and KD using 1:1 global fit analysis Fortebio software as shown below in Table 1. Affinity was determined by averaging KD values for curves with $R^2$ values >0.95. The 250 nM anti-STAT3 VHH13 data point was omitted as it is an outlier. It was determined that the anti-STAT3 VHH13 (SEQ ID NO:3) sdAb affinity was $1.16 \times 10^{-7}$. The affinity of anti-KRAS VHH was not determined.

TABLE 1

Local Fit Analysis

| Sensor Type | Sample ID | Loading Sample ID | VHH Conc. (nM) | KD (M) | kon (1 Ms) | koff (1/s) | Full R^2 |
|---|---|---|---|---|---|---|---|
| APS (Aminopropylsilane) | ANTI-STAT3 VHH13 | STAT3 20 µg/ml | 1000 | 1.168E−07 | 3.16E+05 | 3.69E−02 | 0.985 |
| APS (Aminopropylsilane) | ANTI-STAT3 VHH13 | STAT3 20 µg/ml | 500 | 1.012E−07 | 4.04E+05 | 4.09E−02 | 0.974 |
| APS (Aminopropylsilane) | ANTI-STAT3 VHH13 | STAT3 20 µg/ml | 250 | <1.0E−12 | 4.69E+91 | 5.11E−02 | 0.980 |
| APS (Aminopropylsilane) | ANTI-STAT3 VHH13 | STAT3 20 µg/ml | 125 | 1.474E−07 | 3.09E+05 | 4.55E−02 | 0.991 |
| APS (Aminopropylsilane) | ANTI-STAT3 VHH13 | STAT3 20 µg/ml | 62.5 | 9.921E−08 | 2.71E+05 | 2.69E−02 | 0.975 |
| APS (Aminopropylsilane) | ANTI-STAT3 VHH13 | STAT3 20 µg/ml | 31.3 | 1.53E−06 | 6.75E+04 | 1.03E−01 | 0.656 |
| APS (Aminopropylsilane) | ANTI-kras | STAT3 20 µg/ml | 1000 | 6.75E−08 | 1.19E+04 | 8.01E−04 | 0.917 |
| APS (Aminopropylsilane) | ANTI-kras | STAT3 20 µg/ml | 500 | 2.916E−08 | 1.65E+04 | 4.80E−04 | 0.890 |
| APS (Aminopropylsilane) | ANTI-kras | STAT3 20 µg/ml | 250 | 4.324E−09 | 8.93E+04 | 3.86E−04 | 0.276 |
| APS (Aminopropylsilane) | ANTI-kras | STAT3 20 µg/ml | 125 | NA | NA | NA | NA |
| APS (Aminopropylsilane) | ANTI-kras | STAT3 20 µg/ml | 62.5 | NA | NA | NA | NA |
| APS (Aminopropylsilane) | ANTI-kras | STAT3 20 µg/ml | 31.3 | NA | NA | NA | NA |

Example 2

Immunoprecipitation Studies

The specificity of STAT3 sdAbs was assayed in human breast cancer cells. In this example, MDA-MB-231 human breast cancer cells were grown to 50% to 70% confluence. The cells were then disrupted in freshly prepared ice-cold lysis buffer (20 mM HEPES, pH 7.9, 400 mM NaCl, 0.1% NP-40, 10% glycerol, 1 mM sodium vanadate, 1 mM sodium fluoride, 1 mM dithiothreitol, 1 mM phenylmethylsulfonyl fluoride, 10 µg/mL aprotinin, 10 µg/mL leupeptin) for 45 minutes on ice. Lysates were then centrifuged, the supernatant collected, and protein concentration was determined using a modified Lowry method (Bio Rad, Hercules, Calif.). Total protein (1 mg) was incubated with 1.5 mg of Dynabeads (Invitrogen) with sdAbs against STAT3, a positive control (STAT3, cat #SC-482, Santa Cruz Biotechnology, Dallas, Tex.), or negative control (STAT-1, cat #9172, Cell Signaling, Danvers, Mass.) for 1 hour at 4° C. Beads were then washed. Following the final wash, 60 µl of lysis buffer was added, and the resulting supernatant was subject to Western blot analysis. Briefly, samples were separated on 10% polyacrylamide gels and transferred to a nitrocellulose membrane. The membranes were blocked, then incubated with appropriate primary and secondary antibodies. Anti-STAT3 antibody, used as a positive control, was from Cell Signaling (Cat #4904, Danvers, Mass.). The chemiluminescence reaction was performed using the ECL system from Santa Cruz Biotechnology (Dallas, Tex.).

Figure 3:
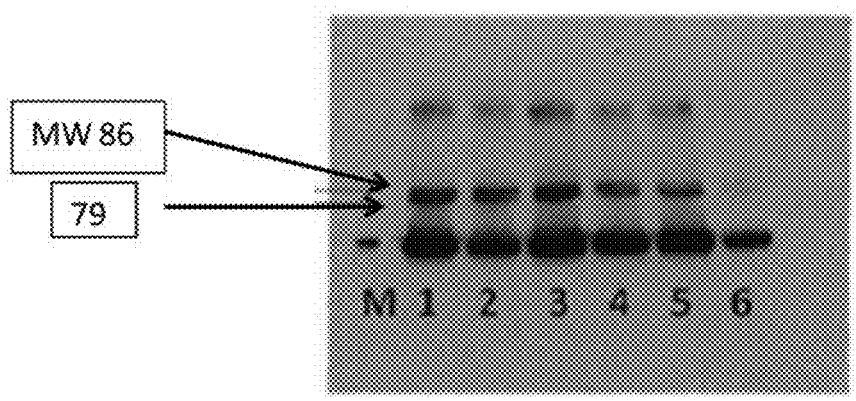
FIG. 3 depicts the results of an immunoprecipitation assay using anti-STAT3 bacterial VHH13 STAT3 (SEQ ID NO:3) and anti-STAT3 bacterial VHH14 STAT3 (SEQ ID NO:4)

As illustrated in FIG. 3, endogenous STAT3 immunoprecipitated with all sdAbs tested at varying amounts. M is the Marker lane containing the marker, lane 1 contained STAT3 VHH13 (SEQ ID NO:3) produced and isolated from mammalian cells, lane 2 contained STAT3 VHH14 (SEQ ID NO:4) produced and isolated from mammalian cells, lane 3 contained STAT3 VHH13 (SEQ ID NO:3) produced and isolated from bacterial cells, lane 4 contained STAT3 VHH14 (SEQ ID NO:4) produced and isolated from bacterial cells, lane 5 was the positive STAT3 antibody, lane 6 used STAT-1 as a negative control, showed no band.

Example 3

Anti-STAT3 Bacterial VHH13 Binds with High Affinity to Cell Lines Continuing Constitutively Activated STAT3

The specificity of bacterial anti-STAT3 VHH13 (SEQ ID NO:3) using constitutively activated STAT3 in human (PANC-1 and DU145) and murine (4T1) cell lines was assayed. Commercial HeLa cells were also treated with interferon gamma (INFΓ) in order to induce phosphorylated STAT3. The PC-3 STAT3 null cell line was used as a negative control.

The cells were grown to 50% to 70% confluence, then disrupted in freshly prepared ice-cold lysis buffer as described above for 45 minutes on ice. Lysates were then centrifuged, the supernatant collected, and protein concentration was determined as described above. Total protein (1 mg) was incubated with 1.5 mg of Dynabeads (Invitrogen) containing the bacterial anti-STAT3 VHH13 (SEQ ID NO:3) or negative control (KRAS, Creative Biolabs, Shirley, N.Y.) for 1 hour at 4° C. Beads were then washed. Following the final wash, 60 µl of lysis buffer was added, and the resulting supernatant was subject to Western Blot analysis as described in Example 2.

Figure 4:
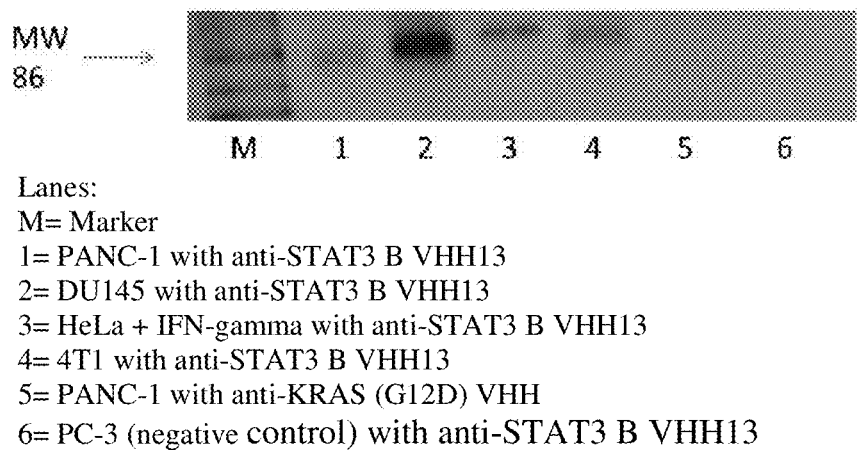
FIG. 4 depicts the results of an immunoprecipitation assay using anti-STAT3 bacterial VHH13 STAT3 (SEQ ID NO:3)

As illustrated in FIG. 4, endogenous STAT3 was immunoprecipitated by bacterial VHH13 STAT3 (SEQ ID NO:3) in the constitutively activated STAT3 cell lines: PANC-1 (lane 1), DU145 (lane 2), and 4T1 (lane 4). Furthermore, anti-STAT3 VHH13 (SEQ ID NO:3) sdAb bound to the Phospho-STAT3 in HeLa lysate (lane 3). No bands were noted for either PANC-1 KRAS, lane 3, or PC-3 (negative control), lane 6. These results indicate that anti-STAT3 VHH13 (SEQ ID NO:3) sdAb can bind both phosphorylated and un-phosphorylated STAT3.

Example 4

Cytotoxicity Studies of Anti-STAT3 SDABS in MDA-MB-231 Cancer Cell Lines

In this example, the anti-proliferative effects of anti-STAT3 sdAbs were assayed using the human breast cancer cell line MDA-MB-231. For the experiments, MDA-MB-231 cells were grown until they reached a confluency of 90%. At that time, cells were washed, trypsinized and counted using a Coulter Counter (Beckman, Brea, Calif.). The proliferation studies were carried out using the 3-[4,5-dimethylthiaolyl]-2,5-diphenyltetrazolium bromide (MTT) assay. For this, cells were seeded in a 96-well plate at a density of $5 \times 10^3$ per well as indicated by the manufacturer (Roche Diagnostics Corporation, Indianapolis, Ind.). Cells were allowed to adhere for 24 hours and then the sdAbs were added at the appropriate concentrations (i.e., 0, 0.5, 1.0, 10.0, or 100 µg/ml). Cells were counted on day 3. For the 5-day treated cells, fresh media containing the sdAbs was refreshed on day 3. At the time of termination, 10 µl of MTT reagent (0.5 mg/mL) was added to each well as indicated by the manufacturer. After a 4 hour incubation period, 100 µl of solubilization solution was added and the plate was placed in the incubator overnight. All the plates were read at 570 nm using the Biotek plate reader (Winooski, Vt.).

All data were analyzed using GraphPad InStat 3 (GraphPad Software, Inc., La Jolla, Calif.). Treatments groups were compared with vehicle control group using one-way ANOVA. If a significant difference ($p<0.05$) was observed, the Tukey-Kramer multiple comparison test was conducted.

Based on the MTT experiment, the bacterial VHH13 anti-STAT3 (SEQ ID NO:3) sdAb was found to be effective in inhibiting cell growth at days 3 and 5 post-treatment, as shown in Tables 2-5 below.

TABLE 2

Mean Absorbance (570 nM) ± S.E. Day 3 Post Treatment with Anti-STAT3 sdAbs in MDA-MB-231 Cells

| Treatment | Control | 0.5 µg/ml | 1.0 µg/ml | 10.0 µg/ml | 100 µg/ml | p-value* |
|---|---|---|---|---|---|---|
| H.VHH13 | 0.444 ± 0.030 | 0.504 ± 0.043 | 0.545 ± 0.060 | 0.603 ± 0.025 | 0.272 ± 0.011 | 0.001 |
| H.VHH14 | 0.404 ± 0.011 | 0.485 ± 0.040 | 0.402 ± 0.017 | 0.588 ± 0.020 | 0.416 ± 0.030 | 0.002 |
| B.VHH13 | 0.550 ± 0.036 | 0.685 ± 0.018 | 0.716 ± 0.023 | 0.355 ± 0.033 | 0.059 ± 0.001 | <0.0001 |
| B.VHH14 | 0.593 ± 0.014 | 0.666 ± 0.022 | 0.644 ± 0.045 | 0.456 ± 0.048 | 0.255 ± 0.005 | <0.0001 |

*One Way Analysis of Variance (ANOVA); Tukey-Kramer Multiple Comparison Test

TABLE 3

Effects of Anti-STAT3 sdAb Treatment on MDA-MB-231 Cell Proliferation after 3 Days of Treatment

| Treatment | µg/ml | % Inhibition | p-value* |
|---|---|---|---|
| H.VHH13 | 0.5 | | NS |
| | 1.0 | | NS |
| | 10.0 | | NS |
| | 100.0 | 38.7 | P < 0.05 |
| H.VHH14 | 0.5 | | NS |
| | 1.0 | 0.5 | NS |
| | 10.0 | | NS |
| | 100.0 | | NS |
| B.VHH13 | 0.5 | | NS |
| | 1.0 | | NS |
| | 10.0 | 35.5 | P < 0.001 |
| | 100.0 | 89.3 | P < 0.001 |
| B.VHH14 | 0.5 | | NS |
| | 1.0 | | NS |
| | 10.0 | 23.1 | P < 0.05 |
| | 100.0 | 57.0 | P < 0.001 |

*One Way Analysis of Variance (ANOVA); Tukey-Kramer Multiple Comparison Test

TABLE 4

Mean Absorbance (570 nM) ± S.E. Day 5 Post Treatment with Anti-STAT3 sdAb in MDA-MB-231 Cells

| Treatment | Control | 0.5 µg/ml | 1.0 µg/ml | 10.0 µg/ml | 100 µg/ml | p-value* |
|---|---|---|---|---|---|---|
| H.VHH13 | 1.100 ± 0.088 | 0.955 ± 0.013 | 0.963 ± 0.018 | 0.832 ± 0.028 | 0.721 ± 0.025 | 0.0012 |
| H.VHH14 | 0.983 ± 0.023 | 0.890 ± 0.021 | 0.935 ± 0.037 | 0.804 ± 0.015 | 0.797 ± 0.010 | 0.0007 |
| B.VHH13 | 0.804 ± 0.046 | 0.761 ± 0.055 | 0.653 ± 0.024 | 0.506 ± 0.030 | 0.083 ± 0.005 | <0.0001 |
| B.VHH14 | 0.677 ± 0.015 | 0.733 ± 0.038 | 0.794 ± 0.023 | 0.640 ± 0.011 | 0.549 ± 0.023 | <0.0001 |

*One Way Analysis of Variance (ANOVA); Tukey-Kramer Multiple Comparison Test

TABLE 5

Effects of Anti-STAT3 sdAb Treatment on MDA-MB-231 Cell Proliferation after 5 Days of Treatment

| Treatment | µg/ml | % Inhibition | p-value* |
|---|---|---|---|
| H.VHH13 | 0.5 | 13.2 | NS |
| | 1.0 | 12.5 | NS |
| | 10.0 | 24.4 | P < 0.01 |
| | 100.0 | 34.5 | P < 0.001 |
| H.VHH14 | 0.5 | 9.5 | NS |
| | 1.0 | 4.9 | NS |
| | 10.0 | 18.2 | P < 0.001 |
| | 100.0 | 18.9 | P < 0.001 |
| B.VHH13 | 0.5 | 5.4 | NS |
| | 1.0 | 18.8 | NS |
| | 10.0 | 37.1 | P < 0.001 |
| | 100.0 | 89.7 | P < 0.001 |
| B.VHH14 | 0.5 | 0 | NS |
| | 1.0 | 0 | NS |
| | 10.0 | 5.5 | NS |
| | 100.0 | 18.9 | P < 0.05 |

*One Way Analysis of Variance (ANOVA); Tukey-Kramer Multiple Comparison Test

Example 5

Cytotoxicity Studies of Anti-STAT3 SDABS in Human Breast (MDA-MB-231) and Pancreatic (PANC-1) Cancer Cell Lines In this Example, the anti-proliferative effects of anti-STAT3 VHH13 (SEQ ID NO:3) and the VHH14 (SEQ ID NO:4) sdAbs were assayed using the human breast cancer cell line MDA-MB-231 and the human pancreatic cancer cell line PANC-1. For the experiments, MDA-MB-231 and PANC-1 cells were grown until they were 90% confluent. At that time, cells were washed, trypsinized and counted using a Coulter Counter (Beckman, Brea, Calif.). The proliferation studies were carried out using the MTT assay described above. For the 5-day treated cells, fresh media containing the anti-STAT3 sdAbs was refreshed on day 3.

All data were analyzed using GraphPad InStat 3. Treatments groups were compared with vehicle control group using one-way ANOVA. If a significant difference ($p<0.05$) was observed, the Tukey-Kramer multiple comparison test was conducted.

Based on the MTT experiment, both the VHH13 (SEQ ID NO:3) and the VHH14 (SEQ ID NO:4) were found to inhibit cell growth in both the MDA-MB-231 and PANC-1 cancer cells, as shown in Tables 6-13 below.

TABLE 6

Mean Absorbance (570 nM) ± S.E. Day 3 Post Treatment With sdAbs in the MDA-MB-231 Cells

| Treatment | Experiment | Control | 10.0 μg/ml | 100 μg/ml | p-value* |
|---|---|---|---|---|---|
| B.VHH13 | 1 | 0.550 ± 0.036 | 0.355 ± 0.033 | 0.059 ± 0.001 | <0.0001 |
| | 2 | 0.735 ± 0.092 | 0.489 ± 0.019 | 0.449 ± 0.054 | 0.0355 |
| | 3 | 0.627 ± 0.033 | 0.432 ± 0.060 | 0.078 ± 0.001 | 0.0002 |
| | 4 | 0.648 ± 0.090 | 0.576 ± 0.061 | 0.063 ± 0.002 | 0.0011 |
| Overall Mean | | 0.640 ± 0.038 | 0.463 ± 0.047 | 0.163 ± 0.10 | 0.0019 |
| B.VHH14 | 1 | 0.593 ± 0.014 | 0.456 ± 0.048 | 0.255 ± 0.005 | 0.0005 |
| | 2 | 0.624 ± 0.046 | 0.499 ± 0.018 | 0.357 ± 0.019 | 0.0025 |
| | 3 | 0.816 ± 0.088 | 0.502 ± 0.048 | 0.308 ± 0.021 | 0.0026 |
| | 4 | 0.729 ± 0.051 | 0.559 ± 0.041 | 0.287 ± 0.021 | 0.0007 |
| Overall Mean | | 0.691 ± 0.051 | 0.504 ± 0.021 | 0.302 ± 0.043 | <0.0001 |

*One Way Analysis of Variance (ANOVA); Tukey-Kramer Multiple Comparison Test

TABLE 7

Mean Absorbance (570 nM) ± S.E. Day 5 Post Treatment with Anti-STAT3 sdAbs in MDA-MB-231 Cells

| Treatment | Experiment | Control | 10.0 μg/ml | 100 μg/ml | p-value* |
|---|---|---|---|---|---|
| B.VHH13 | 1 | 0.804 ± 0.046 | 0.506 ± 0.030 | 0.083 ± 0.005 | <0.0001 |
| | 2 | 0.561 ± 0.024 | 0.417 ± 0.011 | 0.266 ± 0.015 | <0.0001 |
| | 3 | 0.970 ± 0.048 | 0.814 ± 0.052 | 0.105 ± 0.005 | <0.0001 |
| | 4 | 0.757 ± 0.118 | 0.665 ± 0.036 | 0.087 ± 0.004 | 0.011 |
| Overall Mean | | 0.773 ± 0.084 | 0.601 ± 0.088 | 0.135 ± 0.044 | 0.0005 |
| B.VHH14 | 1 | 0.677 ± 0.015 | 0.640 ± 0.011 | 0.549 ± 0.023 | 0.0047 |
| | 2 | 0.456 ± 0.037 | 0.338 ± 0.023 | 0.274 ± 0.032 | 0.0166 |
| | 3 | 0.983 ± 0.019 | 0.930 ± 0.044 | 0.578 ± 0.039 | 0.0004 |
| | 4 | 1.092 ± 0.053 | 0.842 ± 0.052 | 0.499 ± 0.036 | 0.0004 |
| Overall Mean | | 0.802 ± 0.145 | 0.688 ± 0.131 | 0.475 ± 0.0690 | 0.2022 |

*One Way Analysis of Variance (ANOVA); Tukey-Kramer Multiple Comparison Test

TABLE 8

Mean Absorbance (570 nM) ± S.E. Day 3 Post Treatment with Anti-STAT3 sdAbs in the PANC-1 Cells

| Treatment | Experiment | Control | 10.0 μg/ml | 100 μg/ml | p-value* |
|---|---|---|---|---|---|
| B.VHH13 | 1 | 0.756 ± 0.045 | 0.432 ± 0.015 | 0.307 ± 0.012 | <0.0001 |
| | 2 | 1.347 ± 0.189 | 0.491 ± 0.087 | 0.169 ± 0.094 | 0.0019 |
| | 3 | 1.025 ± 0.056 | 0.493 ± 0.029 | 0.166 ± 0.028 | <0.0001 |
| Overall Mean | | 1.043 ± 0.171 | 0.472 ± 0.020 | 0.214 ± 0.047 | 0.0034 |
| H.VHH13 | 1 | 1.541 ± 0.097 | 1.066 ± 0.153 | 0.732 ± 0.015 | 0.0046 |
| | 2 | 1.611 ± 0.119 | 1.353 ± 0.119 | 0.762 ± 0.654 | 0.3527 |
| | 3 | 1.074 ± 0.040 | 0.897 ± 0.154 | 0.700 ± 0.082 | 0.1092 |
| Overall Mean | | 1.409 ± 0.169 | 1.105 ± 0.133 | 0.731 ± 0.181 | 0.0238 |
| H.VHH14 | 1 | 1.195 ± 0.205 | 0.920 ± 0.133 | 0.808 ± 0.239 | 0.4161 |
| | 2 | 1.423 ± 0.038 | 1.183 ± 0.114 | 0.993 ± 0.088 | 0.0338 |
| | 3 | 1.293 ± 0.169 | 1.163 ± 0.044 | 0.916 ± 0.088 | 0.1330 |
| Overall Mean | | 1.304 ± 0.066 | 1.089 ± 0.085 | 0.906 ± 0.054 | 0.0188 |

*One Way Analysis of Variance (ANOVA); Tukey-Kramer Multiple Comparison Test

TABLE 9

Mean Absorbance (570 nM) ± S.E. Day 5 Post
Treatment with Anti-STAT3 sdAbs in PANC-1 Cells

| Treatment | Experiment | Control | 10.0 µg/ml | 100 µg/ml | p-value* |
|---|---|---|---|---|---|
| B.VHH13 | 1 | 0.687 ± 0.047 | 0.433 ± 0.036 | 0.243 ± 0.024 | 0.0004 |
|  | 2 | 1.670 ± 0.196 | 0.869 ± 0.053 | 0.211 ± 0.006 | 0.0004 |
|  | 3 | 1.389 ± 0.044 | 0.627 ± 0.073 | 0.203 ± 0.013 | <0.0001 |
| Overall Mean |  | 1.249 ± 0.292 | 0.643 ± 0.126 | 0.219 ± 0.012 | 0.0208 |
| H.VHH13 | 1 | 1.462 ± 0.150 | 1.128 ± 0.105 | 0.839 ± 0.117 | 0.0349 |
|  | 2 | 1.792 ± 0.202 | 1.341 ± 0.095 | 0.911 ± 0.079 | 0.0113 |
|  | 3 | 1.605 ± 0.289 | 1.161 ± 0.140 | 0.820 ± 0.005 | 0.0638 |
| Overall Mean |  | 1.620 ± 0.096 | 1.210 ± 0.066 | 0.857 ± 0.028 | 0.0007 |
| H.VHH14 | 1 | 1.992 ± 0.105 | 1.859 ± 0.033 | 0.095 ± 0.003 | <0.0001 |
|  | 2 | 1.517 ± 0.050 | 1.165 ± 0.015 | 1.169 ± 0.050 | 0.0015 |
|  | 3 | 1.579 ± 0.134 | 1.081 ± 0.103 | 0.998 ± 0.049 | 0.0136 |
| Overall Mean |  | 1.696 ± 0.149 | 1.368 ± 0.247 | 0.754 ± 0.333 | 0.0967 |

*One Way Analysis of Variance (ANOVA); Tukey-Kramer Multiple Comparison Test

TABLE 10

Mean Growth Inhibition Post 3 Days of Anti-STAT3 sdAbs Treatment on MDA-MB-231 Cell Proliferation

| Treatment | Experiment | P-value[a] | 10.0 µg/ml | P-value[b] | 100 µg/ml | P-value[b] |
|---|---|---|---|---|---|---|
| B.VHH13 | 1 | P < 0.0001 | 35.5 | P < 0.001 | 89.3 | P < 0.001 |
|  | 2 | P = 0.03 | 33.5 | ns | 38.9 | P < 0.05 |
|  | 3 | P = 0.0001 | 31.1 | P < 0.05 | 87.6 | P < 0.001 |
|  | 4 | P = 0.0001 | 11.1 | ns | 90.3 | P < 0.01 |
| Overall Average % Inhibition |  |  | 27.8 |  | 76.5 |  |
| B.VHH14 | 1 | P < 0.001 | 23.1 | P < 0.05 | 57.0 | P < 0.001 |
|  | 2 | P = 0.03 | 20.0 | ns | 42.8 | P < 0.01 |
|  | 3 | P = 0.03 | 38.5 | P < 0.05 | 62.3 | P < 0.01 |
|  | 4 | P = 0.006 | 23.3 | ns | 60.6 | P < 0.001 |
| Overall Average % Inhibition |  |  | 26.2 |  | 55.7 |  |

[a]One-way Analysis of Variance (ANOVA);
[b]Post test = Tukey-Kramer Multiple Comparisons Test

TABLE 11

Mean Growth Inhibition Post 5 days of Anti-STAT3
sdAbs Treatment on MDA-MB-231 Cell Proliferation

| Treatment | Experiment | P-value[a] | 10.0 µg/ml | P-value[b] | 100 µg/ml | P-value[b] |
|---|---|---|---|---|---|---|
| B.VHH13 | 1 | P < 0.0001 | 37.1 | P < 0.001 | 89.7 | P < 0.001 |
|  | 2 | P < 0.0001 | 25.7 | P < 0.001 | 52.6 | P < 0.001 |
|  | 3 | P < 0.0001 | 16.1 | ns | 89.2 | P < 0.001 |
|  | 4 | P = 0.001 | 12.2 | ns | 88.5 | P < 0.01 |
| Overall Average % Inhibition |  |  | 22.8 |  | 80.0 |  |
| B.VHH14 | 1 | P < 0.0001 | 5.5 | ns | 18.9 | P < 0.05 |
|  | 2 | P = 0.02 | 25.9 | ns | 39.9 | P < 0.05 |

TABLE 11-continued

Mean Growth Inhibition Post 5 days of Anti-STAT3
sdAbs Treatment on MDA-MB-231 Cell Proliferation

| Treatment | Experiment | P-value[a] | 10.0 µg/ml | P-value[b] | 100 µg/ml | P-value[b] |
|---|---|---|---|---|---|---|
|  | 3 | P = 0.0004 | 5.4 | ns | 41.2 | P < 0.001 |
|  | 4 | P = 0.0004 | 22.9 | P < 0.05 | 54.3 | P < 0.001 |
| Overall Average % Inhibition |  |  | 14.9 |  | 38.6 |  |

[a]One-way Analysis of Variance (ANOVA);
[b]Post test = Tukey-Kramer Multiple Comparisons Test

TABLE 12

Mean Growth Inhibition Post 3 Days of Anti-STAT3
sdAbs Treatment on PANC-1 Cell Proliferation

| Treatment | Experiment | P-value[a] | 10.0 µg/ml | P-value[b] | 100 µg/ml | P-value[b] |
|---|---|---|---|---|---|---|
| B.VHH13 | 1 | P < 0.0001 | 42.9 | P < 0.001 | 59.4 | P < 0.001 |
|  | 2 | P = 0.03 | 63.5 | P < 0.05 | 87.5 | P < 0.01 |
|  | 3 | P < 0.0001 | 51.9 | P < 0.001 | 83.8 | P < 0.001 |
| Overall Average % Inhibition |  |  | 52.8 |  | 76.9 |  |
| H.VHH13 | 1 | P = 0.005 | 30.8 | P < 0.05 | 52.5 | P < 0.01 |
|  | 2 | P = 0.002 | 16.0 | ns | 52.7 | P < 0.01 |
|  | 3 | P = 0.11 | 16.5 | ns | 34.8 | ns |
| Overall Average % Inhibition |  |  | 21.1 |  | 46.7 |  |
| H.VHH14 | 1 | P = 0.42 | 23.0 | ns | 32.4 | ns |
|  | 2 | P = 0.03 | 16.9 | ns | 30.2 | P < 0.05 |
|  | 3 | P = 0.13 | 10.1 | ns | 29.2 | ns |
| Overall Average % Inhibition |  |  | 16.7 |  | 30.6 |  |

[a]One-way Analysis of Variance (ANOVA);
[b]Post test = Tukey-Kramer Multiple Comparisons Test

TABLE 13

Mean Growth Inhibition Post 5 Days of Anti-STAT3
sdAbs Treatment on PANC-1 Cell Proliferation

| Treatment | Experiment | P-value[a] | 10.0 µg/ml | P-value[b] | 100 µg/ml | P-value[b] |
|---|---|---|---|---|---|---|
| B.VHH13 | 1 | P = 0.0004 | 37.0 | P < 0.01 | 64.6 | P < 0.001 |
|  | 2 | P = 0.0004 | 48.0 | P < 0.01 | 87.4 | P < 0.001 |
|  | 3 | P < 0.0001 | 54.9 | P < 0.001 | 85.4 | P < 0.001 |
| Overall Average % Inhibition |  |  | 46.6 |  | 79.1 |  |
| H.VHH13 | 1 | P = 0.03 | 22.8 | ns | 42.6 | P < 0.05 |
|  | 2 | P = 0.01 | 25.2 | ns | 49.2 | P < 0.01 |
|  | 3 | P = 0.06 | 27.7 | ns | 48.9 | ns |
| Overall Average % Inhibition |  |  | 25.2 |  | 46.9 |  |
| H.VHH14 | 1 | P = 0.08 | 26.8 | ns | 14.8 | ns |
|  | 2 | P = 0.002 | 23.2 | P < 0.01 | 22.9 | P < 0.01 |
|  | 3 | P = 0.02 | 31.5 | P < 0.05 | 36.8 | P < 0.05 |
| Overall Average % Inhibition |  |  | 27.2 |  | 24.8 |  |

[a]One-way Analysis of Variance (ANOVA);
[b]Post test = Tukey-Kramer Multiple Comparisons Test

Example 6

Anti-Proliferative Actions of STAT3 SDABS in the Human Breast Cancer and Human Prostate Cancer Cell Lines The anti-proliferative effects of the STAT3 VHH13 (SEQ ID NO:3) sdAb were assayed in the human breast cancer cell line MDA-MB-231 and the human prostate cancer cell lines DU145. For the experiments, cancer cells were grown until they reached 90% confluence. At that time, cells were washed, trypsinized, and counted using a Coulter Counter (Beckman, Brea, Calif.). The proliferation studies done using the MTT assay as described above.

The anti-proliferative properties of anti-STAT3 bacterial VHH13 (SEQ ID NO:3) sdAb on MDA-MB-231 cells were compared to its actions on DU145 cells. As shown in Table 14, MDA-MB-231 cells treated with the anti-STAT3 (SEQ ID NO:3) sdAbs showed an average growth inhibition of 29.6 and 91.2 at 50.0 and 100 µg/ml, respectively. In the DU145 cells, a similar growth inhibition (31.2 and 92.1% for 50.0 and 100 µg/ml, respectively) was seen as set forth in Table 15.

Cells were kept at 37° C. in a humidified atmosphere of 5% $CO_2$. Cell culture supplies were obtained from Life Technologies, Inc., (Grand Island, N.Y.). The MTT reagent was purchased from Sigma Aldrich (St. Louis, Mo.).

For the experiments, cancer cells were grown until they reached 90% confluency. At that time, cells were washed, trypsinized and counted using a Coulter Counter (Beckman, Brea, Calif.). The proliferation studies were carried out using the MTT assay as described above.

The anti-proliferative properties of Anti-STAT3 Bacterial VHH13 (SEQ ID NO:3) sdAbs were evaluated on five breast cancer cells of representing various classifications (Table 16). As shown in Table 17, all cell lines at 72 hours post treatment showed significant growth inhibition. The greatest growth inhibition was noted at 100 and 200 µg/ml dose for all cell lines. The half maximal inhibitory concentration ($IC_{50}$) for growth in the cell lines tested were: 10.1±2.4, 12.36±1.5, 14.8±1.6, and 25.2±14.7 for the MDA-MB-231, MDA-MB-468, MCF-7, and BT474 cell lines, respectively. These data suggest that the triple negative breast cancer cell lines require the lowest concentration of VHH13 (SEQ ID NO:3) sdAbs to achieve the $IC_{50}$ as compared to estrogen/progesterone positive cell lines (i.e., MCF-7) or HER2 amplified cell lines (i.e., BT474).

TABLE 14

Anti-proliferative Actions of Anti-STAT3 Bacterial VHH13 sdAbs on MDA-MB-231 Breast Cancer Cells

| | Experiment 1 Absorbance (% Inhibition) | Experiment 2 Absorbance (% Inhibition) | Experiment 3 Absorbance (% Inhibition) | Average Absorbance (% Inhibition) | p-value* |
|---|---|---|---|---|---|
| control | 0.93 | 1.25 | 1.46 | 1.21 | |
| 50 µg | 0.82 (12.0) | 0.99 (20.5) | 0.64 (56.2) | 0.82 (32.6) | NS |
| 100 µg | 0.07 (93.1) | 0.12 (90.1) | 0.14 (90.5) | 0.11 (91.0) | <0.001 |

*One Way Analysis of Variance (ANOVA); Tukey-Kramer Multiple Comparison Test

TABLE 15

Anti-proliferative Actions of Anti-STAT3 Bacterial VHH13 sdAbs on DU145 Prostate Cancer Cells

| | Experiment 1 Absorbance (% Inhibition) | Experiment 2 Absorbance (% Inhibition) | Experiment 3 Absorbance (% Inhibition) | Average Absorbance (% Inhibition) | p-value* |
|---|---|---|---|---|---|
| control | 1.05 | 1.58 | 1.61 | 1.41 | |
| 50 µg | 0.68 (35.7) | 1.2 (55.5) | 1.03 (35.8) | 0.98 (30.5) | NS |
| 100 µg | 0.13 (87.4) | 0.12 (95.7) | 0.06 (96.1) | 0.10 (92.7) | <0.001 |

*One Way Analysis of Variance (ANOVA); Tukey-Kramer Multiple Comparison Test

Example 7

Anti-Proliferative Effects of STAT3 VHH13 (SEQ ID NO:3) SDABS on Human Cancer Cell Lines To test the anti-proliferative effects of the STAT3 VHH13 (SEQ ID NO:3) sdAbs using the human cancer cell lines: MDA-MB-231, MDA-MB-468, MCF-7, BT474, and DU145 as shown in Table 16.

All human cancer cell lines were obtained from American Type Culture Collection (Manassas, Va.). Cell lines were maintained and cultured in RPMI 1640 media (MDA-MB-231, MDA-MB-468, MCF-7, BT474) or MEM-E (DU145) containing 10% fetal bovine serum, 2 mM L-glutamine and 1% antibiotic-antimycotic solution (10 units/mL penicillin, 10 µg/mL streptomycin and 25 µg/mL amphotericin B).

TABLE 16

Breast Cancer Cell Line Characteristics

| Cell line | Disease | Immunoprofile | Classification |
|---|---|---|---|
| MDA-MB-231 | adenocarcinoma | ER−, PR−, HER2− | Basal; Claudin-low |
| MDA-MB-468 | adenocarcinoma | ER−, PR−, Her2− | Basal |
| MDA-MB-453 | metastatic carcinoma | ER, PR, HER2− | Unclassified |
| BT474 | ductal carcinoma | Her2 amplified | Luminal B |
| MCF-7 | adenocarcinoma | ER+, PR+, HER2+ | Luminal A |

TABLE 17

Inhibition of Breast Cancer Cell Lines by
Anti-STAT3 VHH13 (SEQ ID NO. 3) sdAbs

| Cell Line | Treatment (μg/ml) | Mean Abs | % Inhibition | p-value |
|---|---|---|---|---|
| BT474 | 0 | 0.634 | | |
| | 0.39 | 0.322 | 49.3 | P < 0.001 |
| | 0.78 | 0.462 | 27.2 | P < 0.001 |
| | 1.56 | 0.502 | 20.8 | P < 0.01 |
| | 3.13 | 0.446 | 29.7 | P < 0.001 |
| | 6.25 | 0.469 | 26.1 | P < 0.001 |
| | 12.5 | 0.363 | 42.7 | P < 0.001 |
| | 25 | 0.256 | 59.6 | P < 0.001 |
| | 50 | 0.145 | 77.2 | P < 0.001 |
| | 100 | 0.046 | 92.8 | P < 0.001 |
| | 200 | 0.040 | 93.8 | P < 0.001 |
| MCF-7 | 0 | 0.590 | | |
| | 0.39 | 0.818 | 0 | |
| | 0.78 | 0.785 | 0 | |
| | 1.56 | 0.823 | 0 | |
| | 3.13 | 0.689 | 0 | |
| | 6.25 | 0.435 | 22.1 | NS |
| | 12.5 | 0.327 | 41.6 | P < 0.01 |
| | 25 | 0.212 | 62.1 | P < 0.001 |
| | 50 | 0.057 | 89.9 | P < 0.001 |
| | 100 | 0.038 | 93.2 | P < 0.001 |
| | 200 | 0.040 | 92.9 | P < 0.001 |
| MDA-MB-468 | 0 | 0.253 | | |
| | 0.39 | 0.311 | 0 | |
| | 0.78 | 0.289 | 0 | |
| | 1.56 | 0.201 | 20.6 | |
| | 3.13 | 0.223 | 11.9 | |
| | 6.25 | 0.230 | 9.1 | |
| | 12.5 | 0.130 | 48.6 | P < 0.001 |
| | 25 | 0.067 | 73.5 | P < 0.001 |
| | 50 | 0.042 | 83.4 | P < 0.001 |
| | 100 | 0.038 | 85.0 | P < 0.001 |
| | 200 | 0.040 | 84.4 | P < 0.001 |
| MDA-MB-231 | 0 | 0.502 | | |
| | 0.39 | 0.603 | 0 | |
| | 0.78 | 0.576 | 0 | |
| | 1.56 | 0.570 | 0 | |
| | 3.13 | 0.445 | 11.4 | P < 0.001 |
| | 6.25 | 0.312 | 37.8 | P < 0.001 |
| | 12.5 | 0.224 | 55.4 | P < 0.001 |
| | 25 | 0.196 | 60.9 | P < 0.001 |
| | 50 | 0.130 | 74.2 | P < 0.001 |
| | 100 | 0.041 | 91.8 | P < 0.001 |
| | 200 | 0.042 | 91.7 | P < 0.001 |

The actions of anti-STAT3 bacterial VHH13 (SEQ ID NO:3) sdAb was also evaluated in the human prostate cancer cell line DU145, as shown in Table 18. The anti-STAT3 bacterial VHH13 (SEQ ID NO:3) sdAb showed dose-dependent growth inhibition in all cancer cells tested.

TABLE 18

Effect of Anti-STAT3 VHH13 sdAbs
on Prostate Cancer Cell Lines

| | Treatment (mg/ml) | Mean Abs | % Inhibition | p-value |
|---|---|---|---|---|
| DU145 | 0 | 0.771 | | |
| DU145 | 0.39 | 0.906 | 0 | |
| DU145 | 0.78 | 1.023 | 0 | |
| DU145 | 1.56 | 0.967 | 0 | |
| DU145 | 3.13 | 0.783 | 0 | |
| DU145 | 6.25 | 0.770 | 0 | |
| DU145 | 12.5 | 0.560 | 27.4 | P < 0.05 |
| DU145 | 25 | 0.359 | 53.5 | P < 0.001 |
| DU145 | 50 | 0.161 | 79.1 | P < 0.001 |
| DU145 | 100 | 0.039 | 95.0 | P < 0.001 |
| DU145 | 200 | 0.039 | 95.0 | P < 0.001 |

Example 8

Maximum Tolerated Dose of Anti-STAT3 Bacterial VHH13 (SEQ ID NO:3) in BALB/C Mice In this Example, the tolerance of anti-STAT3 bacterial VHH13 (SEQ ID NO:3) sdAb was assayed in test animals using the human breast cancer cell line MDA-MB-231. For the experiment, a total of 9 BALB/C nude female mice (6 to 7 weeks old) were divided into three groups according to body weights. (Table 19) Mice (n=3) received either vehicle (PBS) or anti-STAT3 bacterial VHH13 (SEQ ID NO:3) sdAb at 250 or 500 μg/kg body weight/day for five days. During the study, mortality/morbidity was performed twice daily. Body weights were recorded on days 1, 4, and 6 of the study as well as on the day of study termination (Day 13). Toxicity was assessed by body weight measurements and mouse behavior compared to vehicle control mice. Upon completion of treatment phase, animals were followed for an additional week to note any abnormalities in body weights and/or general health post treatment.

TABLE 19

Experimental Design of Maximum Tolerated Dose Study

| Group | # Mice | Treatment | Dose | Route | Frequency |
|---|---|---|---|---|---|
| 1 | 3 | PBS Vehicle | — | IP | 5 days |
| 2 | 3 | Bacterial VHH13 | 250 μg/kg b.w. | IP | 5 days |
| 3 | 3 | Bacterial VHH13 | 500 μg/kg b.w. | IP | 5 days |

As illustrated in Table 20, there was no significant difference in body weights among the groups, and anti-STAT3 bacterial VHH13 (SEQ ID NO:3) sdAb was not associated with any drug-related deaths at either dosing level. Additionally, no behavior changes were observed in the animals treated with anti-STAT3 bacterial VHH13 (SEQ ID NO:3) sdAb as compared to the control mice.

TABLE 20

| | Mean body weights ± S.E | | | | |
|---|---|---|---|---|---|
| Group | Randomization | Day 1 | Day 4 | Day 6 | Day 13 |
| Vehicle | 17.1 ± 0.06 | 17.1 ± 0.07 | 17.8 ± 0.12 | 18.1 ± 0.09 | 18.8 ± 0.20 |
| 250 μg/kg | 17.1 ± 0.06 | 17.2 ± 0.03 | 17.2 ± 0.15 | 17.5 ± 0.15 | 18.1 ± 0.21 |
| 500 μg/kg | 17.1 ± 0.17 | 17.1 ± 0.09 | 17.8 ± 0.18 | 18.0 ± 0.20 | 18.5 ± 0.18 |
| p-value* | >0.9999 | 0.52 | 0.05 | 0.07 | 0.11 |

*One Way Analysis of Variance (ANOVA); Tukey-Kramer Multiple Comparison Test

Example 9

Activity of Bacterial Anti-STAT3 VHH13 (SEQ ID NO:3) in Nude BALB/C Mice Xenograft and Human Breast Cancer and Human Pancreatic Cancer Cells In this example, the activity of anti-STAT3 bacterial VHH13 (SEQ ID NO:3) sdAb was evaluated in mice using the MDA-MB-231 human breast cancer xenograft model and the PANC-1 human pancreatic cancer xenograft model. Dosing schedules were as follows: Group 1 (n=6; PBS; IP) daily for 14 days [QD×14]; and Group 2 (n-12; 500 µg/kg bw; IP), every day for 14 days [QD×14]. An observation period of 5 days followed the drug administration.

The human breast cancer cell lines (MDA-MB-231 and PANC-1) were obtained from American Type Culture Collection (ATCC) (Manassas, Va.). The MDA-MB-231 cells were growth in MEM (Life Technologies, Grand Island, N.Y.) supplemented with 10% FBS (Atlanta Biologicals, Flowery Branch, Ga.) and Penicillin-Streptomycin-Glutamine (Life Technologies, Grand Island, N.Y.). The PANC-1 cells were grown in RPMI 1640 media (Life Technologies, Grand Island, N.Y.) supplemented with 10% FBS and Penicillin-Streptomycin-Glutamine. All cells were grown in the presence of 5% $CO_2$ at 37° C. in an incubator.

Athymic nude-Foxnl$^{nu}$ male mice aged 4 to 5 weeks were purchased from Harlan Laboratories (Indianapolis, Ind.). Animals were quarantined for one week and housed five mice per cage, with a 12-hr light-dark cycle, and a relative humidity of 50%. Drinking water and diet were supplied to the animals ad libitum. All animals were housed under pathogen-free conditions and experiments were performed in accordance with the IIT Research Institute Animal Use and Care Committee. For the MDA-MB-231 xenograft study, cells ($4\times10^6$) in a 100-µL final volume of MEM media were injected subcutaneously into right flanks of mice. For the PANC-1 xenograft study, cells ($5\times10^6$) in a 100-µL final volume of RPMI media were injected subcutaneously into right flanks of mice. Tumor measurements for both models were initiated as soon as the tumors were palpable. Thereafter, tumors were measured twice weekly. Animals were randomized when tumors reach a range size of 75 to 175 mm$^3$, control (n=6) and a treatment (n=12) groups were randomized using the stratified random sampling algorithm. Treatment (anti-STAT3 bacterial VHH13 (SEQ ID NO:3) sdAb) or Vehicle (PBS) was initiated the day following randomization. The treatment was well tolerated and associated with no drug-related deaths. No significant body weight loss was noted.

For the MDA-MB-231 xenograft study, the randomization Mean (±SE) tumor size was: 103.01±11.89 and 102.61±9.60 for control and treatment groups respectively. Mean body weights (±SE) at randomization were: 32.08±0.76 and 30.27+0.75 for Group 1 and Group 2, respectively. Table 21 shows the mean body weights (±SE) for the entire study.

TABLE 21

Mean body weights ± S.E.

| Treatment | Day 1 | Day 6 | Day 9 | Day 12 | Day 16 | Day 20 |
|---|---|---|---|---|---|---|
| Vehicle | 31.0 ± 0.83 | 32.1 ± 0.76 | 31.9 ± 0.66 | 32.1 ± 0.68 | 32.0 ± 0.71 | 32.5 ± 0.88 |
| Anti-STAT3 VHH13 | 29.2 ± 0.71 | 30.3 ± 0.75 | 30.4 ± 0.79 | 29.9 ± 0.72 | 30.6 ± 0.74 | 30.6 ± 0.77 |
| p-value* | 0.16 | 0.18 | 0.27 | .09 | 0.28 | 0.17 |

*Two-tail T-Test

Figure 5:
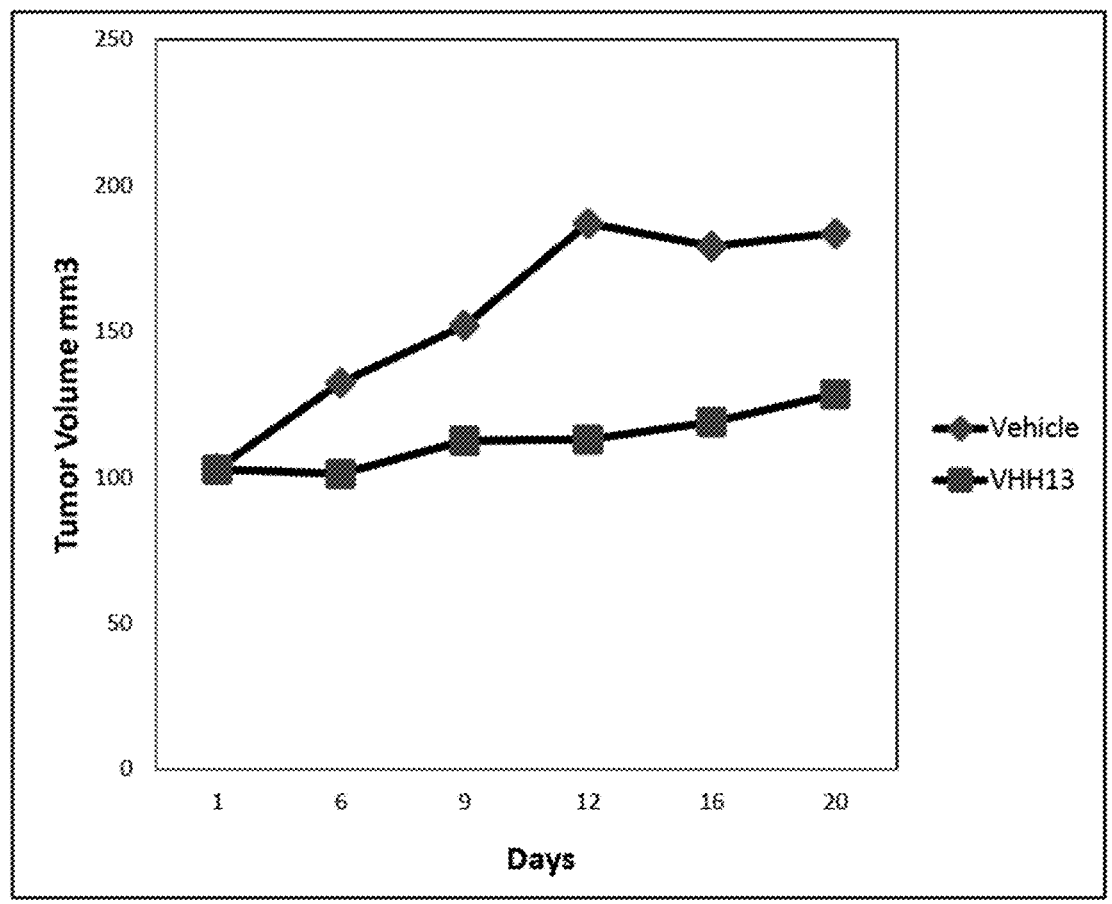
FIG. 5 illustrates the growth inhibition of anti-STAT3 bacterial VHH13 (SEQ ID NO:3) sdAb in the MDA-MB-231 xenograft model, dosed at 0.5 mg/kg/day.

On day 14 of dosing, the mean tumor size (±SE) for the control was 179.11±19.39 versus 118.86±15.94 for treatment group. Mean body weights (±SE) at termination were: 31.98±0.71 and 30.55±0.74 for Group 1 and Group 2, respectively. Table 22 summarizes the tumor volumes (±SE) for entire study. The % mean tumor growth inhibition in the treatment group was 33.64%. The tumor doubling times were as follows: Group 1: 44.27 days; and Group 2: 61.06 days. FIG. 5 illustrates the growth inhibition of anti-STAT3 bacterial VHH13 (SEQ ID NO:3) sdAb in the MDA-MB-231 xenograft model. Anti-STAT3 bacterial VHH13 (SEQ ID NO:3) sdAb showed significant growth inhibition (p=0.047). Thus, anti-STAT3 bacterial VHH13 (SEQ ID NO:3) sdAb has chemotherapeutic activity in the MDA-MB-231 human breast cancer model system.

TABLE 22

Individual Tumor Measurements (mm$^3$) for the MDA-MB-231 Xenograft Model

| Group | Animal # | Day 1 | Day 6 | Day 9 | Day 12 | Day 16 | Day 20 |
|---|---|---|---|---|---|---|---|
| 1 | 1 | 117.43 | 141.72 | 135.00 | 139.31 | 127.93 | 133.19 |
|   | 2 | 130.30 | 142.83 | 206.15 | 256.99 | 244.06 | 243.00 |
|   | 3 | 78.00 | 105.97 | 114.04 | 144.06 | 154.50 | 158.94 |
|   | 4 | 118.24 | 162.41 | 171.39 | 225.59 | 181.32 | 217.97 |
|   | 5 | 71.10 | 109.03 | 133.13 | 168.80 | 187.73 | 164.45 |

TABLE 22-continued

Individual Tumor Measurements (mm³) for the MDA-MB-231 Xenograft Model

| Group | Animal # | Day 1 | Day 6 | Day 9 | Day 12 | Day 16 | Day 20 |
|---|---|---|---|---|---|---|---|
| Mean | | 103.01 | 132.39 | 151.94 | 186.95 | 179.11 | 183.51 |
| S.E. | | 11.89 | 10.82 | 16.42 | 23.28 | 19.39 | 20.28 |
| 2 | 6 | 123.94 | 114.91 | 129.22 | 176.04 | 170.09 | 162.98 |
| | 7 | 85.93 | 101.06 | 112.60 | 112.24 | 139.56 | 96.43 |
| | 8 | 147.34 | 148.72 | 169.69 | 185.08 | 170.07 | 256.71 |
| | 9 | 115.91 | 103.64 | 108.37 | 141.21 | 144.51 | 119.42 |
| | 10 | 73.23 | 82.59 | 110.13 | 91.22 | 166.77 | 285.88 |
| | 11 | 163.73 | 178.23 | 183.79 | 165.52 | 214.28 | 129.51 |
| | 12 | 75.54 | 83.94 | 103.68 | 119.88 | 104.26 | 99.48 |
| | 13 | 70.04 | 89.24 | 102.60 | 75.25 | 57.65 | 95.23 |
| | 14 | 101.62 | 65.09 | 82.02 | 68.01 | 61.41 | 61.83 |
| | 15 | 67.83 | 62.21 | 59.00 | 77.04 | 65.49 | 82.73 |
| | 16 | 131.93 | 75.28 | 76.21 | 53.55 | 73.66 | 51.61 |
| | 17 | 74.28 | 109.06 | 111.92 | 89.94 | 58.56 | 100.07 |
| Mean | | 102.61 | 101.16 | 112.44 | 112.92 | 118.86 | 128.49 |
| S.E. | | 9.6 | 9.8 | 10.3 | 12.9 | 15.9 | 21.1 |
| P-value | | 0.98 | 0.08 | 0.06 | 0.01 | 0.05 | 0.14 |

For the PANC-1 xenograft study, the randomization Mean (+SE) tumor sizes were 107.01±4.54 in the control and 110.58±6.18 in the treatment groups. Mean body weights (±SE) at randomization were: 29.0±0.81 and 28.5±0.70 for Group 1 and Group 2, respectively. Mean body weights (±SE) at termination were: 31.2±0.99 and 30.1±0.75 for Group 1 and Group 2, respectively. Table 23 summarizes the mean body weights (±SE) for entire study. On day 14 of dosing, the mean tumor size (±SE) for control was 287.30±33.94 versus 318.74+29.76 for treatment group. Table 24 summarizes the tumor volumes (±SE) for entire study.

TABLE 23

Mean body weights ± S.E.

| Treatment | 2/19 | 2/24 | 2/27 | 3/2 | 3/6 | 3/10 |
|---|---|---|---|---|---|---|
| Vehicle Control | 31.0 ± 0.83 | 32.1 ± 0.76 | 31.9 ± 0.66 | 32.1 ± 0.68 | 32.0 ± 0.71 | 32.5 ± 0.88 |
| Anti-STAT3 | 29.2 ± 0.71 | 30.3 ± 0.75 | 30.4 ± 0.79 | 29.9 ± 0.72 | 30.6 ± 0.74 | 30.6 ± 0.77 |

The tumor doubling times were as follows: Group 1: 22.44 days, and Group 23.02 days. Anti-STAT3 bacterial VHH13 (SEQ ID NO:3) sdAb showed no significant growth inhibition in the PANC-1 human pancreatic cancer model system.

TABLE 24

Individual Tumor Measurements (mm³) for the PANC-1 xenograft Model

| Group | Animal # | 2/19 | 2/24 | 2/27 | 3/2 | 3/6 | 3/10 |
|---|---|---|---|---|---|---|---|
| 1 | 1 | 99.77 | 117.96 | 134.67 | 161.27 | 160.79 | 195.58 |
| | 2 | 117.54 | 137.14 | 221.14 | 241.27 | 303.70 | 321.45 |
| | 3 | 120.30 | 210.99 | 276.05 | 322.17 | 394.96 | 732.07 |
| | 4 | 111.65 | 135.91 | 215.87 | 340.97 | 334.08 | 382.06 |
| | 5 | 90.88 | 96.35 | 165.26 | 156.28 | 223.17 | 314.97 |
| | 6 | 107.05 | 156.56 | 192.98 | 324.34 | 307.13 | 573.99 |
| Mean | | 107.87 | 142.49 | 201.00 | 257.72 | 287.30 | 420.02 |
| S.E. | | 11.11 | 16.01 | 20.00 | 34.35 | 33.94 | 80.34 |
| 2 | 7 | 96.31 | 193.71 | 275.06 | 317.53 | 395.37 | 540.66 |
| | 8 | 89.24 | 90.03 | 112.43 | 125.51 | 189.63 | 235.08 |
| | 9 | 80.62 | 148.97 | 196.38 | 187.24 | 299.84 | 530.46 |
| | 10 | 108.03 | 144.14 | 234.46 | 240.39 | 288.75 | 421.61 |
| | 11 | 77.66 | 116.21 | 313.19 | 290.38 | 411.66 | 197.67 |
| | 12 | 129.68 | 143.20 | 290.67 | 224.92 | 261.44 | 343.04 |
| | 13 | 108.99 | 182.30 | 239.00 | 254.64 | 342.19 | 464.00 |
| | 14 | 123.27 | 171.03 | 223.34 | 226.88 | 248.69 | 324.30 |
| | 15 | 144.53 | 136.03 | 198.47 | 226.04 | 247.97 | 273.58 |
| | 16 | 120.96 | 136.48 | 226.43 | 338.06 | 564.71 | 883.81 |
| | 17 | 112.69 | 144.76 | 167.12 | 225.70 | 223.06 | 326.19 |
| | 18 | 134.95 | 189.64 | 193.14 | 248.01 | 351.63 | 364.44 |

TABLE 24-continued

Individual Tumor Measurements (mm³) for the PANC-1 xenograft Model

| Group | Animal # | 2/19 | 2/24 | 2/27 | 3/2 | 3/6 | 3/10 |
|---|---|---|---|---|---|---|---|
| Mean | | 110.58 | 149.71 | 222.47 | 242.11 | 318.74 | 408.74 |
| S.E. | | 6.18 | 8.79 | 15.90 | 16.30 | 29.76 | 53.25 |
| P-value | | 0.78 | 0.67 | 0.43 | 0.64 | 0.53 | 0.91 |

Example 10

MDA-MB-231 Xenograft Study

In this Example, the efficacy of anti-STAT3 bacterial VHH13 (SEQ ID NO:3) sdAb in the MDA-MB-231 human breast xenograft model was further evaluated. The dosing schedules were as follows: Group 1 (n=4; PBS; IP) twice a day for 14 days [BID×14]; Group 2 (n=4; 1 mg/kg bw; IP), twice a day for 14 days [BID×14]; Group 3 (n=4; 2 mg/kg bw; IP) twice a day for 14 days [BID×14]; and Group 4 (n=4; 2 mg/kg bw; IP) once a day for 14 days [QD×14]. An observation period of 7 days followed administration.

The human breast cancer cell lines MDA-MB-231 and athymic nude-Foxnl$^{nu}$ female mice were described above.

MDA-MB-231 cells at a density of $5 \times 10^6$ were injected subcutaneously into the right flank of the mice at a final volume of 100-μL in MEM media. Tumor measurements were initiated as soon as the tumors were palpable. Thereafter, tumors were measured twice weekly. Animals are randomized when tumors reach a range size of 55 to 150 mm³ using the stratified random sampling algorithm. Treatment (anti-STAT3 bacterial VHH13 (SEQ ID NO:3) sdAb) or Vehicle (PBS) was initiated the day following randomization.

The randomization Mean (±SE) tumor size was: 92.08±13.24, 82.38±5.17, 77.47±7.17, and 104.71±14.64 for Groups 1, 2, 3, and 4 respectively. As shown in Table 25, mean body weights (±SE) at randomization were: 23.65±0.72, 23.45±0.66, 23.10±0.20, and 22.45±1.25 for Groups 1, 2, 3, and 4, respectively.

As shown in Table 26, at day 14 of dosing, the mean tumor size (±SE) for control group was 221.51±57.32 versus 67.12±10.66, 58.27±22.54, and 131.44±22.86, for treatment group 2, 3, and 4, respectively. At the time of termination (day 42) mean tumor size (±S.E.) was: 255.42±65.46, 55.98±6.94, 41.15±13.21, and 145.51±52.32, for groups 1, 2, 3, and 4, respectively. Mean body weights (±SE) at termination were: 24.80±0.49, 23.25±1.20, 24.00±0.32, and 23.2±1.46 for Groups 1, 2, 3, and 4, respectively. The max mean % net weight loss (day) was: 0.7 (36), 1.5 (23), 1.8 (36), and 2.2 (29) for Groups 1, 2, 3, and 4, respectively.

Also as shown in Table 26, the mean growth inhibition in the treatment groups was 78.3, 75.2, and 55.9, for Groups 2, 3, and 4, respectively. The tumor doubling times were: Group 1: 20.56 days; Group 2: 34.54 days; Group 3: 30.07 days; and Group 4: 27.17 days. There was a growth delay of 13.99, 9.52, and 6.61 days for Groups 2, 3 and 4, respectively. The % treatment/control values for treatment groups were: Group 2: –33.75 (tumor stasis); Group 3: –54.4 (tumor regression); and Group 4: 10.28 (tumor inhibition). FIG. 6 illustrates the growth inhibition of anti-STAT3 bacterial VHH13 (SEQ ID NO:3) sdAb in the MDA-MB-231 xenograft model.

Administration of anti-STAT3 bacterial VHH13 (SEQ ID NO:3) sdAb was associated with a significant growth inhibition in Group 2 (p=0.02) [1 mg/kg; BID×14] and Group 3 (p=0.02) [2 mg/kg; BID×14]. Furthermore, three out of four tumors showed significant regression. Based on these data, it is concluded that anti-STAT3 bacterial VHH13 (SEQ ID NO:3) sdAb has chemotherapeutic activity in the MDA-MB-231 human breast cancer model system.

TABLE 25

Mean Body Weights ± S.E.

| | | Date/Study Day | | | | | | |
|---|---|---|---|---|---|---|---|---|
| | | Dosing | | | | | Recovery | |
| Group | Schedule | 6/23 20 | 6/26 23 | 6/29 26 | 7/2 29 | 7/6 33 | 7/9 36 | 7/15 42 |
| 1 | PBS; BID x14 | 23.65 ± 0.72 | 23.85 ± 0.60 | 24.18 ± 0.67 | 24.05 ± 0.63 | 24.30 ± 0.67 | 24.13 ± 0.72 | 24.80 ± 0.49 |
| 2 | 1 mg/kg; BID x 14 | 23.45 ± 0.66 | 23.10 ± 0.68 | 23.13 ± 0.74 | 23.13 ± 0.95 | 23.08 ± 1.01 | 23.13 ± 1.09 | 23.25 ± 1.20 |
| 3 | 2 mg/kg; BID x 14 | 23.10 ± 0.20 | 23.10 ± 0.14 | 23.20 ± 0.07 | 23.85 ± 0.39 | 23.80 ± 0.24 | 23.38 ± 0.23 | 24.00 ± 0.32 |
| 4 | 2 mg/kg; QD x 14 | 22.45 ± 1.25 | 22.35 ± 1.32 | 22.58 ± 1.46 | 22.08 ± 1.44 | 22.73 ± 1.47 | 22.55 ± 1.46 | 23.20 ± 1.38 |

TABLE 26

Individual Tumor Measurements (mm³) for the MDA-MB-231 Xenograft Model

| | Animal # | 6/23/15 (20) | 6/26/15 (23) | 6/29/15 (26) | 7/2/15 (29) | 7/6/15 (33) | 7/9/15 (36) | 7/15/15 (42) |
|---|---|---|---|---|---|---|---|---|
| Group 1 | | | | | | | | |
| | 001 | 93.38 | 119.07 | 159.80 | 197.91 | 210.95 | 243.31 | 265.61 |
| | 002 | 116.07 | 241.31 | 313.16 | 339.13 | 362.30 | 390.48 | 426.32 |

TABLE 26-continued

Individual Tumor Measurements (mm³) for the MDA-MB-231 Xenograft Model

|  | Animal # | 6/23/15 (20) | 6/26/15 (23) | 6/29/15 (26) | 7/2/15 (29) | 7/6/15 (33) | 7/9/15 (36) | 7/15/15 (42) |
|---|---|---|---|---|---|---|---|---|
|  | 003 | 55.67 | 83.45 | 98.22 | 135.50 | 198.19 | 204.96 | 218.29 |
|  | 004 | 104.82 | 112.09 | 118.44 | 111.07 | 114.61 | 115.31 | 111.45 |
| Mean Absolute |  | 92.49 | 138.98 | 172.41 | 195.90 | 221.51 | 238.51 | 255.42 |
| Mean Relative |  | 100.00% | 150.27% | 186.41% | 211.82% | 239.51% | 257.89% | 276.17% |
| S.E. Mean |  | 13.12 | 34.97 | 48.64 | 51.12 | 51.56 | 57.32 | 65.46 |
| % Inhibition Mean |  |  |  |  |  |  |  |  |
| Median Absolute |  | 99.10 | 115.58 | 139.12 | 166.71 | 204.57 | 224.13 | 241.95 |
| Median Relative |  | 100.00% | 116.62% | 140.38% | 168.22% | 206.42% | 226.16% | 244.14% |
| S.E. Median |  | 13.66 | 37.49 | 52.30 | 53.83 | 52.48 | 57.91 | 65.92 |
| % Inhibition Median |  |  |  |  |  |  |  |  |
| Group 2 |  |  |  |  |  |  |  |  |
|  | 005 | 73.15 | 54.54 | 59.17 | 57.21 | 56.20 | 37.13 | 39.17 |
|  | 006 | 80.11 | 76.56 | 80.34 | 88.75 | 99.09 | 87.42 | 72.18 |
|  | 007 | 97.22 | 79.99 | 78.44 | 59.90 | 55.90 | 53.66 | 60.35 |
|  | 008 | 81.21 | 53.58 | 54.34 | 67.43 | 57.30 | 29.02 | 52.23 |
| Mean Absolute |  | 82.92 | 66.17 | 68.07 | 68.32 | 67.12 | 51.81 | 55.98 |
| Mean Relative |  | 100.00% | 79.79% | 82.09% | 82.39% | 80.95% | 62.48% | 67.51% |
| S.E. Mean |  | 5.09 | 7.03 | 6.62 | 7.14 | 10.66 | 12.93 | 6.94 |
| % Inhibition Mean |  | 10.34% | 52.39% | 60.52% | 65.12% | 69.70% | 78.28% | 78.08% |
| Median Absolute |  | 80.66 | 65.55 | 68.80 | 63.66 | 56.75 | 45.40 | 56.29 |
| Median Relative |  | 100.00% | 81.27% | 85.30% | 78.93% | 70.36% | 56.28% | 69.79% |
| S.E. Median |  | 5.25 | 7.04 | 6.63 | 7.63 | 12.23 | 13.45 | 6.94 |
| % Inhibition Median |  | 18.61% | 43.28% | 50.54% | 61.81% | 72.26% | 79.75% | 76.74% |
| Group 3 |  |  |  |  |  |  |  |  |
|  | 009 | 56.41 | 43.61 | 33.13 | 31.76 | 34.11 | 50.33 | 18.94 |
|  | 010 | 84.06 | 85.18 | 61.75 | 80.69 | 110.72 | 89.11 | 73.89 |
|  | 011 | 82.87 | 54.78 | 34.92 | 54.38 | 78.47 | 78.68 | 51.30 |
|  | 012 | 86.73 | 44.01 | 23.09 | 16.99 | 9.78 | 18.71 | 20.48 |
| Mean Absolute |  | 77.52 | 56.89 | 38.22 | 45.95 | 58.27 | 59.21 | 41.15 |
| Mean Relative |  | 100.00% | 73.39% | 49.31% | 59.28% | 75.17% | 76.38% | 53.09% |
| S.E. Mean |  | 7.08 | 9.78 | 8.26 | 13.90 | 22.54 | 15.79 | 13.21 |
| % Inhibition Mean |  | 16.19% | 59.06% | 77.83% | 76.54% | 73.69% | 75.18% | 83.89% |
| Median Absolute |  | 83.46 | 49.39 | 34.02 | 43.07 | 56.29 | 64.51 | 35.89 |
| Median Relative |  | 100.00% | 59.18% | 40.76% | 51.60% | 67.44% | 77.29% | 43.00% |
| S.E. Median |  | 7.87 | 10.69 | 8.61 | 14.00 | 22.56 | 16.08 | 13.56 |
| % Inhibition Median |  | 15.78% | 57.27% | 75.54% | 74.17% | 72.49% | 71.22% | 85.17% |
| Group 4 |  |  |  |  |  |  |  |  |
|  | 013 | 88.56 | 108.35 | 105.80 | 102.94 | 183.39 | 159.78 | 291.06 |
|  | 014 | 78.73 | 51.51 | 54.20 | 70.39 | 84.29 | 55.83 | 42.03 |
|  | 015 | 113.20 | 85.29 | 69.30 | 103.16 | 103.20 | 87.15 | 130.64 |
|  | 016 | 141.91 | 130.82 | 87.49 | 145.68 | 154.89 | 117.63 | 118.31 |
| Mean Absolute |  | 105.60 | 93.99 | 79.20 | 105.54 | 131.44 | 105.10 | 145.51 |
| Mean Relative |  | 100.00% | 89.01% | 75.00% | 99.94% | 124.47% | 99.52% | 137.79% |
| S.E. Mean |  | 14.11 | 16.94 | 11.18 | 15.44 | 22.86 | 22.17 | 52.32 |
| % Inhibition Mean |  | −14.18% | 32.37% | 54.06% | 46.13% | 40.66% | 55.94% | 43.03% |
| Median Absolute |  | 100.88 | 96.82 | 78.40 | 103.05 | 129.05 | 102.39 | 124.47 |
| Median Relative |  | 100.00% | 95.98% | 77.71% | 102.15% | 127.92% | 101.49% | 123.38% |
| S.E. Median |  | 14.37 | 17.02 | 11.19 | 15.50 | 22.90 | 22.22 | 53.72 |
| % Inhibition Median |  | −1.80% | 16.23% | 43.65% | 38.19% | 36.92% | 54.32% | 48.55% |

Example 11

Efficacy of Anti-STAT3 Bacterial VHH13 (SEQ ID NO:3) SDAB on Three Human Cancer Xenograft Models In this Example, the efficacy of anti-STAT3 bacterial VHH13 (SEQ ID NO:3) sdAb was evaluated in the MDA-MB-231 Human Breast, PANC-1 Pancreatic, and DU145 Prostate cancer xenograft models.

Athymic Nude-Foxnl$^{nu}$ mice, MDA-MB-231 breast cancer cells, PANC-1 pancreatic cancer and the DU145 prostate cancer cell lines were described above. The body weight of the mice ranged from 17 to 19 g (34 females) and 21 to 23 g (16 males) on Day 1 of the study.

Cells in early passages (4 to 10) were used for implantation into the mice and were harvested during log phase growth. MDA-MB-231 ($5\times10^6$), DU145 ($5\times10^6$), and PANC-1 ($1.5\times10^6$) were injected subcutaneously into the right flank of the mice at a final volume of 100-μL of media. Tumor measurements were initiated as soon as the tumors were palpable. Thereafter, tumors were measured twice weekly.

Animals were randomized using the stratified random sampling algorithm when tumors reach a range size of: 74-120 mm³ (MDA-MB-231), 89-146 mm³ (DU145), or 60-160 mm³ (PANC-1). Treatment (containing anti-STAT3 bacterial VHH13 (SEQ ID NO:3) sdAb and referred to herein as SBT-100) or Vehicle (PBS) was initiated the day following randomization, referred to as day 1.

Anti-STAT3 bacterial VHH13 (SEQ ID NO:3) sdAb was supplied as a pre-formulated solution at a concentration of 0.651 mg/ml and was stored at −20° C. until ready to use. The stock solution was diluted in sterile PBS pH 7.6 to provide a 5 mg/kg in a dosing volume of 10 mL/kg. The working solution was prepared every 7 days, aliquoted onto seven vials and stored at 4° C. On each day of treatment, only the needed vial was brought to room temperature. All leftover sdAb material was retained at 4° C. as need for the next dose. At day 8, any remaining sdAb material was discarded and a fresh batch prepared.

Two groups (control and SBT-100) of mice per tumor model were dosed according to the protocol shown in Table 27. Dosing schedules were as follows: Group 1 (n=4; PBS) twice a day for 14 days [BID×14]; Group 2 (n=4; SBT-100, 5 mg/kg bw), twice a day for 14 days [BID×14]. Both the vehicle (PBS pH 7.6) and SBT100 were administered intraperitoneally (i.p.) twice a day, six hours apart for fourteen days. Dosing was conducted according to individual animal weights. A recovery period of 7 days followed administration.

TABLE 27

Experimental Design of Xenograft Study

| Model | # of cells inoculated/mouse | Group | # Mice | Agent | Dose (mg/kg) | Route | Schedule |
|---|---|---|---|---|---|---|---|
| MDA-MB-231 | 5 × 10$^8$ | 1 | 4 | Control (PBS) | 0 | IP | BIDx14 |
|  |  | 2 | 4 | SBT-100 | 5 | IP | BIDx14 |
| PANC-1 | 1.5 × 10$^8$ | 1 | 4 | Control (PBS) | 0 | IP | BIDx14 |
|  |  | 2 | 4 | SBT-100 | 5 | IP | BIDx14 |
| DU145 | 5 × 10$^8$ | 1 | 4 | Control (PBS) | 0 | IP | BIDx14 |
|  |  | 2 | 4 | SBT-100 | 5 | IP | BIDx14 |

Study Log Study Director Animal Study Management Software

Study Log Study Director Animal Study Management Software (San Francisco, Calif.) was used to randomize animals, collect data (e.g., dosing, body weights, tumors measurements, clinical observations), and conduct data analyses.

In the MDA-MB-231 tumor xenograft model, animals were randomized on day 23 post-inoculation with a mean (±SE) tumor size of: 77.98±21.58 and 84.71±5.56 for Groups 1 and 2, respectively. Mean body weights (±SE) at randomization were: 20.04±0.62 and 23.7±1.84 for Groups 1 and 2, respectively. Table 28 summarizes the mean body weights (±SE) for entire study. At last day of dosing (Day 14), the mean tumor size (±SE) for control group was 168.28±51.57 versus 83.81±22.65 for SBT-100 treated mice. Table 29 summarizes the tumor volumes (±SE) for entire study. At the time of termination (day 28) mean tumor size (±S.E.) was: 270.49±112.35 and 91.72±33.17, for Groups 1 and 2, respectively. Mean body weights (±SE) at termination were: 25.36±1.07 and 24.25±1.68 for Groups 1 and 2, respectively. At the end of the study, the mean tumor growth inhibition in the SBT-100 treated group was 85.8% (p=0.006). FIG. 7 illustrates the mean tumor volume. The tumor doubling times were 25.78 days versus 111.6 days for Group 1 and Group 2, respectively. The % treatment/control for Group 2 was 13.35 (tumor inhibition).

TABLE 28

Mean Body Weights for Mice in MDA-MB-231

| Group | Animal ID | Phase | | | | | | |
|---|---|---|---|---|---|---|---|---|
| | | Dosing | | | | | Recovery | |
| | | 8/28 | 9/1 | 9/4 | 9/8 | 9/11 | 9/15 | 9/18 |
| Control | 001 | 23.40 | 24.80 | 24.60 | 25.00 | 24.70 | 23.30 | 25.10 |
| Control | 002 | 22.40 | 22.50 | 22.60 | 22.70 | 22.80 | 20.60 | 23.10 |
| Control | 003 | 23.70 | 24.80 | 25.20 | 24.80 | 24.30 | 23.30 | 25.20 |
| Control | 004 | 23.70 | 24.70 | 25.10 | 25.30 | 24.90 | 22.90 | 25.40 |
| Mean | | 23.30 | 24.20 | 24.38 | 24.45 | 24.18 | 22.53 | 24.70 |
| Median | | 23.55 | 24.75 | 24.85 | 24.90 | 24.50 | 23.10 | 25.15 |
| SD | | 0.62 | 1.13 | 1.21 | 1.18 | 0.95 | 1.30 | 1.07 |
| % Change | | 0.00 | 3.82 | 4.56 | 4.89 | 3.73 | −3.38 | 5.97 |
| SBT-100 | 005 | 21.70 | 21.70 | 21.70 | 22.40 | 22.60 | 21.40 | 22.20 |
| SBT-100 | 006 | 25.00 | 24.30 | 24.30 | 24.70 | 25.30 | 24.40 | 25.00 |
| SBT-100 | 007 | 22.60 | 23.00 | 23.10 | 23.10 | 23.80 | 22.80 | 23.70 |
| SBT-100 | 008 | 25.50 | 25.30 | 25.50 | 26.10 | 25.80 | 25.60 | 26.10 |
| Mean | | 23.7 | 23.575 | 23.65 | 24.075 | 24.375 | 23.55 | 24.25 |
| Median | | 23.8 | 23.65 | 23.7 | 23.9 | 24.55 | 23.6 | 24.35 |
| SD | | 1.84 | 1.56 | 1.63 | 1.66 | 1.46 | 1.84 | 1.68 |
| % Change | | 0.00 | −0.45 | −0.15 | 1.65 | 2.96 | −0.63 | 2.38 |

TABLE 29

Tumor Volumes for MDA-MB-231

| | | Phase | | | | | | | | |
|---|---|---|---|---|---|---|---|---|---|---|
| | | Pre-Dosing | | | Dosing | | | | Recovery | |
| Group | Animal ID | 8/21 | 8/24 | 8/27 | 8/28 | 9/1 | 9/4 | 9/8 | 9/11 | 9/15 | 9/18 |
| Control | 001 | 51.00 | 55.80 | 80.94 | 76.35 | 83.66 | 94.11 | 110.78 | 129.99 | 162.81 | 184.15 |
| Control | 002 | 75.19 | 77.22 | 121.13 | 120.73 | 145.12 | 179.21 | 203.15 | 234.05 | 308.70 | 428.44 |
| Control | 003 | 57.04 | 57.81 | 75.32 | 81.06 | 93.25 | 114.27 | 181.87 | 242.88 | 295.93 | 408.67 |
| Control | 004 | 42.92 | 51.67 | 106.54 | 92.23 | 116.96 | 142.60 | 191.58 | 213.48 | 286.91 | 303.19 |
| Mean | | 56.54 | 60.63 | 95.98 | 92.59 | 109.75 | 132.55 | 171.84 | 205.10 | 263.59 | 331.11 |
| Median | | 54.02 | 56.80 | 93.74 | 86.64 | 105.10 | 128.44 | 186.72 | 223.76 | 291.42 | 355.93 |
| SD | | 13.71 | 11.36 | 21.58 | 19.91 | 27.42 | 36.92 | 41.63 | 51.57 | 67.78 | 112.35 |
| SBT-100 | 005 | 72.25 | 64.45 | 80.02 | 74.07 | 56.81 | 49.44 | 68.70 | 73.04 | 93.32 | 116.07 |
| SBT-100 | 006 | 61.50 | 63.08 | 80.67 | 79.60 | 71.92 | 67.08 | 87.54 | 115.80 | 116.97 | 120.44 |
| SBT-100 | 007 | 37.41 | 35.15 | 91.93 | 91.85 | 50.02 | 50.32 | 46.10 | 63.85 | 66.57 | 80.57 |
| SBT-100 | 008 | 43.80 | 56.95 | 86.22 | 79.94 | 59.23 | 60.19 | 54.10 | 82.57 | 79.47 | 49.78 |
| Mean | | 53.74 | 54.91 | 84.71 | 81.37 | 59.49 | 56.76 | 64.11 | 83.81 | 89.08 | 91.72 |
| Median | | 52.65 | 60.02 | 83.45 | 79.77 | 58.02 | 55.25 | 61.40 | 77.81 | 86.40 | 98.32 |
| SD | | 16.00 | 13.57 | 5.56 | 7.49 | 9.16 | 8.43 | 18.21 | 22.65 | 21.56 | 33.17 |
| % T/C | | 0.0 | 32.3 | 84.0 | 81.6 | 13.6 | 5.9 | 9.2 | 20.7 | 17.6 | 13.4 |
| p-value | | | 0.800 | 0.542 | 0.351 | 0.332 | 0.013 | 0.007 | 0.003 | 0.005 | 0.003 | 0.006 |

In the DU145 tumor xenograft model, animals were randomized on day 17 post-inoculation with a mean (±SE) tumor size of: 111.87±20.53 and 111.23±25.16 for Groups 1 and 2, respectively. Mean body weights (±SE) at randomization were: 29.10±1.94 and 30.68±1.56 for Groups 1 and 2, respectively. Table 30 summarizes the mean body weights (±SE) for entire study. At last day of dosing (Day 14), the mean tumor size (±SE) for control group was 621.81±276.25 versus 364.14±51.64 for SBT-100 treated mice. Table 31 summarizes the tumor volumes (±SE) for entire study. At the time of termination (day 28) mean tumor size (±S.E.) was: 819.42±351.88 and 601.83±131.51, for Groups 1 and 2, respectively. Mean body weights (±SE) at termination were: 29.20±2.33 and 29.60±1.04 for Groups 1 and 2, respectively. At the end of the study, the mean tumor growth inhibition in the SBT-100 treated group was 26.6% (p=0.29). FIG. 8 illustrates the mean tumor volume. The tumor doubling times were 14.57 days versus 18.19 days for Group 1 and Group 2, respectively. The % treatment/control for Group 2 was 74.8.

TABLE 30

Mean Body Weights for Mice in DU145

| | | Phase | | | | | | |
|---|---|---|---|---|---|---|---|---|
| | | Dosing | | | | | Recovery | |
| Group | Animal ID | 9/4 | 9/8 | 9/11 | 9/15 | 9/18 | 9/22 | 9/25 |
| Control | 001 | 29.60 | 28.10 | 29.30 | 28.40 | 28.30 | 29.00 | 29.90 |
| Control | 002 | 29.70 | 30.10 | 31.20 | 30.10 | 30.40 | 29.90 | 30.00 |
| Control | 003 | 30.80 | 30.10 | 31.00 | 31.70 | 31.20 | 31.10 | 31.10 |
| Control | 004 | 26.30 | 25.70 | 26.60 | 25.20 | 26.10 | 26.20 | 25.80 |
| Mean | | 29.10 | 28.50 | 29.53 | 28.85 | 29.00 | 29.05 | 29.20 |
| Median | | 29.65 | 29.10 | 30.15 | 29.25 | 29.35 | 29.45 | 29.95 |
| SD | | 1.94 | 2.09 | 2.13 | 2.78 | 2.29 | 2.09 | 2.33 |
| % Change | | 0.00 | −2.07 | 1.46 | −0.99 | −0.37 | −0.19 | 0.27 |
| SBT-100 | 005 | 30.90 | 30.20 | 27.90 | 29.80 | 29.90 | 30.50 | 30.10 |
| SBT-100 | 006 | 28.40 | 26.20 | 27.30 | 26.90 | 27.50 | 29.10 | 28.50 |
| SBT-100 | 007 | 31.70 | 31.20 | 31.50 | 30.40 | 30.70 | 31.20 | 30.80 |
| SBT-100 | 008 | 31.70 | 29.70 | 30.20 | 28.20 | 28.10 | 28.80 | 29.00 |
| Mean | | 30.68 | 29.33 | 29.23 | 28.83 | 29.05 | 29.90 | 29.60 |
| Median | | 31.30 | 29.95 | 29.05 | 29.00 | 29.00 | 29.80 | 29.55 |
| SD | | 1.56 | 2.17 | 1.97 | 1.58 | 1.50 | 1.14 | 1.04 |
| % Change | | 0.00 | −4.47 | −4.74 | −6.00 | −5.23 | −2.39 | −3.40 |

TABLE 31

Tumor Volumes for DU145

| | | Phase | | | | | | | | | |
|---|---|---|---|---|---|---|---|---|---|---|---|
| | | Pre-Dosing | | | | Dosing | | | | Recovery | |
| Group | Animal ID | 8/24 | 8/27 | 8/31 | 9/3 | 9/4 | 9/8 | 9/11 | 9/15 | 9/18 | 9/22 | 9/25 |
| Control | 001 | 39.18 | 41.27 | 38.41 | 92.80 | 93.22 | 121.16 | 203.79 | 310.41 | 409.15 | 430.31 | 450.89 |
| Control | 002 | 45.05 | 35.99 | 64.98 | 95.50 | 103.83 | 135.42 | 225.62 | 327.76 | 478.14 | 534.48 | 599.97 |
| Control | 003 | 46.65 | 22.37 | 88.76 | 127.98 | 141.49 | 213.24 | 384.15 | 930.74 | 1,023.13 | 1,084.09 | 1,198.93 |
| Control | 004 | 17.06 | 36.44 | 65.73 | 131.20 | 138.33 | 227.23 | 289.78 | 338.79 | 576.83 | 926.90 | 1,027.90 |

TABLE 31-continued

Tumor Volumes for DU145

| Group | Animal ID | Pre-Dosing | | | | Dosing | | | | | Recovery | |
|---|---|---|---|---|---|---|---|---|---|---|---|---|
| | | 8/24 | 8/27 | 8/31 | 9/3 | 9/4 | 9/8 | 9/11 | 9/15 | 9/18 | 9/22 | 9/25 |
| Mean | | 36.98 | 34.02 | 64.47 | 111.87 | 119.22 | 174.26 | 275.84 | 476.93 | 621.81 | 743.95 | 819.42 |
| Median | | 42.11 | 36.22 | 65.36 | 111.74 | 121.08 | 174.33 | 257.70 | 333.27 | 527.49 | 730.69 | 813.93 |
| SD | | 13.67 | 8.12 | 20.58 | 20.53 | 24.32 | 53.70 | 80.91 | 302.77 | 276.25 | 311.67 | 351.88 |
| SBT- | 005 | 33.80 | 23.32 | 35.67 | 86.02 | 89.21 | 151.92 | 145.67 | 386.92 | 325.85 | 474.31 | 498.83 |
| SBT- | 006 | 59.44 | 41.00 | 54.21 | 98.56 | 121.39 | 148.44 | 206.10 | 357.62 | 391.02 | 518.25 | 588.67 |
| SBT- | 007 | 42.30 | 35.11 | 77.90 | 144.06 | 145.78 | 115.05 | 106.70 | 248.12 | 316.24 | 454.78 | 528.83 |
| SBT- | 008 | 69.37 | 50.18 | 71.23 | 116.28 | 118.70 | 134.16 | 147.52 | 320.22 | 423.45 | 604.72 | 790.96 |
| Mean | | 51.23 | 37.40 | 59.75 | 111.23 | 118.77 | 137.39 | 151.50 | 328.22 | 364.14 | 513.01 | 601.83 |
| Median | | 50.87 | 38.06 | 62.72 | 107.42 | 120.05 | 141.30 | 146.60 | 338.92 | 358.43 | 496.28 | 558.75 |
| SD | | 16.13 | 11.25 | 18.90 | 25.16 | 23.17 | 16.76 | 40.98 | 59.97 | 51.64 | 66.65 | 131.51 |
| % T/C | | 0.00 | −26.9 | 29.1 | 78.8 | 81.7 | 65.4 | 42.1 | 70.6 | 56.9 | 69.9 | 74.8 |
| p-value | | | 0.226 | 0.643 | 0.747 | 0.970 | 0.980 | 0.238 | 0.034 | 0.372 | 0.116 | 0.197 | 0.291 |

In the PANC-1 tumor xenograft model, animals were randomized on day 22 post-inoculation with a mean (±SE) tumor size of: 78.74±40.21 and 93.84±36.31 for Groups 1 and 2, respectively. Mean body weights (±SE) at randomization were: 22.50±1.47 and 24.23±1.63 for Groups 1 and 2, respectively. Table 32 summarizes the mean body weights (±SE) for entire study. At last day of dosing (Day 14), the mean tumor size (±SE) for control group was 204.95±178.90 versus 159.03±28.01 for SBT-100 treated mice. Table 33 summarizes the tumor volumes (±SE) for entire study. At the time of termination (day 28) mean tumor size (±S.E.) was: 284.77±288.88 and 203.02±30.34, for groups 1 and 2, respectively. Mean body weights (±SE) at termination were: 27.38±1.07 and 26.23±1.19 for Groups 1 and 2, respectively. At the end of the study, the mean tumor growth inhibition in the SBT-100 treated group was 41.78% (p=0.35). FIG. 9 illustrates the mean tumor volume. The tumor doubling times were 18.51 days versus 35.70 days for Group 1 and Group 2, respectively. The % treatment/control for Group 2 was 52.79.

TABLE 32

Mean Body Weights for Mice in PANC-1

| Group | Animal ID | Dosing | | | | | Recovery | |
|---|---|---|---|---|---|---|---|---|
| | | 9/9 | 9/11 | 9/15 | 9/18 | 9/22 | 9/25 | 9/29 |
| Control | 001 | 26.50 | 26.60 | 25.80 | 27.10 | 25.70 | 26.10 | 27.20 |
| Control | 002 | 24.30 | 24.60 | 23.90 | 25.10 | 24.40 | 25.00 | 25.60 |
| Control | 003 | 27.60 | 26.50 | 26.30 | 26.20 | 26.10 | 27.50 | 28.20 |
| Control | 004 | 25.10 | 25.30 | 24.20 | 25.10 | 24.70 | 25.90 | 26.90 |
| Mean | | 22.50 | 22.80 | 23.04 | 24.30 | 24.58 | 25.90 | 27.38 |
| Median | | 25.80 | 25.90 | 25.00 | 25.65 | 25.20 | 26.00 | 27.05 |
| SD | | 1.47 | 0.97 | 1.18 | 0.97 | 0.81 | 1.03 | 1.07 |
| % Change | | 0.00 | −0.39 | −3.15 | 0.12 | −2.41 | 1.05 | 4.33 |
| SBT-100 | 005 | 22.60 | 22.80 | 21.40 | 22.50 | 22.60 | 22.90 | 24.80 |
| SBT-100 | 006 | 26.00 | 25.10 | 24.90 | 25.70 | 25.10 | 25.40 | 27.10 |
| SBT-100 | 007 | 23.10 | 22.30 | 22.40 | 22.70 | 23.10 | 23.50 | 25.70 |
| SBT-100 | 008 | 25.20 | 25.00 | 25.20 | 25.40 | 26.20 | 25.40 | 27.30 |
| Mean | | 24.23 | 23.80 | 23.48 | 24.08 | 24.25 | 24.30 | 26.23 |
| Median | | 24.15 | 23.90 | 23.65 | 24.05 | 24.10 | 24.45 | 26.40 |
| SD | | 1.63 | 1.46 | 1.87 | 1.71 | 1.69 | 1.29 | 1.19 |
| % Change | | 0.00 | −1.71 | −3.14 | −0.63 | 0.13 | 0.39 | 8.39 |

TABLE 33

Tumor Volumes for PANC-1

| Group | Animal ID | Pre-Dosing | | | Dosing | | | | | Recovery | |
|---|---|---|---|---|---|---|---|---|---|---|---|
| | | 8/31 | 9/3 | 9/8 | 9/9 | 9/11 | 9/15 | 9/18 | 9/22 | 9/25 | 9/29 |
| Control | 001 | 54.91 | 56.79 | 94.23 | 94.37 | 94.69 | 123.90 | 135.77 | 206.74 | 220.31 | 223.91 |
| Control | 002 | 46.38 | 75.43 | 81.99 | 81.62 | 88.44 | 130.01 | 151.06 | 140.52 | 145.62 | 202.22 |
| Control | 003 | 0.00 | 27.50 | 57.30 | 59.60 | 99.77 | 107.02 | 142.23 | 140.55 | 168.68 | 187.27 |
| Control | 004 | 0.00 | 0.00 | 152.17 | 159.98 | 227.02 | 380.54 | 502.06 | 514.93 | 574.44 | 781.45 |
| Mean | | 20.26 | 32.54 | 78.74 | 80.91 | 104.18 | 151.29 | 189.83 | 204.95 | 226.81 | 284.77 |
| Median | | 23.19 | 42.15 | 88.11 | 87.99 | 97.23 | 126.95 | 146.64 | 173.65 | 194.50 | 213.06 |
| SD | | 29.45 | 33.13 | 40.21 | 43.18 | 66.52 | 130.48 | 179.63 | 178.90 | 200.56 | 288.88 |
| SBT- | 005 | 39.60 | 64.75 | 76.44 | 78.07 | 57.54 | 93.17 | 112.98 | 140.09 | 173.92 | 245.84 |

TABLE 33-continued

Tumor Volumes for PANC-1

| | Animal | Pre-Dosing | | | Dosing | | | | | Recovery | |
|---|---|---|---|---|---|---|---|---|---|---|---|
| Group | ID | 8/31 | 9/3 | 9/8 | 9/9 | 9/11 | 9/15 | 9/18 | 9/22 | 9/25 | 9/29 |
| SBT- | 006 | 40.31 | 37.27 | 68.57 | 73.13 | 76.46 | 113.30 | 130.49 | 192.56 | 205.55 | 189.42 |
| SBT- | 007 | 85.71 | 91.27 | 147.61 | 149.02 | 123.95 | 116.01 | 157.50 | 171.29 | 175.68 | 200.97 |
| SBT- | 008 | 48.72 | 55.19 | 82.73 | 83.18 | 86.90 | 102.48 | 105.65 | 132.19 | 136.93 | 175.84 |
| Mean | | 53.58 | 62.12 | 93.84 | 95.85 | 86.21 | 106.24 | 126.65 | 159.03 | 173.02 | 203.02 |
| Median | | 44.51 | 59.97 | 79.59 | 80.62 | 81.68 | 107.89 | 121.73 | 155.69 | 174.80 | 195.19 |
| SD | | 21.82 | 22.52 | 36.31 | 35.69 | 27.94 | 10.49 | 23.05 | 28.01 | 28.10 | 30.34 |
| % T/C | | 0.0 | 0.0 | 42.6 | 44.2 | 27.4 | 34.4 | 38.0 | 49.7 | 51.0 | 52.8 |
| p-value | | | 0.174 | 0.310 | 0.927 | 0.917 | 0.296 | 0.272 | 0.286 | 0.350 | 0.343 | 0.355 |

Example 12

Efficacy of Anti-STAT3 Bacterial VHH13 (SEQ ID NO:3) SDAB in the ER+/PR+ (MCF-7) Human Breast Tumor Xenograft Model This Example demonstrates the efficacy of anti-STAT3 bacterial VHH13 (SEQ ID NO:3) sdAb in the MCF-7 human breast tumor xenograft model in nude mice.

Female athymic nude mice (Crl:NU(Ncr)-Foxnl$^{nu}$, Charles River) were twelve weeks old with a body weight (BW) range of 23.0 to 30.1 g on Day 1 of the study. The animals were fed and housed as described above.

MCF-7 human breast carcinoma cells were obtained and cultured as described above, and used for the mouse xenograph. Three days prior to tumor cell implantation, estrogen pellets (0.36 mg estradiol, 60-day release, Innovative Research of America, Sarasota, Fla.) were implanted subcutaneously between the scapulae of each test animal using a sterilized trocar.

The tumor cells used for implantation were harvested during log phase growth and resuspended in phosphate buffered saline (PBS) at a concentration of $1 \times 10^8$ cells/mL. On the day of implantation, each test mouse received $1 \times 10^7$ MCF-7 cells (0.1 mL cell suspension) implanted subcutaneously in the right flank and tumor growth was monitored as the average size approached the target range of 100-150 mm$^3$. Twenty-one days later, designated as Day 1 of the study, the animals were sorted into two groups each consisting of four mice with individual tumor volumes ranging from 108 to 144 mm$^3$ and group mean tumor volumes from 117 to 123 mm$^3$.

Anti-STAT3 bacterial VHH13 (SEQ ID NO:3) sdAb was provided as a pre-formulated ready to dose solution at a concentration 0.41867 mg/mL in 1 mL aliquots and were stored at −20° C. until needed. The 0.41867 mg/mL solution provided 1 mg/kg dosage in a dosing volume of 23.88 mL/kg. On each day of treatment, only needed vials of anti-STAT3 bacterial VHH13 (SEQ ID NO:3) sdAb were thawed to room temperature. All leftover dosing suspensions were retained at 4° C. as needed for the next dose.

Two groups of athymic nude mice were dosed according to the protocol shown in Table 34. All vehicle (control) and anti-STAT3 bacterial VHH13 (SEQ ID NO:3) sdAb doses were administered intraperitoneally (i.p.) three times daily, six hours apart for fourteen days, with two doses delivered on Day 1 and one dose delivered on the morning of Day 15 (tid×14, first day 2 doses). The dosing volume for vehicle and anti-STAT3 bacterial VHH13 (SEQ ID NO:3) sdAb was 0.478 mL per 20 grams of body weight (23.88 mL/kg) and was scaled to the body weight of each individual animal. Group 1 received the vehicle and served as the benchmark group for tumor engraftment and progression, as well as the control. Group 2 was given anti-STAT3 bacterial VHH13 (SEQ ID NO:3) sdAb at 1 mg/kg.

TABLE 34

Protocol Design for the Study

| | | Treatment Regimen | | | |
|---|---|---|---|---|---|
| Group | n | Agent | mg/kg | Route | Schedule |
| 1 | 4 | vehicle | — | ip | tid x 14 first Day 2 doses |
| 2 | 4 | VHH13 | 1 | ip | tid x 14 first Day 2 doses |

Tumors were measured twice weekly, and each animal was euthanized when its neoplasm reached the predetermined endpoint volume (1000 mm$^3$) or at the end of the study, day 39, whichever came first. When a tumor reached the endpoint volume, the animal was documented as euthanized for tumor progression (TP), with the date of euthanasia. The time to endpoint (TTE) for each mouse was calculated by the following equation:

$$TTE = \frac{\log_{10}(\text{endpoint volume}) - b}{m}$$

where TTE is expressed in days, endpoint volume is expressed in mm$^3$, b is the intercept, and m is the slope of the line obtained by linear regression of a log-transformed tumor growth data set. The data set consists of the first observation that exceeded the endpoint volume used in analysis and the three consecutive observations that immediately preceded the attainment of this endpoint volume. The calculated TTE is usually less than the TP date, the day on which the animal was euthanized for tumor size. Animals that did not reach the endpoint volume were assigned a TTE value equal to the last day of the study (D39). Any animal classified as having died from treatment-related (TR) causes was to be assigned a TTE value equal to the day of death. Any animal classified as having died from non-treatment-related (NTR) causes was to be excluded from TTE calculations.

Treatment efficacy was determined from tumor growth delay (TGD), which is defined as the increase in the median TTE, in days, for a treatment group compared to the control group:

$$TDG = T - C$$

The percent increase in the median TTE, relative to the control group, is $$\% \text{ TGD} = \frac{T - C}{C} \times 100$$

where:
T=median TTE for a treatment group, and
C=median TTE for the designated control group.

Treatment efficacy in each group may be indicated by the median tumor volume, MTV(n), which was defined as the median tumor volume on the last day of the study (D39) in the number of animals remaining (n) whose tumors had not attained the endpoint volume.

Treatment efficacy may also be determined from the incidence and magnitude of regression responses observed during the study. Treatment may cause partial regression (PR) or complete regression (CR) of the tumor in an animal. In a PR response, the tumor volume was 50% or less of its D1 volume for three consecutive measurements during the course of the study, and equal to or greater than 13.5 mm$^3$ for one or more of these three measurements. In a CR response, the tumor volume was less than 13.5 mm$^3$ for three consecutive measurements during the course of the study. Any animal with a CR response at the end of the study was additionally classified as a tumor-free survivor (TFS).

Animals were weighed daily for the first five days, then twice weekly for the remainder of the study. The mice were observed frequently for health and overt signs of any adverse treatment related TR side effects, and noteworthy clinical observations were recorded. Individual body weight loss was monitored per protocol, and any animal with weight loss exceeding 30% for one measurement, or exceeding 25% for three measurements, was to be euthanized for health as a TR death. If group mean body weight recovered, dosing may resume in that group, but at a lower dose or less frequent dosing schedule. Acceptable toxicity was defined as a group mean BW loss of less than 20% during the study and not more than one TR death among ten treated animals, or 10%. Any dosing regimen resulting in greater toxicity is considered above the maximum tolerated dose (MTD). A death was to be classified as TR if it was attributable to treatment side effects as evidenced by clinical signs and/or necropsy, or may also be classified as TR if due to unknown causes during the dosing period or within 14 days of the last dose. A death was classified as NTR if there was evidence that the death was related to the tumor model, rather than treatment-related. NTR deaths are further categorized as NTRa (due to accident or human error), NTRm (due to necropsy-confirmed tumor dissemination by invasion or metastasis), and NTRu (due to unknown causes).

Prism 6.07 (GraphPad) for Windows was employed for graphical analyses. Statistics were not employed due to small sample size.

A scatter plot was constructed to show TTE values for individual mice, by group; this plot shows NTR deaths, which were excluded from all other figures. Individual animal, group median and mean tumor volumes were plotted as functions of time. When an animal exited the study because of tumor size or TR death, its final recorded tumor volume was included with the data used to calculate the median volume at subsequent time points. A Kaplan-Meier plot was constructed to show the percentage of animals in each group remaining on study versus time. Tumor growth curves were truncated after two TR deaths occurred in the same group. Group mean BW changes over the course of the study were graphed as percent change, ±SEM, from Day 1. Tumor growth and BW change curves were truncated after more than half the assessable mice in a group exited the study. FIG. 10 illustrates the mean tumor volume in the study.

Table 35 provides the mean BW losses, TR and NTR deaths for the mice. Clinical signs were recorded when observed, as shown in Tables 36-38. No TR deaths occurred during the study. Bodyweight losses were variable, severe for one animal in each group, and resulted from estrogen effects. Clinical observations including weight loss, enlarged uterine horns, and bladder crystals were present in both groups and were also attributable to estrogen effects. Estrogen toxicity resulted in two non-treatment related deaths in each group. The treatment evaluated in the study was acceptably tolerated.

TABLE 35

Response Summary

| Group | n | Treatment Regimen Agent | mg/kg | Route | Schedule | Median TTE | % T-C | TGD | MTV (n) D39 | Regressions PR | CR | TFS | Mean BW Nadir | Deaths TR | NTR |
|---|---|---|---|---|---|---|---|---|---|---|---|---|---|---|---|
| 1 | 2 | Vehicle | — | ip | tid × 14 first Day 2 doses | 23.2 | — | — | — | 0 | 0 | 0 | −15.6% Day 25 | 0 | 2 |
| 2 | 2 | VHH13 | 1 | ip | tid × 14 first Day 2 doses | 32.9 | 9.7 | 42 | — | 0 | 0 | 0 | −21.8% Day 32 | 0 | 2 |

TABLE 36

Body Weight
Body Weight

| | \multicolumn{15}{c}{Date} |
|---|---|---|---|---|---|---|---|---|---|---|---|---|---|---|
| | Jul. 27, 2015 | Jul. 28, 2015 | Jul. 29, 2015 | Jul. 30, 2015 | Jul. 31, 2015 | Aug. 3, 2015 | Aug. 6, 2015 | Aug. 10, 2015 | Aug. 13, 2015 | Aug. 17, 2015 | Aug. 20, 2015 | Aug. 24, 2015 | Aug. 27, 2015 | Aug. 31, 2015 | Sep. 3, 2015 |
| | \multicolumn{15}{c}{Day of Study} |
| A# | 1 Wt (g) | 2 Wt (g) | 3 Wt (g) | 4 Wt (g) | 5 Wt (g) | 8 Wt (g) | 11 Wt (g) | 15 Wt (g) | 18 Wt (g) | 22 Wt (g) | 25 Wt (g) | 29 Wt (g) | 32 Wt (g) | 36 Wt (g) | 39 Wt (g) |
| \multicolumn{16}{c}{Group I: vehicle (ip, tid × 14 first Day 2 doses)} |
| 1 | 27.50 | 28.60 | 28.10 | 29.30 | 29.40 | | | | | \multicolumn{6}{l}{NTRa on Aug. 1, 2015} |
| 2 | 26.30 | 27.30 | 27.40 | 27.30 | 27.40 | 26.80 | 26.40 | 26.50 | 26.60 | 27.20 | | \multicolumn{4}{l}{TP on Aug. 17, 2015} |
| 3 | 30.10 | 31.00 | 30.50 | 30.00 | 31.10 | 29.50 | 28.20 | 26.00 | 22.50 | 23.60 | 23.80 | \multicolumn{4}{l}{TP on Aug. 20, 2015} |
| 4 | 23.00 | 24.20 | 24.40 | | 25.00 | | | | | \multicolumn{6}{l}{NTRu on Aug. 3, 2015} |
| Mean | 26.7 | 27.8 | 27.6 | 27.9 | 28.2 | 28.2 | 27.3 | 26.3 | 24.6 | 25.4 | 23.8 | | | | |
| STDEV | 2.9 | 2.8 | 2.5 | 2.2 | 2.6 | 1.9 | 1.3 | 0.4 | 2.9 | 2.5 | | | | | |
| n | 4 | 4 | 4 | 4 | 4 | 2 | 2 | 2 | 2 | 2 | 1 | | | | |
| \multicolumn{16}{c}{Group 2: VHH13 (1 mg/kg, ip, tid × 14 first Day 2 doses)} |
| 1 | 28.90 | 29.30 | 28.50 | 29.60 | 28.80 | 28.70 | 27.80 | 28.30 | 28.20 | 28.80 | 29.00 | 28.90 | \multicolumn{3}{l}{TP on Aug. 24, 2015} |
| 2 | 25.30 | 27.00 | 26.40 | 26.40 | 26.30 | 25.90 | 25.80 | 26.00 | 24.50 | 21.90 | 20.10 | 21.10 | 21.20 | 23.80 | 24.20 |
| 3 | 27.20 | 25.40 | 23.90 | | | | | | | \multicolumn{6}{l}{NTRu on Jul. 30, 2015} |
| 4 | 27.60 | 27.50 | 27.10 | 27.30 | 27.20 | 26.90 | 26.10 | | | \multicolumn{6}{l}{NTRu on Aug. 8, 2015} |
| Mean | 27.3 | 27.3 | 26.5 | 27.8 | 27.4 | 27.2 | 26.6 | 27.2 | 26.4 | 25.4 | 24.6 | 25 | 21.2 | 23.8 | 24.2 |
| STDEV | 1.5 | 1.6 | 1.9 | 1.7 | 1.3 | 1.4 | 1.1 | 1.6 | 2.6 | 4.9 | 6.3 | 5.5 | | | |
| n | 4 | 4 | 4 | 3 | 3 | 3 | 3 | 2 | 2 | 2 | 2 | 2 | 1 | 1 | 1 |

TABLE 37

Tumor Measurement
Caliper Measurement

| | \multicolumn{12}{c}{Date} |
|---|---|---|---|---|---|---|---|---|---|---|---|---|
| | \multicolumn{2}{c}{Jul. 27, 2015} | \multicolumn{2}{c}{Jul. 30, 2015} | \multicolumn{2}{c}{Aug. 3, 2015} | \multicolumn{2}{c}{Aug. 6, 2015} | \multicolumn{2}{c}{Aug. 10, 2015} | \multicolumn{2}{c}{Aug. 13, 2015} |
| | \multicolumn{12}{c}{Day of Study} |
| | \multicolumn{2}{c}{1} | \multicolumn{2}{c}{4} | \multicolumn{2}{c}{8} | \multicolumn{2}{c}{11} | \multicolumn{2}{c}{15} | \multicolumn{2}{c}{18} |
| A# | W (mm) | L (mm) | W (mm) | L (mm) | W (mm) | L (mm) | W (mm) | L (mm) | W (mm) | L (mm) | W (mm) | L (mm) |
| \multicolumn{13}{c}{Group 1: vehicle (ip, tid × 14 first Day 2 doses)} |
| 1 | 6 | 6 | 7 | 8 | \multicolumn{8}{l}{NTRa on Aug. 1, 2015} |
| 2 | 5 | 9 | 7 | 9 | 8 | 12 | 9 | 13 | 10 | 13 | 10 | 13 |
| 3 | 6 | 7 | 7 | 10 | 9 | 10 | 10 | 12 | 11 | 12 | 11 | 12 |
| 4 | 6 | 8 | 7 | 11 | \multicolumn{8}{l}{NTRa on Aug. 3, 2015} |
| \multicolumn{13}{c}{Group 2: VHH13 (1 mg/kg, ip, tid × 14 first Day 2 doses)} |
| 1 | 6 | 6 | 7 | 8 | 8 | 10 | 9 | 10 | 9 | 10 | 9 | 10 |
| 2 | 6 | 6 | 6 | 7 | 7 | 8 | 7 | 8 | 8 | 9 | 8 | 9 |
| 3 | 6 | 7 | | | \multicolumn{8}{l}{NTRu on Jul. 30, 2015} |
| 4 | 6 | 7 | 6 | 8 | 7 | 10 | 8 | 10 | \multicolumn{4}{l}{NTRu on Aug. 8, 2015} |

| | \multicolumn{12}{c}{Date} |
|---|---|---|---|---|---|---|---|---|---|---|---|---|
| | \multicolumn{2}{c}{Aug. 17, 2015} | \multicolumn{2}{c}{Aug. 20, 2015} | \multicolumn{2}{c}{Aug. 24, 2015} | \multicolumn{2}{c}{Aug. 27, 2015} | \multicolumn{2}{c}{Aug. 31, 2015} | \multicolumn{2}{c}{Sep. 3, 2015} |
| | \multicolumn{12}{c}{Day of Study} |
| | \multicolumn{2}{c}{22} | \multicolumn{2}{c}{25} | \multicolumn{2}{c}{29} | \multicolumn{2}{c}{32} | \multicolumn{2}{c}{36} | \multicolumn{2}{c}{39} |
| A# | W (mm) | L (mm) | W (mm) | L (mm) | W (mm) | L (mm) | W (mm) | L (mm) | W (mm) | L (mm) | W (mm) | L (mm) |
| \multicolumn{13}{c}{Group 1: vehicle (ip, tid × 14 first Day 2 doses)} |
| 1 | \multicolumn{8}{l}{NTRa on Aug. 1, 2015} | | | | |
| 2 | 12 | 15 | \multicolumn{6}{l}{TP on Aug. 17, 2015} | | | | |
| 3 | 11 | 13 | 12 | 14 | \multicolumn{4}{l}{TP on Aug. 20, 2015} | | | | |
| 4 | \multicolumn{8}{l}{NTRa on Aug. 3, 2015} | | | | |
| \multicolumn{13}{c}{Group 2: VHH13 (1 mg/kg, ip, tid × 14 first Day 2 doses)} |
| 1 | 10 | 11 | 12 | 12 | 13 | 13 | \multicolumn{4}{l}{TP on Aug. 24, 2015} | | |
| 2 | 9 | 10 | 9 | 10 | 10 | 10 | 10 | 10 | 12 | 12 | 13 | 13 |

TABLE 37-continued

| | Tumor Measurement<br>Caliper Measurement |
|---|---|
| 3 | NTRu on Jul. 30, 2015 |
| 4 | NTRu on Aug. 8, 2015 |

TABLE 38

Tumor Volume

| | | | | | | | Date | | | | | |
|---|---|---|---|---|---|---|---|---|---|---|---|---|
| | Jul. 27, 2015 | 14 Jul. 30, 2015 | Aug. 3, 2015 | Aug. 6, 2015 | Aug. 10, 2015 | Aug. 13, 2015 | Aug. 17, 2015 | Aug. 20, 2015 | Aug. 24, 2015 | Aug. 27, 2015 | Aug. 31, 2015 | Sep. 3, 2015 |
| | | | | | | | Day of Study | | | | | |
| A# | TV (mm$^3$) | TV (mm$^3$) | 8 TV (mm$^3$) | 11 TV (mm$^3$) | 15 TV (mm$^3$) | 18 TV (mm$^3$) | 22 TV (mm$^3$) | 25 TV (mm$^3$) | 29 TV (mm$^3$) | 32 TV (mm$^3$) | 36 TV (mm$^3$) | 39 TV (mm$^3$) |
| | | | | | Group 1: vehicle (ip, tid × 14 first Day 2 doses) | | | | | | | |
| 1 | 108 | 196 | | | | | NTRa on Aug. 1, 2015 | | | | | |
| 2 | 113 | 221 | 384 | 527 | 650 | 650 | 1080 | | TP on Aug. 17, 2015 | | | |
| 3 | 126 | 245 | 405 | 600 | 726 | 726 | 787 | 1008 | TP on Aug. 20, 2015 | | | |
| 4 | | 270 | | | | | NTRu on Aug. 3, 2015 | | | | | |
| Mean | 122.6 | 232.8 | 394.5 | 563.3 | 688 | 688 | 933.3 | 1008 | | | | |
| SEM | 8.1 | 15.8 | 10.5 | 36.8 | 38 | 38 | 146.8 | | | | | |
| n | 4 | 4 | | | 222221 | | | | | | | |
| | | | | Group 2: VHH13 (1 mg/kg, ip, tid × 14 first Day 2 doses) | | | | | | | |
| 1 | 108 | 196 | 320 | 405 | 405 | 405 | 550 | 864 | 1099 | TP on Aug. 24, 2015 | | |
| 2 | 108 | 126 | 196 | 196 | 288 | 288 | 405 | 405 | 500 | 500 | 864 | 1099 |
| 3 | 126 | | | | NTRu on Jul. 30, 2015 | | | | | | | |
| 4 | 126 | 144 | 245 | 320 | | | NTRu on Aug. 8, 2015 | | | | | |
| Mean | 117 | 155.3 | 253.7 | 307 | 346.5 | 346.5 | 477.5 | 634.5 | 799.3 | 500 | 864 | 1098.5 |
| SEM | 5.2 | 21 | 36.1 | 60.7 | 58.5 | 58.5 | 72.5 | 229.5 | 299.3 | | | |
| n | 4 | 3 | 3 | | | | 322222111 | | | | | |

Because two out of the four mice in the control group and also in the treatment group died of estrogen toxicity, no statistical conclusion could be determined. With the data available, the median tumor growth and mean tumor volume were reduced in the treatment group when compared to the control group. This difference was present during the 14 days of treatment but also to day 25 of the study. It took the control group 25 days to reach a tumor volume of 1000 mm$^3$, whereas the treatment group took 36 days to reach a tumor volume of 1000 mm$^3$. This suggests that anti-STAT3 bacterial VHH13 (SEQ ID NO:3) sdAb slows the growth of MCF-7 tumor in vivo. Throughout the study both the control group and the treatment group maintained similar weights. This suggests that the anti-STAT3 bacterial VHH13 (SEQ ID NO:3) sdAb did not cause toxicity with respect to weight loss.

Example 13

Treatment of Human HER2+ (BT474) Breast Cancer with Anti-STAT3 Bacterial VHH13 (SEQ ID NO:3) SDAB in Xenograft Mice In this Example, the efficacy of anti-STAT3 bacterial VHH13 (SEQ ID NO:3) sdAb was determined in the BT474 human breast tumor xenograft in CB.17 SCID mice.

Two groups of 8-12 week old CB.17 SCID mice containing xenographs of 1 mm$^3$ BT474 tumor fragments in their flank were treated according to the protocol shown in Table 39 when the tumors reached an average size of 100-150 mm$^3$. All vehicle (PBS control) and anti-STAT3 bacterial VHH13 (SEQ ID NO:3) sdAb (shown in Table 39 as SB-01) doses were administered intraperitoneally (i.p.) three times daily, six hours apart for fourteen days, with two doses delivered on Day 1 (tid×14, first day 2 doses). The dosing volume for vehicle and anti-STAT3 bacterial VHH13 (SEQ ID NO:3) sdAb was 0.478 mL per 20 grams of body weight (23.88 mL/kg) and was scaled to the body weight of each individual animal. Group 1 received the vehicle and served as the benchmark group for tumor engraftment and progression, as well as the control. Group 2 was given anti-STAT3 bacterial VHH13 (SEQ ID NO:3) sdAb at 1 mg/kg.

TABLE 39

Study protocol

| | | | Regimen 1 | | | |
|---|---|---|---|---|---|---|
| Group | N | Agent | Vehicle | mg/kg | Route | Schedule |
| 1# | 4 | vehicle | — | | ip | tid × 14 first day 2 doses |
| 2 | 4 | SB-01 | | 1 | ip | tid × 14 first day 2 doses |

During the first 14 days of the study, the treatment group received anti-STAT3 B VHH13 and the control group only received the vehicle. As shown in Table 40, during this time, the treatment group maintained and gained weight throughout the study while the control group had lower weights throughout the study. This suggests that the treatment group did not experience toxicity from anti-STAT3 bacterial VHH13 (SEQ ID NO:3) sdAb with respect to weight loss. Both groups mean tumor volume and median tumor volume were similar, and exactly the same on day 15 of the study. On day 59 of the study, both groups reached a tumor volume of 700 cubic mm$^3$. This suggests that the anti-STAT3 bacterial VHH13 (SEQ ID NO:3) sdAb did not reduce the growth of BT474 tumors in vivo when compared to the control group. FIG. 11 illustrates the group mean tumor volume.

human pancreatic cancer cell line PANC-1. For the experiments, the PANC-1 cells were grown until they reached a confluency of 90%. At that time, proliferation studies were carried out using the MTT assay as described above.

The anti-proliferative properties of anti-KRAS (G12D) (SEQ ID NO:2) sdAb on PANC-1 cells three days post treatment are shown in Table 41. PANC-1 cells treated with the anti-KRAS (G12D) (SEQ ID NO:2) sdAb showed an average growth inhibition of 19.9 and 37.7 at 50.0 and 100 µg/ml, respectively.

TABLE 40

BT474 Response Summary

| Group | n | Agent | Vehicle | mg/kg | Route | Schedule | TTE | T-C | % TGD | Stat Sign | MTV (n) Day 60 | PR | CR | TFS | BW Nadir | TR | NTRm | NTR |
|---|---|---|---|---|---|---|---|---|---|---|---|---|---|---|---|---|---|---|
| 1# | 4 | vehicle | — | | ip | tid × 14 first day 2 doses | 49.2 | — | — | | 288 (2) | 0 | 0 | 0 | −9.1% (3) | 0 | 0 | 0 |
| 2 | 4 | SB-01 | | 1 | ip | tid × 14 first day 2 doses | 60.0 | 10.8 | 22 | | 550 (3) | 0 | 0 | 0 | — | 0 | 0 | 0 |

Control Group

Example 14

Production of Mouse Monoclonal Antibody Directed Against Anti-STAT3 Bacterial VHH13 (SEQ ID NO:3) SDAB In this Example, mouse monoclonal antibodies were generated towards the sdAb of the invention. The animals used were BALB/c female mice, 8-10 week. A water-soluble adjuvant was used (CBL). The HAT and the HT used were from Sigma-Aldrich.

Anti-STAT3 bacterial VHH13 (SEQ ID NO:3) sdAb was used to immunize three mice and make hybridoma cell lines. The mice were immunized three times each with water-soluble adjuvant. In one mouse, the serum titer reached 1/51200. The mouse was sacrificed and hybridoma cell lines were made by fusing spleen cells with myeloma cell line Sp2/0.

The fused cells were seeded into 96 well plates by limited dilution. The fused cells were cultured in the presence of HAT, and 651 single clones were tested. Of the 651 single clones, 27 positive clones were identified that specifically bound to anti-STAT3 bacterial VHH13 (SEQ ID NO:3) sdAb antigen.

Example 15

Cytotoxicity of KRAS (G12D) Single Domain Antibodies on PANC-1 Human Pancreatic Cancer Cells This Example demonstrates the anti-proliferative effects of the anti-KRAS (G12D) (SEQ ID NO:2) sdAb using the

TABLE 41

Anti-proliferative Actions of Anti-KRAS (G12D) (SEQ ID NO: 2) sdAb on PANC-1 Cancer Cells

| | Mean Abs ± SE | % Inhibition |
|---|---|---|
| control | 0.281 ± 0.017 | |
| 50 µg/ml | 0.225 ± 0.006 | 19.9 |
| 100 µg/ml | 0.175 ± 0.016 | 37.7 |

Thus, the anti-KRAS (G12D) (SEQ ID NO:2) sdAb showed dose-dependent growth inhibition in the PANC-1 human pancreatic cancer cells.

Example 16

In Vitro Growth Inhibition by TNF-A SDAB

This Example demonstrates the method development to determine TNF-α concentration and evaluation of the inhibition of TNF-α function. The concentration of TNF-α required to show measurable modulation of activity in the U937 human lung lymphoblast cell line was evaluated by quantitation of the ATP present, which signals the presence of metabolically active cells using Promega's Cell Titer-Glo® Luminescent Cell Viability assay.

The U937 cells were seeded in a clear polystyrene 96-well microculture plate (Corning® Costar® 96-well flat bottom plate, Cat. #3997) in a total volume of 90 µL/well. After 24 hours of incubation in a humidified incubator at 37° C. with 5% CO$_2$ and 95% air, 5 µL of 20×, serially diluted TNF-α in growth medium was added to each well in duplicate (10 pt dose response, highest concentration 20 ng/mL). Additionally, 5 µL of 20×, diluted staurosporine in growth medium was added to each well in duplicate (concentration 1 nM).

After 24 hours of culture in the presence of test agents, the concentration of compound required to show measurable modulation of TNF-α activity in the U937 cell line as evaluated by quantitation of the ATP present. Percent cell growth was calculated relative to untreated control wells. All tests were performed in duplicate at each concentration level.

The $EC_{50}$ value for the test agents was estimated using Prism 6.05 by curve-fitting the data using the following four parameter-logistic equation:

$$Y = \frac{Top - Bottom}{1 + (X/IC_{50})^n} + Bottom$$

where Top is the maximal % of control absorbance, Bottom is the minimal % of control absorbance at the highest agent concentration, Y is the % of control absorbance, X is the agent concentration, $IC_{50}$ is the concentration of agent that inhibits cell growth by 50% compared to the control cells, and n is the slope of the curve.

FIGS. 12 and 13 demonstrate that TNF-α is cytotoxic to the U937 cells. The $IC_{50}$ for TNF-α against U937 is 95.10 pg/ml. The TNF-α curve shows a dose titration killing effect.

FIG. 14 demonstrates that TNF-α cytotoxicity against U937 is inhibited by the three different anti-TNF-α VHHs. When anti-TNF-α VHH62 (SEQ ID NO:47) sdAb, anti-TNF-α VHH 66 (SEQ ID NO:45) sdAb, and anti-TNF-α VHH69 (SEQ ID NO:46) sdAb were incubated with a constant dose of TNF-α, at $EC_{50}$, all three anti-TNF-α VHHs inhibit killing of U937 by TNF-α. The $IC_{50}$ of anti-TNF-α VHH62 (SEQ ID NO:47) sdAb was approximately 713.6 ug/ml. The $IC_{50}$ of anti-TNF-α VHH69 (SEQ ID NO:46) sdAb was greater than 208.055 ug/ml. The $IC_{50}$ of anti-TNF-α VHH66 (SEQ ID NO:45) sdAb could not be determined because it completely inhibited the cytotoxicity of TNF-α from concentrations of about $1\times10^2$ ug/ml to $1\times10^2$ ug/ml of anti-TNF-α VHH66 (SEQ ID NO:45) sdAb. In this concentration range of anti-TNF-α VHH66 (SEQ ID NO:45) sdAb, there is an increase in U937 cell growth, and thus complete inhibition of TNF-α activity.

Example 17

Anti-Proliferative Effects of STAT3 VHH13 (SEQ ID NO:3) SDAB on Glioblastoma, Osteosarcoma and Fibrosarcoma Cell Lines The anti-proliferative effects of the STAT3 VHH13 (SEQ ID NO:3) sdAb was assayed using HT1080, SJSA and U87 mg cells. The treatment time and dose is shown in Table 42, as is the percent growth inhibition is shown in Table 42. The $IC_{50}$ of STAT3 VHH13 (SEQ ID NO:3) sdAb in HT1080 cells was 33 μg/ml. The $IC_{50}$ of STAT3 VHH13 (SEQ ID NO:3) sdAb for SJSA cells was 51 μg/ml. The $IC_{50}$ of anti-STAT3 VHH13 (SEQ ID NO:3) sdAb for U87 mg cells was 65 μg/ml. The results show statistically significant suppression with anti-STAT3 VHH13 (SEQ ID NO:3) sdAb within three days after treatment.

TABLE 42

| Growth Inhibition | | |
|---|---|---|
| Dose (μg/ml) | Absorbance ± S.E. | % Inhibition |
| HT1080 cells treated for 72 hr. with SBT-100 | | |
| 0 | 1.58 ± 0.07 | |
| 12.5 | 1.36 ± 0.09 | 14 |

TABLE 42-continued

| Growth Inhibition | | |
|---|---|---|
| Dose (μg/ml) | Absorbance ± S.E. | % Inhibition |
| 25 | 1.09 ± 0.01 | 31 |
| 50 | 0.42 ± 0.04 | 73 |
| 100 | 0.27 ± 0.01 | 83 |
| 200 | 0.22 ± 0.02 | 86 |
| SJSA cells treated for 72 hr. with SBT-100 | | |
| 0 | 1.52 ± 0.15 | |
| 12.5 | 1.52 ± 0.10 | 0 |
| 25 | 1.36 ± 0.09 | 11 |
| 50 | 0.90 ± 0.04 | 41 |
| 100 | 0.27 ± 0.01 | 82 |
| 200 | 0.26 ± 0.01 | 83 |
| U87mg cells treated for 72 hr. with SBT-100 | | |
| 0 | 0.555 ± 0.02 | |
| 12.5 | 0.702 ± 0.04 | 0 |
| 25 | 0.687 ± 0.03 | 0 |
| 50 | 0.456 ± 0.01 | 18 |
| 100 | 0.271 ± 0.02 | 51 |
| 200 | 0.211 ± 0.03 | 62 |

Example 18

Anti-Proliferative Effects of STAT3 VHH13 (SEQ ID NO:3) SDABS on Human Cancer Cell Lines in Combination with Chemotherapy The anti-proliferative effects of the STAT3 VHH13 (SEQ ID NO:3) sdAb was assayed using the human cancer cell line PANC-1 with or without the chemotherapy drug Gemcitabine.

The PANC-1 cell line was maintained as described above. The cells were treated with STAT3 VHH13 (SEQ ID NO:3) sdAb (denoted SBT-100) alone, Gemcitabine alone, or with a combination of STAT3 VHH13 (SEQ ID NO:3) sdAb and Gemcitabine. Addition of 10 micromolar Gemcitabine ($IC_{50}$ concentration) showed a 48% growth inhibition of PANC-1 cells three days after treatment. When 100 μg/ml STAT3 VHH13 (SEQ ID NO:3) sdAb was added to the cells, there was a 68% growth inhibition of PANC-1 cells three days after treatment. The combination of 10 micromolar Gemcitabine and 100 μg/ml STAT3 VHH13 (SEQ ID NO:3) sdAb resulted in an 80% growth inhibition of PANC-1 cells three days after treatment. Similarly, the combination of Gemcitabine (at ⅛th it's IC50 conc.) and 100 μg/ml STAT3 VHH13 (SEQ ID NO:3) sdAb resulted in a 75% growth inhibition of PANC-1 cells three days after treatment.

Table 43 shows the growth inhibition of PANC-1 cells treated for 72 hours with STAT3 VHH13 (SEQ ID NO:3) sdAb (100 μg/ml) alone or in combination with Gemcitabine (5 or 10 μM) prepared in water.

TABLE 43

| Growth Inhibition of PANC-1 Cells | | |
|---|---|---|
| Treatment | % Inhibition | p-value |
| Vehicle | | |
| SBT-100 | 77 | p < 0.001 |
| Gemcitabine (5 μM) | 38 | p < 0.001 |
| Gemcitabine (10 μM) | 35 | p < 0.001 |
| SBT-100 + Gem (5 μM) | 87 | p < 0.001 |
| SBT-100 + Gem (10 μM) | 81 | p < 0.001 |

The growth inhibition was dose dependent, as shown in Table 44.

TABLE 44

Growth Inhibition of PANC-1 Cells

| Treatment | Absorbance | ±SE | % Inhibition | P-value |
|---|---|---|---|---|
| Vehicle Control | 1.050 | 0.075 | | |
| Gemcitabine 10 µM | 0.543 | 0.037 | 48 | p < 0.001 |
| Gemcitabine 5 µM | 0.631 | 0.012 | 40 | p < 0.001 |
| Gemcitabine 2.5 µM | 0.681 | 0.017 | 35 | p < 0.01 |
| Gemcitabine 1.25 µM | 0.861 | 0.077 | 18 | ns |
| Gemcitabine 0.625 µM | 1.050 | 0.162 | 0 | ns |
| Gemcitabine 0.313 µM | 0.997 | 0.054 | 5 | ns |
| Gemcitabine 0.156 µM | 1.210 | 0.062 | 0 | ns |
| Gemcitabine 0.078 µM | 1.230 | 0.039 | 0 | ns |
| Gemcitabine 0.039 µM | 1.240 | 0.014 | 0 | ns |
| Gemcitabine 0.020 µM | 1.560 | 0.101 | 0 | ns |
| SBT-100 100 µg/ml | 0.333 | 0.050 | 68 | p < 0.001 |
| Gemcitabine 10 µM + SBT-100 100 µg/ml | 0.234 | 0.041 | 78 | p < 0.001 |
| Gemcitabine 5 µM + SBT-100 100 µg/ml | 0.294 | 0.044 | 72 | p < 0.001 |
| Gemcitabine 2.5 µM + SBT-100 100 µg/ml | 0.240 | 0.036 | 77 | p < 0.001 |
| Gemcitabine 1.25 µM + SBT-100 100 µg/ml | 0.204 | 0.013 | 81 | p < 0.001 |
| Gemcitabine 0.625 µM + SBT-100 100 µg/ml | 0.232 | 0.008 | 78 | p < 0.001 |
| Gemcitabine 0.313 µM + SBT-100 100 µg/ml | 0.276 | 0.010 | 74 | p < 0.001 |
| Gemcitabine 0.156 µM + SBT-100 100 µg/ml | 0.290 | 0.047 | 72 | p < 0.001 |
| Gemcitabine 0.078 µM + SBT-100 100 µg/ml | 0.265 | 0.015 | 75 | p < 0.001 |
| Gemcitabine 0.039 µM + SBT-100 100 µg/ml | 0.446 | 0.039 | 56 | p < 0.001 |
| Gemcitabine 0.020 µM + SBT-100 100 µg/ml | 0.457 | 0.002 | 56 | p < 0.001 |

Example 19

Treatment of PANC-1 Cells with Anti-STAT3 Bacterial VHH13 (SEQ ID NO:3) SDAB in Xenograft Mice In this Example, the efficacy of anti-STAT3 bacterial VHH13 (SEQ ID NO:3) sdAb was determined in PANC-1 xenograft in mice. The $1.5 \times 10^6$ PANC-1 cells were injected into nude mice, and large xenograft tumors were grown to between 100-150 mm³. The mice were divided into four groups. As shown in Table 45, the groups were left untreated, treated for 14 days with STAT3 VHH13 (SEQ ID NO:3) sdAb alone, treated with Gemcitabine alone, or treated with a combination of STAT3 VHH13 (SEQ ID NO:3) (SBT-100) sdAb and Gemcitabine, followed by a 7 day recovery period. Body weight (Table 46) and inhibition of tumor growth (Table 47) was measured on days 1, 5, 8, 12, 15, 19, and 22.

TABLE 45

Treatment

| Model | # of cells inoculated/ mouse | Group | # of mice | Agent | Dose (mg/kg) | Route | Schedule | Mean Tumour Size (mm³) Day 1 |
|---|---|---|---|---|---|---|---|---|
| PANC-1 | 1.5 × 10⁶ | 1 | 10 | Control (PBS) | 0 | IP | BID × 14 | 125.31 ± 16.5 |
| | | 2 | 6 | STB-100 | 5 | IP | BID × 14 | 107.34 ± 29.46 |
| | | 3 | 6 | Gemcitabine | 20 | IP | QD × 7 | 122.23 ± 23.46 |
| | | 4 | 6 | SBT-100 + Gemcitabine | 5 + 20 | IP | BID × 14 + QD × 7 | 115.87 ± 10.01 |

As shown in Table 46, there was no substantial weight loss observed in mice after the different treatment regimens.

TABLE 46

Body Weight

| BODY WEIGHT (g) | Day 1 | | Day 5 | | Day 8 | | Day 12 | | Day 15 | | Day 19 | | Day 22 | |
|---|---|---|---|---|---|---|---|---|---|---|---|---|---|---|
| | Mean | SEM | Mean | SEM | Mean | SEM | Mean | SEM | Mean | SEM | Mean | SEM | Mean | SEM |
| Control | 23.84 | 0.81 | 24.41 | 0.89 | 24.02 | 0.80 | 24.06 | 0.91 | 23.73 | 0.86 | 24.22 | 0.92 | 24.55 | 0.87 |
| 5 mg/g SBT-100 BID | 23.68 | 0.50 | 24.35 | 0.72 | 23.72 | 0.62 | 23.25 | 0.47 | 23.72 | 0.48 | 24.38 | 0.50 | 24.63 | 0.43 |
| 20 mg/kg Gemcitabine | 23.77 | 0.68 | 23.47 | 0.60 | 23.37 | 0.46 | 23.13 | 0.43 | 212.98 | 0.56 | 23.97 | 0.37 | 24.55 | 0.46 |
| 5 mg/kg SBT-100 + 20 mg/kg Gemcitabine | 22.93 | 0.90 | 22.30 | 0.80 | 22.03 | 0.76 | 21.68 | 0.63 | 21.85 | 0.80 | 22.85 | 0.82 | 23.53 | 0.81 |

PANC-1 tumors demonstrated enhanced inhibition after treatment with either STAT3 VHH13 (SEQ ID NO:3) sdAb alone or Gemcitabine alone. However, treatment with a combination of STAT3 VHH13 (SEQ ID NO:3) sdAb and Gemcitabine resulted in a synergistic inhibition of tumor growth, as seen in Table 48. Combination treatment resulted in increased inhibition of tumor growth as compared to the inhibition seen with either compound alone.

hematoxylin for 45 seconds, and then rinsed three times with water for five minutes followed by 45 seconds with Scott's tap water substitute.

As seen in FIG. 15, anti-STAT3 VHH13 (SEQ ID NO:3) sdAb can be seen in neurons and glial cells, indicating that anti-STAT3 VHH13 (SEQ ID NO:3) sdAb can cross the blood-brain barrier. Anti-STAT3 VHH13 (SEQ ID NO:3) sdAb can also be seen in the cytoplasm of the living cancer

TABLE 47

Tumor Growth

| TUMOR VOLUMES (mm$^3$) | Day 1 | | Day 5 | | Day 8 | | Day 12 | | Day 15 | | Day 19 | | Day 22 | | |
|---|---|---|---|---|---|---|---|---|---|---|---|---|---|---|---|
| | Mean | SEM | Mean | SEM | Mean | SEM | Mean | SEM | Mean | SEM | Mean | SEM | Mean | SEM | p Value |
| Control | 125.31 | 16.15 | 188.50 | 22.66 | 200.72 | 24.42 | 238.05 | 21.52 | 320.80 | 34.54 | 407.55 | 42.23 | 483.19 | 51.64 | |
| 5 mg/g SBT-100 BID | 107.34 | 29.46 | 145.86 | 28.86 | 149.12 | 43.88 | 188.78 | 31.64 | 233.25 | 56.43 | 332.68 | 82.01 | 390.59 | 115.03 | $p < -0.05$ |
| 20 mg/kg Gemcitabine | 122.23 | 23.46 | 165.57 | 41.17 | 183.88 | 25.61 | 191.6 | 35.30 | 246.48 | 27.01 | 312.74 | 40.96 | 411.93 | 43.33 | $p < -0.01$ |
| 5 mg/kg SBT-100 + 20 mg/kg Gemcitabine | 115.87 | 10.01 | 152.90 | 19.60 | 169.92 | 23.99 | 169.42 | 14.14 | 207.00 | 19.43 | 259.31 | 45.72 | 330.88 | 34.96 | $p < -0.001$ |

Table 48 depicts the percent inhibition of tumor growth after the indicated treatment. The combination of STAT3 VHH13 (SEQ ID NO:3) sdAb and Gemcitabine resulted in an increased inhibition of tumor growth as compared to cells treated with either STAT3 VHH13 (SEQ ID NO:3) sdAb or Gemcitabine alone.

TABLE 48

Inhibition of Tumor Growth

| % INHIBITION OF CONTROL | Day 12 | Day 15 | Day 19 | Day 22 |
|---|---|---|---|---|
| 5 mg/kg SBT-100 BID | 20.70 | 27.29 | 18.37 | 19.17 |
| 20 mg/kg Gemcitabine | 19.51 | 23.17 | 23.26 | 14.93 |
| 5 mg/kg SBT-100 + 20 mg/kg Gemcitabine | 28.83 | 35.48 | 36.37 | 31.52 |

Example 20

STAT3 VHH13 (SEQ ID NO:3) SDAB is Localized in Brain and Tumor Cells

Various tissues from the xenograft mice with a MDA-MB-231 tumor as described in Example 11 were taken for immunohistochemical analysis. Slides were made from the tissues using standard procedures. The slides were then blocked with blocking serum. A 1:50 dilution of the primary antibody, in this case a STAT3 rabbit monoclonal antibody (Cell Signaling Inc., Danvers, Mass., Catalog #4904), was made with buffer containing 1.5% blocking buffer for 1.5 hours at room temperature in a humidity chamber. The slides were then rinsed with phosphate buffered saline (PBS). The slides were then incubated in prediluted biotinylated panspecific universal secondary antibody for 10 minutes, followed by a PBS rinse. The slides were then incubated in streptavidin/peroxidase complex reagent for 5 minutes, followed by a PBS rinse. The slides were then incubated in peroxidase substrate solution for 15 minutes, followed by a rinse in distilled water. The slides were counterstained with Gill's #1 cells, as can be seen in FIG. 16. These results show that anti-STAT3 VHH13 (SEQ ID NO:3) sdAb can cross the cell membrane into cells without exogenous targeting sequences or compounds.

Example 21

Internalization of Anti-STAT3 VHH13 (SEQ ID NO:3) SDAB and TNF-A VHH66 (SEQ ID NO:45) SDAB in MDA-MB 231 and PANC-1 Cells MDA-MB 231 and PANC-1 cell lines were plated at low density on chamber slides and left overnight for cell attachment. The next day, the chambers were rinsed with fresh media and STAT3 VHH13 (SEQ ID NO:3) sdAb (diluted 1:10 in media) or TNF-α VHH66 (SEQ ID NO:45) sdAb was added to the chamber. An anti-HIV-1 Reverse Transcriptase (RT) sdAb was used as a negative control.

The slides were incubated for 18 hours after sdAb addition. The chambers were briefly rinsed with media and fixed in ice-cold methanol for 5-10 min. The chambers were then dried and stained with a fluorescent anti-His tag antibody (1:200) (Novus Biologicals, Littleton, Colo.) for 45 min at room temperature. The slides were rinsed in PBS for 5 minutes and mounted.

Both the MDA-MB 231 cells and PANC-1 cells incubated with STAT3 VHH13 (SEQ ID NO:3) sdAb showed positive cytoplasmic staining, as shown in FIGS. 17 and 18 respectively. Similarly, both the MDA-MB 231 cells and PANC-1 cells incubated with TNF-α VHH66 (SEQ ID NO:45) sdAb showed positive cytoplasmic staining, as shown in FIGS. 19 and 20, respectively. As expected, no staining was seen in either cell line with the anti-HIV-1 RT sdAb.

Example 22

Anti-STAT3 VHH13 (SEQ ID NO:3) SDAB Binds KRAS, Mutant KRAS and Mutant STAT3

Protein binding experiments were performed on a Biacore 3000 (General Electric Company, Fairfield, Conn.) at 25° C.

The assay buffer contained 10 mM HEPES buffer (pH 7.4), 150 mM NaCl, 3 mM EDTA, and 0.05% P20. The regeneration buffer contained 10 mM glycine HCl pH 1.75, and the immobilization buffer contained 10 mM sodium acetate, pH 5.0. The flow rate used for capturing the ligand was 5 ul/min. The flow rate used for kinetics analysis was 30 ul/min.

The ligands used for the protein binding experiment were human KRAS and human STAT3. The ligands were directly immobilized by amine coupling (EDC/NHS) at a response unit (RU) of 1000, 420, and 1800 on flow cell 2 and 3 for KRAS and 4 for STAT3, respectively, on a CM5 sensor chip. Flow cell 1 was kept blank and used for background subtraction. The un-occupied sites on the CM5 chip were blocked with 1M ethanol amine. For binding analysis, the analyte, anti-STAT3 VHH13 (SEQ ID NO:3) sdAb or anti-KRAS (G12D) (SEQ ID NO:2) sdAb was flowed over the sensor chip. Binding of analyte to the ligand was monitored in real time. The affinity constant (KD=kd/ka) was calculated from the observed on rate (ka) of off rate (kd), as shown in Table 49. Full kinetic analysis was performed at analyte concentrations as indicated. Chi square analysis was carried out between the actual sensorgram and the sensorgram generated from the BIAnalysis software to determine the accuracy of the analysis. A chi square value within 1-2 is considered accurate and below 1 is highly accurate.

The anti-STAT3 VHH13 (SEQ ID NO:3) sdAb bound both KRAS and STAT3 ligands. The anti-KRAS (G12D) (SEQ ID NO:2) sdAb anti-KRAS VHH analyte bound the KRAS ligand, but not the STAT3 ligand.

Example 23

Anti-STAT3 VHH13 (SEQ ID NO:3) SDAB Binds KRAS, Mutant KRAS and Mutant STAT3

Protein binding experiments were performed on a Biacore 3000 as described above. The ligands used for the protein binding experiment were anti-STAT5-31 sdAb (SEQ ID NO:83), anti-KRAS (G12D) (SEQ ID NO:2) sdAb and anti-STAT3 VHH13 (SEQ ID NO:3) sdAb. The ligands were directly immobilized by amine coupling (EDC/NHS) on a CM5 sensor chip at a response unit (RU) of 440, 140, and 1000 on flow cells 2, 3 and 4, respectively. Flow cell 1 was kept blank and used for background subtraction. The un-occupied sites on the CM5 chip were blocked with 1M ethanol amine. For binding analysis, the analyte, STAT5, normal human KRAS, or mutant human KRAS (12 ASP) was flowed over the sensor chip. Binding of analyte to the ligand was monitored in real time. The affinity constant (KD=kd/ka) was calculated from the observed on rate (ka) of off rate (kd). Full kinetic analysis was performed at analyte concentrations as indicated. Chi square analysis was carried out between the actual sensorgram and the sensorgram generated from the BIAnalysis software to determine the accuracy of the analysis. A chi square value within 1-2 is considered accurate and below 1 is highly accurate.

As shown in Table 50, STAT3, normal and mutant KRAS, as well as STAT5 ligands bound the anti-STAT3 VHH13 (SEQ ID NO:3) sdAb ligand, but not STAT5-31 VHH. anti-KRAS (G12D) (SEQ ID NO:2) sdAb bound the human KRAS protein, but not STAT5 or mutant KRAS (12 ASP).

TABLE 49

| | | | Kinetic Analysis | | | | |
|---|---|---|---|---|---|---|---|
| Ligand | Analyte | ka (1/Ms) | kd (1/s) | Rmax | KD (M) | Conc. (nM) | Chi2 |
| Hu.KRAS 1000 RU Flow cell 2 | Anti-STAT VHH13 | $3.66 \times 10^4$ | $4.62 \times 10^{-3}$ | 11.8 | $1.26 \times 10^{-7}$ | 0 | 0.0783 |
| | | | | | | 12.5 | |
| | | | | | | 25 | |
| | | | | | | 50 | |
| | | | | | | 100 | |
| | | | | | | 100 | |
| | | | | | | 200 | |
| Hu.KRAS 420 RU Flow cell 3 | Anti-KRAS VHH | $3.96 \times 10^3$ | $4.56 \times 10^{-3}$ | 358 | $1.15 \times 10^{-6}$ | 0 | 0.223 |
| | | | | | | 12.5 | |
| | | | | | | 25 | |
| | | | | | | 50 | |
| | | | | | | 100 | |
| | | | | | | 100 | |
| | | | | | | 200 | |
| Hu.STAT3 1800 RU Flow cell 4 | Anti-STAT VHH13 | $7.58 \times 10^4$ | $1.70 \times 10^{-3}$ | 17.6 | $2.24 \times 10^{-8}$ | 0 | 0.194 |
| | | | | | | 12.5 | |
| | | | | | | 25 | |
| | | | | | | 50 | |
| | | | | | | 100 | |
| | | | | | | 100 | |
| | | | | | | 200 | |
| Hu.STAT3 1800 RU | Anti-KRAS VHH | NA | NA | NA | NA | 0-200 | NA |

TABLE 50

Kinetic Analysis

| Ligand | Analyte | ka (1/Ms) | kd (1/s) | Rmax | KD (M) | Conc. (nM) | Chi2 | Result |
|---|---|---|---|---|---|---|---|---|
| STAT5-31 VHH (440 RU) | STAT5 protein | NA | NA | NA | NA | 500 | NA | No binding |
| STAT5-31VHH (440 RU) | hu.KRAS full | NA | NA | NA | NA | 500 | NA | No binding |
| STAT5-31 VHH (440 RU) | hu.KRAS 12 ASP | NA | NA | NA | NA | 500 | NA | No binding |
| anti-KRAS (G12D) (SEQ ID NO: 2) sdAb (140 RU) | STAT5 protein | NA | NA | NA | NA | 500 | NA | No binding |
| anti-KRAS (G12D) (SEQ ID NO: 2) sdAb (140 RU) | hu.KRAS full protein | $1.86 \times 10^5$ | $5.52 \times 10^{-3}$ | 8.94 | $2.96 \times 10^{-8}$ | 500 | 0.42 | Binding |
| Anti-KRAS (G12D) VHH (140 RU) | Hu.KRAS 12ASP | NA | NA | NA | NA | 500 | NA | No binding |
| Anti-STAT3 VHH13 (1000 RU) | STAT5 protein | $2.99 \times 10^4$ | $7.90 \times 10^{-4}$ | 27.2 | $2.64 \times 10^{-8}$ | 500 | 0.0719 | Binding |
| Anti-STAT3 VHH13 (1000 RU) | Hu.KRAS full protein | $5.09 \times 10^4$ | $2.76 \times 10^{-4}$ | 36 | $5.42 \times 10^{-9}$ | 500 | 0.338 | Binding |
| Anti-STAT3 VHH13 (1000 RU) | Hu.KRAS 12ASP | $2.62 \times 10^4$ | $8.06 \times 10^{-7}$ | 12.9 | $3.08 \times 10^{-11}$ | 500 | 0.0546 | Binding |

Example 24

Activity of Anti-STAT3 SDABS

To determine whether the anti-STAT3sdAbs were able to inhibit the induction of the reporter cell line by interleukin-6, the activity of the two anti-STAT3 sdAbs were evaluated in a STAT3 reporter Thaw and Use GloResponse™ cell assay from Promega (Madison, Wis.).

Anti-STAT3 VHH13 (SEQ ID NO:3) sdAb, anti-STAT3 VHH14 (SEQ ID NO:4) sdAb, anti-TNF-α VHH69 (SEQ ID NO:46) sdAb, and BBI608 (napabucasin) (Selleckchem, Houston, Tex.) were used. The concentration used for the assay was at 55.8 and 10 µg/mL for anti-STAT3 VHH13 (SEQ ID NO:3) sdAb, 84.3 and 10 µg/mL for anti-STAT3 VHH14 (SEQ ID NO:4) sdAb, 50.5 and 10 µg/mL for anti-TNF-α VHH69 (SEQ ID NO:46) sdAb and 4.16 and 2 µM for BBI608.

The antibody blocking protocol provided with the Thaw and Use GloResponse™ SIE-luc2P/HEK293 cells was utilized with some modifications. The modifications consisted of pretreating the cells with test article for 48 or 24 hours prior to induction with IL-6.

The assay was performed over 4 days. On assay day 1, GloResponse™ SIE-luc2P/HEK 293 cells were thawed and dispensed into 96-well plates at $1 \times 10^4$ cells/well. The sdAbs and BBI608 control were prepared in assay medium (DMEM supplemented with 10% FBS) and added to triplicate wells. Media was added to wells designated for IL-6 positive and negative controls. All plates were then incubated at 37° C. with 5% $CO_2$ humidity. On assay day 2, an identical set of test article dilutions to day 1 were prepared and added to triplicate wells. Media was added to wells designated for IL-6 positive and negative controls.

IL-6 induction occurred on assay day 3. A 10× IL-6 stock (ThermoFisher, Hanover Park, Ill.) at the $EC_{80}$ concentration (40 ng/mL final concentration) was prepared in assay medium and added to the appropriate test article and IL-6 control ("+IL6") wells on each plate. A triplicate set of wells were designated as "−IL-6" and received assay media only. Plates were again incubated at 37° C. with 5% $CO_2$ humidity.

Detection was performed utilizing the Promega Bio-Glo™ Luciferase Assay System. On assay day 4, the Bio-Glo™ reagent was reconstituted per the manufacturer's instructions. At the end of induction, the plates were removed from the incubator and allowed to equilibrate to ambient temperature for 10-15 minutes. The Bio-Glo™ Reagent was then added to each well. After approximately 3-5 minutes, the relative luminescence units (RLU) was measured using the Veritas Microplate Luminator (Turner Biosystems, Sunnyvale, Calif.).

Statistical analysis by ANOVA with Dunnett Multiple Comparisons Test using the +IL6 as the control column was performed. The Pierce BCA Protein Assay Kit (Thermo Scientific, Rockford, Ill.) was utilized to determine protein concentration. Cells were plated and treated with test article and IL-6 in parallel with the reporter assay. On assay day 4, cells were lysed and harvested for protein concentration utilizing the BCA kit.

Data from the STAT3 Reporter Assay and the BCA protein concentration results are reported in Tables 51 and 52. STAT3 Reporter Assay results were reported as a RLU value. The values were not normalized to protein concentration, although at the highest level of anti-STAT3 VHH13 (SEQ ID NO:3) sdAb, a decrease in protein concentration was observed.

TABLE 51

STAT3 Reporter Assay, 24 Hour Treatment Prior to IL6 Induction

| | −IL6 | +IL6 | VHH13 55.8 µg/mL | VHH13 10 µg/mL | VHH14 84.3 µg/mL | VHH14 10 µg/mL | BB1608 4.16 µM | BB1608 2 µM | VHH69 50.5 µg/mL | VHH69 10 µg/mL | Media |
|---|---|---|---|---|---|---|---|---|---|---|---|
| Luminescence (RLU) | 359 | 132340 | 11445 | 169890 | 520343 | 203210 | 28 | 33 | 194320 | 184364 | 19 |
| Luminescence (RLU) | 604 | 175040 | 12058 | 191537 | 503880 | 223150 | 31 | 39 | 198330 | 165776 | 27 |
| Luminescence (RLU) | 489 | 174030 | 10992 | 164397 | 465649 | 218125 | 41 | 41 | 203139 | 159115 | 31 |
| Average RLU | 483 | 160470 | 11498 | 175275 | 496624 | 214828 | 33 | 38 | 198596 | 169752 | 26 |
| Standard Deviation | 123 | 24367 | 535 | 14349 | 28060 | 10371 | 7 | 4 | 4416 | 13086 | 6 |
| % CV | 25 | 15 | 5 | 8 | 6 | 5 | 20 | 11 | 2 | 8 | 24 |
| Average RLU with Media Blank | 457 | 160444 | 11473 | 175249 | 496598 | 214803 | 8 | 12 | 198571 | 169726 | N/A |
| Fold-Induction RLU/RLU of −IL6 | | 351 | 25 | 383 | 1086 | 470 | 0 | 0 | 434 | 371 | N/A |
| Protein concentration | 252 | 270 | 180 | 277 | 270 | 189 | 174 | 425 | 213 | 237 | N/A |

TABLE 52

STAT3 Reporter Assay, 48 Hour Treatment Prior to IL6 Induction

| | −IL6 | +IL6 | VHH13 55.8 µg/mL | VHH13 10 µg/mL | VHH14 84.3 µg/mL | VHH14 10 µg/mL | BB1608 4.16 µM | BB1608 2 µM | VHH69 50.5 µg/mL | VHH69 10 µg/mL | Media |
|---|---|---|---|---|---|---|---|---|---|---|---|
| Luminescence (RLU) | 634 | 172542 | 104 | 168740 | 494706 | 241785 | 25 | 26 | 237816 | 191241 | 33 |
| Luminescence (RLU) | 476 | 158914 | 96 | 188307 | 488307 | 236843 | 31 | 42 | 220259 | 171796 | 28 |
| Luminescence (RLU) | 485 | 169797 | 68 | 189606 | 458771 | 218982 | 32 | 31 | 219104 | 155927 | 37 |
| Average RLU | 532 | 167084 | 89 | 182218 | 480595 | 232537 | 29 | 33 | 225726 | 172988 | 33 |
| Standard Deviation | 89 | 7208 | 19 | 11690 | 19169 | 11996 | 4 | 8 | 10486 | 17687 | 5 |
| % CV | 17 | 4 | 21 | 6 | 4 | 5 | 13 | 25 | 5 | 10 | 14 |
| Average RLU with Media Blank | 499 | 167052 | 57 | 182185 | 480562 | 232504 | −3 | 0 | 225694 | 172955 | N/A |
| Fold-Induction RLU/RLU of −IL6 | | 335 | 0 | 365 | 963 | 466 | 0 | 0 | 452 | 347 | N/A |
| Protein concentration | 211 | 199 | 92 | 223 | 229 | 216 | 165 | 324 | 208 | 222 | N/A |

Data was analyzed using an ANOVA. The data was shown to be statistically significant at both 24 and 48 hour treatment time points; a P value of <0.0001 was obtained. Inhibition of IL-6 was seen in the wells treated with the highest concentration of anti-STAT3 VHH13 (SEQ ID NO:3) sdAb and with the positive control (BB1608) with both the 24 hours and 48 hours treatment (P values <0.01). Some of the lower RLU value with the highest concentration of anti-STAT3 VHH13 (SEQ ID NO:3) sdAb can be attributed to the decrease in cell numbers (based on protein analysis). The decrease in protein is approximately 2-fold while the decrease in RLU is greater than 10-fold at 24 hours and greater than 1,000-fold at 48 hours. Both concentrations of anti-STAT3 VHH14 (SEQ ID NO:4) sdAb and the highest concentrations of anti-TNF-α VHH69 (SEQ ID NO:46) sdAb showed an enhancement of the IL-6 induction (P values <0.05 and <0.01). The results indicate that anti-STAT3 VHH13 (SEQ ID NO:3) sdAb can enter a cell and can suppress IL-6 production, with results comparable to a small molecule inhibitor of STAT3.

Example 25

Anti-STAT3 SDAB Suppresses IL-6 Production

Anti-STAT3 VHH13 (SEQ ID NO:3) suppressed IL-6 production in HEp-2, MDA-MB-231, and PANC-1 cell lines. The cells were grown to confluence on chamber slides. Anti-STAT3 VHH13 (SEQ ID NO:3) sdAb was added to duplicate chambers (1:10 dilution in media) overnight in a 37° C. incubator. As a negative control, no antibody was added to duplicate chambers. The slides were washed, and either serum-free media alone or 100 ng/ml recombinant human IL-6 (Peprotech, Rocky Hill, N.J.) in serum free media was added to the slides for 15 min at 37° C. The media was then removed and the chamber slides were fixed in ice cold 100% methanol for 10 min at −20° C.

Immunofluorescence assays were performed on the fixed slides. First, the slides were blocked with 3% BSA in PBS was done for one hour at room temperature. The primary antibody, Stat3(124H6) mouse monoclonal antibody (Cell Signaling Technology, Danvers, Mass.) was added to the slides at a 1:1000 dilution overnight in dark box at 4° C. The following day, the slides were washed and the secondary Alexa Fluor 488 anti-mouse IgG antibody (Cell Signaling Technology) was added at a 1:500 dilution and incubated for 1 hour at room temperature. The slides were then washed, mounted with mounting media and viewed with a fluorescence microscope.

Cells that were pre-treated with anti-STAT3 VHH13 (SEQ ID NO:3) sdAb alone showed Stat3 staining in the cytoplasm (FIG. 21 shows HEp-2 cells, but similar results were seen with MDA-MB-231 and PANC-1 cells). The nucleus of cells treated with IL-6 stained positive for Stat3 (FIG. 22). The cells that were pre-treated with anti-STAT3 VHH13 (SEQ ID NO:3) sdAb followed by treatment with IL-6 did not stain positive for Stat3 in the nucleus, but rather showed Stat3 staining in the cytoplasm (FIG. 23). Thus, anti-STAT3 VHH13 (SEQ ID NO:3) sdAb blocks the translocation of Stat3 to the nucleus following IL-6 treatment.

Example 26

VEGF-A Analysis in Retinal Cells Treated with Anti-STAT3 SDAB

Inhibition of the vascular endothelial growth factor A (VEGF-A) production was assessed in retinal cells exposed to anti-STAT3 sdAb, in particular anti-STAT3 VHH13 (SEQ ID NO:3) sdAb. For Experiment 1, the retinal cell line ARPE-19 (ATCC, Manassas, Va.) were plated at $5 \times 10^4$ cells/well into a 24-well plate and grown to confluence. All incubations with cells were performed in a 37° C., 5% $CO_2$ humidified incubator. The media was replaced with growth media (DMEM:HAM12) containing 1% FBS and incubated overnight. The media was then removed and replaced with media containing anti-STAT3 VHH13 (SEQ ID NO:3) sdAb at 0.5 µg/mL, anti-STAT3 VHH13 (SEQ ID NO:3) sdAb at 0.1 µg/ml, anti-STAT-3 monoclonal antibody (Abcam, Cambridge Mass.), or media alone, and incubated for 24 or 72 hours. At that time, the supernatant was removed and stored at ≤−65° C. for ELISA analysis. Cells were lysed using RIPA lysis buffer (ThermoFisher Scientific, Rockford, Ill.) and the protein content of the cell lysate was measured in the BCA assay (ThermoFisher Scientific) according to the kit instructions. VEGF-A was measured utilizing the Human VEGF-A ELISA Kit (ThermoFisher Scientific) in accordance with the kit instructions.

For Experiment 2, the assay was performed in a 96-well plate format. ARPE-19 cells were plated at $1.5 \times 10^4$ cells/well into three 96-well plates and allowed to grow to confluence. The media was replaced with growth media (DMEM:HAM12) containing 1% FBS and incubated overnight. The media was then replaced with media containing anti-STAT3 VHH13 (SEQ ID NO:3) sdAb at 100, 10, 1 or 0.1 µg/ml, anti-EMP2 antibody (Abcam), or media, and incubated for 12, 24 or 48 hours. At the appropriate time point, the supernatant was removed and stored at ≤−65° C. for ELISA analysis. Cells were lysed using RIPA lysis buffer and the protein content of the cell lysate was measured in the BCA assay according to the kit instructions. VEGF-A was measured utilizing the Human VEGF-A ELISA Kit. For both experiments, statistical analysis by ANOVA with Dunnett Multiple Comparisons Test using the negative control as the control column was performed.

ELISA results were reported as pictograms (pg) VEGF-A/mL and then adjusted for the dilution of samples in the ELISA (1:2 for Experiment 1 and 1:5 for Experiment 2). The ELISA results were then normalized for protein content. Data from Experiment 1 is reported in Table 53 and Table 54. For samples collected at 24 hours, inhibition of VEGF-A was not definitively detected. At 0.5 µg/mL anti-STAT3 VHH13 (SEQ ID NO:3) sdAb, triplicate wells ranged from 61.9 to 115 pg VEGF-A/µg of protein which was similar to the negative control (NC) media only wells which ranged from 59.3 to 105 pg VEFG/µg protein. The positive control (PC) (anti-STAT3 monoclonal antibody) ranged from 48.8 to 66.4 pg VEFG/µg protein slightly lower but overlapping the range seen with the negative control. Statistical analysis confirmed that the variation seen was not statistically significant (P value >0.05). The samples collected at 72 hours were higher than the top standard curve.

TABLE 53

Experiment 1 VEGF-A ELISA Results

| Sample | Result (pg VEGF-A per mL) | Mean Result (pg VEGF-A per mL) | Std. Dev. | CV % | Adj. Result* (pg VEGF-A per mL) | Mean (pg VEGF-A per mL) | Std. Dev. | % Negative Control |
|---|---|---|---|---|---|---|---|---|
| STAT3 VHH13 at 0.5 µg/well 24 Hr Well 1 | 466 808 | 637 | 241.6 | 37.9 | 1274 | 2664 | 1303.3 | 92.0 |
| STAT3 VHH13 at 0.5 µg/well 24 Hr Well 2 | 1277 1580 | 1429 | 214.2 | 15.0 | 2857 | | | |
| STAT3 VHH13 at 0.5 µg/well 24 Hr Well 3 | 1823 2036 | 1930 | 150.5 | 7.8 | 3859 | | | |
| STAT3 VHH13 at 0.1 µg/well 24 Hr Well 1 | 464 575 | 520 | 78.3 | 15.1 | 1040 | 2060 | 1280.0 | 71.1 |
| STAT3 VHH13 at 0.1 µg/well 24 Hr Well 2 | 1478 2018 | 1748 | 1748 | 381.6 | 3496 | | | |
| STAT3 VHH13 at 0.1 µg/well 24 Hr Well 3 | 727 917 | 822 | 822 | 134.7 | 1644 | | | |
| PC (anti-STAT3 antibody @ 1:500 dil) 24 Hr Well 1 | 551 777 | 664 | 159.9 | 24.1 | 1328 | 1970 | 556.6 | 68.0 |
| PC (anti-STAT3 antibody @ 1:500 dil) 24 Hr Well 2 | 1082 1228 | 1155 | 1155 | 103.2 | 2311 | | | |
| PC (anti-STAT3 antibody @ 1:500 dil) 24 Hr Well 3 | 1086 | 1136 | 1136 | 70.6 | 2272 | | | |

TABLE 53-continued

Experiment 1 VEGF-A ELISA Results

| Sample | Result (pg VEGF-A per mL) | Mean Result (pg VEGF-A per mL) | Std. Dev. | CV % | Adj. Result* (pg VEGF-A per mL) | Mean (pg VEGF-A per mL) | Std. Dev. | % Negative Control |
|---|---|---|---|---|---|---|---|---|
| NC (media only) 24 Hr Well 1 | 928 | 1008 | 113.5 | 11.3 | 2016 | 2896 | 826.1 | 100.0 |
| NC (media only) 24 Hr Well 2 | 1668 | 1828 | 1828 | 226.1 | 3655 | | | |
| NC (media only) 24 Hr Well 3 | 1496 | 1508 | 1508 | 17.2 | 3016 | | | |
| STAT3 VHH13 at 0.5 µg/well 72 Hr Well 1 | >6,000 >6,000 | 1289811 | 481845.2 | 37.4 | >12,000 | | | |
| STAT3 VHH13 at 0.5 µg/well 72 Hr Well 2 | >6,000 >6,000 | 320652 | 1461.5 | 0.5 | >12,000 | | | |
| STAT3 VHH13 at 0.5 µg/well 72 Hr Well 3 | >6,000 >6,000 | 351430 | 166765.9 | 47.5 | >12,000 | | | |
| STAT3 VHH13 at 0.1 µg/well 72 Hr Well 1 | >6,000 >6,000 | 896832 | 338049.2 | 37.7 | >12,000 | | | |
| STAT3 VHH13 at 0.1 µg/well 72 Hr Well 2 | >6,000 >6,000 | 4936142 | 0.0 | 0.0 | >12,000 | | | |
| STAT3 VHH13 at 0.1 µg/well 72 Hr Well 3 | >6,000 >6,000 | 282889 | 86269.8 | 30.5 | >12,000 | | | |
| PC (anti-STAT3 antibody @ 1:500 dil) 72 Hr Well 1 | >6,000 >6,000 | Range? | Range? | Range? | >12,000 | | | |
| PC (anti-STAT3 antibody @ 1:500 dil) 72 Hr Well 2 | >6,000 >6,000 | 10802 | 215.7 | 2.0 | >12,000 | | | |
| PC (anti-STAT3 antibody @ 1:500 dil) 72 Hr Well 3 | >6,000 >6,000 | Range? | Range? | Range? | >12,000 | | | |
| NC (media only) 72 Hr Well 1 | >6,000 >6,000 | 45898 | 41321.1 | 90.0 | >12,000 | | | |
| NC (media only) 72 Hr Well 2 | 1065 5769 | 3417 | 3326.5 | 97.3 | 6835 | | | |
| NC (media only) 72 Hr Well 3 | >6,000 >6,000 | 418930 | 170327.2 | 40.7 | >12,000 | | | |

*All samples tested at a 1:2 dilution

TABLE 54

Experiment 1 VEGF-A Normalized Results

| Sample | pg VEGF-A per well# | Protein Conc. (µg/mL) | Total protein per well# | pg VEGF-A per µg protein | Mean (pg VEGF-A per µg protein) | Std. Dev. | % Control |
|---|---|---|---|---|---|---|---|
| STAT3 VHH13 at 0.5 µg/well 24 Hr Well 1 | 637 | 206 | 10 | 62 | 99 | 41.7 | 115.8 |
| STAT3 VHH13 at 0.5 µg/well 24 Hr Well 2 | 1429 | 315 | 16 | 91 | | | |
| STAT3 VHH13 at 0.5 µg/well 24 Hr Well 3 | 1930 | 268 | 13 | 144 | | | |
| STAT3 VHH13 at 0.1 µg/well 24 Hr Well 1 | 520 | 245 | 12 | 42 | 66 | 37 | 76.8 |
| STAT3 VHH13 at 0.1 µg/well 24 Hr Well 2 | 1748 | 323 | 16 | 108 | | | |
| STAT3 VHH13 at 0.1 µg/well 24 Hr Well 3 | 822 | 357 | 18 | 46 | | | |
| PC (anti-STAT3 antibody @ 1:500 dil) 24 Hr Well 1 | 664 | 272 | 14 | 49 | 58 | 8.9 | 68.4 |
| PC (anti-STAT3 antibody @ 1:500 dil) 24 Hr Well 2 | 1155 | 387 | 19 | 60 | | | |
| PC (anti-STAT3 antibody @ 1:500 dil) 24 Hr Well 3 | 1136 | 342 | 17 | 66 | | | |

TABLE 54-continued

Experiment 1 VEGF-A Normalized Results

| Sample | pg VEGF-A per well[#] | Protein Conc. (μg/mL) | Total protein per well[#] | pg VEGF-A per μg protein | Mean (pg VEGF-A per μg protein) | Std. Dev. | % Control |
|---|---|---|---|---|---|---|---|
| NC (media only) 24 Hr Well 1 | 1008 | 340 | 17 | 59 | 85 | 23.5 | 100.0 |
| NC (media only) 24 Hr Well 2 | 1828 | 348 | 17 | 105 | | | |
| NC (media only) 24 Hr Well 3 | 1508 | 329 | 16 | 92 | | | |

[#]Based on collecting 0.5 ml of supernatant per well and the addition of 0.05 μl per well of RIPA buffer.

Data from Experiment 2 is reported in Table 55 and Table 56. Data was analyzed using an ANOVA. The data was shown to be statistically significant at all time points. For the 12 and 48 hour treatments a P value of <0.0001 was obtained and for the 24 hour treatment the P value was 0.0004. At 100 μg/mL anti-STAT3 VHH13, less VEGF-A was detected. At 48 hours, the pg VEGF-A/μg protein for the 100 μg/mL anti-STAT3 VHH13 treatment was at 11% of the negative control (P<0.01). Similar decreases in VEGF-A were seen with the 12 and 24 hour treatments (20.1% and 7.5% decrease respectively; P values of <0.01 for both). This decrease in VEGF-A was not seen with lower concentrations of anti-STAT3 VHH13. It should be noted that less protein was also detected from the wells with 100 μg/mL anti-STAT3 VHH13, which could be due to the inhibition of cell growth and proliferation, resulting in the lower concentrations of protein seen in Experiment 2.

TABLE 55

Experiment 2 VEGF-A ELISA Results

| Sample | Result (pg VEGF-A per mL) | Mean Result (pg VEGF-A per mL) | Std. Dev. | CV % | Adj. Result* (pg VEGF-A per mL) | Mean (pg VEGF-A per mL) | Std. Dev. | % Negative Control |
|---|---|---|---|---|---|---|---|---|
| STAT3 VHH13 at 0.1 μg/well 12 Hr Well 1 | 29.44 27.64 | 28.54 | 1.272 | 4.5 | 142.71 | 159.7 | 23.13 | 123.8 |
| STAT3 VHH13 at 0.1 μg/well 12 Hr Well 2 | 29.74 30.38 | 30.06 | 0.455 | 1.5 | 150.31 | | | |
| STAT3 VHH13 at 0.1 μg/well 12 Hr Well 3 | 36.84 37.57 | 37.2 | 0.519 | 1.4 | 186.02 | | | |
| STAT3 VHH13 at 1 μg/well 12 Hr Well 1 | 26.74 24.91 | 25.82 | 1.3 | 5 | 129.12 | 142.5 | 16.67 | 110.5 |
| STAT3 VHH13 at 1 μg/well 12 Hr Well 2 | 26.62 28.24 | 27.43 | 1.15 | 4.2 | 137.14 | | | |
| STAT3 VHH13 at 1 μg/well 12 Hr Well 3 | 33.18 31.29 | 32.23 | 1.337 | 4.1 | 161.16 | | | |
| STAT3 VHH13 at 10 μg/well 12 Hr Well 1 | 29.66 31.2 | 30.43 | 1.092 | 3.6 | 152.14 | 139.00 | 15.4 | 107.8 |
| STAT3 VHH13 at 10 μg/well 12 Hr Well 2 | 24.52 24.31 | 24.41 | 0.151 | 0.6 | 122.07 | | | |
| STAT3 VHH13 at 10 μg/well 12 Hr Well 3 | 27.98 29.18 | 28.58 | 0.848 | 3 | 142.92 | | | |
| STAT3 VHH13 at 100 μg/well 12 Hr Well 1 | 5.09 4.62 | 4.86 | 0.327 | 6.7 | 24.27 | 23.8 | 0.79 | 18.5 |
| STAT3 VHH13 at 100 μg/well 12 Hr Well 2 | 5.3 4.41 | 4.86 | 0.623 | 12.8 | 24.27 | | | |
| STAT3 VHH13 at 100 μg/well 12 Hr Well 3 | 4.83 4.33 | 4.58 | 0.356 | 7.8 | 22.91 | | | |
| NC (media only) 12 Hr Well 1 | 28.76 28.76 | 26.76 | 0 | 0 | 143.78 | 128.9 | 23.87 | 100 |
| NC (media only) 12 Hr Well 2 | 28.58 28.07 | 28.33 | 0.363 | 1.3 | 141.63 | | | |
| NC (media only) 12 Hr Well 3 | 20.52 20.05 | 20.28 | 0.311 | 1.6 | 101.4 | | | |
| PC (anti-STAT3 antibody @ 1:500 dil) 12 Hr Well 1 | 25.76 24.86 | 25.31 | 0.634 | 2.5 | 12656 | 120.1 | 12.65 | 93.2 |
| PC (anti-STAT3 antibody @ 1:500 dil) 12 Hr Well 2 | 20.77 21.45 | 21.11 | 0.482 | 2.3 | 105.55 | | | |
| PC (anti-STAT3 antibody @ 1:500 dil) 12 Hr Well 3 | 28.33 22.99 | 25.66 | 3.777 | 14.7 | 128.28 | | | |
| STAT3 VHH13 at 0.1 μg/well 24 Hr Well 1 | 58.86 52.60 | 55.73 | 4.431 | 8 | 278.66 | 287.4 | 14 | 93.6 |

TABLE 55-continued

Experiment 2 VEGF-A ELISA Results

| Sample | Result (pg VEGF-A per mL) | Mean Result (pg VEGF-A per mL) | Std. Dev. | CV % | Adj. Result* (pg VEGF-A per mL) | Mean (pg VEGF-A per mL) | Std. Dev. | % Negative Control |
|---|---|---|---|---|---|---|---|---|
| STAT3 VHH13 at 0.1 µg/well 24 Hr Well 2 | 59.52 52.51 | 56.02 | 4.959 | 8.9 | 280.09 | | | |
| STAT3 VHH13 at 0.1 µg/well 24 Hr Well 3 | 64.54 56.89 | 60.72 | 5.413 | 8.9 | 303.58 | | | |
| STAT3 VHH13 at 1 µg/well 24 Hr Well 1 | 78.44 70.78 | 74.61 | 5.413 | 7.3 | 373.06 | 327.9 | 39.69 | 106.8 |
| STAT3 VHH13 at 1 µg/well 24 Hr Well 2 | 68.61 56.23 | 62.42 | 8.755 | 14 | 312.11 | | | |
| STAT3 VHH13 at 1 µg/well 24 Hr Well 3 | 63.71 55.71 | 59.71 | 5.658 | 9.5 | 298.74 | | | |
| STAT3 VHH13 at 10 µg/well 24 Hr Well 1 | 57.85 54.04 | 55.95 | 2.696 | 4.8 | 279.74 | 350.7 | 72.26 | 1142 |
| STAT3 VHH13 at 10 µg/well 24 Hr Well 2 | 72.69 66.53 | 69.61 | 4.356 | 6.3 | 348.06 | | | |
| STAT3 VHH13 at 10 µg/well 24 Hr Well 3 | 84.97 84.71 | 84.84 | 0.19 | 0.2 | 424.20 | | | |
| STAT3 VHH13 at 100 µg/well 24 Hr Well 1 | 6.01 5.67 | 5.84 | 0.238 | 4.1 | 29.21 | 19.2 | 8.66 | 6.3 |
| STAT3 VHH13 at 100 µg/well 24 Hr Well 2 | 2.82 2.9 | 2.86 | 0.059 | 2.1 | 14.31 | | | |
| STAT3 VHH13 at 100 µg/well 24 Hr Well 3 | 2.61 3.03 | 2.82 | 0.296 | 10.5 | 14.10 | | | |
| NC (media only) 24 Hr Well 1 | 62.91 61.5 | 62.21 | 0.997 | 1.6 | 311.04 | 307.1 | 45.18 | 100 |
| NC (media only) 24 Hr Well 2 | 51.81 52.21 | 52.01 | 0.278 | 0.5 | 260.04 | | | |
| NC (media only) 24 Hr Well 3 | 70.61 69.45 | 70.03 | 0.815 | 1.2 | 350.15 | | | |
| PC (anti-STAT3 antibody @ 1:500 dil) 24 Hr Well 1 | 48.11 42.11 | 45.11 | 4.238 | 9.4 | 225.54 | 264.1 | 8.66 | 6.3 |
| PC (anti-STAT3 antibody @ 1:500 dil) 24 Hr Well 2 | 55.27 48.72 | 51.99 | 4.633 | 8.9 | 259.95 | | | |
| PC (anti-STAT3 antibody @ 1:500 dil) 24 Hr Well 3 | 59.44 63.27 | 61.35 | 2.708 | 4.4 | 306.75 | | | |
| STAT3 VHH13 at 0.1 µg/well 48 Hr Well 1 | 195.75 182.85 | 189.30 | 9.122 | 4.8 | 946.50 | 966 | 45.18 | 100 |
| STAT3 VHH13 at 0.1 µg/well 48 Hr Well 2 | 173.80 166.73 | 170.27 | 4.997 | 2.9 | 851.33 | | | |
| STAT3 VHH13 at 0.1 µg/well 48 Hr Well 3 | 220.87 219.22 | 220.04 | 1.17 | 0.5 | 1100.22 | | | |
| STAT3 VHH13 at 1 µg/well 48 Hr Well 1 | 168.84 181.59 | 175.22 | 9.012 | 5.1 | 876.08 | 1004.7 | 40.76 | 86 |
| STAT3 VHH13 at 1 µg/well 48 Hr Well 2 | 195.75 212.03 | 203.89 | 11.508 | 5.6 | 1019.44 | | | |
| STAT3 VHH13 at 1 µg/well 48 Hr Well 3 | 225.75 221.67 | 223.71 | 2.880 | 1.3 | 1118.55 | | | |
| STAT3 VHH13 at 10 µg/well 48 Hr Well 1 | 194.18 188.16 | 191.17 | 4.257 | 2.2 | 955.85 | 925.1 | 125.59 | 99.3 |
| STAT3 VHH13 at 10 µg/well 48 Hr Well 2 | 194.77 198.36 | 196.56 | 2.538 | 1.3 | 982.81 | | | |
| STAT3 VHH13 at 10 µg/well 48 Hr Well 3 | 158.85 175.83 | 167.34 | 12.002 | 7.2 | 836.69 | | | |
| STAT3 VHH13 at 100 µg/well 48 Hr Well 1 | 7.83 7.72 | 7.78 | 0.082 | 1.1 | 38.88 | 35.6 | 5.54 | 3.7 |
| STAT3 VHH13 at 100 µg/well 48 Hr Well 2 | 7.49 8.03 | 7.76 | 0.384 | 5 | 38.78 | | | |
| STAT3 VHH13 at 100 µg/well 48 Hr Well 3 | 5.86 5.83 | 5.85 | 0.027 | 0.5 | 29.23 | | | |
| NC (media only) 48 Hr Well 1 | 202.96 188.16 | 195.55 | 10.455 | 5.3 | 977.76 | 972.4 | 32.87 | 100 |
| NC (media only) 48 Hr Well 2 | 209.84 191.09 | 200.46 | 13.254 | 6.6 | 1002.32 | | | |
| NC (media only) 48 Hr Well 3 | 205.67 169.23 | 187.45 | 25.767 | 13.7 | 937.23 | | | |
| PC (anti-STAT3 antibody @ 1:500 dil) 48 Hr Well 1 | 186.06 168.89 | 177.48 | 12.142 | 6.8 | 887.38 | 887.7 | 41.95 | 91.3 |

TABLE 55-continued

Experiment 2 VEGF-A ELISA Results

| Sample | Result (pg VEGF-A per mL) | Mean Result (pg VEGF-A per mL) | Std. Dev. | CV % | Adj. Result* (pg VEGF-A per mL) | Mean (pg VEGF-A per mL) | Std. Dev. | % Negative Control |
|---|---|---|---|---|---|---|---|---|
| PC (anti-STAT3 antibody @ 1:500 dil) 48 Hr Well 2 | 196.49 175.44 | 185.96 | 14.884 | 8 | 929.82 | | | |
| PC (anti-STAT3 antibody @ 1:500 dil) 48 Hr Well 3 | 177.32 161.04 | 169.18 | 11.512 | 6.8 | 845.90 | | | |

*All samples tested at a 1:2 dilution

TABLE 56

Experiment 2 VEGF-A Normalized Results

| Sample | pg VEGF-A per mL.# | Protein Conc. (µg/mL) | ML RIPA buffer/well | Total protein per well | pg VEGF-A per µg protein | Mean (pg VEGF-A per µg protein) | Std. Dev. | % Control |
|---|---|---|---|---|---|---|---|---|
| STAT3 VHH13 at 0.1 µg/well 12 Hr Well 1 | 14.3 | 67 | 0.1 | 6.7 | 2.1 | 2.540 | 0.5 | 134.4 |
| STAT3 VHH13 at 0.1 µg/well 12 Hr Well 2 | 15 | 62 | 0.1 | 6.2 | 2.4 | | | |
| STAT3 VHH13 at 0.1 µg/well 12 Hr Well 3 | 18.6 | 61 | 0.1 | 6.1 | 3 | | | |
| STAT3 VHH13 at 1 µg/well 12 Hr Well 1 | 12.9 | 66 | 0.1 | 6.6 | 2 | 2.273 | 0.4 | 120.3 |
| STAT3 VHH13 at 1 µg/well 12 Hr Well 2 | 13.7 | 63 | 0.1 | 6.3 | 2.2 | | | |
| STAT3 VHH13 at 1 µg/well 12 Hr Well 3 | 16.1 | 60 | 0.1 | 6 | 2.7 | | | |
| STAT3 VHH13 at 10 µg/well 12 Hr Well 1 | 15.2 | 61 | 0.1 | 6.1 | 2.5 | 2.148 | 0.3 | 113.7 |
| STAT3 VHH13 at 10 µg/well 12 Hr Well 2 | 12.2 | 64 | 0.1 | 6.4 | 1.9 | | | |
| STAT3 VHH13 at 10 µg/well 12 Hr Well 3 | 14.3 | 70 | 0.1 | 7 | 2 | | | |
| STAT3 VHH13 at 100 µg/well 12 Hr Well 1 | 2.4 | 64 | 0.1 | 6.4 | 0.4 | 0.4 | 0.380 | 0 |
| STAT3 VHH13 at 100 µg/well 12 Hr Well 2 | 2.4 | 62 | 0.1 | 6.2 | 0.4 | | | |
| STAT3 VHH13 at 100 µg/well 12 Hr Well 3 | 2.3 | 62 | 0.1 | 6.2 | 0.4 | | | |
| NC (media only) 12 Hr Well 1 | 14.4 | 73 | 0.1 | 7.3 | 2 | 1.889 | 0.3 | 100 |
| NC (media only) 12 Hr Well 2 | 14.2 | 67 | 0.1 | 6.7 | 2.1 | | | |
| NC (media only) 12 Hr Well 3 | 10.1 | 64 | 0.1 | 6.4 | 1.6 | | | |
| PC (anti-STAT3 antibody @ 1:500 dil) 12 Hr Well 1 | 12.7 | 66 | 0.1 | 6.6 | 1.9 | 1.917 | 0.2 | 101.5 |
| PC (anti-STAT3 antibody @ 1:500 dil) 12 Hr Well 2 | 10.6 | 61 | 0.1 | 6.1 | 1.7 | | | |
| PC (anti-STAT3 antibody @ 1:500 dil) 12 Hr Well 3 | 12.8 | 61 | 0.1 | 6.1 | 2.1 | | | |

TABLE 56-continued

Experiment 2 VEGF-A Normalized Results

| Sample | pg VEGF-A per mL[#] | Protein Conc. (µg/mL) | ML RIPA buffer/well | Total protein per well | pg VEGF-A per µg protein | Mean (pg VEGF-A per µg protein) | Std. Dev. | % Control |
|---|---|---|---|---|---|---|---|---|
| STAT3 VHH13 at 0.1 µg/well 24 Hr Well 1 | 27.9 | 83 | 0.089 | 7.4 | 3.8 | 4.152 | 0.5 | 94.1 |
| STAT3 VHH13 at 0.1 µg/well 24 Hr Well 2 | 28 | 72 | 0.097 | 7.0 | 4.0 | | | |
| STAT3 VHH13 at 0.1 µg/well 24 Hr Well 3 | 30.4 | 73 | 0.089 | 6.5 | 4.7 | | | |
| STAT3 VHH13 at 1 µg/well 24 Hr Well 1 | 37.3 | 68 | 0.1 | 6.8 | 5.5 | 4.084 | 1.6 | 92.5 |
| STAT3 VHH13 at 1 µg/well 24 Hr Well 2 | 31.2 | 71 | 0.1 | 7.1 | 4.4 | | | |
| STAT3 VHH13 at 1 µg/well 24 Hr Well 3 | 29.9 | 126 | 0.1 | 12.6 | 2.4 | | | |
| STAT3 VHH13 at 10 µg/well 24 Hr Well 1 | 28 | 64 | 0.1 | 6.4 | 4.4 | 5.290 | 0.9 | 119.8 |
| STAT3 VHH13 at 10 µg/well 24 Hr Well 2 | 34.8 | 64 | 0.1 | 6.4 | 5.4 | | | |
| STAT3 VHH13 at 10 µg/well 24 Hr Well 3 | 42.4 | 70 | 0.1 | 7 | 6.1 | | | |
| STAT3 VHH13 at 100 µg/well 24 Hr Well 1 | 2.9 | 62 | 0.1 | 6.2 | 0.5 | 0.329 | 0.1 | 7.5 |
| STAT3 VHH13 at 100 µg/well 24 Hr Well 2 | 1.4 | 56 | 0.1 | 5.6 | 0.3 | | | |
| STAT3 VHH13 at 100 µg/well 24 Hr Well 3 | 1.4 | 54 | 0.1 | 5.4 | 0.3 | | | |
| NC (media only) 24 Hr Well 1 | 31.1 | 76 | 0.095 | 7.2 | 4.3 | 4.414 | 1.1 | 100 |
| NC (media only) 24 Hr Well 2 | 26 | 77 | 0.1 | 7.7 | 3.4 | | | |
| NC (media only) 24 Hr Well 3 | 35 | 105 | 0.06 | 6.3 | 5.6 | | | |
| PC (anti-STAT3 antibody @ 1:500 dil) 24 Hr Well 1 | 22.6 | 73 | 0.087 | 6.4 | 3.6 | 3.838 | 0.3 | 86.9 |
| PC (anti-STAT3 antibody @ 1:500 dil) 24 Hr Well 2 | 26 | 72 | 0.096 | 6.9 | 3.8 | | | |
| PC (anti-STAT3 antibody @ 1:500 dil) 24 Hr Well 3 | 30.7 | 73 | 0.1 | 7.3 | 4.2 | | | |
| STAT3 VHH13 at 0.1 µg/well 48 Hr Well 1 | 94.7 | 74 | 0.091 | 6.7 | 14.1 | 14.067 | 1 | 107.4 |
| STAT3 VHH13 at 0.1 µg/well 48 Hr Well 2 | 85.1 | 74 | 0.088 | 6.5 | 13.1 | | | |
| STAT3 VHH13 at 0.1 µg/well 48 Hr Well 3 | 110 | 73 | 0.1 | 7.3 | 15.1 | | | |
| STAT3 VHH13 at 1 µg/well 48 Hr Well 1 | 87.6 | 72 | 0.098 | 7.1 | 12.4 | 13.796 | 1.5 | 105.4 |
| STAT3 VHH13 at 1 µg/well 48 Hr Well 2 | 101.9 | 77 | 0.097 | 7.5 | 13.6 | | | |
| STAT3 VHH13 at 1 µg/well 48 Hr Well 3 | 111.9 | 73 | 0.1 | 7.3 | 15.3 | | | |
| STAT3 VHH13 at 10 µg/well 48 Hr Well 1 | 95.6 | 71 | 6.8 | 6.8 | 14 | 13.696 | 1.8 | 104.6 |

TABLE 56-continued

Experiment 2 VEGF-A Normalized Results

| Sample | pg VEGF-A per mL[#] | Protein Conc. (µg/mL) | ML RIPA buffer/well | Total protein per well | pg VEGF-A per µg protein | Mean (pg VEGF-A per µg protein) | Std. Dev. | % Control |
|---|---|---|---|---|---|---|---|---|
| STAT3 VHH13 at 10 µg/well 48 Hr Well 2 | 98.3 | 67 | 6.4 | 6.4 | 15.3 | | | |
| STAT3 VHH13 at 10 µg/well 48 Hr Well 3 | 83.7 | 71 | 701 | 7.1 | 11.8 | | | |
| STAT3 VHH13 at 100 µg/well 48 Hr Well 1 | 3.9 | 27 | 2.7 | 2.7 | 1.4 | 1.458 | 0.1 | 11.1 |
| STAT3 VHH13 at 100 µg/well 48 Hr Well 2 | 3.9 | 25 | 2.5 | 2.5 | 1.6 | | | |
| STAT3 VHH13 at 100 µg/well 48 Hr Well 3 | 3.9 | 22 | 2.1 | 2.1 | 1.4 | | | |
| NC (media only) 48 Hr Well 1 | 97.8 | 75 | 7.5 | 7.5 | 13 | 13.092 | 0.6 | 100 |
| NC (media only) 48 Hr Well 2 | 100.2 | 83 | 7.3 | 7.3 | 13.7 | | | |
| NC (media only) 48 Hr Well 3 | 93.7 | 78 | 7.5 | 7.5 | 12.5 | | | |
| PC (anti-STAT3 antibody @ 1:500 dil) 48 Hr Well 1 | 88.7 | 69 | 6.8 | 6.8 | 131 | 13.412 | 1 | 102.4 |
| PC (anti-STAT3 antibody @ 1:500 dil) 48 Hr Well 2 | 93 | 68 | 6.4 | 6.4 | 14.5 | | | |
| PC (anti-STAT3 antibody @ 1:500 dil) 48 Hr Well 3 | 84.6 | 68 | 6.7 | 6.7 | 12.6 | | | |

[#]Based on collecting 0.1 ml of supernatant.

The treatment of retinal cells with 100 µg/mL of anti-STAT3 VHH13 (SEQ ID NO:3) sdAb decreased the production of VEGF-A. This may be associated with the inhibition of STAT3 and subsequent effect on the growth and proliferation of the retinal cells.

Example 27

Anti-STAT3 VHH13 (SEQ ID NO:3) SDAB Specificity

Experiments were performed to assess the specificity of multiple STAT sdAbs including STAT3 sdAb and the STAT5 sdAb bind to other STAT proteins using an ELISA format. A panel of STAT proteins (STAT 1, STAT 2, STAT 3, STAT 4, STAT 5a, STAT 5b and STAT 6) were used.

The test articles for this study were STAT 3 VHH labeled Process Intermediate III from Anthem Biosciences (Bangalore, India), anti-STAT3 VHH13 (SEQ ID NO:3) sdAb, and STAT5-31 (SEQ ID NO:83) sdAb. The test articles were tested at 10, 1, 0.1 and 0.01 µg/mL.

A standard sandwich ELISA format was utilized. For each ELISA, wells on a 96-well plate were coated with one of the STAT proteins at 0.5 µg/mL in carbonate buffer. Plates were incubated overnight at 2-8° C. After the incubation, plates were washed (3×) and blocked (3% BSA in PBS) for at least one hour at room temperature.

After removal of the blocking buffer and washing (3×), samples were added to the appropriate wells of the ELISA plates and incubated at room temperature with shaking (150 rpm) for at least one hour. The secondary antibody was then added to each well and incubated with shaking for at least one hour at room temperature. On Run 1, the secondary antibody was rabbit anti-llama biotinylated antigen at 1:5,000 dilution. For Run 2, in addition to the rabbit anti-lama, the his-probe (H-3) biotin labeled secondary antibody at a 1:1,000 dilution was tested in parallel.

After the incubation with secondary antibody, the plates were again washed (3×) and horseradish peroxidase (HRP) at a 1:25,000 dilution was added to each well. Plates were incubated with shaking for at least one hour at room temperature. One last wash (3×) was performed followed by the addition of TMB (Tetramethylbenzidine) substrate. After a 20 to 22 minute incubation at room temperature, stop solution was added to halt the colorimetric reaction. The absorbance at 450 nm was measured on a VersaMax instrument utilizing SoftMax Pro GxP version 5.4 software from Molecular Devices.

The STAT3 VHH from Anthem, anti-STAT3 VHH13 (SEQ ID NO:3) sdAb, and STAT5-31 (SEQ ID NO:83) sdAb were detected in each of the STAT 1, STAT 2, STAT 3, STAT 4, STAT 5a, STAT 5b and STAT 6 ELISA. Mean $OD_{450}$ values are shown in Table 57. The STAT 3 VHH from Anthem showed a higher specify to STAT 3 as indicated by a higher OD value as compared with the other ELISAs. The anti-STAT3 VHH13 (SEQ ID NO:3) sdAb had higher values in the STAT 3 and STAT 4 ELISA. The STAT5-31 (SEQ ID NO:83) sdAb had higher values in both the STAT 5a and the STAT 1 ELISA; however, the overall values seen with the STAT5-31 (SEQ ID NO:83) sdAb were considerably lower than those seen with the anti-STAT3 VHH13 (SEQ ID NO:3) sdAb in the same ELISAs. While it was demonstrated that these VHHs are not specific for their targeted STAT some preferential specificity was shown.

TABLE 57

STAT Specificity Mean OD450 Value*

| Sample | Concentration µg/mL | STAT 1 | STAT 2 | STAT 3 | STAT 4 | STAT 5a | STAT 5b | STAT 6 |
|---|---|---|---|---|---|---|---|---|
| STAT 3 VHH from Anthem | 0.01 | 0.008 | 0.007 | 0.007 | 0.008 | 0.005 | 0.008 | 0.007 |
| | 0.1 | 0.009 | 0.007 | 0.045 | 0.020 | 0.020 | 0.023 | 0.019 |
| | 1 | 0.203 | 0.270 | 0.776 | 0.237 | 0.250 | 0.264 | 0.261 |
| | 10 | 1.990 | 2.266 | 3.243 | 2.246 | 2.153 | 2.354 | 2.265 |
| STAT 3 VHH13 | 0.01 | 0.026 | 0.023 | 0.063 | 0.083 | 0.107 | 0.038 | 0.044 |
| | 0.1 | 0.159 | 0.186 | 0.431 | 0.833 | 0.821 | 0.499 | 0.413 |
| | 1 | 1.938 | 1.846 | 2.759 | 3.140 | 2.725 | 2.297 | 2.094 |
| | 10 | 3.163 | 3.336 | 3.669 | 3.674 | 3.322 | 3.377 | 3.205 |
| STAT 5-31 | 0.01 | 0.024 | 0.007 | 0.009 | 0.006 | 0.017 | 0.005 | 0.009 |
| | 0.1 | 0.015 | 0.000 | 0.000 | 0.000 | 0.000 | 0.000 | 0.000 |
| | 1 | 0.056 | 0.015 | 0.014 | 0.012 | 0.000 | 0.009 | 0.007 |
| | 10 | 0.122 | 0.076 | 0.088 | 0.085 | 0.158 | 0.051 | 0.048 |

*Mean $OD_{450}$ values from duplicate wells

The results show that the STAT3 VHH from Anthem and anti-STAT3 VHH13 (SEQ ID NO:3) sdAb bind to STAT proteins with an increased affinity for the STAT3 protein. The STAT5-31 (SEQ ID NO:83) sdAb binds to STAT 1, STAT 2, STAT 3, STAT 4, STAT 5a, STAT 5b and STAT 6 proteins with an increased affinity for the STAT 5a protein.

Example 28

Anti-TNF-A SDABS Bind to TNF-A Protein

In this Example, the binding of anti-TNF-α sdAbs to active human TNF-α full length protein was assessed using an enzyme linked immunosorbent assay (ELISA) format. Additionally, the feasibility of utilizing a secondary antibody targeted to the his tag portion of the sdAbs was assessed.

The test articles for this study were anti-TNF-α VHH62 (SEQ ID NO:47) sdAb, TNF-α VHH66 (SEQ ID NO:45) sdAb, and anti-TNF-α VHH69 (SEQ ID NO:46) sdAb (Experiment 1). Subsequently, additional lots of anti-TNF-α VHH62 (SEQ ID NO:47) sdAb and VHH69 (Experiment 4), as well as anti-TNF-α VHH66 (SEQ ID NO:45) sdAb (Experiment 5) were received. For the testing of the secondary antigen (Experiments 2 and 3), the following sdAb molecules were included: anti-STAT3 VHH13 (SEQ ID NO:3) sdAb, anti-STAT3 VHH14 (SEQ ID NO:4) sdAbs, anti-KRAS (G12D) (SEQ ID NO:2) sdAb, and a commercially available anti-Stat3 antibody (Abcam, Cambridge, Mass.).

For the assays to assess the binding of the sdAbs to TNF-α protein (Experiment 1, 4 and 5), a standard sandwich ELISA format was utilized. For each ELISA, wells on a 96-well plate were coated with TNF proteins (Abcam, Cambridge, Mass.) at 0.5, 0.25 or 0.125 µg/mL in carbonate buffer for the initial experiment and at 0.5 µg/mL only for subsequent assays. Plates were incubated overnight at 2-8° C. After the incubation, plates were washed (3x) and blocked (3% Bovine Serum Albumin (BSA) in Phosphate Buffered Saline (PBS)) for at least one hour at room temperature.

After removal of the blocking buffer and washing (3x), samples were added to the appropriate wells of the ELISA plates and incubated at room temperature with shaking (150 rpm) for at least one hour. The secondary antibody (rabbit anti-llama biotinylated antibody at either a 1:5,000 or 10,000 dilution) was added to each well and incubated with shaking for at least one hour at room temperature.

After the incubation with secondary antibody, the plates were again washed (3x) and horseradish peroxidase (HRP) at either a 1:25,000 or 1:50,000 dilution was added to each well. Plates were incubated with shaking for at least one hour at room temperature. A final wash (3x) was performed followed by the addition of TMB (Tetramethylbenzidine) substrate. After a 20 to 25 minute incubation at room temperature, stop solution was added to halt the colorimetric reaction. The absorbance at 450 nm was measured on a VersaMax instrument utilizing SoftMax Pro GxP version 5.4 software from Molecular Devices (Sunnyvale, Calif.).

Two assays (Experiment 2 and 3) were performed to assess the binding of the secondary antibody to the sdAbs. A similar ELISA method was utilized except the sdAbs were directly coated onto the assay plate at a concentration of 1 µg/mL. Plates were incubated overnight at 2-8° C. After the incubation, plates were washed (3x) and blocked (3% BSA in PBS) for at least one hour at room temperature.

After removal of the blocking buffer and washing (3x), the secondary antibodies, either rabbit anti-llama biotinylated antibody or his-probe (H-3) biotin labeled antibody at was then added at a 1:5,000 dilution to each well and incubated with shaking for at least one hour at room temperature. Only the rabbit anti-llama biotinylated antibody was used in Experiment 2. Both antibodies were run in parallel in Experiment 3.

After the incubation with secondary antibody, the plates were again washed (3x) and HRP at a 1:50,000 dilution was added to each well. Plates were incubated with shaking for at least one hour at room temperature. One last wash (3x) was performed followed by the addition of TMB substrate and plates were incubated at room temperature. For the anti-llama biotinylated antibody stop solution was added to halt the colorimetric reaction at 10 minutes. The his-probe (H-3) biotin labeled antibody was allowed to incubate for 20 minutes prior to stopping. The absorbance at 450 nm was measured as before.

For Experiment 1, a checkerboard of coating antigen concentration (0.5, 0.25, and 0.125 µg/mL), secondary antibody (1:5,000 and 1:10,000) and HRP (1:25,000 and 1:50,000) were assessed for signal to noise against 1 µg/mL of each sdAb. Signal/Noise ratios are provided in Table 58 for anti-TNF-α VHH62 (SEQ ID NO:47) sdAb, anti-TNF-α VHH66 (SEQ ID NO:45) sdAb and anti-TNF-α VHH69 (SEQ ID NO:46) sdAb respectively. Both anti-TNF-α VHH62 (SEQ ID NO:47) sdAb and anti-TNF-α VHH69 (SEQ ID NO:46) sdAb had little to no detection (i.e. very low OD values) indicating poor binding of the sdAbs to the TNF-α protein or to the rabbit anti-Llama secondary antibody. The anti-TNF-α VHH66 (SEQ ID NO:45) sdAb demonstrated good binding to the TNF-α protein with signal to noise ratios as high as 44.8.

TABLE 58

TNF ELISA Signal/Noise Ratio Experiment 1

| Coating antigen (μg/mL) | Rabbit anti-Llama Secondary Antibody (1:X dilution) | HRP (1:X dilution) | Signal/Noise Ratio | | |
|---|---|---|---|---|---|
| | | | anti-TNF-α VHH62 (SEQ ID NO: 47) sdAb | TNF-α VHH66 (SEQ ID NO: 45) sdAb | TNF-α VHH69 (SEQ ID NO: 46) sdAb |
| 0.5 | 5,000 | 25,000 | 2.0 | 40.4 | 8.0 |
| 0.5 | 5,000 | 50,000 | 1.9 | 44.8 | 7.5 |
| 0.5 | 10,000 | 25,000 | 1.7 | 41.9 | 5.9 |
| 0.5 | 10,000 | 50,000 | 1.5 | 32.4 | 3.7 |
| 0.25 | 5,000 | 25,000 | 1.5 | 35.3 | 3.2 |
| 0.25 | 5,000 | 50,000 | 1.4 | 28.7 | 2.4 |
| 0.25 | 10,000 | 25,000 | 1.4 | 25.7 | 2.1 |
| 0.25 | 10,000 | 50,000 | 1.3 | 18.5 | 1.9 |
| 0.125 | 5,000 | 25,000 | 1.1 | 11.8 | 1.6 |
| 0.125 | 5,000 | 50,000 | 1.1 | 12.4 | 1.6 |
| 0.125 | 10,000 | 25,000 | 1.1 | 11.4 | 1.5 |
| 0.125 | 10,000 | 50,000 | 0.9 | 7.3 | 1.3 |

The binding of the secondary antibody was assessed in Experiments 2 and 3 to determine if the lack of detection with anti-TNF-α VHH62 (SEQ ID NO:47) sdAb and anti-TNF-α VHH69 (SEQ ID NO:46) sdAb was due to binding to the coating antigen or to the secondary antibody. Data is shown in Table 59 below. Additional VHH molecules were included in these ELISAs as indicated. In Experiment 2, high $OD_{450}$ values (>1) were obtained with all but the anti-TNF-α VHH69 (SEQ ID NO:46) sdAb. This indicates that the rabbit anti-llama Secondary Antibody is an appropriate antibody for these ELISAs. For Experiment 3, an anti-his secondary antibody was compared to the anti-llama secondary antibody. For all but one sdAb, anti-STAT3 VHH14 (SEQ ID NO:4), lower $OD_{450}$ values were obtained with the anti-his secondary antibody.

A comparison of data obtained between Experiment 2 and Experiment 3 showed a decrease in OD values for several of the sdAbs tested. For Experiment 3 the 1:100 dilution of sdAb that had been prepared for Experiment 2 was utilized instead of preparing a fresh dilution (this was done to conserve material as several were in limited supply). The 1:100 dilution had been prepared in PBS and stored at −20° C. for three months. The decrease in $OD_{450}$ values is an indication of sample stability. Either storing the dilute solution and/or freeze thawing the samples resulted in the decreased stability.

TABLE 59

Comparison of Secondary Biotinylated Antibodies in Experiments 2 and 3

| Sample | $OD_{450}$ Values | | |
|---|---|---|---|
| | Rabbit anti-Llama Secondary Antibody Experiment 2 | Rabbit anti-Llama Secondary Antibody Experiment 3 | His-probe (H-3) Experiment 3 |
| Anti-STAT3 VHH14 (SEQ ID NO: 4) sdAb | 2.813 | 2.439 | 3.416 |

TABLE 59-continued

Comparison of Secondary Biotinylated Antibodies in Experiments 2 and 3

| Sample | $OD_{450}$ Values | | |
|---|---|---|---|
| | Rabbit anti-Llama Secondary Antibody Experiment 2 | Rabbit anti-Llama Secondary Antibody Experiment 3 | His-probe (H-3) Experiment 3 |
| Anti-KRAS (G12D) (SEQ ID NO: 2) sdAb | 1.924 | 1.307 | 0.577 |
| Anti-STAT3 VHH13 (SEQ ID NO: 3) sdAb | 1.313 | 0.363 | 0.360 |
| Anti-TNF-α VHH62 (SEQ ID NO: 47) sdAb | 1.485 | 2.341 | 0.196 |
| Anti-TNF-α VHH66 (SEQ ID NO: 45) sdAb | 2.057 | 2.682 | 0.181 |
| Anti-TNF-α VHH69 (SEQ ID NO: 46) sdAb | 0.499 | 0.443 | 0.153 |
| Anti-Stat 3 commercial antibody | Not tested | 3.076 | 0.018① |

①Documentation does not indicate that this VHH has a his-tag.

New batches of anti-TNF-α VHH62 (SEQ ID NO:47) sdAb and anti-TNF-α VHH69 (SEQ ID NO:46) sdAb were tested using four 10-fold serial dilutions starting at 1 μg/mL. Again very little detection was seen with the anti-TNF-α VHH62 (SEQ ID NO:47) sdAb (data not shown). The original receipt performed better than the new receipt; however, OD values were poor (<0.2 $OD_{450}$). For anti-TNF-α VHH69 (SEQ ID NO:46) sdAb, sufficient OD values were obtained to demonstrate a dose response of $OD_{450}$ to concentration of sdAb, as shown in FIG. 22. A comparison of the old and new lot of anti-TNF-α VHH69 (SEQ ID NO:46) sdAb showed similar results with the new batch having slightly higher OD values.

Two new batches of anti-TNF-α VHH66 (SEQ ID NO:45) sdAb were tested in Experiment 5 alongside the original batch. Each sdAb was tested at four 10-fold dilutions starting at 1 μg/mL. Similar detection was seen with all three batches (data not shown). Of the conditions tested, the combination of 0.5 μg/mL coating antigen, secondary antibody at 1:5,000 and HRP at 1:25,000 was shown to be optimal.

The final experiment performed was to confirm that the results from the ELISA testing were due to binding to the TNF-α protein and not non-specific binding of the sdAb. For this determination, a comparison was made between wells coated with 0.5 μg/mL of coating antigen and non-coated wells. The results are provided in Table 60. As previously seen, 1 μg/mL of anti-TNF-α VHH62 (SEQ ID NO:47) sdAb was not detected in either coated or non-coated wells. Both the anti-TNF-α VHH66 (SEQ ID NO:45) sdAb and anti-TNF-α VHH69 (SEQ ID NO:46) sdAb (at 1 m/mL) were detected in coated wells but not in non-coated wells. This experiment confirms that the detection seen with the previous experiments was due to the specific binding of the VHH to the coating antigen and not due to non-specific binding.

TABLE 60

Assessment of Non-specific Binding

| | OD450 Values | | |
|---|---|---|---|
| | anti-TNF-α VHH62 (SEQ ID NO: 47) sdAb | TNF-α VHH66 (SEQ ID NO: 45) sdAb | TNF-α VHH69 (SEQ ID NO: 46) sdAb |
| Coated | 0.005 | 3.863 | 1.948 |
| Non-Coated | −0.001 | 0.009 | 0.007 |

The results showed that both anti-TNF-α VHH66 (SEQ ID NO:45) sdAb and anti-TNF-α VHH69 (SEQ ID NO:46) sdAb demonstrated binding to the TNF-α protein. Detection of anti-TNF-α VHH62 (SEQ ID NO:47) sdAb was not demonstrated. Of the three anti-TNF-α sdAbs tested, anti-TNF-α VHH66 (SEQ ID NO:45) sdAb demonstrated the best affinity to the TNF-α protein. Additional preparations of each sdAb demonstrated similar results, indicating consistency between batch preparations.

Example 29

Cytotoxicity of Anti-TNF-α VHH66 SDAB (SEQ ID NO 45) on L929 Fibroblast Cells

This Example demonstrates the anti-proliferative effects of the anti-TNF-α VHH66 (SEQ ID NO:45) sdAb. The activity of the anti-TNF-α VHH66 (SEQ ID NO:45) sdAb was assessed by incubating the anti-TNF-α VHH66 (SEQ ID NO:45) sdAb with a cytotoxic dose of TNFα, followed by evaluating the mixture for the inhibition of cytotoxicity in the TNFα sensitive mouse fibroblast cell line L929 (ATCC, Manassas, Va.).

Promega's protocol for determining bioactivity in rhTNF-α using L929 cells was modified to show inhibition of the cytotoxicity of TNF-α. L929 cells were grown to near confluency at 37° C. with 5% $CO_2$ and humidity in a 96-well plate. The cells were plated at 20,000 cells/well for Assay 1 and incubated approximately 48 hours. For Assay 2, 40,000 cells/well were plated and incubated approximately 24 hours.

Human recombinant TNF-α (Sigma-Aldrich, Saint Louis, Mo.) was prepared at a 4× concentration of 2 µg/mL in assay medium (DMEM supplemented with 10% FBS; 0.5 µg/mL final concentration in the assay). Next, the anti-TNF-α VHH66 (SEQ ID NO:45) sdAb was serially diluted in assay medium at 4× concentration. The final assay concentrations using three separate batches of anti-TNF-α VHH66 (SEQ ID NO:45) sdAb, designated Batch A, Batch B, and Batch C. For Assay 1, 10-fold dilutions ranging from 100 µg/mL to 0.01 µg/mL (Batch B and C), and 52 to 0.0052 µg/mL (Batch A). For Assay 2, Batches B and C were tested at a final concentration range (2-fold dilutions) of 40 µg/mL to 0.3125 µg/mL. Equal volumes of the TNF-α and the appropriate anti-TNF-α VHH66 (SEQ ID NO:45) sdAb (or assay media) were mixed and incubated for 30 minutes at 37° C. The medium was then aspirated off the cells and replaced with assay media containing actinomycin D (final concentration 1 µg/mL) or assay media only (designated as media only wells). The TNF-α/anti-TNF-α VHH66 (SEQ ID NO:45) sdAb mixtures were then added to the appropriate wells in quadruplicate. In addition to the media only control wells (no actinomycin D, no TNF-α), TNF-α (with actinomycin D) and actinomycin D only (no TNF-α) control wells were included. After incubating for 24 hours at 37° C. with 5% $CO_2$ and humidity, a MTS/PMS solution (Cell Titer 96 AQueous Non-Radioactive Cell Proliferation Assay, Promega, Madison Wis.) was added to each well. The plate was incubated for 4 hours at 37° C. with 5% $CO_2$ and humidity. The absorbance was then read at 490 nm on a VersaMax instrument utilizing SoftMax Pro GxP version 5.4 software from Molecular Devices (Sunnyvale, Calif.).

Dose response curves were generated and the $EC_{50}$ value (the value at which the effective concentration is half of the maximal) was determined for each sdAb. For Assay 1, the $EC_{50}$ value for Batch A was 2.9 µg/mL. The $EC_{50}$ value for Batch B was 1.2 µg/mL and the $EC_{50}$ value for Batch C was 2.3 µg/mL. The percent cytotoxicity for the control wells and test samples are provided in Table 61 and 62, respectively.

TABLE 61

Percent Toxicity for Controls (Assay 1) % Toxicity
% Toxicity
Sample Replicate #

| | Sample | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Actinomycin D only (no TNFα) | 18.6 | 0 | 0 | 0 | 0 | 0 | 0 | 0 | 0 | 5.4 | 2.3 | 3.5 |
| Media only (no TNF-α) | 0 | 0 | 0 | 0 | 0 | 0 | 0 | 0 | 0 | 0 | 0 | 0 |
| TNFα (0.5 µg/mL) | 101.9 | 102.6 | 102.7 | 102.1 | 101.8 | 101.8 | 102.1 | 102.1 | 101.7 | 101.6 | 101.8 | 102.1 |

TABLE 62

Percent Toxicity for Test Samples (Assay 1)

| Test Sample | Sample Replicate # | | | | Mean % | Standard Deviation |
|---|---|---|---|---|---|---|
| Batch A | | | | | | |
| 52 µg/mL | 31.4 | 28.3 | 19.6 | 23.2 | 25.6 | 4.55 |
| 5.2 µg/mL | 48.4 | 28.1 | 30.1 | 27.3 | 33.5 | 8.68 |
| 0.52 µg/mL | 78.6 | 70.5 | 71.4 | 67.9 | 72.1 | 3.97 |
| 0.052 µg/mL | 101.5 | 101.1 | 101.2 | 101.5 | 101.3 | 0.18 |
| 0.0052 µg/mL | 102.0 | 101.6 | 101.9 | 102.1 | 101.9 | 0.19 |
| Batch B | | | | | | |
| 100 µg/mL | 15.4 | 7.7 | 4.8 | 5.7 | 8.4 | 4.18 |
| 10 µg/mL | 35.7 | 34.7 | 31.6 | 32.2 | 33.6 | 1.70 |
| 1 µg/mL | 34.6 | 34.4 | 34.8 | 33.0 | 34.2 | 0.71 |
| 0.1 µg/mL | 101.2 | 101.7 | 101.7 | 102.0 | 101.7 | 0.29 |
| 0.01 µg/mL | 102.1 | 102.4 | 102.1 | 102.3 | 102.2 | 0.13 |
| 100 µg/mL | 15.4 | 7.7 | 4.8 | 5.7 | 8.4 | 4.18 |
| Batch C | | | | | | |
| 100 µg/mL | 18.8 | 15.0 | 15.7 | 38.2 | 21.9 | 9.50 |
| 10 µg/mL | 34.6 | 32.8 | 33.8 | 32.4 | 33.4 | 0.86 |

TABLE 62-continued

Percent Toxicity for Test Samples (Assay 1)

| Test Sample | Sample Replicate # | | | | Mean % | Standard Deviation |
|---|---|---|---|---|---|---|
| 1 µg/mL | 44.9 | 42.1 | 41.6 | 45.7 | 43.6 | 1.76 |
| 0.1 µg/mL | 102.0 | 102.3 | 102.0 | 101.7 | 102.0 | 0.21 |
| 0.01 µg/mL | 102.1 | 102.3 | 102.4 | 102.1 | 102.2 | 0.13 |

For Assay 2, the concentration range was narrowed in order to further refine the $EC_{50}$ value. Values of 4.5 µg/mL and 6.2 µg/mL were determined for Batch B and C, respectively. The percent cytotoxicity for the control wells and test samples are provided in Table 63 and 64, respectively.

TABLE 63

Percent Toxicity for Controls (Assay 2)
% Toxicity
Sample Replicate #

| | Sample | | | | | | | |
|---|---|---|---|---|---|---|---|---|
| | 1 | 2 | 3 | 4 | 5 | 6 | 7 | 8 |
| Actinomycin D only (no TNFα) | 2.3 | 0 | 10.4 | --1 | 0 | 0 | 0.4 | 0 |
| Media only (no TNFα) | 0 | 0 | 0 | 0 | 0 | 0 | 0 | 0 |
| TNFα (0.5 µg/mL) | 98.0 | 97.5 | 97.7 | 97.4 | 98 | 97.4 | 97.4 | 97.2 |

[1]Well was masked as an outlier (Q-test performed).

TABLE 64

Percent Toxicity for Test Samples (Assay 1)

| Test Sample | Sample Replicate # | | | | Mean % | Standard Deviation |
|---|---|---|---|---|---|---|
| Batch B | | | | | | |
| 40 µg/mL | 12.1 | 9.6 | 9.2 | 11.0 | 10.5 | 1.15 |
| 20 µg/mL | 10.5 | 5.7 | 6.5 | 7.7 | 7.6 | 1.82 |
| 10 µg/mL | 30.1 | 31.2 | 15.1 | 13.7 | 22.5 | 8.15 |
| 5 µg/mL | 40.6 | 39.6 | 25.1 | 23.6 | 32.2 | 7.90 |
| 2.5 µg/mL | 96.3 | 96.2 | 84.5 | 82.6 | 89.9 | 6.39 |
| Batch C | | | | | | |
| 40 µg/mL | 10.5 | 6.5 | 10.6 | 4.0 | 7.9 | 2.79 |
| 20 µg/mL | 5.5 | 2.6 | 9.7 | 2.5 | 5.1 | 2.93 |
| 10 µg/mL | 14.0 | 11.9 | 26.6 | 25.6 | 19.5 | 6.63 |
| 5 µg/mL | 44.9 | 42.5 | 85.7 | 86.3 | 64.9 | 21.17 |
| 2.5 µg/mL | 96.9 | 96.3 | 97.3 | 97.3 | 97.0 | 0.41 |
| 1.25 µg/mL | 97.5 | 97.3 | 97.7 | 97.4 | 97.5 | 0.15 |

Activity against TNF-α was demonstrated for all three batches of anti-TNFα VHH66 as shown by the reduction in TNF cytotoxicity. The difference between Batch B and C was less than 2-fold. Batch A demonstrated <2-fold difference as compared to Batch C and slightly higher then 2-fold difference compared to Batch B.

Example 30

Anti-STAT3 and Anti-VP24 Zika and Ebola Virus Infection Assays

This example demonstrates the effect anti-Stat3 sdAbs and anti-VP24 sdAbs have on infection with the Zika virus and the Ebola virus. Anti-STAT3 VHH13 (SEQ ID NO:3) sdAb and anti-Ebola virus VP24-5 (SEQ ID NO:84) were tested in Zika/Vero and Ebola/Hela and Ebola/HFF virus infection assays. The amino acid sequence of SEQ ID NO: 84 is MGDVQLVESGGDSVRAGGSLQLSCKASGYTYNSRVDIRSMGWFRQYPGKE
REGVATINIRNSVTYYADSVKGRFTISQDNAKNTVYLQMNALKPEDTAMY
YCALSDRFAAQVPARYGIRPSDYNYWGEGTLVTVSSSSGLE The materials used consisted of the following cell lines: 1) Vero cells infected with Zika; 2) Hela cells infected with Ebola; and 3) HHF-1 cells infected with Ebola. The antibodies were made in an aqueous buffer at concentrations indicated in Table 65.

TABLE 65

Concentrations of Antibodies

| VHH13 (SEQ ID NO: 3) | 556.7 ug/ml |
|---|---|
| VP24-5 (SEQ ID NO: 84) | 524.1 ug/ml |

The antibodies were manually dispensed 2 hours before infection into the assay wells with cells. Titration was done in 10× intermediate dilution in media (with no serum) starting at 55.6 ug/ml (final) for anti-STAT3 VHH13 (SEQ ID NO:3) and 52.4 ug/ml (final) for VP24-5 (SEQ ID NO:84). Antibody activity was tested in a 10-point dose response with 2-fold step dilution in a 384-well assay plate. The titration was repeated 4 times on a single plate (n=4) for Zika and EBOV/HFF and 3 times (n=3) for EBOV/Hela.

Column 2 was used as "blank control" BC with cells not infected with virus. Column 3 was used as "neutral control" NC-infected, treated with DMSO only. E864 and AQ were used as control compounds and tittered in dose response starting at 2.5 uM for E864 and 10 uM for AQ with 2-fold step dilution.

2 hours after treatment the cells were infected with Zika/DAKAR D41525 Senegal strain at MOI=0.3, EBOv (Makon) at MOI=2.0 for Hela cells and MOI=18 for HFF. The infection was stopped after 48 hours by fixing cells with a formalin solution. To detect infected cells, an immunostaining was done with anti-Flavi virus epitope (mm D1-4G2 anti-Env P antibodies for detecting Zika infection and mm 6D8 anti-GP Ab for Ebola infection. Images were acquired by the PE Opera confocal platform using a 10× objective and were analyzed using Acapella software. The signal for GP-staining was converted into % infection and the number of nuclei per well was used to determine the % cell count (or viability of cells) in comparison to infected but untreated controls, n=16. The data was analyzed using GeneData software. % of Infection was converted into % Inhibition (% INH) for each well using plate controls. The results are shown in Tables 66A, 66B, 67 and 68.

TABLE 66A

Plate Statistics

| Index | Cell line | Pathogen | MOI | Plate ID | Date |
|---|---|---|---|---|---|
| 1 | Hela | EBOV (Makona) | 2 | AA00005885 | Apr. 26, 2017 |
| 2 | HFF | EBOV (Makona) | 18 | AA00005112 | Apr. 26, 2017 |
| 3 | Vero | Zika (Senegal) | 0.3 | AA00005886 | Apr. 26, 2017 |

TABLE 66B

Plate Statistics

| Index | Well Masking | Nuclei - Number, NC | % Infection | Z' Factor | Number of Analyzed Fields | AQ, EC50 [uM] | E864, EC50 [nM] |
|---|---|---|---|---|---|---|---|
| 1 | 0% | 4321 | 79.10 | 0.89 | 5 | 3.53 ± 0.36 | 199.4 ± 15.04 |
| 2 | 0% | 2259 | 92.27 | 0.88 | 5 | 4.56 ± 0.46 | |
| 3 | 2% | 6388 | 42.56 | 0.44 | 5 | 3.70 ± 1.35 | 246.4 ± 61.97 |

TABLE 67

Curve Fitting Results for EBOV

| Compound ID | Cell line | Pathogen | Plate ID | Fit Model | EC50 ug/m | SD | EC90 ug/ml | CC50 ug/ml | CC50/ EC50 |
|---|---|---|---|---|---|---|---|---|---|
| VHH13 (SEQ ID NO: 3) | Hela | EBOV (Makona) | AA00005885 | 2pHill (AC50, n) | 19.02 | 3.0524 | 58.72 | 31 | 1.6 |
| VP24-5 (SEQ ID NO: 55) | Hela | EBOV (Makona) | AA00005885 | 4pHill (AC50, n, S0, Sinf) | >52.4 | — | — | >52.4 | — |
| VHH13 (SEQ ID NO: 3) | HFF | EBOV (Makona) | AA00005112 | 3pHill (AC50, n, S0) | 38.36 | 2.7858 | 66.43 | 31 | 0.8 |
| VP24-5 (SEQ ID NO: 55) | HFF | EBOV (Makona) | AA00005112 | Constant | >52.4 | — | — | >52.4 | — |

TABLE 68

Curve Fitting Results for ZikV

| Compound ID | Cell line | Pathogen | Plate ID | Fit Model | EC50 ug/m | SD | EC90 ug/ml | CC50 ug/ml | CC50/ EC50 |
|---|---|---|---|---|---|---|---|---|---|
| VHH13 (SEQ ID NO: 3) | Vero E6 | Zika (Senegal) | AA00005886 | 2pHill (AC50, n) | 11.04 | 3.5011 | 48.11 | 31 | 2.8 |
| VHH-VP24 | Vero E6 | Zika (Senegal) | AA00005886 | Constant | >52.4 | — | — | >52.4 | — |

Example 31

IC50 Studies on Six Human Cancer Cell Lines Using VHH13 (SEQ ID NO:3) SDAB

The objective of these studies was to test the antiproliferative effects of the VHH13 (SEQ ID NO:3) SDAB (SBT-100) using the human cancer cell lines: U87MG, SJSA-1 and HT1080 (single treatment [SBT-100]), SJSA-1 (combination treatment: SBT-100 and Doxorubicin), PANC-1 (combination SBT-100 and gemcitabine), and SJSA-1 (comparison studies with SBT-100 from Creative Biolab versus SBT-100 from CuriRx Inc).

For the experiments, the cells were grown until to 90% confluence, when they were washed, trypsinized, and counted using a Coulter Counter (Beckman, Brea, Calif.). The proliferation studies were carried out using the 3-[4,5-dimethylthiaolyl]-2,5-diphenyltetrazolium bromide (MTT) assay (Roche Diagnostics Corporation, Indianapolis, Ind.). For this, cells were seeded in a 96-well plate at a density of $5 \times 10^3$ (U87MG, HT1080, PANC-1, SJSA-1) or $1 \times 10^3$ (SJSA-1; experiment 5a) cells per well. Cells were allowed to adhere for 24 hours and treated at the appropriate concentrations as described in Table 69 for the different experiments. At Day 3, 10 μl of MTT reagent (0.5 mg/mL) was added to each well as indicated by the manufacturer. After a 4 hour incubation period, 100 μL of solubilization solution was added and the plate was placed in the incubator overnight. All the plates were read at 570 nm wavelength using the Biotek plate reader (Winooski, Vt.).

TABLE 69

Dose levels of SBT-100, Gemcitabine, and Doxorubicin for cell proliferation studies

| Experiments | Test Article #1 | Dose(s) μg/ml | Test Article #2 | Dose(s) μM |
|---|---|---|---|---|
| 1) HT1080 | SBT-100 | 0 | N/A | |
| 2) SJSA-1 | | 12.5 | | |
| 3) U87MG | | 25 | | |
| | | 50 | | |
| | | 100 | | |
| | | 200 | | |
| 4) PANC-1 | SBT-100 | 0 | Gemcitabine | 0 |
| | | 100 | | 0.02 |
| | | | | 0.04 |
| | | | | 0.08 |
| | | | | 0.16 |
| | | | | 0.31 |
| | | | | 0.63 |
| | | | | 1.25 |
| | | | | 2.50 |

TABLE 69-continued

Dose levels of SBT-100, Gemcitabine, and Doxorubicin for cell proliferation studies

| Experiments | Test Article #1 | Dose(s) µg/ml | Test Article #2 | Dose(s) µM |
|---|---|---|---|---|
| | | | | 5.00 |
| | | | | 10.00 |
| 5a) SJSA-1 | SBT-100 | 0 | Doxorubicin | 0 |
| | | 3.13 | | 0.03 |
| | | 6.25 | | 0.06 |
| | | 12.5 | | 0.13 |
| | | 25.0 | | 0.25 |
| | | 50.0 | | 0.50 |
| | | 100.0 | | 1.00 |
| 5b) SJSA-1 | SBT-100 | 0 | Doxorubicin | 0 |
| | | 3.13 | | 0.31 |
| | | 6.25 | | 0.63 |
| | | 12.5 | | 1.25 |
| | | 25.0 | | 2.50 |
| | | 50.0 | | 5.00 |
| | | 100.0 | | 10.00 |
| 6) MDA-MB-231 | MPT His Tag SBT-100 | 50, 100 | N/A | |
| | MPT B1 (pH 5.0) | 50, 100 | | |
| | MPT B2 (pH 7.4) | 50, 100 | | |
| | MPT B3 (pH 7.4) | 50, 100 | | |
| | Creative Biolabs (1/14) PBS Control | 50, 100 | | |
| 7) SJSA-1 | SBT100 PO4 | 50, 100 | N/A | |
| | SBT100 SUCC | 50, 100 | | |
| | SBT100 SUCC-PROLINE | 50, 100 | | |
| | Creative Biolabs (5/16) | 50, 100 | | |

As shown in Table 70, treatment of cells with anti-STAT3 VHH13 (SEQ ID NO:3) (SBT-100) showed a significant growth inhibition. The IC50 were calculated to be: 33, 51, and 65 µg/ml for HT1080, SJSA-1, and U87MG, respectively.

TABLE 70

Anti-proliferative actions of SBT-100 on the HT1080 Human fibrosarcoma cell line, SJSA1 Human Bone Osteosarcoma cell line and U87MG Human Glioblastoma cell line.

| Dose (µg/ml) | Absorbance ± S.E. | % Inhibition | |
|---|---|---|---|
| HT1080 cells treated for 72 hr. with SBT-100 | | | |
| 0 | 1.58 ± 0.07 | | |
| 12.5 | 1.36 ± 0.09 | 14 | |
| 25 | 1.09 ± 0.01 | 31 | IC50 = 33 µg/ml |
| 50 | 0.42 ± 0.04 | 73 | |
| 100 | 0.27 ± 0.01 | 83 | |
| 200 | 0.22 ± 0.02 | 86 | |
| SJSA cells treated for 72 hr. with SBT-100 | | | |
| 0 | 1.52 ± 0.15 | | |
| 12.5 | 1.52 ± 0.10 | 0 | |
| 25 | 1.36 ± 0.09 | 11 | IC50 = 51 µg/ml |
| 50 | 0.90 ± 0.04 | 41 | |
| 100 | 0.27 ± 0.01 | 82 | |
| 200 | 0.26 ± 0.01 | 83 | |
| U87mg cells treated for 72 hr. with SBT-100 | | | |
| 0 | 0.555 ± 0.02 | | |
| 12.5 | 0.702 ± 0.04 | 0 | |
| 25 | 0.687 ± 0.03 | 0 | IC50 = 65 µg/ml |
| 50 | 0.456 ± 0.01 | 18 | |
| 100 | 0.271 ± 0.02 | 51 | |
| 200 | 0.211 ± 0.03 | 62 | |

PANC-1 Human Pancreatic cells treated with anti-STAT3 VHH13 (SEQ ID NO:3) (SBT-100) alone or in combination with Gemcitabine were evaluated. For these studies, PANC-1 cells were treated with SBT-100 (100 µg/ml) and increasing concentrations of Gemcitabine (0 to 10 µM) for 72 hours. Two experiments using different sources of Gemcitabine (Biovison #1759, Gemcitabine Hydrochloride; and Selleckchem #S1714, Gemcitabine Free Base) were conducted. Results for the two studies are shown in Table 71.

TABLE 71

PANC-1 cells treated with Gemcitabine alone or in combination with SBT-100

| | Gemcitabine Free Base Selleckchem #S1714 | | | | Gemcitabine Hydrochloride Biovision #1759 | | | |
|---|---|---|---|---|---|---|---|---|
| Treatment | Abs | ±SE | % Inh | p-value | Abs | ±SE | % Inh | p-value |
| Vehicle Control | 1.050 | 0.075 | | | 1.020 | 0.068 | | |
| Gemcitabine 10 µM | 0.543 | 0.037 | 48 | p < 0.001 | 0.576 | 0.006 | 46 | p < 0.001 |
| Gemcitabine 5 µM | 0.631 | 0.012 | 40 | p < 0.001 | 0.654 | 0.018 | 36 | p < 0.001 |
| Gemcitabine 2.5 µM | 0.681 | 0.017 | 35 | p < 0.01 | 0.762 | 0.022 | 25 | p < 0.001 |
| Gemcitabine 1.25 µM | 0.861 | 0.077 | 18 | ns | 0.852 | 0.019 | 16 | p < 0.05 |
| Gemcitabine 0.625 µM | 1.050 | 0.162 | 0 | ns | 1.001 | 0.026 | 2 | ns |
| Gemcitabine 0.313 µM | 0.997 | 0.054 | 5 | ns | 1.084 | 0.054 | 0 | ns |
| Gemcitabine 0.156 µM | 1.210 | 0.062 | 0 | ns | 1.405 | 0.041 | 0 | p < 0.001 |
| Gemcitabine 0.078 µM | 1.230 | 0.039 | 0 | ns | 1.405 | 0.034 | 0 | p < 0.001 |
| Gemcitabine 0.039 µM | 1.240 | 0.014 | 0 | ns | 1.550 | 0.037 | 0 | p < 0.001 |
| Gemcitabine 0.020 µM | 1.560 | 0.101 | 0 | ns | 1.631 | 0.056 | 0 | p < 0.001 |
| SBT-100 100 µg/ml | 0.333 | 0.050 | 68 | p < 0.001 | 0.381 | 0.023 | 63 | p < 0.001 |
| Gemcitabine 10 µM + | 0.234 | 0.041 | 78 | p < 0.001 | 0.350 | 0.001 | 66 | p < 0.001 |
| Gemcitabine 5 µM + SBT-100 100 µg/ml | 0.294 | 0.044 | 72 | p < 0.001 | 0.314 | 0.010 | 69 | p < 0.001 |
| Gemcitabine 2.5 µM + SBT-100 100 µg/ml | 0.240 | 0.036 | 77 | p < 0.001 | 0.295 | 0.018 | 71 | p < 0.001 |
| Gemcitabine 1.25 µM + SBT-100 100 µg/ml | 0.204 | 0.013 | 81 | p < 0.001 | 0.296 | 0.023 | 71 | p < 0.001 |
| Gemcitabine 0.625 µM + SBT-100 100 µg/ml | 0.232 | 0.008 | 78 | p < 0.001 | 0.319 | 0.008 | 69 | p < 0.001 |
| Gemcitabine 0.313 µM + SBT-100 100 µg/ml | 0.276 | 0.010 | 74 | p < 0.001 | 0.326 | 0.005 | 68 | p < 0.001 |

TABLE 71-continued

PANC-1 cells treated with Gemcitabine alone or in combination with SBT-100

| Treatment | Gemcitabine Free Base Selleckchem #S1714 | | | | Gemcitabine Hydrochloride Biovision #1759 | | | |
|---|---|---|---|---|---|---|---|---|
| | Abs | ±SE | % Inh | p-value | Abs | ±SE | % Inh | p-value |
| Gemcitabine 0.156 μM + SBT-100 100 μg/ml | 0.290 | 0.047 | 72 | p < 0.001 | 0.336 | 0.012 | 67 | p < 0.001 |
| Gemcitabine 0.078 μM + SBT-100 100 μg/ml | 0.265 | 0.015 | 75 | p < 0.001 | 0.294 | 0.024 | 71 | p < 0.001 |
| Gemcitabine 0.039 μM + SBT-100 100 μg/ml | 0.446 | 0.039 | 56 | p < 0.001 | 0.059 | 0.000 | *** | p < 0.001 |
| Gemcitabine 0.020 μM + SBT-100 100 μg/ml | 0.457 | 0.002 | 56 | p < 0.001 | 0.344 | 0.011 | 66 | p < 0.001 |

Based on the results of the IC50 studies, further experiments were done to asses anti-STAT3 VHH13 (SEQ ID NO:3) sdAb (SBT-100) in combination with an established chemotherapeutic agent (i.e., Doxorubicin). For these studies, cells were plated in 96 wells at a density of $1 \times 10^6$ (Experiment 5a) or $5 \times 10^6$ (Experiment 5b). In both experiments, one drug was kept constant (i.e., SBT-100 at 50 μg/ml 5a, or 25 μg/ml 5b) and the other drug (i.e., Doxorubicin) was used at increasing concentrations. When Doxorubicin was kept constant (i.e., 62.5 μM 5a or 1 μM 5b) SBT-100 was then administered at increasing concentrations. For both experiments, cells were exposed to the drugs for 72 hours. The dose of Doxorubicin for experiment 5a was based on the literature, however, significant inhibition was not reached. For experiment 5b, the dose levels for Doxorubicin and the cell density were increased. In both experiments, anti-STAT3 VHH13 (SEQ ID NO:3) sdAb (SBT-100) showed significant inhibition at dose levels of 50 and 100 μg/ml. Similarly, doxorubicin showed significant dose-dependent inhibition at all dose levels tested. When both drugs are combined, the effects on the PANC-1 cells are synergistic.

TABLE 72

SJSA-1 Human Bone Osteosarcoma Cells Treated with anti-STAT3 VHH13 (SEQ ID NO: 3) sdAb (SBT-100) alone or in combination with Doxorubicin SJSA-1 cells treated for 72 hours
SJSA-1 cells treated for 72 hours

| | Mean Abs (±SD) | % inhibition | p-value |
|---|---|---|---|
| SBT-100 Dose (μg/ml) | | | |
| 0 | 0.241 ± 0.034 | | |
| 3.13 | 0.278 ± 0.057 | 0 | ns |
| 6.25 | 0.258 ± 0.097 | 0 | ns |
| 12.5 | 0.231 ± 0.046 | 4 | ns |
| 25 | 0.221 ± 0.034 | 8 | ns |
| 50 | 0.066 ± 0.003 | 73 | 0.05 |
| 100 | 0.058 ± 0.002 | 76 | 0.01 |
| Doxorubicin (μM) | | | |
| 0 | 0.388 ± 0.040 | | |
| 0.0313 | 0.281 ± 0.031 | 28 | 0.05 |
| 0.0625 | 0.277 ± 0.035 | 29 | 0.05 |
| 0.125 | 0.257 ± 0.026 | 34 | 0.01 |
| 0.25 | 0.245 ± 0.038 | 37 | 0.01 |
| 0.5 | 0.248 ± 0.038 | 36 | 0.01 |
| 1 | 0.197 ± 0.012 | 49 | 0.001 |

TABLE 72-continued

SJSA-1 Human Bone Osteosarcoma Cells Treated with anti-STAT3 VHH13 (SEQ ID NO: 3) sdAb (SBT-100) alone or in combination with Doxorubicin SJSA-1 cells treated for 72 hours
SJSA-1 cells treated for 72 hours

| | Mean Abs (±SD) | % inhibition | p-value |
|---|---|---|---|
| Constant dose level of SBT-100 (50 μg/ml) with a dose range of Doxorubicin (μM) | | | |
| Doxorubicin (μM) | | | |
| 0 | 0.311 ± 0.024 | | |
| 0.0313 | 0.09 ± 0.013 | 71 | 0.001 |
| 0.0625 | 0.087 ± 0.013 | 72 | 0.001 |
| 0.125 | 0.088 ± 0.008 | 72 | 0.001 |
| 0.25 | 0.086 ± 0.011 | 72 | 0.001 |
| 0.5 | 0.078 ± 0.008 | 75 | 0.001 |
| 1 | 0.057 ± 0.00 | 82 | 0.001 |
| Constant dose of doxorubicin (62.5 μM) with a dose range of SBT-100 (μg/ml) | | | |
| SBT-100 Dose (μg/ml) | | | |
| 0 | 0.353 ± 0.046 | | |
| 3.13 | 0.204 ± 0.031 | 42 | 0.001 |
| 6.25 | 0.176 ± 0.023 | 50 | 0.001 |
| 12.5 | 0.185 ± 0.024 | 48 | 0.001 |
| 25 | 0.187 ± 0.028 | 47 | 0.001 |
| 50 | 0.069 ± 0.012 | 80 | 0.001 |
| 100 | 0.057 ± 0.006 | 84 | 0.001 |

TABLE 73

SJSA-1 Human Bone Osteosarcoma Cells Treated with anti-STAT3 VHH13 (SEQ ID NO: 3) sdAb (SBT-100) alone or in combination with Doxorubicin SJSA-1 cells treated for 72 hours
SJSA-1 cells treated for 72 hours_Experiment 2

| | Mean Abs (±SD) | % inhibition | p-value |
|---|---|---|---|
| SBT-100 Dose (μg/ml) | | | |
| 0 | 0.789 ± 0.091 | | |
| 3.13 | 0.774 ± 0.068 | 0 | ns |
| 6.25 | 0.835 ± 0.058 | 0 | ns |
| 12.5 | 0.800 ± 0.058 | 0 | ns |
| 25 | 0.781 ± 0.057 | 1 | ns |
| 50 | 0.460 ± 0.038 | 42 | 0.001 |
| 100 | 0.091 ± 0.002 | 88 | 0.001 |
| Doxorubicin (μM) | | | |
| 0 | 0.751 ± 0.009 | | |
| 0.313 | 0.519 ± 0.004 | 31 | 0.001 |
| 0.625 | 0.530 ± 0.024 | 29 | 0.001 |

TABLE 73-continued

SJSA-1 Human Bone Osteosarcoma Cells Treated with anti-STAT3 VHH13 (SEQ ID NO: 3) sdAb (SBT-100) alone or in combination with Doxorubicin SJSA-1 cells treated for 72 hours SJSA-1 cells treated for 72 hours_Experiment 2

|  | Mean Abs (±SD) | % inhibition | p-value |
|---|---|---|---|
| 1.25 | 0.469 ± 0.016 | 38 | 0.001 |
| 2.50 | 0.353 ± 0.004 | 53 | 0.001 |
| 5.00 | 0.358 ± 0.003 | 52 | 0.001 |
| 10.0 | 0.414 ± 0.007 | 45 | 0.001 |
| Constant dose level of SBT-100 (25 µg/ml) with a dose range of Doxorubicin (µM) | | | |
| Doxorubicin (µM) | | | |
| 0 | 0.723 ± 0.015 | | |
| 0.313 | 0.553 ± 0.018 | 24 | 0.001 |
| 0.625 | 0.566 ± 0.030 | 22 | 0.001 |
| 1.25 | 0.434 ± 0.011 | 40 | 0.001 |
| 2.50 | 0.385 ± 0.013 | 47 | 0.001 |
| 5.00 | 0.261 ± 0.004 | 64 | 0.001 |
| 10.0 | 0.193 ± 0.012 | 73 | 0.001 |
| Constant dose level of doxorubicin (1 µM) with a dose range of SBT-100 (µm/ml) | | | |
| SBT-100 Dose (µg/ml) | | | |
| 0 | 0.868 ± 0.067 | | |
| 3.13 | 0.502 ± 0.103 | 42 | 0.001 |
| 6.25 | 0.405 ± 0.129 | 53 | 0.001 |
| 12.5 | 0.458 ± 0.047 | 47 | 0.001 |
| 25 | 0.444 ± 0.017 | 49 | 0.001 |
| 50 | 0.340 ± 0.074 | 61 | 0.001 |
| 100 | 0.265 ± 0.125 | 70 | 0.001 |

An efficacy study was conducted using anti-STAT3 VHH13 (SEQ ID NO:3) sdAb (SBT-100) (Creative Biolabs) and anti-STAT3 VHH13 (SEQ ID NO:3) sdAb (SBT-100) produced by Microprotein Technologies inc (i.e., MPT His Tag, MPT B1 (pH 5.0), MPT B2 (pH7.4) and MPT B3 (pH 7.4). The results are shown in Table 74. While the greatest inhibition was noted for MPT His Tag, it was noted the test article had a cloudy appearance and that cells exposed to this drug appeared to lose normal morphology within a few hours of exposure. Other samples tested showed a more similar response to that of the SBT-100 produced by Creative Biolabs.

TABLE 74

MDA-MB-231 Cells treated with anti-STAT3 VHH13 (SEQ ID NO: 3) sdAb (SBT-100) from Creative Biolabs and Microprotein Technologies Dose Level MPT Tagless

| Dose Level | Control | MPT His Tag* | B1 (pH 5.0) | B2 (pH 7.4) | B3 (7.4) | Creative Biolabs (1/14/16) |
|---|---|---|---|---|---|---|
| 100 µg/ml | 1.001 | 0.74 | 0.65 | 0.771 | 0.221 | 0.44 |
|  | 1.039 | 0.8 | 0.656 | 0.778 | 0.213 | 0.398 |
|  | 1.037 | 0.82 | 0.624 | 0.723 | 0.214 | 0.442 |
| Mean | 1.03 | 0.079 | 0.643 | 0.757 | 0.216 | 0.427 |
| SE | 0.012 | 0.002 | 0.01 | 0.017 | 0.003 | 0.014 |
| % Inhibition |  | 92.3 | 37.6 | 2.5 | 79.0 | 58.5 |

| Dose Level | Control | MPT His Tag* | B1 (pH 5.0) | B2 (pH 7.4) | B3 (7.4) | CB (1/14/16) |
|---|---|---|---|---|---|---|
| 50 µg/ml | 0.809 | 0.095 | 0.924 | 0.647 | 0.819 | 0.827 |
|  | 0.84 | 0.091 | 0.741 | 0.916 | 0.854 | 0.807 |
|  | 0.843 | 0.102 | 0.834 | 0.916 | 0.819 | 0.874 |
|  |  | 0.1 | 0.749 | 0.668 | 0.78 | 0.79 |
|  |  | 0.087 | 0.771 | 0.813 | 0.832 | 0.76 |
|  |  | 0.092 | 0.77 | 0.809 | 0.828 | 0.771 |
| Mean | 0.831 | 0.0945 | 0.798 | 0.795 | 0.822 | 0.805 |
| SE | 0.011 | 0.002 | 0.028 | 0.048 | 0.01 | 0.017 |

*Cloudy; appears to kill cells within hours-very toxic to cells

A comparison study was conducted using anti-STAT3 VHH13 (SEQ ID NO:3) sdAb (SBT-100) from Creative Biolabs and compared its efficacy with that of anti-STAT3 VHH13 (SEQ ID NO:3) sdAb (SBT-100) produced by Curirx. For this study, SJSA-1 cells were treated with anti-STAT3 VHH13 (SEQ ID NO:3) sdAb (SBT-100) produced by Creative Biolabs or with the different samples of anti-STAT3 VHH13 (SEQ ID NO:3) sdAb (SBT-100) produced by Curirx (i.e., Succinate-Proline, Succinate, P04). The anti-STAT3 VHH13 (SEQ ID NO:3) sdAb (SBT-100) was tested at three dose levels: 0, 50 or 100 µg/ml. For each sample their respective buffers were used as vehicle controls. The study was terminated at 72 hours post-treatment. As shown in Table 75, all anti-STAT3 VHH13 (SEQ ID NO:3) sdAb (SBT-100) treated samples tested showed highly significant growth inhibition at the highest dose tested (100 µg/ml) while only the Creative Biolab and the Curirx P04 buffer based show significant growth inhibition at the 50 µg/ml dose level.

TABLE 75

Comparison study of SJSA-1 Human Bone Osteosarcoma Cancer Cells treated with anti-STAT3 VHH13 (SEQ ID NO: 3) sdAb (SBT-100)

| Source | Treatment | Mean Abs (570 nm) | ±SD | % Inhibition | p-value |
|---|---|---|---|---|---|
| Creative Biolabs | PBS | 0.439 | 0.059 | | |
| | 50 µg/ml | 0.242 | 0.044 | 44.9 | <0.001 |
| | 100 µg/ml | 0.058 | 0.002 | 86.9 | <0.001 |
| Curirx-Succinate-Proline | Succinate-Proline | 0.425 | 0.051 | | |
| | 50 µg/ml | 0.367 | 0.038 | 13.7 | ns |
| | 100 µg/ml | 0.054 | 0.002 | 87.2 | <0.001 |
| Curirx-Succinate | Succinate | 0.542 | 0.128 | | |
| | 50 µg/ml | 0.516 | 0.028 | 4.7 | ns |
| | 100 µg/ml | 0.054 | 0.001 | 90.1 | <0.001 |
| Curirx-P04 | P04 | 0.749 | 0.119 | | |
| | 50 µg/ml | 0.278 | 0.068 | 62.8 | <0.001 |
| | 100 µg/ml | 0.054 | 0.002 | 92.8 | <0.001 |

Cumulatively, these studies show support for anti-STAT3 VHH13 (SEQ ID NO:3) sdAb (SBT-100) as a chemotherapeutic agent (alone or in combination with established chemotherapeutic agents) against various types of cancers including: Pancreatic (PANC-1), Osteosarcoma (SJSA-1), fibrosarcoma (HT1080) (U87MG) Glioblastoma (U87MG) and breast cancer (MDA-MB-231).

Example 32

Efficacy of SBT-100 and Doxorubicin on SJSA-1 Bone Osteosarcoma Subcutaneous Xenograft Model The objective of this study was to evaluate the efficacy of anti-STAT3 VHH13 (SEQ ID NO:3) sdAb (SBT-100) alone or in combination with Doxorubicin on SJSA-1 Bone Osteosarcoma Subcutaneous Xenograft Model.

5 to 6 week old athymic mice (Hsd: Athymic Nude-Fox1nu, Charles River laboratories) were fed ad libitum autoclaved water and PicoLab Rodent Diet 20 Irradiated consisting of 20% crude protein, 4.5% crude fat, and 6.0% crude fiber. The mice were housed on autoclaved bedding in plastic shoebox cages with filter. The animals were kept in a 12-hour light cycle at 20-26° C. (68-78.8° F.) and 30-70% humidity.

The SJSA-1 Bone Osteosarcoma cell line was obtained from American Type Culture collection (ATCC, Manassas, Va.). The SJSA-1 cells were cultured in RPMI-1640 medium containing 10% fetal bovine serum and 1% of 100× Penicilin-streptomycin glutamine. Cells were cultured in a humidified incubator at 37° C., in 5% $CO_2$ and 95% air.

Tumor cells in passage three were used for the implantation and were harvested during log phase growth. SJSA-1 ($1 \times 10^6$) were injected subcutaneously into the right flank at a final volume of 100-µL of media. Tumor measurements were initiated as soon as the tumors were palpable. Thereafter, tumors were measured twice weekly. Tumors were measured in two dimensions using calipers and volume was calculated using the formula:

$$\text{Tumor volume (mm}^3\text{)} = \frac{w^2 \times l}{2}$$

Where w=width and l=length in mm of a tumor. Tumor weight may be estimated with the assumption that 1 mg is equivalent to 1 $mm^3$ or tumor volume. Animals are randomized using the stratified random sampling algorithm using animal body weights (g). Treatment was initiated the day following randomization.

Anti-STAT3 VHH13 (SEQ ID NO:3) sdAb (SBT-100) was provided as a pre-formulated ready to dose solution (Lot No. 11152012-VHH026E_Anti-STAT3_VHH13). The dosing solution was supplied at 0.558 mg/mL in 1 mL aliquots and stored at −20° C. until needed for dosing. On each day of treatment, only needed vials of SBT-100 were thawed to room temperature. All leftover dosing suspensions were retained at 4° C. as needed for the next dose. Doxorubicin was purchased from Selleckchem (Houston, Tex.). Sterile water was used as a vehicle to dissolve Doxorubicin.

Athymic nude mice were dosed as indicated in Table 76. All treatments were administered via intraperitoneal (IP). Vehicle and anti-STAT3 VHH13 (SEQ ID NO:3) sdAb (SBT-100) were administered twice daily, six hours; the dosing level was 5.0 mg/kg twice a day (BID) for 14 days. Doxorubicin was dosed at a dose level of 7.0 mg/kg on days 1, 8 and 14.

TABLE 76

| | | | Doseage | | |
|---|---|---|---|---|---|
| Group | # Mice | TA | Dose (mg/kg) | Schedule | Route |
| 1 | 9 | PBS | 0 | BIDx14 | IP |
| 2 | 7 | SBT-100 | 5.0 | BIDx14 | IP |
| 3 | 7 | Doxorubicin | 7.0 | Days 1, 8, and 14 | IP |
| 4 | 7 | SBT-100 and Doxorubicin | 5.0/7.0 | BID x14 (SBT-100) & Days 1, 8, and 14 (Doxorubicin) | IP |

SJSA-1 Tumor Xenograft Model animals were quarantined for one week after arrival. The animals were then inoculated with SJSA-1 ($1 \times 10^6$) cells and randomized based on body weights. Treatment was initiated 8 days post-inoculation. Mean (±SE) tumor size was shown to be as follows: 39.66±12.48 (n=9), 31.31±11.59 (n=7), 16.52±5.93 (n=7), and 34.86±11.42 (n=7) for Groups 1, 2, 3, and 4 respectively. Table 77 summarizes the mean and median tumor measurements for the entire study. Mean body weights (±SE) at randomization were: 22.28±0.63 (Groups 1), 21.96±0.43 (Group 2), 23.26±0.42 (Group 3) and 21.56±0.43 (Group 4). Table 78 summarizes the mean and median body weights (±SE) for entire study.

TABLE 77

SJSA-1 Human Osteosarcoma Subcutaneous Xenograft Model Summary of Tumor Measurements (mm³)

| | | \multicolumn{7}{c}{Date/Study Day post implant Dosing} | | | | | | |
|---|---|---|---|---|---|---|---|---|
| Group | Animal ID | 5/26<br>9 | 5/30<br>13 | 6/2<br>16 | 6/6<br>20 | 6/7<br>21 | 6/9<br>23 | 6/13<br>27 |
| 1 | 001 | 41.59 | 59.20 | 62.67 | 157.81 | 176.52 | 345.34 | 1,026.02 |
| 1 | 002 | 0.00 | 11.16 | 42.12 | 84.18 | 90.11 | 154.67 | 365.59 |
| 1 | 003 | 13.66 | 36.49 | 163.74 | 234.36 | 333.88 | 461.26 | 1,194.54 |
| 1 | 004 | 14.65 | 56.77 | 235.84 | 253.93 | 302.38 | 390.15 | 1,138.99 |
| 1 | 005 | 120.48 | 125.58 | 340.31 | 711.65 | 1,012.21 | 1,102.51 | 2,529.62 |
| 1 | 006 | 22.68 | 52.53 | 103.20 | 192.63 | 261.71 | 340.11 | 584.01 |
| 1 | 007 | 21.02 | 76.68 | 165.63 | 286.11 | 307.94 | 490.44 | 919.47 |
| 1 | 008 | 71.90 | 159.96 | 292.14 | 487.89 | 602.12 | 689.81 | 2,606.85 |
| 1 | 009 | 50.99 | 134.65 | 156.84 | 371.01 | 507.23 | 720.72 | 2,341.61 |
| | Mean Abs | 39.66 | 79.22 | 173.61 | 308.84 | 399.34 | 521.67 | 1,411.86 |
| | SD Mean | 37.44 | 49.78 | 100.44 | 191.72 | 277.18 | 279.72 | 854.02 |
| | SE Mean | 12.48 | 16.59 | 33.48 | 63.91 | 92.39 | 93.24 | 284.67 |
| | Median Abs | 22.68 | 59.20 | 163.74 | 253.93 | 307.94 | 461.26 | 1,138.99 |
| | SE Med | 13.85 | 18.04 | 33.66 | 66.79 | 97.88 | 95.65 | 300.58 |
| 2 | 010 | 15.75 | 106.64 | 139.83 | 191.62 | 271.05 | 308.49 | 707.34 |
| 2 | 011 | 19.98 | 28.26 | 36.05 | 70.70 | 115.97 | 201.00 | 474.71 |
| 2 | 012 | 0.00 | 0.00 | 11.02 | 59.97 | 96.53 | 185.39 | 380.72 |
| 2 | 013 | 69.47 | 126.45 | 200.95 | 616.53 | 901.18 | 1,359.67 | 2,500.29 |
| 2 | 014 | 10.46 | 38.25 | 187.82 | 180.38 | 155.51 | 197.83 | 351.21 |
| 2 | 015 | 79.76 | 420.78 | 358.90 | 450.45 | 602.51 | 756.79 | 1,699.89 |
| 2 | 016 | 23.77 | 85.60 | 126.46 | 200.68 | 198.86 | 332.80 | 1,275.63 |
| | Mean Abs | 31.31 | 115.14 | 151.57 | 252.90 | 334.52 | 477.43 | 1,055.68 |
| | SD Mean | 30.67 | 142.13 | 115.91 | 205.52 | 303.26 | 436.98 | 812.51 |
| | SE Mean | 11.59 | 53.72 | 43.81 | 77.68 | 114.62 | 165.16 | 307.10 |
| | % Inh Mean | 21.06% | −45.34% | 12.69% | 18.11% | 16.23% | 8.48% | 25.23% |
| | Median Abs | 19.98 | 85.60 | 139.83 | 191.62 | 198.86 | 308.49 | 707.34 |
| | SE Med | 12.48 | 55.06 | 44.07 | 81.61 | 127.30 | 178.99 | 338.43 |
| | % Inh Med | 11.92% | −44.59% | 14.60% | 24.54% | 35.42% | 33.12% | 37.90% |
| | % T/C | n/a | n/a | 71.23 | 73.26 | 76.22 | 79.47 | 69.91 |
| | p-value | 0.64 | 0.49 | 0.69 | 0.58 | 0.66 | 0.81 | 0.41 |
| 3 | 017 | 23.19 | 48.43 | 102.31 | 61.44 | 85.16 | 105.84 | 163.53 |
| 3 | 018 | 15.21 | 20.77 | 37.33 | 68.71 | 115.50 | 142.33 | |
| 3 | 019 | 14.32 | 132.27 | 105.65 | 114.42 | 133.21 | 217.29 | 268.16 |
| 3 | 020 | 16.69 | 104.16 | 118.75 | 93.72 | 119.94 | 151.94 | |
| 3 | 021 | 0.00 | 25.81 | 57.55 | 75.00 | 160.89 | 116.95 | |
| 3 | 022 | 0.00 | 132.66 | 51.55 | 69.85 | | | |
| 3 | 023 | 46.20 | 72.93 | 73.50 | 72.16 | 94.40 | 117.30 | |
| | Mean Abs | 16.52 | 76.72 | 78.09 | 79.33 | 118.18 | 141.94 | 215.84 |
| | SD Mean | 15.69 | 47.44 | 31.11 | 18.40 | 27.26 | 40.78 | 73.99 |
| | SE Mean | 5.93 | 17.93 | 11.76 | 6.95 | 11.13 | 16.65 | 52.32 |
| | % Inh Mean | 58.36% | 3.16% | 55.02% | 74.31% | 70.41% | 72.79% | 84.71% |
| | Median Abs | 15.21 | 72.93 | 73.50 | 72.16 | 117.72 | 129.81 | 215.84 |
| | SE Med | 5.96 | 18.00 | 11.91 | 7.55 | 11.13 | 17.51 | 52.32 |
| | % Inh Med | 32.94% | −23.18% | 55.11% | 71.58% | 61.77% | 71.86% | 81.05% |
| | % T/C | n/a | 107.14 | 51.96 | 30.35 | 36.16 | 30.43 | 17.91 |
| | p-value | 0.15 | 0.92 | 0.03 | 0.01 | 0.03 | 0.01 | 0.09 |
| 4 | 024 | 35.18 | 33.03 | 71.08 | 59.73 | 63.34 | 99.24 | 104.58 |
| 4 | 025 | 10.45 | 39.28 | 70.76 | 88.40 | 115.41 | 211.40 | |
| 4 | 026 | 0.00 | 0.00 | 0.00 | 0.00 | 0.00 | 0.00 | 0.00 |
| 4 | 027 | 30.69 | 53.56 | 63.22 | 72.51 | 65.68 | 93.09 | 159.02 |
| 4 | 028 | 82.90 | 131.03 | 186.81 | 275.94 | 249.53 | 269.40 | 331.49 |
| 4 | 029 | 17.61 | 71.56 | 51.35 | | | | |
| 4 | 030 | 67.21 | 99.41 | 360.89 | 383.26 | 388.92 | 474.13 | 899.01 |
| | Mean Abs | 34.86 | 61.12 | 114.87 | 146.64 | 147.15 | 191.21 | 298.82 |
| | SD Mean | 30.22 | 43.82 | 122.11 | 148.76 | 145.09 | 168.05 | 356.32 |
| | SE Mean | 11.42 | 16.56 | 46.15 | 60.73 | 59.23 | 68.61 | 159.35 |
| | % Inh Mean | 12.11% | 22.85% | 33.83% | 52.52% | 63.15% | 63.35% | 78.83% |
| | Median Abs | 30.69 | 53.56 | 70.76 | 80.45 | 90.55 | 155.32 | 159.02 |
| | SE Med | 11.55 | 16.85 | 49.54 | 67.56 | 64.42 | 70.46 | 174.01 |
| | % Inh Med | −35.33% | 9.53% | 56.79% | 68.32% | 70.60% | 66.33% | 86.04% |
| | % T/C | 0 | −100 | −100 | −100 | −100 | −100 | 0.24 |
| | p-value | 0.79 | 0.46 | 0.31 | 0.10 | 0.06 | 0.02 | 0.02 |

TABLE 78

SJSA-1 Human Osteosarcoma Subcutaneous Xenograft Model Summary of Body Weights (g)

| | | Pre-dosing | Date/Study Day post implant Dosing | | | | | |
|---|---|---|---|---|---|---|---|---|
| Group | Animal ID | 5/24 7 | 5/26 9 | 5/30 13 | 6/2 16 | 6/6 20 | 6/9 23 | 6/13 27 |
| 1 | 001 | 21.60 | 22.40 | 22.80 | 23.20 | 23.30 | 21.10 | 23.40 |
| 1 | 002 | 24.90 | 24.90 | 25.30 | 26.80 | 27.20 | 24.60 | 26.90 |
| 1 | 003 | 21.60 | 23.00 | 22.40 | 22.70 | 22.90 | 20.90 | 24.40 |
| 1 | 004 | 25.30 | 25.30 | 24.90 | 25.30 | 25.30 | 23.20 | 26.20 |
| 1 | 005 | 21.80 | 22.10 | 22.10 | 22.30 | 23.10 | 20.80 | 21.50 |
| 1 | 006 | 20.50 | 21.00 | 20.50 | 20.80 | 20.70 | 21.00 | 22.40 |
| 1 | 007 | 22.10 | 22.50 | 22.80 | 22.60 | 23.40 | 23.80 | 25.10 |
| 1 | 008 | 19.60 | 20.40 | 19.80 | 19.60 | 20.10 | 21.00 | 21.60 |
| 1 | 009 | 23.10 | 23.70 | 23.60 | 24.50 | 24.50 | 24.20 | 24.40 |
| | Mean Abs | 22.28 | 22.81 | 22.69 | 23.09 | 23.39 | 22.29 | 23.99 |
| | Mean Rel | 100.0% | 100.00% | 99.46% | 101.22% | 102.53% | 97.71% | 105.16% |
| | SD Mean | 1.88 | 1.63 | 1.81 | 2.21 | 2.17 | 1.62 | 1.93 |
| | SE Mean | 0.63 | 0.54 | 0.60 | 0.74 | 0.72 | 0.54 | 0.64 |
| | Median Abs | 21.80 | 22.50 | 22.80 | 22.70 | 23.30 | 21.10 | 24.40 |
| | Median Rel | 100.00% | 100.00% | 101.33% | 100.89% | 103.56% | 93.78% | 108.44% |
| | SE Med | n/a | 0.55 | 0.60 | 0.75 | 0.73 | 0.68 | 0.66 |
| 2 | 010 | 22.3 | 21.70 | 23.00 | 23.40 | 23.80 | 24.20 | 25.50 |
| 2 | 011 | 22.1 | 22.00 | 22.00 | 22.60 | 23.70 | 24.40 | 24.50 |
| 2 | 012 | 20.4 | 20.20 | 20.70 | 21.40 | 21.90 | 22.20 | 23.00 |
| 2 | 013 | 23.2 | 22.80 | 22.70 | 23.90 | 25.20 | 25.70 | 26.80 |
| 2 | 014 | 20.9 | 20.80 | 21.90 | 21.90 | 21.40 | 22.30 | 22.90 |
| 2 | 015 | 23.4 | 23.10 | 24.70 | 24.70 | 25.40 | 25.60 | 26.90 |
| 2 | 016 | 21.4 | 21.10 | 21.60 | 22.10 | 22.40 | 22.80 | 24.80 |
| | Mean Abs | 21.96 | 21.67 | 22.37 | 22.86 | 23.40 | 23.89 | 24.91 |
| | Mean Rel | 100.00% | 100.00% | 103.23% | 105.47% | 107.98% | 110.22% | 114.96% |
| | SD Mean | 1.13 | 1.05 | 1.27 | 1.19 | 1.57 | 1.48 | 1.62 |
| | SE Mean | 0.43 | 0.40 | 0.48 | 0.45 | 0.59 | 0.56 | 0.61 |
| | % Inh Mean | n/a | 5.00% | 1.40% | 1.00% | −0.05% | −7.16% | −3.86% |
| | Median Abs | 22.10 | 21.70 | 22.00 | 22.60 | 23.70 | 24.20 | 24.80 |
| | Median Rel | 100.00% | 100.00% | 101.38% | 104.15% | 109.22% | 111.52% | 114.29% |
| | SE Med | n/a | 0.40 | 0.50 | 0.46 | 0.60 | 0.57 | 0.61 |
| | % Inh Med | n/a | 3.56% | 3.51% | 0.44% | −1.72% | −14.69% | −1.64% |
| 3 | 017 | 22.9 | 22.70 | 24.50 | 24.70 | 21.50 | 20.00 | 18.80 |
| 3 | 018 | 22.6 | 23.00 | 22.70 | 22.00 | 21.20 | 19.00 | |
| 3 | 019 | 23 | 22.40 | 23.10 | 22.80 | 19.70 | 18.10 | 17.90 |
| 3 | 020 | 23 | 22.40 | 23.10 | 22.30 | 19.30 | 17.40 | |
| 3 | 021 | 24.8 | 24.40 | 25.00 | 25.00 | 20.30 | 18.50 | |
| 3 | 022 | 24.7 | 24.70 | 25.40 | 25.00 | 19.90 | | |
| 3 | 023 | 21.8 | 21.80 | 21.90 | 22.10 | 19.00 | 18.10 | |
| | Mean Abs | 23.26 | 23.06 | 23.67 | 23.41 | 20.13 | 18.52 | 18.35 |
| | Mean Rel | 100.00% | 100.00% | 102.66% | 101.55% | 87.30% | 80.31% | 79.58% |
| | SD Mean | 1.10 | 1.09 | 1.30 | 1.42 | 0.94 | 0.90 | 0.64 |
| | SE Mean | 0.42 | 0.41 | 0.49 | 0.54 | 0.35 | 0.37 | 0.45 |
| | % Inh Mean | n/a | −1.08% | −4.33% | −1.41% | 13.94% | 16.92% | 23.51% |
| | Median Abs | 23.00 | 22.70 | 23.10 | 22.80 | 19.90 | 18.30 | 18.35 |
| | Median Rel | 100.00% | 100.00% | 101.76% | 100.44% | 87.67% | 80.62% | 80.84% |
| | SE Med | n/a | 0.44 | 0.54 | 0.59 | 0.37 | 0.38 | 0.45 |
| | % Inh Med | n/a | −0.89% | −1.32% | −0.44% | 14.59% | 13.27% | 24.80% |
| 4 | 024 | 21.80 | 19.60 | 19.80 | 19.00 | 18.60 | 17.50 | 16.80 |
| 4 | 025 | 21.40 | 18.50 | 19.80 | 19.10 | 18.00 | 16.60 | |
| 4 | 026 | 20.20 | 20.00 | 20.60 | 18.90 | 19.00 | 17.40 | 17.50 |
| 4 | 027 | 21.90 | 18.80 | 19.30 | 18.70 | 15.60 | 16.00 | 16.30 |
| 4 | 028 | 20.20 | 21.40 | 22.30 | 21.40 | 21.00 | 20.20 | 18.80 |
| 4 | 029 | 23.50 | 20.00 | 18.50 | 18.60 | | | |
| 4 | 030 | 21.90 | 20.10 | 20.80 | 19.80 | 19.00 | 17.40 | 16.70 |
| | Mean Abs | 21.56 | 19.77 | 20.16 | 19.36 | 18.53 | 17.52 | 17.22 |
| | Mean Rel | 100.00% | 100.00% | 101.95% | 97.90% | 93.74% | 88.60% | 87.10% |
| | SD Mean | 1.14 | 0.95 | 1.22 | 0.98 | 1.76 | 1.44 | 0.98 |
| | SE Mean | 0.43 | 0.36 | 0.46 | 0.37 | 0.72 | 0.59 | 0.44 |
| | % Inh Mean | n/a | 13.33% | 11.16% | 16.16% | 20.76% | 21.41% | 28.22% |
| | Median Abs | 21.80 | 20.00 | 19.80 | 19.00 | 18.80 | 17.40 | 16.80 |
| | Median Rel | 100.00% | 100.00% | 99.00% | 95.00% | 94.00% | 87.00% | 84.00% |
| | SE Med | n/a | 0.37 | 0.48 | 0.40 | 0.73 | 0.59 | 0.49 |
| | % Inh Med | n/a | 11.11% | 13.16% | 16.30% | 19.31% | 17.54% | 31.15% |

At the last day of dosing, the mean tumor size (±SE) was 399.34±92.39, 334.52±114.62, 118.18±11.13, and 147.15±59.23 for Group 1, 2, 3, and 4 respectively. At the time of termination mean tumor size (±S.E.) was: 1411.86±284.67, 1055.68±307.10, 215.84±52.32, and 298.82±159.35, for Groups 1, 2, 3, and 4 respectively. A significant growth inhibition was noted for Group 2 (p=0.09) and for Group 3 (p=0.02). Mean body weights (±SE) at termination were: 23.99±0.64, 24.91±0.61, 18.35±0.45, 17.22±0.44 for Groups 1, 2, 3, and 4, respectively. At termination the % body weight change were 11.23, 14.51, −14.99, and −18.33 for Groups 1, 2, 3, and 4, respectively. Table 78 shows the average body weights for the study period. The number of surviving at the end of the study was 9, 7, 2, and 5 for Groups 1, 2, 3, and 4, respectively. At the end of the study, the mean tumor growth inhibition was shown to be: 25.23% (Group 2), 84.71% (Group 3) and 78.83% (Group 4). Table 77 illustrates the mean tumor volume. The tumor doubling times were: 8.22 (Group 1), 8.84 (Group 2), 13.32 (Group 3), and 13.86 (Group 4). The % T/C was 69.91, 17.91 and 0.24 for Groups 2, 3, and 4, respectively.

TABLE 79

Body Weights: SJSA-1 Xenograft Study 2680

| Dates | Control vs. SBT-100 | Control vs. Doxorubicin | Control vs. Combination Doxorubicin and SBT-100 |
|---|---|---|---|
| May 26, 2017 | 0.1316 | 0.7365 | 0.0006 |
| May 30, 2017 | 0.6996 | 0.246 | 0.0068 |
| Jun. 2, 2017 | 0.8066 | 0.7404 | 0.001 |
| Jun. 6, 2017 | 0.9911 | 0.0024 | 0.0005 |
| Jun. 9, 2017 | 0.618 | 0.0002 | <0.0001 |
| Jun. 13, 2017 | 0.3255 | 0.0034 | <0.0001 |
| Two-tailed P-values | | | |

Table 79 illustrates the body weights throughout the study, as compared to the control.

TABLE 80

Comparison of Survival Curves: Groups Control, SBT-100, Doxorubicin and Combination

| Log-rank (Mantel-Cox) Test | |
|---|---|
| Chi square | 15.35 |
| df | 6 |
| P value | 0.0015 |
| P value summary | ** |
| Are the survival curves sig different? | Yes |
| Gehan-Breslow-Wilcoxon Test | |
| Chi square | 5.101 |
| df | 1 |
| P value | 0.0239 |
| P value summary | * |
| Are the survival curves sig different? | Yes |

TABLE 81

Comparison of Survival Curves: Groups Control and Doxorubicin

| Log-rank (Mantel-Cox) Test | |
|---|---|
| Chi square | 9.403 |
| df | 1 |
| P value | 0.0022 |
| P value summary | ** |
| Are the survival curves sig different? | Yes |

TABLE 81-continued

Comparison of Survival Curves: Groups Control and Doxorubicin

| Gehan-Breslow-Wilcoxon Test | |
|---|---|
| Chi square | 8.949 |
| df | 1 |
| P value | 0.0028 |
| P value summary | ** |
| Are the survival curves sig different? | Yes |

TABLE 82

Comparison of Survival Curves: Groups Control and Combination

| Log-rank (Mantel-Cox) Test | |
|---|---|
| Chi square | 2.780 |
| df | 1 |
| P value | 0.0954 |
| P value summary | ns |
| Are the survival curves sig different? | No |
| Gehan-Breslow-Wilcoxon Test | |
| Chi square | 2.769 |
| df | 1 |
| P value | 0.0961 |
| P value summary | ns |
| Are the survival curves sig different? | No |

Tables 80-82 illustrate comparison of the survival curves between the Control group, the SBT-100 group, the Doxorubicin group and the Combination group.

Anti-STAT3 VHH13 (SEQ ID NO:3) sdAb (SBT-100) showed a non-significant decrease in mean tumor size as compared to control. Moreover, while SBT-100 did not increase tumor inhibition in comparison to the Doxorubicin treatment, animals received both SBT-100 and Doxorubicin were less likely to die as compared to animals receiving Doxorubicin alone. Therefore it appears that combining Doxorubicin with anti-STAT3 VHH13 (SEQ ID NO:3) sdAb (SBT-100) is beneficial for treatment. FIG. 24 illustrates the dose response curves for controls E864 and AQ for EBOV/Hela, FIG. 25 illustrates the dose response curves for controls E864 and AQ for EBOV/HFF, FIG. 26 illustrates the dose response curves for controls E864 and AQ for Zika/Vero, FIG. 27 illustrates the dose response curves with test drugs for EBOV/Hela, FIG. 28 illustrates the dose response curves with test drugs for EBOV/HFF; and FIG. 29 illustrates the dose response curves with test drugs for Zika/Vero.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A method of treating viral infections using a single-domain antibody (sdAb), wherein the sdAb comprises the amino acid sequence as set forth in SEQ ID NO:3.

2. The method of claim 1, wherein the viral infection is caused by one or more of a DNA virus, an RNA virus, or a retrovirus.

3. The method of claim 2 wherein the virus is hepatitis A virus, hepatitis B virus, hepatitis C virus, human papillomavirus, polio virus, rabies virus, herpesvirus, West Nile virus, Ebola virus, and Zika virus.

4. The method of claim 1, wherein the sdAb inhibits the replication of Ebola viruses in infected cells.

5. The method of claim 1 wherein the sdAb is used in combination with one or more compounds.

* * * * *